(12) United States Patent
Statsyuk et al.

(10) Patent No.: US 10,273,208 B2
(45) Date of Patent: Apr. 30, 2019

(54) SCREENING METHODS FOR THE BINDING AFFINITY OF CHEMICAL ENTITIES TO BIOLOGICAL MOLECULES AND NEDD4-1 INHIBITORS IDENTIFIED BY THE SCREENING METHODS

(71) Applicant: Northwestern University, Evanston, IL (US)

(72) Inventors: Alexander V. Statsyuk, Evanston, IL (US); Stefan G. Kathman, Evanston, IL (US)

(73) Assignee: Northwestern University, Evanston, IL (US)

( * ) Notice: Subject to any disclaimer, the term of this patent is extended or adjusted under 35 U.S.C. 154(b) by 43 days.

(21) Appl. No.: 15/428,501

(22) Filed: Feb. 9, 2017

(65) Prior Publication Data

US 2017/0152228 A1    Jun. 1, 2017

Related U.S. Application Data

(63) Continuation-in-part of application No. 14/721,829, filed on May 26, 2015, now Pat. No. 9,586,890.

(60) Provisional application No. 62/002,588, filed on May 23, 2014, provisional application No. 62/003,656, filed on May 28, 2014.

(51) Int. Cl.
| | |
|---|---|
| *G01N 33/68* | (2006.01) |
| *H01J 49/00* | (2006.01) |
| *H01J 49/16* | (2006.01) |
| *C07C 235/40* | (2006.01) |
| *C07D 209/42* | (2006.01) |
| *C07D 231/56* | (2006.01) |
| *C07D 307/84* | (2006.01) |
| *C07D 471/04* | (2006.01) |

(52) U.S. Cl.
CPC .......... *C07D 209/42* (2013.01); *C07C 235/40* (2013.01); *C07D 231/56* (2013.01); *C07D 307/84* (2013.01); *C07D 471/04* (2013.01); *G01N 33/6815* (2013.01); *G01N 2500/20* (2013.01); *H01J 49/0027* (2013.01); *H01J 49/165* (2013.01)

(58) Field of Classification Search
CPC .......... G01N 2333/47; G01N 30/8675; G01N 33/5008; G01N 33/5011; G01N 33/5306; G01N 33/542; G01N 33/566; G01N 33/573; G01N 33/6812; G01N 33/6815; G01N 2333/9015; G01N 33/68; G01N 2500/04; C12N 9/96
See application file for complete search history.

(56) References Cited

U.S. PATENT DOCUMENTS

| | | | | |
|---|---|---|---|---|
| 7,713,958 B2 * | 5/2010 | Wan | ..................... | C07D 487/04 514/212.06 |
| 2003/0077653 A1 * | 4/2003 | Baig | ....................... | C12N 9/50 435/7.1 |
| 2009/0117100 A1 * | 5/2009 | Mao | ................. | A61K 47/48569 424/130.1 |
| 2015/0158931 A1 * | 6/2015 | Ovaa | ..................... | A61K 38/57 424/9.1 |

FOREIGN PATENT DOCUMENTS

| | | | | |
|---|---|---|---|---|
| WO | 0172701 A1 | 10/2001 | | |
| WO | WO-0172701 A1 * | 10/2001 | .......... | C07C 233/18 |
| WO | 2004098520 A2 | 11/2004 | | |
| WO | WO-2004098520 A2 * | 11/2004 | .......... | C07D 487/04 |

OTHER PUBLICATIONS

Chemical Abstract Service (CAS) STN Registry Database No. (RN) 606658-18-8 [Entered STN: Oct. 19, 2003] (Year: 2003).*
Kathman et al. Med. Chem. Commun. 2016, 7, 576-585 (Year: 2016).*
Wells et al. PNAS 2000, 97, 9367-9372 (Year: 2000).*
Kathman et al. J. Med. Chem. 2014, 57, 4969-4974 (Year: 2014).*
Chacun-Lefevre et al. Synlett 2001, 6, 848-850. (Year: 2001).*
Castaneto et al. Forensic Toxicology 2015, 33, 295-310. (Year: 2015).*
Dong et al. Bioorg. Med.Chem. Lett. 2010, 20, 2210-2214. (Year: 2010).*
Jakse et al. Heterocycles 2007, 74, 293-307. (Year: 2007).*
Padwa et al. J. Org. Chem. 2014, 79, 3173-3184. (Year: 2014).*
Kawamura et al. Tetrahedron 1995, 36, 3369-3372. (Year: 1995).*
M.Rossi et al., Cell Death Dis. 2014, 5:e1203.
Rotin, D., Kumar, S., Nat. Rev. Mol. Cell Biol. 2009, 10, 398-409.
Scott, D. E.; Coyne, A. G.; Hudson, S. A.; Abell, C. Fragment-Based Approaches in Drug Discovery and Chemical Biology. Biochemistry 2012, 51, 4990-5003.
Shi, Y.J., Wang, J., Chandarlapaty, S., Cross, J., Thompson, C., Rosen, N., Jiang, X., Nat. Struct. Mol. Biol. 2014.
Singh, J.; Petter, R. C.; Baillie, T. A.; Whitty, A. The resurgence of covalent drugs. Nat. Rev. Drug. Discov. 2011, 10, 307-317.
Song, M.S., Carracedo, A., Salmena, L., Song, S.J., Egia, A., Malumbres, M., Pandolfi, P.P., Cell 2011, 144, 187-199.

(Continued)

Primary Examiner — Amanda L Aguirre
(74) Attorney, Agent, or Firm — Andrus Intellectual Property Law, LLP

(57) ABSTRACT

Disclosed are methods for preparing and screening for an inhibitor of the activity of a biological molecule having a catalytic or non-catalytic cysteine residue. The methods including preparing a library of candidate inhibitor molecules by conjugating an electrophile to a plurality of drug molecules where the library of candidate inhibitor molecules thus formed react with cysteine residues. The library of candidate inhibitor molecules then may be reacted with the biological molecule to identify those inhibitor molecule that react with the catalytic or non-catalytic cysteine residue of the biological molecule in order to identify an inhibitor of the biological molecule.

16 Claims, 123 Drawing Sheets
Specification includes a Sequence Listing.

(56) References Cited

OTHER PUBLICATIONS

Vaguine, A.A., Richelle, J., Wodak, S.J. SFCHECK: a unified set of procedures for evaluating the quality of macromolecular structure-factor data and their agreement with the atomic model. Acta Cryst. D 55, 191-205 (1999).
X.J. Wang et al., Cell 2007.
Weerapana, E.; Wang, C.; Simon, G. M.; Richter, F.; Khare, S.; Dillon, M. B.; Bachovchin, D. A.;Mowen, K.; Baker, D.; Cravatt, B. F. Quantitative reactivity profiling predicts functional cysteines in proteomes. Nature 2010, 468, 790-795.
Whitcomb, E. A.; Dudek, E. J.; Liu, Q.; Taylor, A. Novel control of S phase of the cell cycle by ubiquitin-conjugating enzyme H7. Mol. Biol. Cell. 2009, 20, 1-9.
Winn, M.D., Isupov, M.N., Murshudov, G.N. Use of TLS parameters to model anisotropic displacements in macromolecular refinement. Acta Cryst. D 57, 122-133 (2001).
Winn, M.D. et al. Overview of the CCP4 suite and current developments. Acta Cryst. D 67, 235-242 (2011).
Winter, G. Xia2: an expert system for macromolecular crystallography data reduction. J. Appl. Cryst. 43, 186-190 (2010).
Adams, P.D. et al. PHENIX: a comprehensive Python-based system for macromolecular structure solution. Acta Cryst. D 66, 213-221 (2010).
Boase, N.A., Kumar, S., Gene 2015, 557, 113-122; b) Y.J. Shi, J. Wang, S. Chandarlapaty, J. Cross, C. Thompson, N. Rosen, X. Jiang, Nat. Struct. Mol. Biol. 2014.
Byun, S.; Lee, S. Y.; Lee, J.; Jeong, C. H.; Farrand, L.; Lim, S.; Reddy, K.; Kim, J. Y.; Lee, M. H.; Lee, H. J.; Bode, A. M.; Lee, K. W.; Dong, Z. USP8 is a novel target for overcoming gefitinib-resistance in lung cancer. Clin. Cancer Res. 2013, 19, 3894-904.
Y. Cao, C. Wang, X. Zhang, G. Xing, K. Lu, Y. Gu, F. He, L. Zhang, Sci. Rep. 2014, 4, 4965.
Cardoso, R.; Love, R.; Nilsson, C. L.; Bergqvist, S.; Nowlin, D.; Yan, J.; Liu, K. K.; Zhu, J.; Chen, P.; Deng, Y. L.; Dyson, H. J.; Greig, M. J.; Brooun, A. Identification of Cys255 in HIF-1α as a novel site for development of covalent inhibitors of HIF-1α/ARNT PasB domain protein-protein interaction. Protein. Sci. 2012, 21, 1885-1896.
Castaneto et al. "Identification of AB-FUBINACA metabolites in human hepatocytes and urine using high-resolution mass spectrometry" Forensic Toxicology 2015, 33, 295-310.
Chacun-Lefevre et al. "Intramolecular Heck Coupling of Alkenyl 3-Iodoindole-2-carboxamide Derivatives" Synlett 2001, 6, 848-850.
Chen, G.; Heim, A.; Riether, D.; Yee, D.; Milgrom, Y.; Gawinowicz, M. A.; Sames. D. Reactivity of Functional Groups on the Protein Surface: Development of Epoxide Probes for Protein Labeling. J. Am. Chem. Soc. 2003, 125, 8130-8133.
Congreve, M.; Carr, R.; Murray, C.; Jhoti, H. A. Drug Discovery Today 2003, 8, 876-877.
Copeland, R.A., Evaluation of Enzyme Inhibitors in Drug Discovery: A Guide for Medicinal Chemists and Pharmacologists, 2nd Edition, Wiley, p. 347-348, (2013).
Dong et al "Structure-based design of novel human Pin 1 inhibitors (II)" Bioorg. Med. Chem. Lett. 2010, 20, 2210-2214.
Emsley, P., Cowtan, K. Coot: model-building tools for molecular graphics. Acta Cryst. D 60, 2126-2132 (2004).
Erlanson, D. A.; Braisted, A. C.; Raphael, D. R.; Randal, M.; Stroud, R.M.; Gordon, E.M.; Wells, J.A. Site-directed ligand discovery. PNAS 2000, 97, 9367-9372.
Erlanson, D. A.; Wells, J. A; Braisted, A. C. Tethering: fragment-based drug discovery. Annu. Rev. Biophys. Biomol. Struct. 2004, 33, 199-223.
Ettari, R.; Micale, N.; Schirmeister, T.; Gelhaus, C.; Leippe, M.; Nizi, E.; Di Francesco, M. E.; Grasso, S.; Zappalà, M. Novel Peptidomimetics Containing a Vinyl Ester Moiety as Highly Potent and Selective Falcipain-2 Inhibitors. J. Med. Chem. 2009, 52, 2157-60.
French, M.E., Kretzmann, B.R., Hicke, L., J. Biol. Chem. 2009, 284, 12071-12079.
Han et al. J. Virol. 2014, 88, 7294-7306.

Hanzlik, R. P.; Thompson, S. A. Vinylogous Amino Acid Esters: A New Class of Inactivators for Thiol Proteases. J. Med. Chem. 1984, 27, 711-712.
Hershko, A., Ciechanover, A., Annu. Rev. Biochem. 1998, 67, 425-479.
Hu, Y., Furtmann, N., Bajorath, J., J. Med. Chem. 2015, 58, 30-40.
Jakse et al. "Synthesis and Transformation of N,N-Dimethylamino-Methylidene Derivatives of Indolylglycines and some other Dipeptides" Heterocycles 2007, 74, 293-307.
S.E. Kaiser, B.E. Riley, T.A. Shaler, R.S. Trevino, C.H. Becker, H. Schulman, R.R. Kopito, Nat. Methods 2011, 8, 691-U129.
Kamadurai et al., Elife 2013, 2:e00828.
S.G. Kathman, Z. Xu, A.V. Statsyuk, J. Med. Chem. 2014, 57, 4969-4974.
Kawamura et al. "Enantio and Stereocontrolled Syntheses of (−) Semburin, (+) N-Benzoylmeroquinene Aldehyde, (—) Antirhine, and (+) Isocorynantheol from Common (+) Norcamphor" Tetrahedron 1995, 36, 3369-3372.
Kim, A.M. Steffen, M.L. Oldham, J. Chen, J. Huibregtse, EMBO Rep. 2011, 12, 334-341.
Kitz, R.; Wilson, I. B. Esters of Methanesulfonic Acid as Irreversible Inhibitors of Acetylcholinesterase. J. Biol. Chem. 1962, 237, 3245-3249.
Komander, M. Rape, Annu. Rev. Biochem. 2012, 81, 203-229.
Krippendorff B. F.; Neuhaus, R.; Lienau, P.; Reichel, A.; Huisinga, W. Mechanism-Based Inhibition: Deriving KI and kinact Directly from Time-Dependent IC50 Values. J. Biomol. Screen. 2009, 14, 913-23.
Lanning et al., Nat. Chem. Biol. 2014, 10, 760-767.
Laskowski, R.A., Rullmannn, J.A., MacArthur, M.W., Kaptein, R., Thornton, J.M.J. AQUA and PROCHECK-NMR: programs for checking the quality of protein structures solved by NMR. Biomol. NMR 8, 477-486 (1996).
Lebedev, A.A. et al. JLigand: a graphical tool for the CCP4 template-restraint library. Acta Cryst. D 68, 431-440 (2012).
Liu, S.; Hanzlik, R. P. Structure-activity relationships for inhibition of papain by peptide Michael acceptors. J. Med. Chem. 1992, 35, 1067-1075.
Maddika, S. Kavela, N. Rani, V.R. Palicharla, J.L. Pokorny, J.N. Sarkaria, J.J. Chen, Nat. Cell Biol. 2011, 13, 728-U224.
Maspero, E., et al. Structure of the HECT:ubiquitin complex and its role in ubiquitin chain elongation. EMBO Rep. 12 (4), 342-9 (2011).
Maspero, E., Valentini, E., Mari, S., Cecatiello, V., Soffientini, P., Pasqualato, S., Polo, S., Nat. Struct. Mol. Biol. 2013, 20, 696-701.
McCoy, A.J., et al. Phaser crystallographic software. J. Appl. Cryst. 40, 658-674 (2007).
Miller, R. M.; Paavilainen, V. O.; Krishnan, S.; Serafimova, I. M.; Taunton, J. Electrophilic fragment based design of reversible covalent kinase inhibitors. J. Am. Chem. Soc. 2013, 135, 5298-5301.
T. Mund, M.J. Lewis, S. Maslen, H.R. Pelham, Proc. Natl. Acad. Sci. 2014, 111, 16736-16741.
Murshudov, G.N., Vagin, A.A., Dodson, E.J. Refinement of macromolecular structures by the maximum-likelihood method. Acta Cryst. D 53, 240-255 (1997).
Nonoo, R. H.; Armstrong, A.; Mann, D. J. Kinetic Template-Guided Tethering of Fragments. ChemMedChem 2012, 7, 2082-2086.
Padwa et al. "Intramolecular Cycloaddition Reactions of Furo[3,4-b] indoles for Alkaloid Synthesis" J. Org. Chem. 2014, 79, 3173-3184.
Park, S., et al. Mechanism-based small molecule cross-linkers of HECT E3 ubiquitin ligase—substrate pairs. Biochemistry 51, 8327-8329 (2012).
Patick, A. K.; Brothers, M. A.; Maldonado, F.; Binford, S.; Maldonado, O.; Fuhrman, S.; Petersen, A.; Smith III, G. J.; Zalman, L. S.; Burns-Naas, L. A.; Tran, J. Q. In Vitro Antiviral Activity and Single-Dose Pharmacokinetics in Humans of a Novel, Orally Bioavailable Inhibitor of Human Rhinovirus 3C Protease. Antimicrob. Agents Chemother. 2005, 49, 2267-2275.
S. Peter et al., EMBO Mol. Med. 2014, 6, 1525-1541.
Powers, J. C.; Asgian, J. L.; Ekici, O. D.; James, K. E. Irreversible Inhibitors of Serine, Cysteine, and Threonine Proteases. Chem. Rev. 2002, 102, 4639-4750.

(56) References Cited

OTHER PUBLICATIONS

Read, R.J., Schierbeek, A.J.J. A phased translation function. J. Appl. Cryst. 21, 490-495 (1988).
Reddick, J. J.; Cheng, J.; Roush, W. R. Relative Rates of Michael Reactions of 2'-(Phenethyl)thiol with Vinyl Sulfones, Vinyl Sulfonate Esters, and Vinyl Sulfonamides Relevant to Vinyl Sulfonyl Cysteine Protease Inhibitors. Org. Lett. 2003, 5, 1967-1970.
Renukuntla, J.; Vadlapudi, A. D.; Patel, A.; Boddu, S. H.; Mitra, A. K. Approaches for enhancing oral bioavailability of peptides and proteins. Int. J. Pharm. 2013, 447, 75-93.
Rosenthal, P. J. Falcipains and other cysteine proteases of malaria parasites. Adv. Exp. Med. Biol. 2011, 712, 30-48.

* cited by examiner

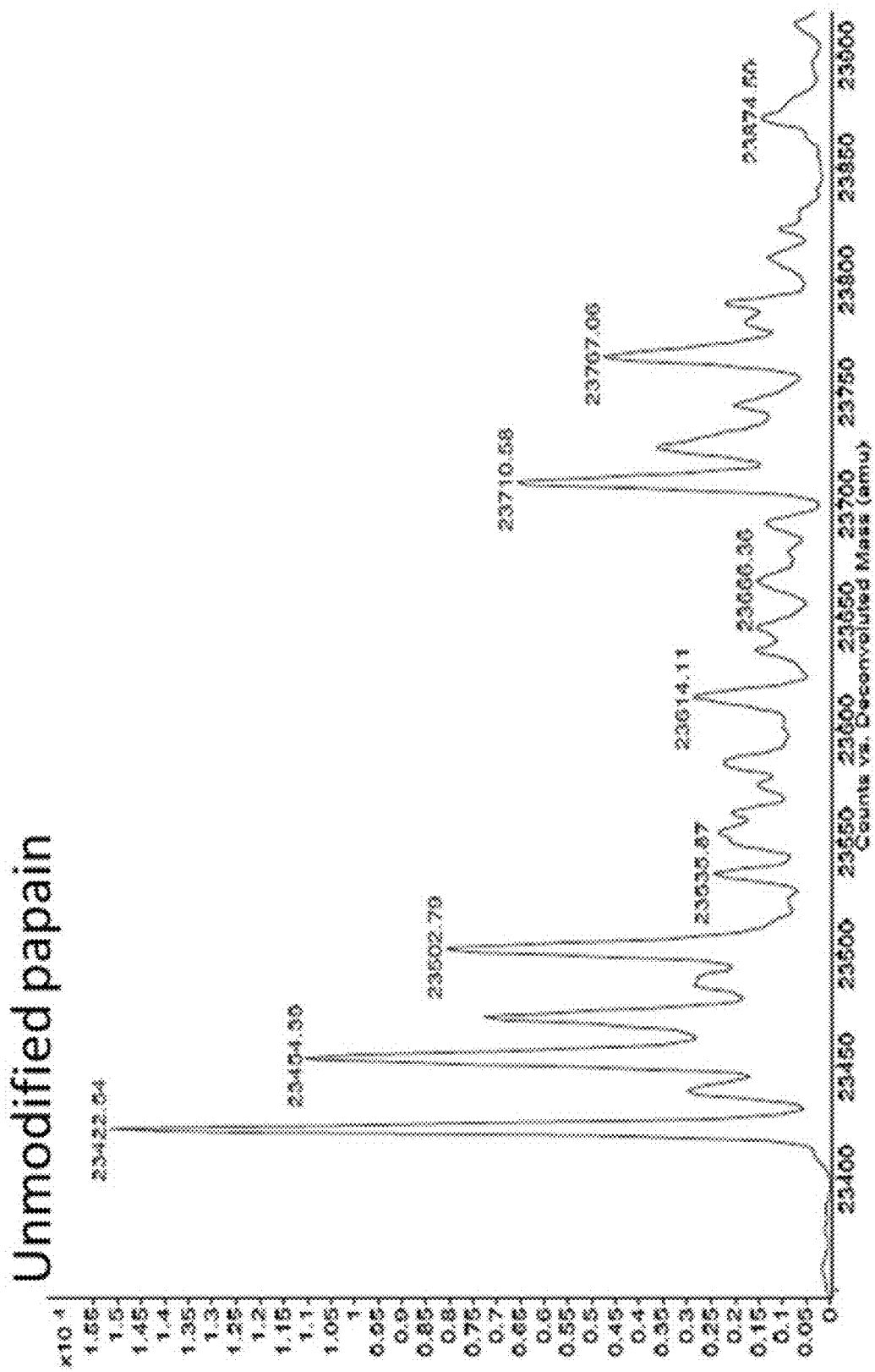
Figure 5C Mix 2 Unmodified papain

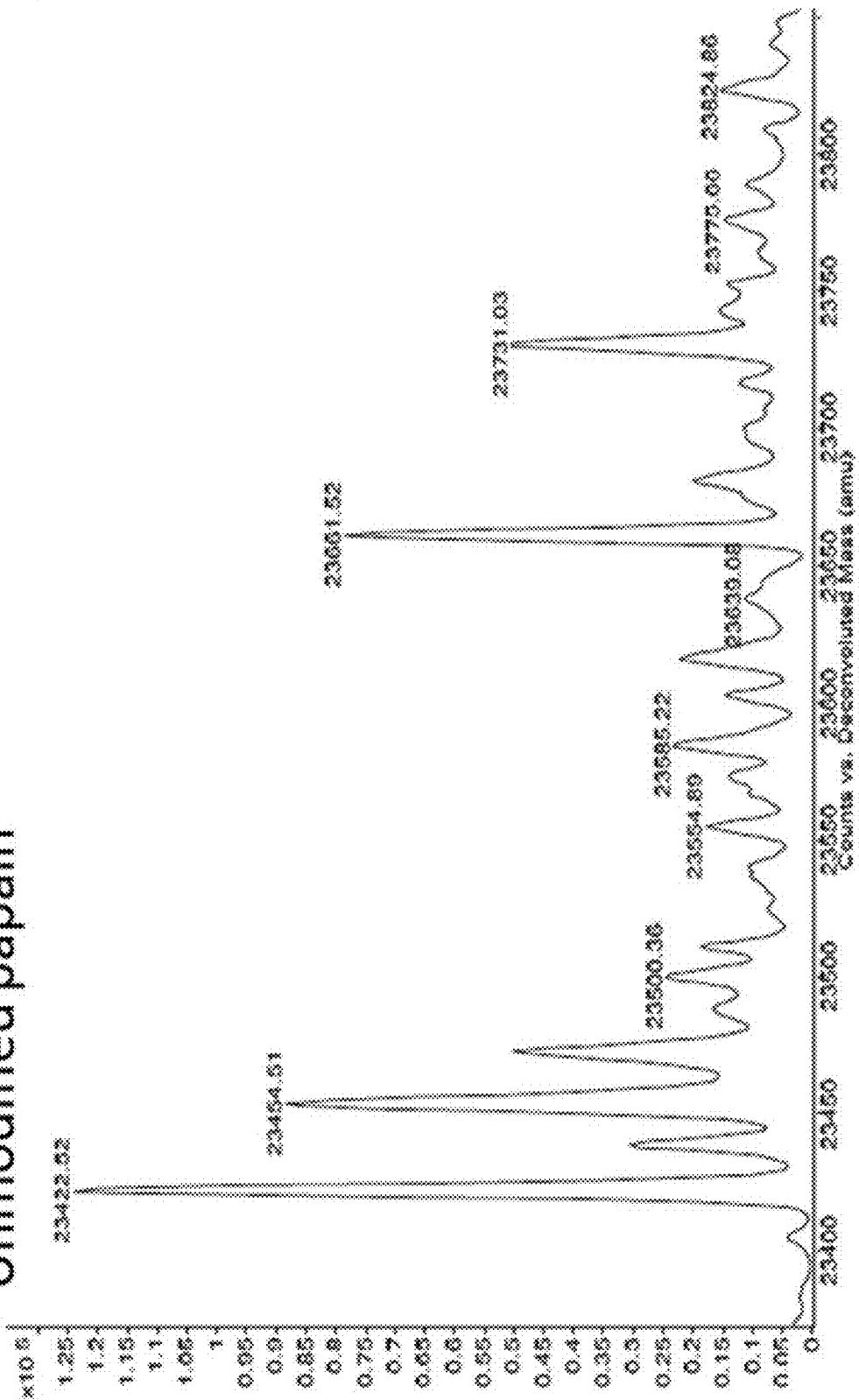

SEQUENCE LISTING

```
<160> NUMBER OF SEQ ID NOS: 6

<210> SEQ ID NO 1
<211> LENGTH: 212
<212> TYPE: PRT
<213> ORGANISM: Carica papaya

<400> SEQUENCE: 1

Ile Pro Glu Tyr Val Asp Trp Arg Gln Lys Gly Ala Val Thr Pro Val
1               5                   10                  15

Lys Asn Gln Gly Ser Cys Gly Ser Cys Trp Ala Phe Ser Ala Val Val
            20                  25                  30

Thr Ile Glu Gly Ile Ile Lys Ile Arg Thr Gly Asn Leu Asn Glu Tyr
        35                  40                  45

Ser Glu Gln Glu Leu Leu Asp Cys Asp Arg Arg Ser Tyr Gly Cys Asn
    50                  55                  60

Gly Gly Tyr Pro Trp Ser Ala Leu Gln Leu Val Ala Gln Tyr Gly Ile
65                  70                  75                  80

His Tyr Arg Asn Thr Tyr Pro Tyr Glu Gly Val Gln Arg Tyr Cys Arg
                85                  90                  95

Ser Arg Glu Lys Gly Pro Tyr Ala Ala Lys Thr Asp Gly Val Arg Gln
            100                 105                 110

Val Gln Pro Tyr Asn Glu Gly Ala Leu Leu Tyr Ser Ile Ala Asn Gln
        115                 120                 125

Pro Val Ser Val Val Leu Glu Ala Ala Gly Lys Asp Phe Gln Leu Tyr
    130                 135                 140

Arg Gly Gly Ile Phe Val Gly Pro Cys Gly Asn Lys Val Asp His Ala
145                 150                 155                 160

Val Ala Ala Val Gly Tyr Gly Pro Asn Tyr Ile Leu Ile Lys Asn Ser
                165                 170                 175

Trp Gly Thr Gly Trp Gly Glu Asn Gly Tyr Ile Arg Ile Lys Arg Gly
            180                 185                 190

Thr Gly Asn Ser Tyr Gly Val Cys Gly Leu Tyr Thr Ser Ser Phe Tyr
        195                 200                 205

Pro Val Lys Asn
    210

<210> SEQ ID NO 2
<211> LENGTH: 418
<212> TYPE: PRT
<213> ORGANISM: Human rhinoviurs

<400> SEQUENCE: 2

Met Ser Pro Ile Leu Gly Tyr Trp Lys Ile Lys Gly Leu Val Gln Pro
1               5                   10                  15
```

```
Thr Arg Leu Leu Leu Glu Tyr Leu Glu Lys Tyr Glu Glu His Leu
            20              25              30

Tyr Glu Arg Asp Glu Gly Asp Lys Trp Arg Asn Lys Lys Phe Glu Leu
        35              40              45

Gly Leu Glu Phe Pro Asn Leu Pro Tyr Ile Asp Gly Asp Val Lys
50              55              60

Leu Thr Gln Ser Met Ala Ile Ile Arg Tyr Ile Ala Asp Lys His Asn
65              70              75              80

Met Leu Gly Gly Cys Pro Lys Glu Arg Ala Glu Ile Ser Met Leu Glu
                85              90              95

Gly Ala Val Leu Asp Ile Arg Tyr Gly Val Ser Arg Ile Ala Tyr Ser
            100             105             110

Lys Asp Phe Glu Thr Leu Lys Val Asp Phe Leu Ser Lys Leu Pro Glu
        115             120             125

Met Leu Lys Met Phe Glu Asp Arg Leu Cys His Lys Thr Tyr Leu Asn
    130             135             140

Gly Asp His Val Thr His Pro Asp Phe Met Leu Tyr Asp Ala Leu Asp
145             150             155             160

Val Val Leu Tyr Met Asp Pro Met Cys Leu Asp Ala Phe Pro Lys Leu
                165             170             175

Val Cys Phe Lys Lys Arg Ile Glu Ala Ile Pro Gln Ile Asp Lys Tyr
            180             185             190

Leu Lys Ser Ser Lys Tyr Ile Ala Trp Pro Leu Gln Gly Trp Gln Ala
        195             200             205

Thr Phe Gly Gly Gly Asp His Pro Pro Lys Ser Asp Leu Val Pro Arg
    210             215             220

Gly Ser Pro Glu Phe Gly Pro Asn Thr Glu Phe Ala Leu Ser Leu Leu
225             230             235             240

Arg Lys Asn Ile Met Thr Ile Thr Thr Ser Lys Gly Glu Phe Thr Gly
                245             250             255

Leu Gly Ile His Asp Arg Val Cys Val Ile Pro Thr His Ala Gln Pro
            260             265             270

Gly Asp Asp Val Leu Val Asn Gly Gln Lys Ile Arg Val Lys Asp Lys
        275             280             285

Tyr Lys Leu Val Asp Pro Glu Asn Ile Asn Leu Glu Leu Thr Val Leu
    290             295             300

Thr Leu Asp Arg Asn Glu Lys Phe Arg Asp Ile Arg Gly Phe Ile Ser
305             310             315             320

Glu Asp Leu Glu Gly Val Asp Ala Thr Leu Val Val His Ser Asn Asn
                325             330             335

Phe Thr Asn Thr Ile Leu Glu Val Gly Pro Val Thr Met Ala Gly Leu
            340             345             350

Ile Asn Leu Ser Ser Thr Pro Thr Asn Arg Met Ile Arg Tyr Asp Tyr
        355             360             365

Ala Thr Lys Thr Gly Gln Cys Gly Gly Val Leu Cys Ala Thr Gly Lys
    370             375             380

Ile Phe Gly Ile His Val Gly Gly Asn Gly Arg Gln Gly Phe Ser Ala
385             390             395             400

Gln Leu Lys Lys Gln Tyr Phe Val Glu Lys Gln Leu Glu Arg Pro His
                405             410             415

Arg Asp

<210> SEQ ID NO 3
```

```
<211> LENGTH: 159
<212> TYPE: PRT
<213> ORGANISM: Homo sapiens

<400> SEQUENCE: 3

Gly Pro Leu Gly Ser Met Ala Ala Ser Arg Arg Leu Met Lys Glu Leu
1               5                   10                  15

Glu Glu Ile Arg Lys Cys Gly Met Lys Asn Phe Arg Asn Ile Gln Val
            20                  25                  30

Asp Glu Ala Asn Leu Leu Thr Trp Gln Gly Leu Ile Val Pro Asp Asn
        35                  40                  45

Pro Pro Tyr Asp Lys Gly Ala Phe Arg Ile Glu Ile Asn Phe Pro Ala
    50                  55                  60

Glu Tyr Pro Phe Lys Pro Pro Lys Ile Thr Phe Lys Thr Lys Ile Tyr
65                  70                  75                  80

His Pro Asn Ile Asp Glu Lys Gly Gln Val Cys Leu Pro Val Ile Ser
                85                  90                  95

Ala Glu Asn Trp Lys Pro Ala Thr Lys Thr Asp Gln Val Ile Gln Ser
            100                 105                 110

Leu Ile Ala Leu Val Asn Asp Pro Gln Pro Glu His Pro Leu Arg Ala
        115                 120                 125

Asp Leu Ala Glu Glu Tyr Ser Lys Asp Arg Lys Lys Phe Cys Lys Asn
    130                 135                 140

Ala Glu Glu Phe Thr Lys Lys Tyr Gly Glu Lys Arg Pro Val Asp
145                 150                 155

<210> SEQ ID NO 4
<211> LENGTH: 395
<212> TYPE: PRT
<213> ORGANISM: Homo sapiens

<400> SEQUENCE: 4

Gly Ser Ser His His His His His His Ser Ser Gly Leu Val Pro Arg
1               5                   10                  15

Gly Ser Pro Thr Val Thr Pro Thr Val Asn Arg Glu Asn Lys Pro Thr
            20                  25                  30

Cys Tyr Pro Lys Ala Glu Ile Ser Arg Leu Ser Ala Ser Gln Ile Arg
        35                  40                  45

Asn Leu Asn Pro Val Phe Gly Gly Ser Gly Pro Ala Leu Thr Gly Leu
    50                  55                  60

Arg Asn Leu Gly Asn Thr Cys Tyr Met Asn Ser Ile Leu Gln Cys Leu
65                  70                  75                  80

Cys Asn Ala Pro His Leu Ala Asp Tyr Phe Asn Arg Asn Cys Tyr Gln
                85                  90                  95

Asp Asp Ile Asn Arg Ser Asn Leu Leu Gly His Lys Gly Glu Val Ala
            100                 105                 110

Glu Glu Phe Gly Ile Ile Met Lys Ala Leu Trp Thr Gly Gln Tyr Arg
        115                 120                 125

Tyr Ile Ser Pro Lys Asp Phe Lys Ile Thr Ile Gly Lys Ile Asn Asp
    130                 135                 140

Gln Phe Ala Gly Tyr Ser Gln Gln Asp Ser Gln Glu Leu Leu Leu Phe
145                 150                 155                 160

Leu Met Asp Gly Leu His Glu Asp Leu Asn Lys Ala Asp Asn Arg Lys
                165                 170                 175

Arg Tyr Lys Glu Glu Asn Asp His Leu Asp Asp Phe Lys Ala Ala
            180                 185                 190
```

```
Glu His Ala Trp Gln Lys His Lys Gln Leu Asn Glu Ser Ile Ile Val
            195                 200                 205

Ala Leu Phe Gln Gly Gln Phe Lys Ser Thr Val Gln Cys Leu Thr Cys
210                 215                 220

His Lys Lys Ser Arg Thr Phe Glu Ala Phe Met Tyr Leu Ser Leu Pro
225                 230                 235                 240

Leu Ala Ser Thr Ser Lys Cys Thr Leu Gln Asp Cys Leu Arg Leu Phe
                245                 250                 255

Ser Lys Glu Glu Lys Leu Thr Asp Asn Asn Arg Phe Tyr Cys Ser His
            260                 265                 270

Cys Arg Ala Arg Arg Asp Ser Leu Lys Lys Ile Glu Ile Trp Lys Leu
        275                 280                 285

Pro Pro Val Leu Leu Val His Leu Lys Arg Phe Ser Tyr Asp Gly Arg
290                 295                 300

Trp Lys Gln Lys Leu Gln Thr Ser Val Asp Phe Pro Leu Glu Asn Leu
305                 310                 315                 320

Asp Leu Ser Gln Tyr Val Ile Gly Pro Lys Asn Leu Lys Lys Tyr
                325                 330                 335

Asn Leu Phe Ser Val Ser Asn His Tyr Gly Gly Leu Asp Gly His
            340                 345                 350

Tyr Thr Ala Tyr Cys Lys Asn Ala Ala Arg Gln Arg Trp Phe Lys Phe
                355                 360                 365

Asp Asp His Glu Val Ser Asp Ile Ser Val Ser Ser Val Lys Ser Ser
370                 375                 380

Ala Ala Tyr Ile Leu Phe Tyr Thr Ser Leu Gly
385                 390                 395

<210> SEQ ID NO 5
<211> LENGTH: 386
<212> TYPE: PRT
<213> ORGANISM: Homo sapiens

<400> SEQUENCE: 5

Gly Pro Leu Gly Ser Arg Asp Tyr Lys Arg Lys Tyr Glu Phe Phe Arg
1               5                   10                  15

Arg Lys Leu Lys Lys Gln Asn Asp Ile Pro Asn Lys Phe Glu Met Lys
            20                  25                  30

Leu Arg Arg Ala Thr Val Leu Glu Asp Ser Tyr Arg Ile Met Gly
        35                  40                  45

Val Lys Arg Ala Asp Phe Leu Lys Ala Arg Leu Trp Ile Glu Phe Asp
50                  55                  60

Gly Glu Lys Gly Leu Asp Tyr Gly Gly Val Ala Arg Glu Trp Phe Phe
65                  70                  75                  80

Leu Ile Ser Lys Glu Met Phe Asn Pro Tyr Tyr Gly Leu Phe Glu Tyr
                85                  90                  95

Ser Ala Thr Asp Asn Tyr Thr Leu Gln Ile Asn Pro Asn Ser Gly Leu
            100                 105                 110

Cys Asn Glu Asp His Leu Ser Tyr Phe Lys Phe Ile Gly Arg Val Ala
        115                 120                 125

Gly Met Ala Val Tyr His Gly Lys Leu Leu Asp Gly Phe Phe Ile Arg
    130                 135                 140

Pro Phe Tyr Lys Met Met Leu His Lys Pro Ile Thr Leu His Asp Met
145                 150                 155                 160

Glu Ser Val Asp Ser Glu Tyr Tyr Asn Ser Leu Arg Trp Ile Leu Glu
```

```
                165                 170                 175
Asn Asp Pro Thr Glu Leu Asp Leu Arg Phe Ile Ile Asp Glu Glu Leu
            180                 185                 190

Phe Gly Gln Thr His Gln His Glu Leu Lys Asn Gly Gly Ser Glu Ile
            195                 200                 205

Val Val Thr Asn Lys Asn Lys Lys Glu Tyr Ile Tyr Leu Val Ile Gln
            210                 215                 220

Trp Arg Phe Val Asn Arg Ile Gln Lys Gln Met Ala Ala Phe Lys Glu
225                 230                 235                 240

Gly Phe Phe Glu Leu Ile Pro Gln Asp Leu Ile Lys Ile Phe Asp Glu
                245                 250                 255

Asn Glu Leu Glu Leu Leu Met Cys Gly Leu Gly Asp Val Asp Val Asn
            260                 265                 270

Asp Trp Arg Glu His Thr Lys Tyr Lys Asn Gly Tyr Ser Ala Asn His
            275                 280                 285

Gln Val Ile Gln Trp Phe Trp Lys Ala Val Leu Met Met Asp Ser Glu
            290                 295                 300

Lys Arg Ile Arg Leu Leu Gln Phe Val Thr Gly Thr Ser Arg Val Pro
305                 310                 315                 320

Met Asn Gly Phe Ala Glu Leu Tyr Gly Ser Asn Gly Pro Gln Ser Phe
                325                 330                 335

Thr Val Glu Gln Trp Gly Thr Pro Glu Lys Leu Pro Arg Ala His Thr
            340                 345                 350

Cys Phe Asn Arg Leu Asp Leu Pro Pro Tyr Glu Ser Phe Glu Glu Leu
            355                 360                 365

Trp Asp Lys Leu Gln Met Ala Ile Glu Asn Thr Gln Gly Phe Asp Gly
            370                 375                 380

Val Asp
385

<210> SEQ ID NO 6
<211> LENGTH: 168
<212> TYPE: PRT
<213> ORGANISM: Homo sapiens

<400> SEQUENCE: 6

Gly Pro Leu Gly Ser Ser Arg Arg Ala Ser Val Gly Ser Pro Glu Phe
1               5                   10                  15

Thr Met Leu Thr Phe Thr Ala Gly Gly Ala Ile Glu Phe Gly Gln Arg
            20                  25                  30

Met Leu Gln Val Ala Ser Gln Ala Ser Arg Gly Glu Val Pro Ser Gly
            35                  40                  45

Ala Tyr Gly Tyr Ser Tyr Met Pro Ser Gly Ala Tyr Val Tyr Pro Pro
            50                  55                  60

Pro Val Ala Asn Gly Met Tyr Pro Cys Pro Pro Gly Tyr Pro Tyr Pro
65                  70                  75                  80

Pro Pro Pro Pro Glu Phe Tyr Pro Gly Pro Met Met Asp Gly Ala
                85                  90                  95

Met Gly Tyr Val Gln Pro Pro Pro Pro Tyr Pro Gly Pro Met Glu
            100                 105                 110

Pro Pro Val Ser Gly Pro Asp Val Pro Ser Thr Pro Ala Ala Glu Ala
            115                 120                 125

Lys Ala Ala Glu Ala Ala Ala Ser Ala Tyr Tyr Asn Pro Gly Asn Pro
            130                 135                 140
```

-continued

| His | Asn | Val | Tyr | Met | Pro | Thr | Ser | Gln | Pro | Pro | Pro | Pro | Tyr | Tyr |
|-----|-----|-----|-----|-----|-----|-----|-----|-----|-----|-----|-----|-----|-----|-----|
| 145 |     |     |     |     | 150 |     |     |     | 155 |     |     |     |     | 160 |

| Pro | Pro | Glu | Asp | Arg | Arg | Thr | Gln |
|-----|-----|-----|-----|-----|-----|-----|-----|
|     |     |     |     | 165 |     |     |     |

SCREENING METHODS FOR THE BINDING AFFINITY OF CHEMICAL ENTITIES TO BIOLOGICAL MOLECULES AND NEDD4-1 INHIBITORS IDENTIFIED BY THE SCREENING METHODS

CROSS-REFERENCE TO RELATED PATENT APPLICATIONS

The present application is a continuation-in-part of U.S. application Ser. No. 14/721,829, filed on May 26, 2015, and issued as U.S. Pat. No. 9,586,890, on Mar. 7, 2017, which application claims the benefit of priority under 35 U.S.C. § 119(e) to U.S. Provisional Patent Application No. 62/002, 588, filed on May 23, 2014 and to U.S. Provisional Patent Application No. 62/003,656, filed on May 28, 2014, the contents of which are incorporated herein by reference in their entireties.

BACKGROUND

The field of the invention relates to methods for screening for the binding affinity of chemical entities to other bioactive molecules and identifying covalent inhibitors of bioactive molecules. In particular, the field of the invention relates to methods for screening for the binding affinity of small molecule inhibitors of bioactive molecules such as enzymes that contain catalytic or non-catalytic cysteines including the neuronal precursor cell-expressed developmentally down-regulated 4-1 ubiquitin ligase (NEDD4-1), and pharmaceutical compositions and therapeutic methods that include or utilize the screened small molecule inhibitors.

Fragment based drug discovery (FBDD) has emerged as a powerful approach to discover drug leads by exploring greater chemical diversity space with smaller libraries.[1] The major challenge, however, is to detect weak binding interactions between drug-like fragments and their protein target. Disulfide tethering was developed as one solution to this problem.[2] In this approach, disulfide-containing fragments are covalently trapped on the protein surface via the reversible formation of disulfide bonds. Subsequent MS of the intact protein can identify the covalently bound fragment. The advantages of this method include screening the fragments as mixtures rather than as separate entities. Screening fragments as mixtures increases the throughput capability of the assay and reduces the number of false positives by introducing competition between the fragments. This has proven to be a general and successful approach.[3] Another technique relies on the use of an α-cyanoacrylamide moiety attached to drug-like fragments that react reversibly with non-catalytic cysteines present at the binding site of the protein of interest.[4]

Whether it is possible to design a robust system where the protein can select the best binder from a mixture of electrophilic fragments under irreversible conditions to identify novel leads is not known. Such an approach would be particularly powerful since the identified fragments can subsequently retain their electrophilic tether while being elaborated into a covalent drug. Irreversible tethering would especially benefit the burgeoning field of covalent drug-discovery.[5]

However, one concern with such an approach is the danger of selecting the most reactive fragment rather than the fragment with the most specific binding affinity to the protein target.[6] If the electrophilic fragments are too reactive, cysteines or other nucleophilic residues present on the protein surface can undergo non-specific covalent modifications by the fragments irrespective of their binding affinity.[7] Alternatively hyper-reactive cysteines or other nucleophilic residues can nonspecifically react with even moderately electrophilic fragments, leading to non-specific covalent modifications of the protein.[8] In addition, no systematic studies have been done to investigate the kinetic reactivity of cysteine reactive electrophiles attached to a large number (~50) drug-like fragments, in order to outline general principles and design rules for irreversible tethering. While this work was in progress Nonoo, et. al. reported the first irreversible tethering method using a small ten-member acrylamide library, which included known reversible thymidylate synthase inhibitor scaffolds.[9] However, hyper-reactive acrylamide in that library has led to one false positive hit, and no systematic studies have been done further to investigate the reactivity of and outline design rules for drug-like libraries for irreversible tethering. Moreover, there are still no reports of irreversible fragment screening of an unbiased library to identify novel and selective binding fragments. Therefore, whether it is possible to rationally design an electrophilic library of drug-like fragments for irreversible tethering is still a concern.

Here, the inventors address this concern and shows that the proper selection of a cysteine reactive electrophile yields a chemical system that can select weakly bound electrophilic fragments from a mixture, and covalently trap the best binders at the highly reactive catalytic cysteine of the model cysteine protease papain. The discovered fragments behave as weak and irreversible inhibitors of papain, and have novel non-peptidic structures. The reported method serves as an entry point to discover non-peptidic inhibitors of other active biological molecule having a catalytic or non-catalytic cysteine residue, which are promising drug targets to treat many diseases.[10]

One such active biological molecule having a catalytic cysteine residue is the neural precursor cell expressed developmentally down-regulated protein 4 (NEDD4 or NEDD4-1). NEDD4-1 is an E3 ubiquitin ligase enzyme that targets proteins for ubiquitination and has been shown to be overexpressed in a wide variety of cancers and thus is a promising drug target for these diseases. It is proposed that NEDD4-1 ubiquitinates and degrades the tumor suppressors p53, LATS, and PTEN, which contributes to its oncogenic properties. Genetic experiments have firmly established the essential role of NEDD4-1 in regulating insulin and IGF-1 growth pathways in cells, two pathways that are upregulated in many human cancers such as Ewing's sarcoma (Nat. Struct. Mol. Biol. 2014 June; 21(6):522-7). Furthermore, NEDD4-1$^{-/+}$ heterozygous mice gained less weight when placed on the high fat diet, which suggests that NEDD4-1 is a potential drug target to treat obesity (Endocrinology. 2015 April; 156(4):1283-91). In addition NEDD4-1 is involved in the degradation of α-synuclein, a key player in Parkinson's disease, which makes NEDD4-1 a promising drug target to treat Parkinson's disease. Therefore, small molecule activators of NEDD4-1 will serve as therapeutics to treat Parkinson's disease. Lastly, NEDD4-1 and its closely related homolog NEDD4-2, which is also a likely target of our inhibitors, have been shown to be essential host proteins for the budding of HIV and Ebola viruses from the host cell (J. Virol. 2014 July; 88(13):7294-306). Therefore, NEDD4 inhibitors are promising host targets to treat HIV.

Unlike protein kinases, efforts to develop small molecule inhibitors of ubiquitin ligases have been mostly unsuccessful. Here, the inventors disclose small molecule inhibitors of the HECT-type ubiquitin ligase NEDD4-1, an enzyme for which there are no reported inhibitors. These compounds serve as therapies for the multitude of diseases in which NEDD4-1 is a factor including, but not limited to, cancer, neurodegenerative disease and spreading of HIV.

SUMMARY

Disclosed are methods for identifying for screening for the binding affinity of chemical entities to other bioactive molecules. The screened chemical entities may be utilized in pharmaceutical compositions or therapeutic methods for treating disease or disorders associated with the bioactive molecules.

The disclosed methods may include methods of screening for an inhibitor of an active biological molecule having a catalytic or non-catalytic cysteine residue, for example, an inhibitor of the neuronal precursor cell-expressed developmentally down-regulated 4-1 ubiquitin ligase (NEDD4-1), including irreversible inhibitors and/or inhibitors that react covalently with the biological molecule. The methods may include: (a) selecting an electrophile that is reactive with cysteine residues; (b) preparing a library of candidate inhibitor molecules by reacting the electrophile with a plurality of candidate drug molecules, wherein the library of candidate inhibitor molecules thus prepared is reactive with cysteine residues; (c) contacting the library of molecules of candidate inhibitor molecules with the biological molecule having the catalytic or non-catalytic cysteine residue; (d) measuring binding of the library of candidate inhibitor molecules to the biological molecule comprising having the catalytic or non-catalytic cysteine residue and/or measuring reactivity between the library of candidate inhibitor molecules and the biological molecule; and (e) screening for the inhibitor based on binding affinity of the library of molecules candidate inhibitor molecules to the biological molecule and/or based on reactivity between the library of candidate inhibitor molecule and the biological molecule. The methods further may include reacting the library of candidate inhibitor molecules with a molecule comprising a cysteine residue and measuring reaction rates of the library of candidate inhibitor molecules with the molecule comprising the cysteine residue. Even further, the methods may include measuring inhibitor activity of the library of candidate inhibitor molecules, or a selected molecule from the screened library of candidate inhibitor molecules, against the activity of one or more biological molecules having a catalytic or non-catalytic cysteine residue.

Inhibitor molecules identified by the disclosed methods may include inhibitors of active biological molecules having catalytic or non-catalytic cysteine residues such as NEDD4-1. Inhibitor molecules identified by the disclosed methods may include irreversible inhibitors of active biological molecules having catalytic or non-catalytic cysteine residues such as NEDD4-1.

In some embodiments, the disclosed inhibitors may include a compounds having formula I, or a salt, ester, amide, or solvate thereof:

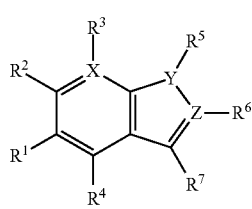

I wherein: X is CH or N; Y is N, O, or S; Z is C or N; $R^1$ is selected from hydrogen, hydroxyl, thiol, halogen, alkoxy, alkylthio, amino, alkylamino, haloalkyl, and haloalkoxy; $R^2$, $R^3$, and $R^4$ are the same or different and are selected from hydrogen, halogen, and alkoxy; $R^5$ and $R^6$ are the same or different and are selected from hydrogen, alkyl, cycloalkyl, aryl, and alkylaryl; and $R^7$ has a formula selected from:'

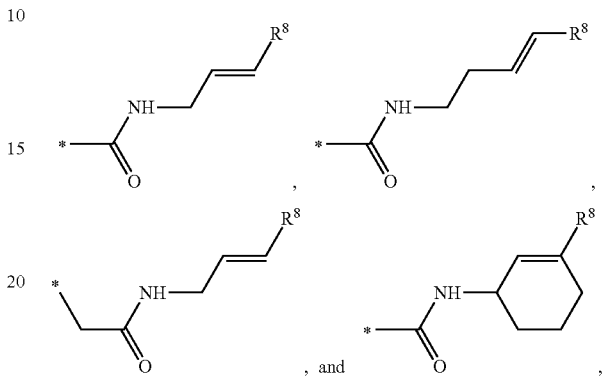

wherein $R^8$ is $COR^9$, COOR, $C(=O)NR_2$, $C(=O)NHR$, $SO_2R^9$ or CN, and $R^9$ is selected from alkyl, aryl, alkoxy, amino, alkylamino, and anilino.

In the disclosed compounds, preferably the compounds contemplated have the formula Ia:

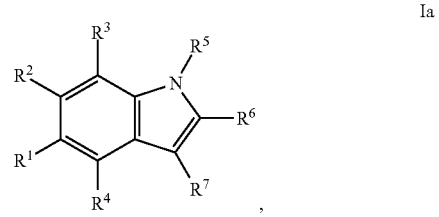

Ia and preferably $R^1$ is methoxy, ethoxy, or hydroxyl.

In the disclosed compounds, preferably $R^7$ has a formula selected from:

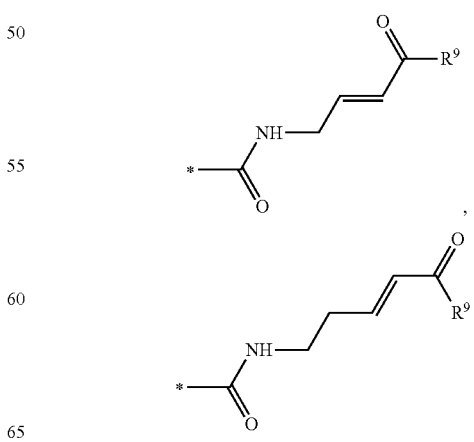

-continued

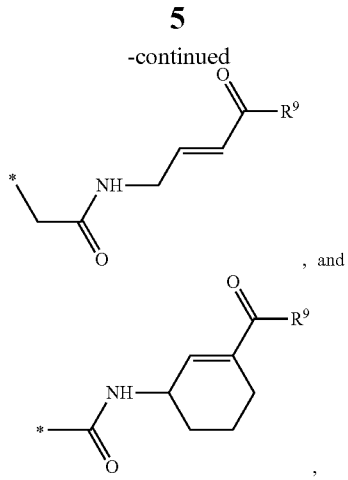

and preferably R⁹ is alkoxy.

Pharmaceutical compositions comprising the disclosed compounds are also contemplated. The pharmaceutical compositions comprise the disclosed compounds and a pharmaceutical carrier. The disclosed compounds or pharmaceutical compositions comprising the disclosed compounds may be administering to treat and/or prevent a disease or disorder in a subject in need thereof.

The methods contemplated herein include methods for treating a disease or disorder that is associated with an active biological molecule having a catalytic or non-catalytic cysteine residue, such as diseases or disorders that are associated with NEDD4-1 activity. The disclosed methods of treatment may include administering to a subject in need thereof an inhibitor of an active biological molecule having a catalytic or non-catalytic cysteine residue, such as an irreversible inhibitor of the active biological molecule having a catalytic or non-catalytic cysteine residue. In particular, the disclosed methods of treatment may include administering to a subject in need thereof an inhibitor of NEDD4-1, such as an irreversible inhibitor of NEDD4-1.

BRIEF DESCRIPTION OF THE FIGURES

FIG. 5A, FIG. 5B, FIG. 5C, FIG. 5D, FIG. 5E, FIG. 5F, FIG. 5G, FIG. 5H, FIG. 5I, FIG. 5J and FIG. 5K. ESI-MS of 10 reaction mixtures containing 10 electrophilic fragments each screened against papain as described. See Table 2 for list of fragments in each reaction mixture. The molecular weight of papain is 23422.56 Da and its amino acid sequence is provided as SEQ ID NO:1. (FIG. 5A) untreated; (FIG. 5B) Mix 1; (FIG. 5C) Mix 2; (FIG. 5D) Mix 3; (FIG. 5E) Mix 4; (FIG. 5F) Mix 5; (FIG. 5G) Mix 6; (FIG. 5H) Mix 7; (FIG. 5I) Mix 8; (FIG. 5J) Mix 9; (FIG. 5K) Mix 10.

(FIG. 14A) Close-up view of the hotspot interface of NEDD4-1 and Ub in the NEDD4-1:Ub complex (PDB ID 2XBB) with the key side chains depicted as sticks. (FIG. 14B) Electrophilic compounds 1-4 used in this work. (FIG. 14C) Intact protein MS shows compounds 1 and 2 (100 μM) monolabel NEDD4-1 HECT domain (10 μM) after 4 h (n.b.: the other peaks on the right side are −27 Da peaks, which are also present in the unlabeled protein). FIG. 14D) 1 mM compound 1 fully labels NEDD4-1 HECT domain after 3 h, with minor non-specific dilabeling.

(FIG. 15A) Enzymatic assay with compounds 1, 2, and 4. NEDD4-1 HECT domain was pretreated with 1% DMSO (lane 1), or 1 mM of compounds 1 (lane 2), 2 (lane 3), or 4 (lane 4) for 3 h before beginning the assay. The reaction mixtures were quenched after 5 min, and polyubiquitin chains were detected by Western blot with anti-ubiquitin antibody. (FIG. 15B) Cartoon depiction of the crystal structure of NEDD4-1:1 with key side chains and the inhibitor shown as spheres. (FIG. 15C) Close-up view of the inhibitor-binding site with the key side chains depicted as sticks and colored by atom type.

Figure 1:
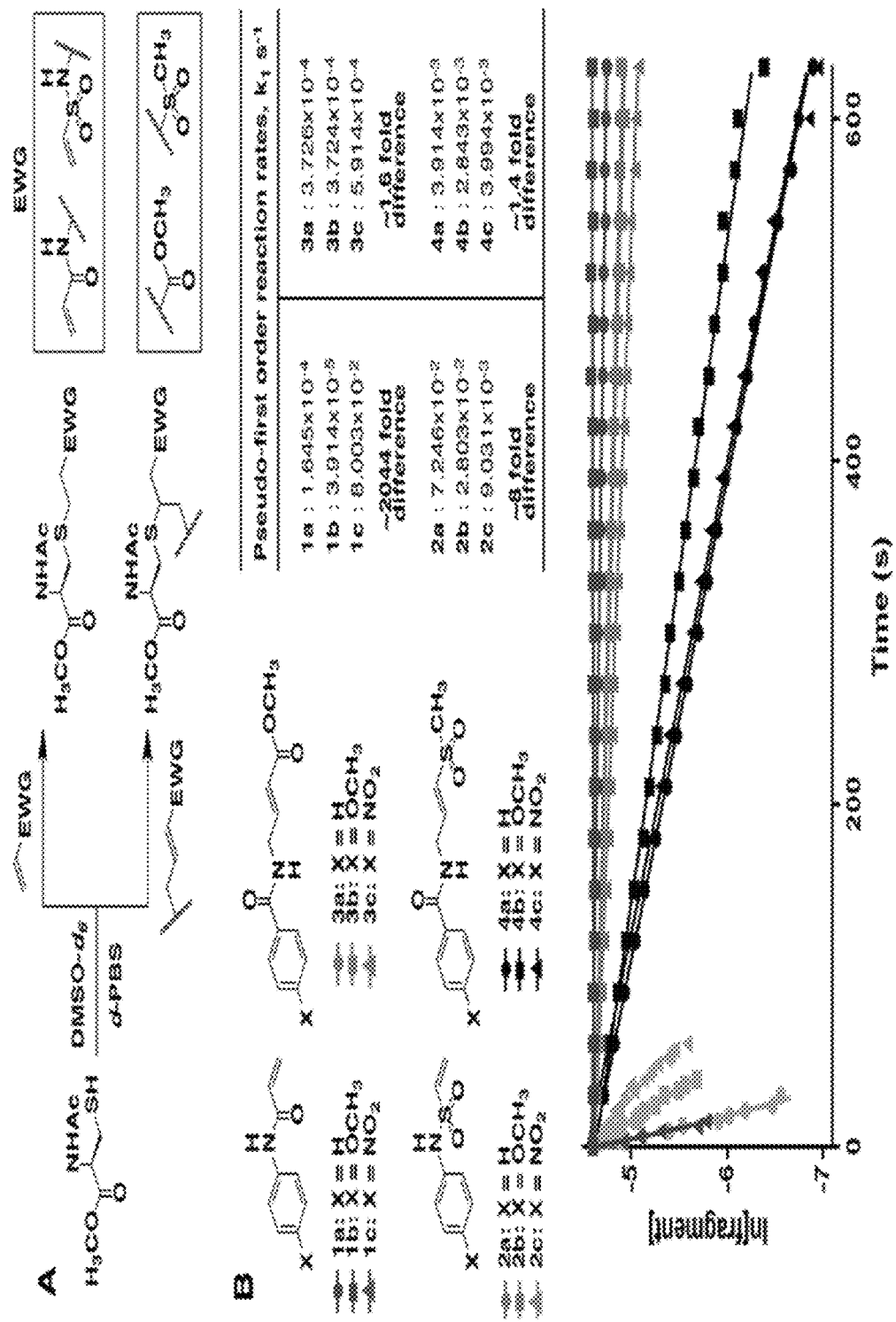
FIG. 1. (A) General scheme of NMR rate studies. (B) Chemical structures of the electrophiles 1-4 tested for suitability for irreversible tethering and their pseudo-first order reaction rates with N-acetylcysteine methylester at pD 8.0 as measured by NMR spectroscopy.

The 2F$_O$-F$_C$ electron density map (mesh, contoured at 1.0 σ) is presented for Cys$^{627}$ and 1.

FIG. 16A, FIG. 16B, FIG. 16C and FIG. 16D. (FIG. 16A) and (FIG. 16B) Compound 6 disrupts the NEDD4-1:Ub interaction as shown by a fluorescence polarization assay. Mean±s.e.m., n=3. (FIG. 16C) Compound 6 inhibits the ability of NEDD4-1 to polyubiquitinate the Wbp2-C-K222 protein substrate. NEDD4-1 was pretreated with 1% DMSO (lane 1), or 100 μM of compound 6 (lane 2) or compound 4 (lane 3) for 1.5 h before beginning the assay. Reaction mixtures were quenched at the indicated times and the amount of ubiquitinated Wbp2-C-K222 was determined using in-gel fluorescence. (FIG. 16D) Quantification of polyubiquitin chains in FIG. 16B. Mean±s.e.m., n=2.

FIG. 17A, FIG. 17B, FIG. 17C, FIG. 17D, FIG. 17E, FIG. 17F, FIG. 17G, FIG. 17H, FIG. 17I, and FIG. 17J. MS screening of NEDD4-1 HECT domain and fragments. Mixtures of fragments are the same as reported previously (ref. 19 of the main manuscript). Mixtures of ten fragments (100 μM each) were incubated with NEDD4-1 HECT domain for 4 h, followed by gel filtration and whole protein ESI-MS.

FIG. 18A, FIG. 18B, FIG. 18C and FIG. 18D. Compounds 1 and 2 selectively modify non-catalytic Cys$^{627}$ of NEDD4-1. Compounds 1 or 2 at 100 μM in 1% DMSO were incubated with the indicated NEDD4-1 HECT domain mutant (10 μM) for 4 h, followed by gel filtration and whole protein ESI-MS.

FIG. 19A, FIG. 19B, FIG. 19C, FIG. 19D, FIG. 19E, FIG. 19F, FIG. 19G, FIG. 19H, FIG. 19I and FIG. 19J. Time and concentration dependent covalent modification of NEDD4-1 with compounds 1 and 2. Compounds 1 or 2 at the indicated concentration in 1% DMSO were incubated with NEDD4-1 HECT domain mutant (10 μM) for the indicated time period, followed by gel filtration and whole protein ESI-MS.

Figure 20A:
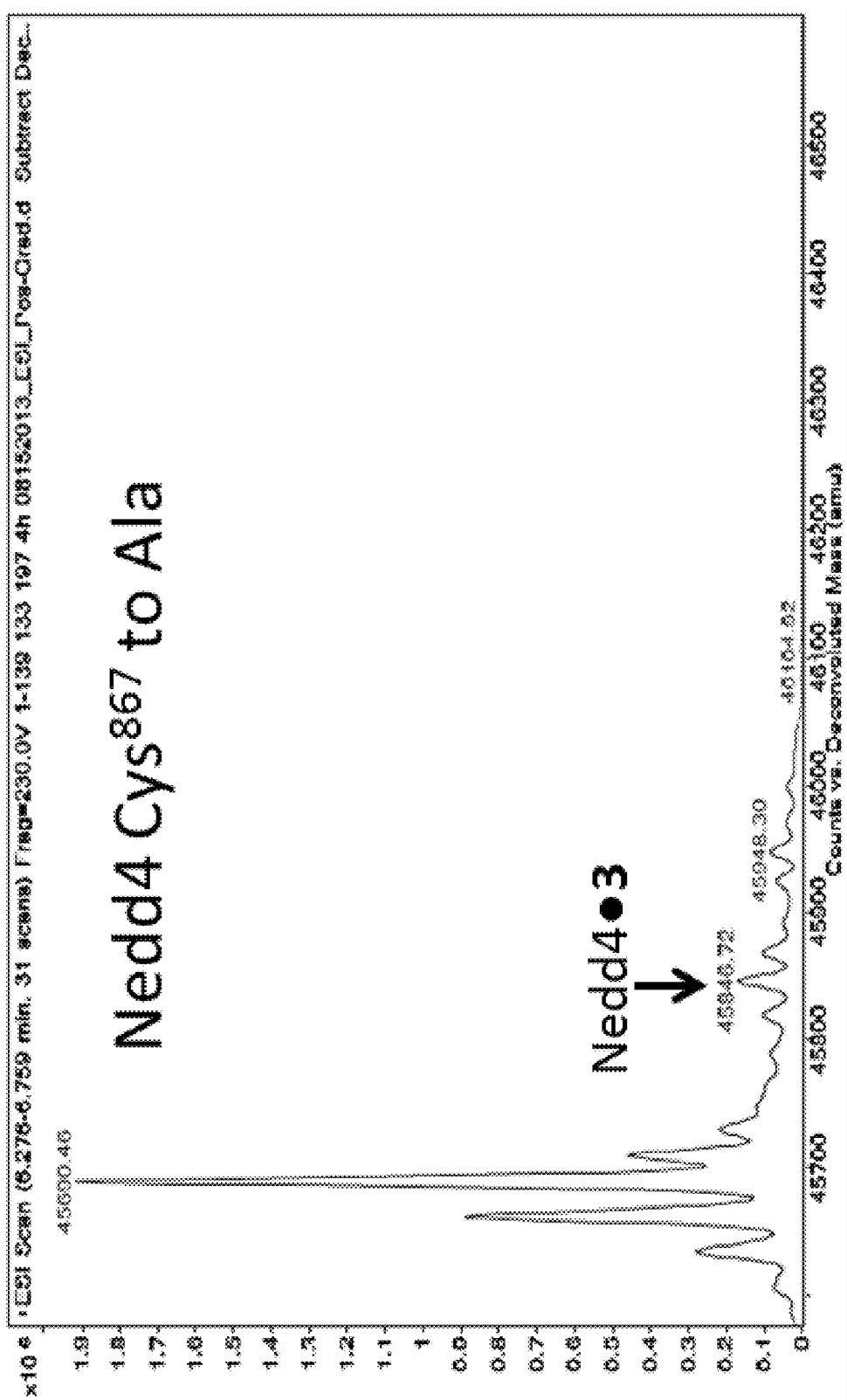
Figure 20B:
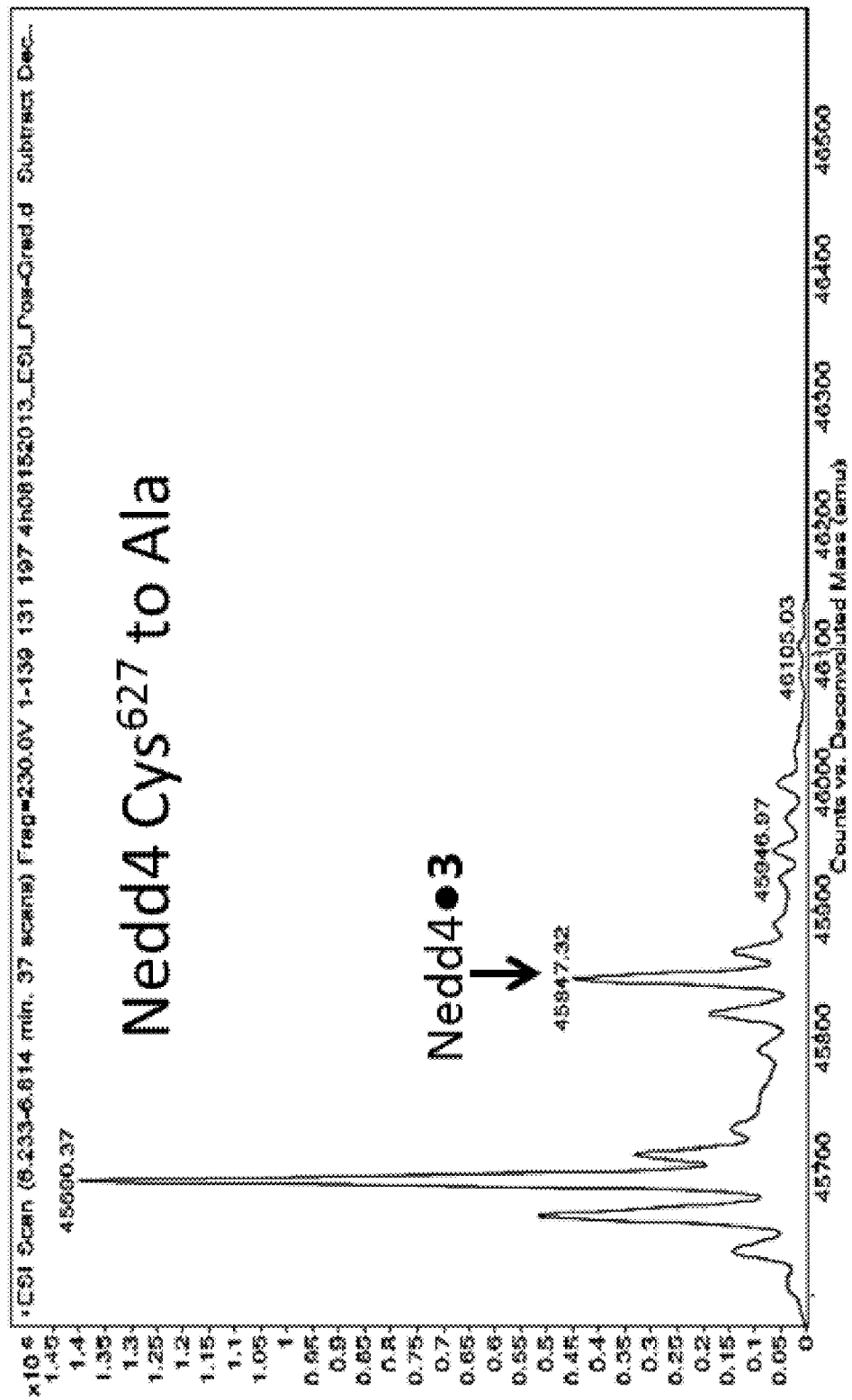
Figure 21A:
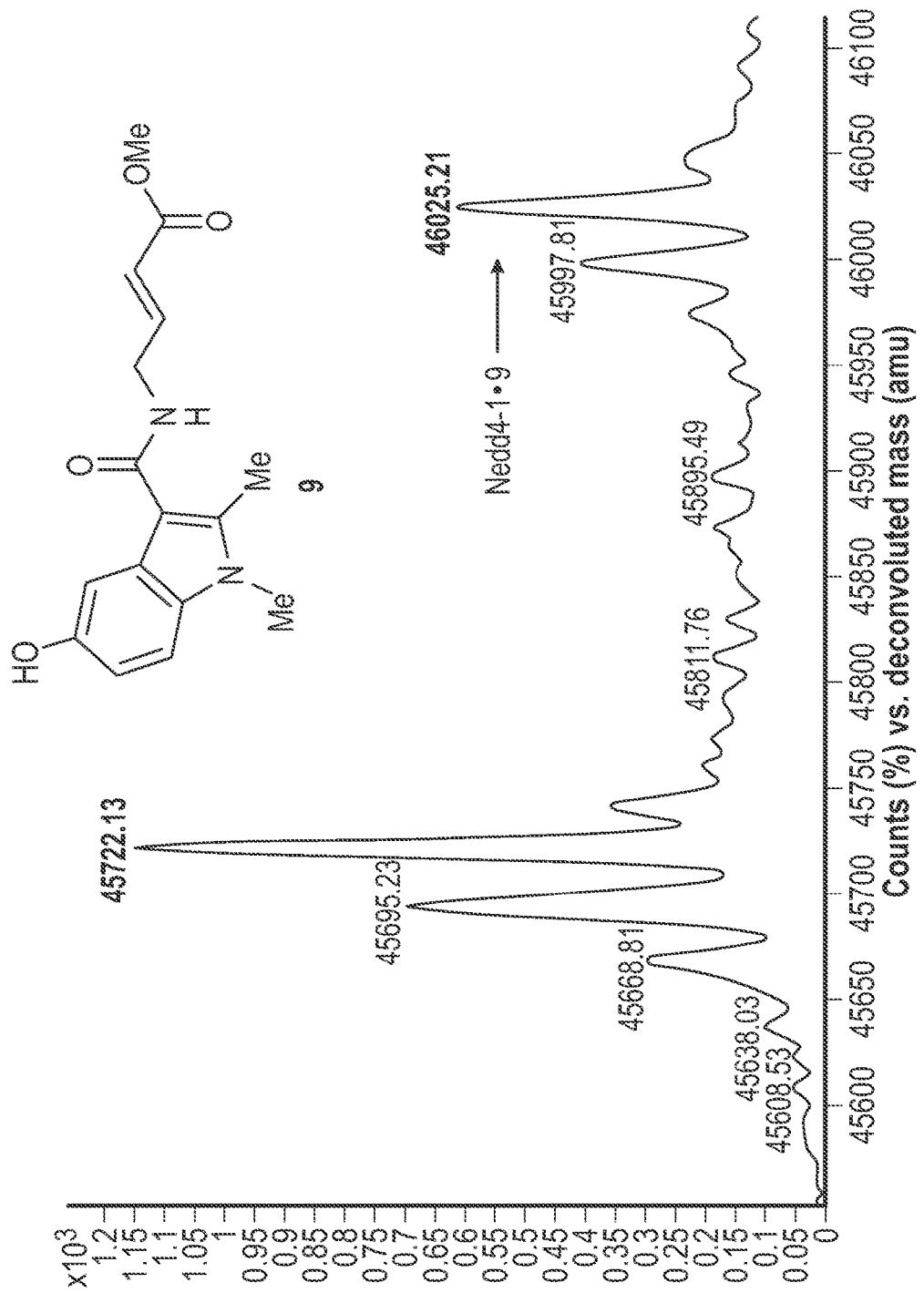
Figure 21B:
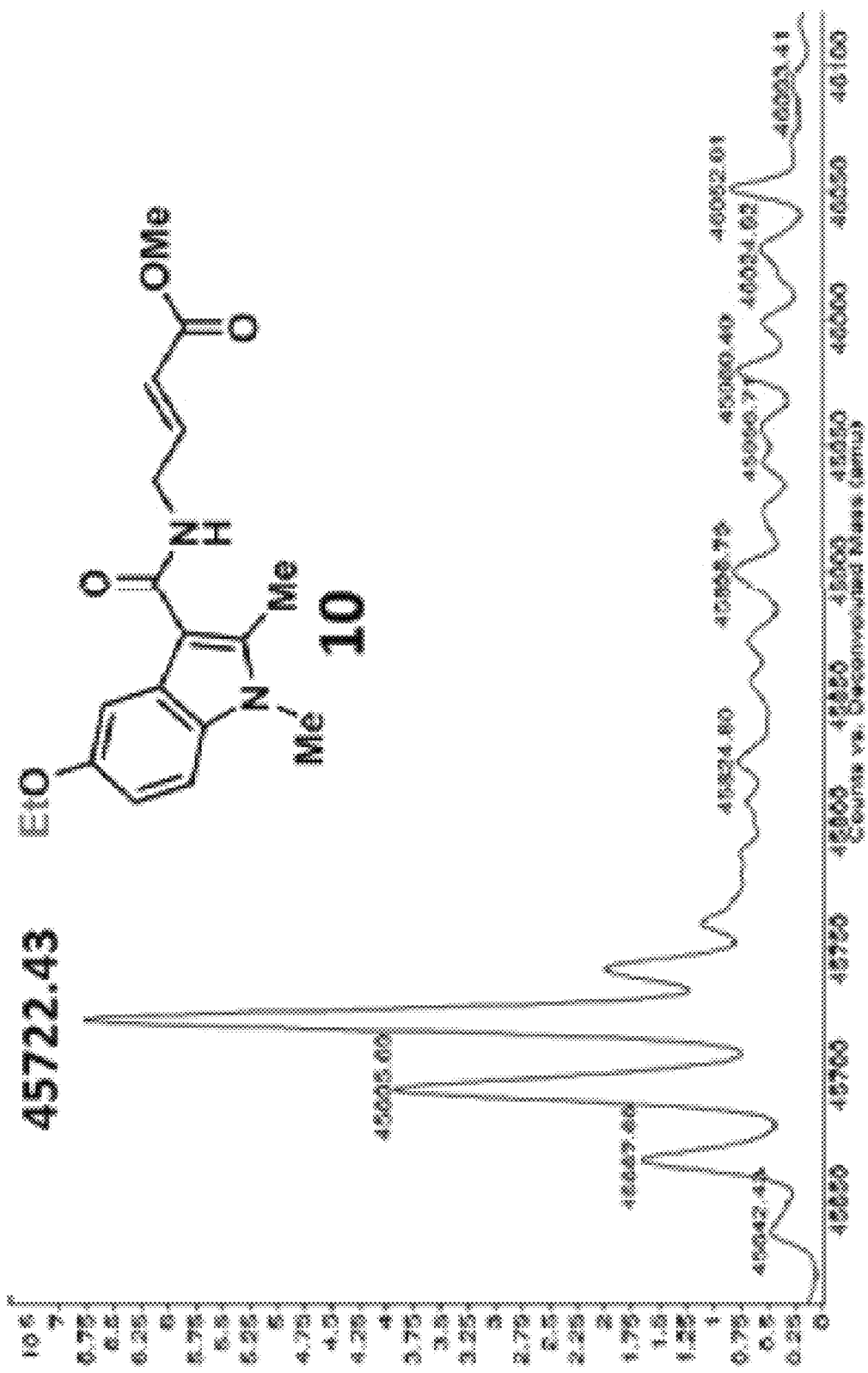
Figure 21C:
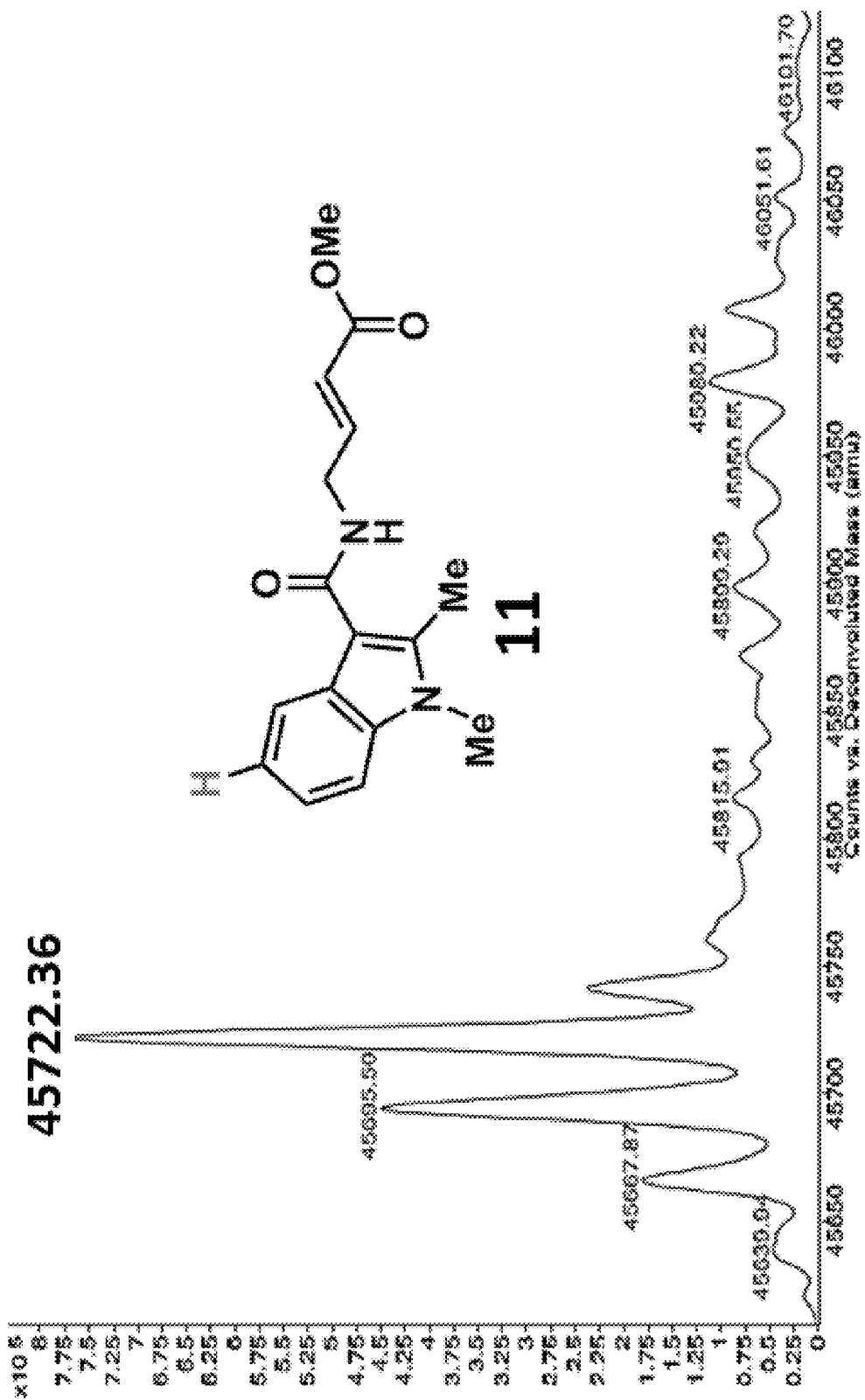
Figure 21D:
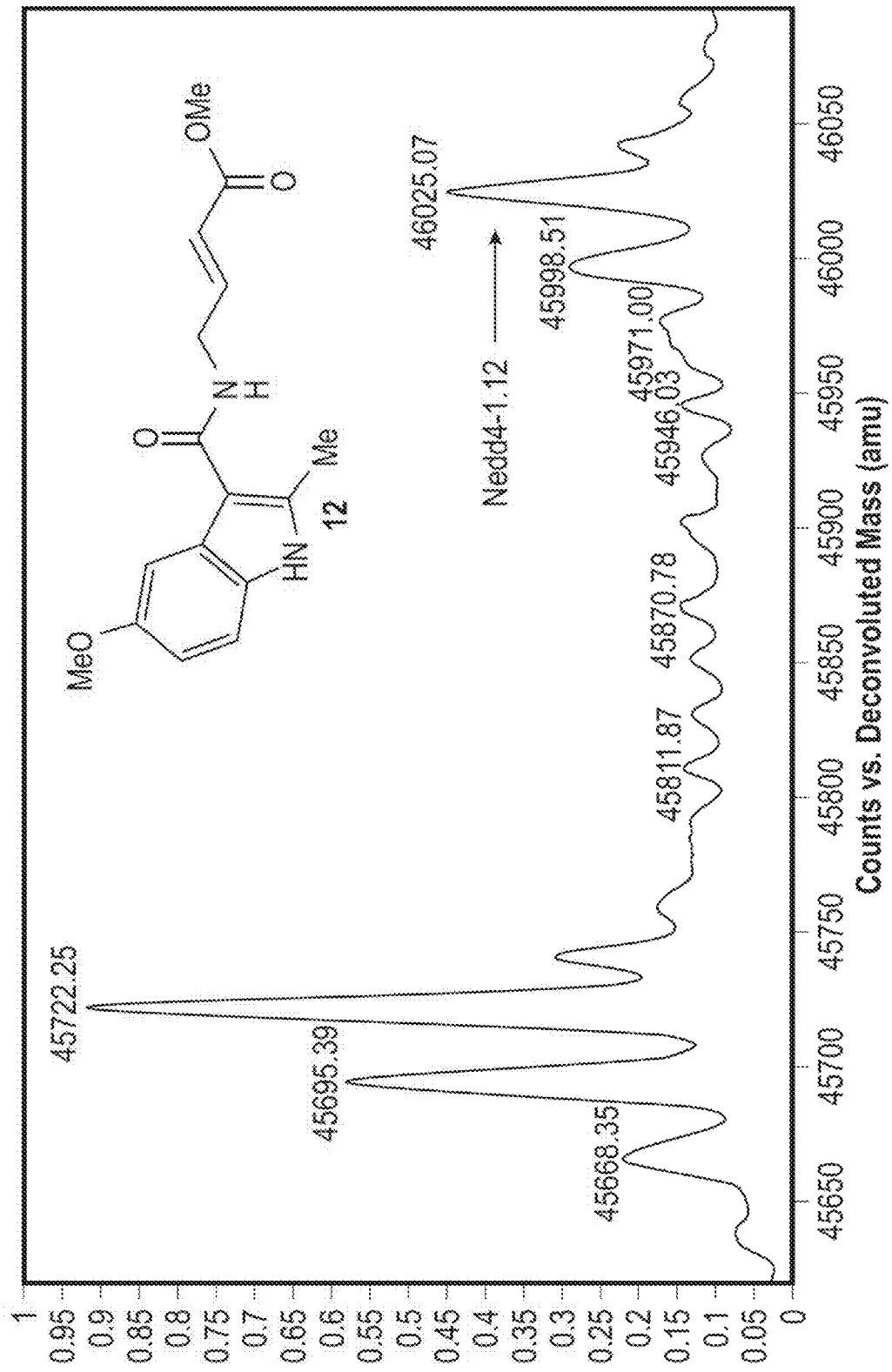
Figure 21E:
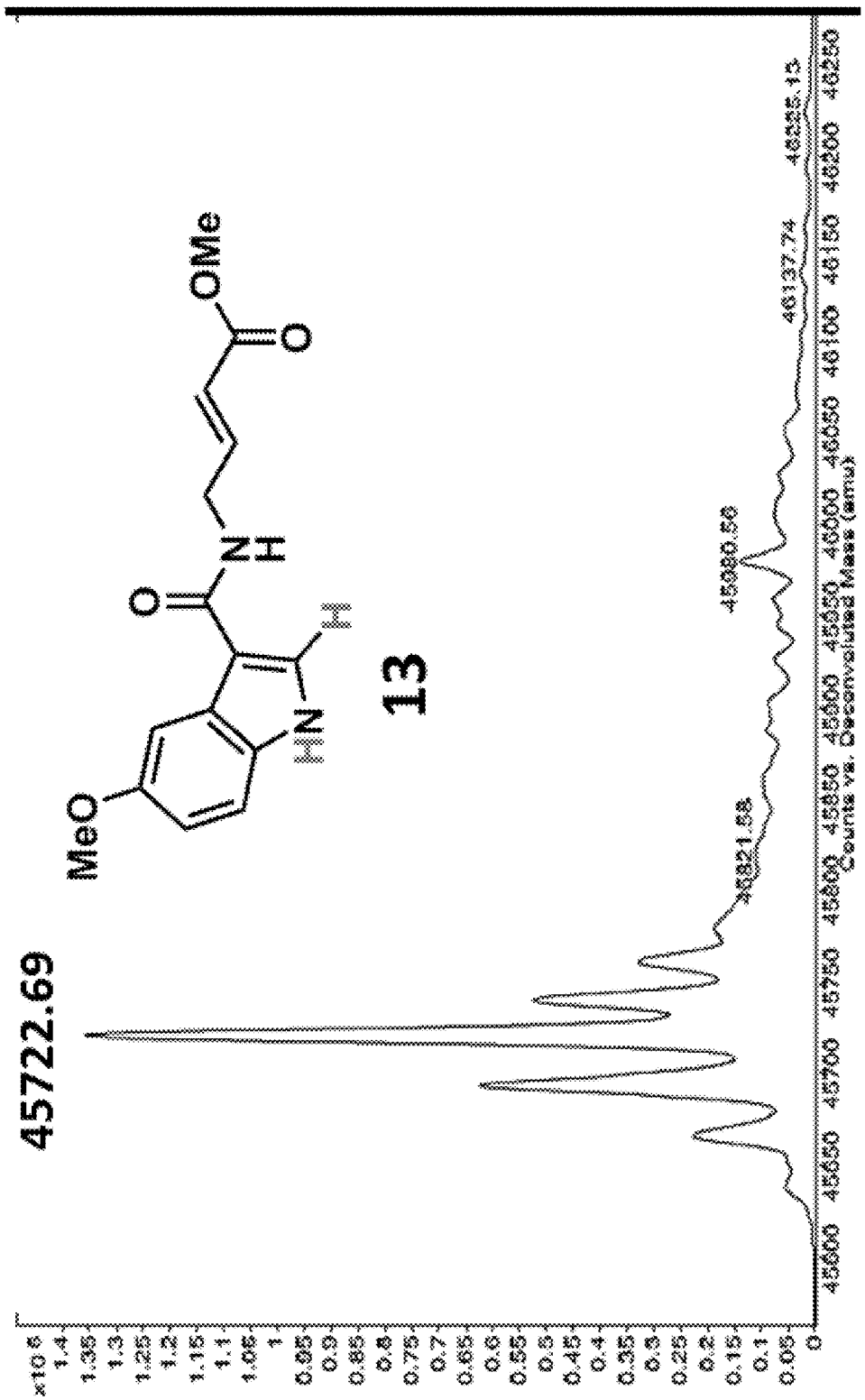
Figure 21F:
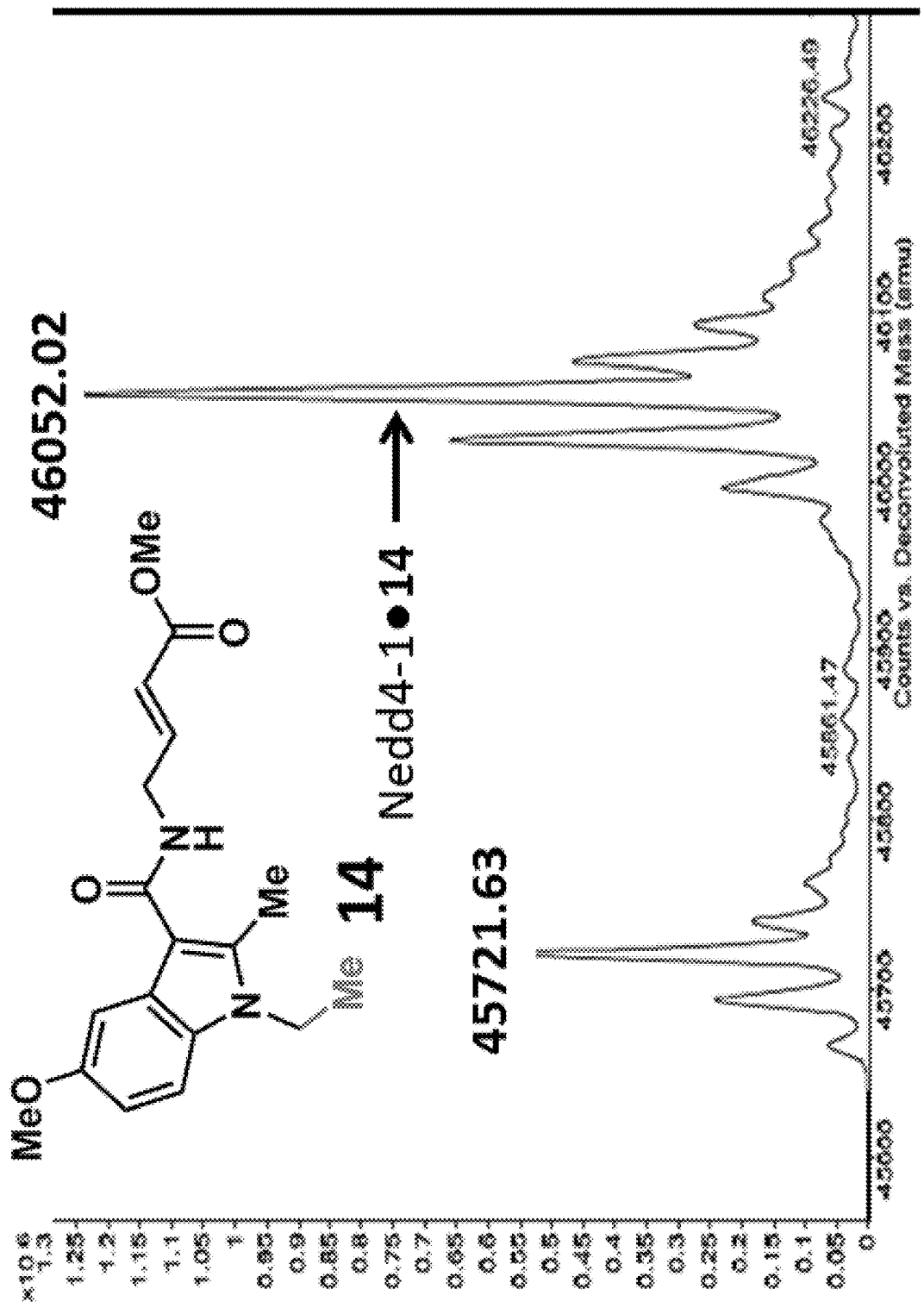

FIG. 20A and FIG. 20B. The catalytic Cys$^{867}$ of NEDD4-1 is more reactive with the non-specific N-acetyl electrophile 3 than Cys$^{627}$, as determined by the corresponding Cys to Ala mutations. Compound 3 at 1 mM in 1% DMSO was incubated with the indicated NEDD4-1 HECT domain mutant (10 μM) for 4 h, followed by gel filtration and whole protein ESI-MS.

FIG. 21A, FIG. 21B, FIG. 21C, FIG. 21D, FIG. 21E and FIG. 21F. Structural changes in 1 impact covalent labeling of NEDD4-1 HECT domain. NEDD4-1 HECT domain (10 μM) was treated with the indicated compounds at 100 μM for 4 h, followed by gel filtration and whole protein ESI-MS. Notably, the 5-position of indole does not tolerate a 5-EtO- substitution, while labeling is improved when N-CH$_3$ is replaced by N-Ethyl.

Figure 22:
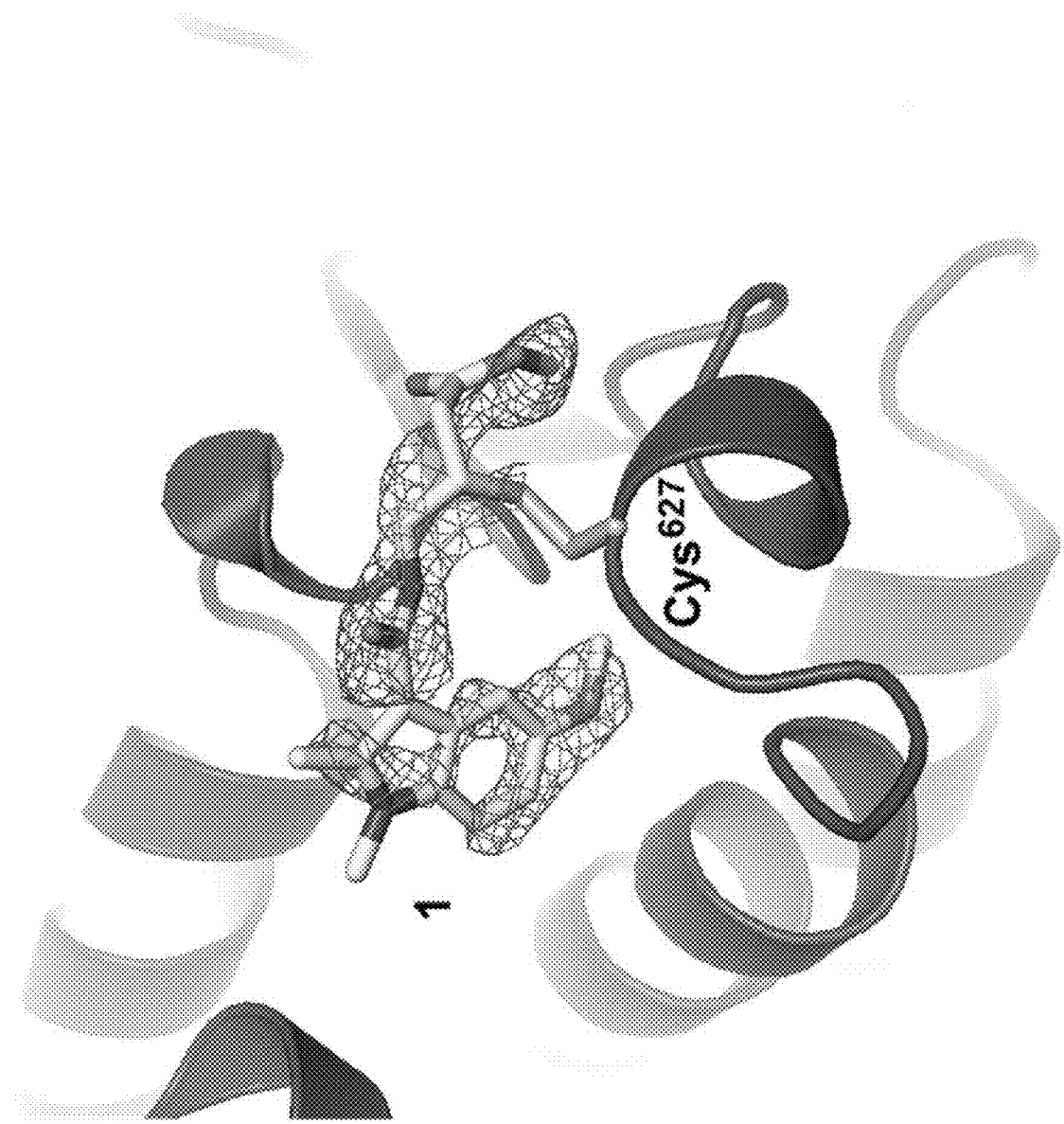

FIG. 22. Inhibitor-binding site with the side chain of Cys$^{627}$ and 1 depicted as sticks and colored by atom type. The 2F$_O$-F$_C$ electron density map (green mesh, contoured at 1.0 σ) was computed after simulated annealing with the inhibitor omitted from the atomic model.

Figure 23:
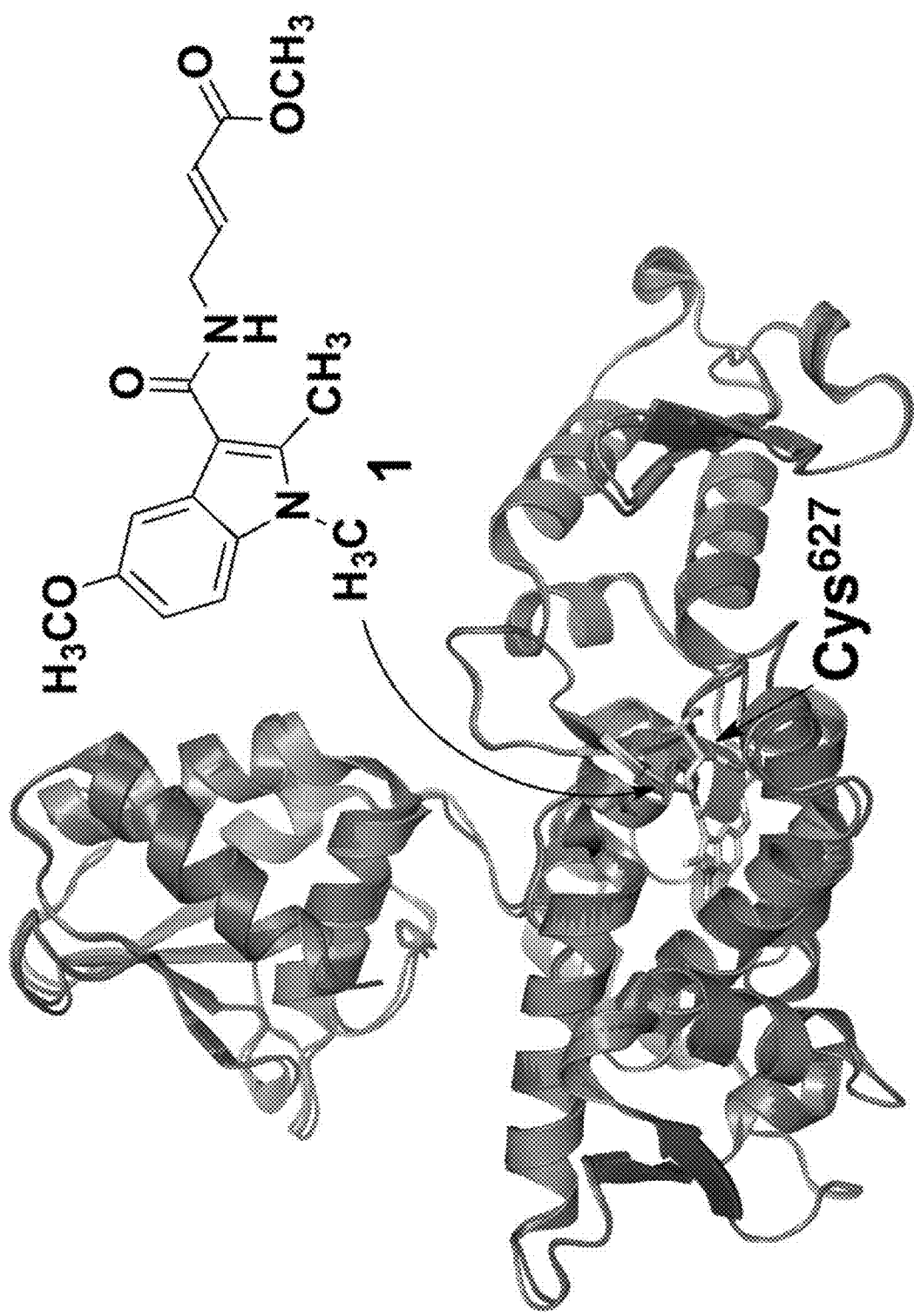

FIG. 23. Superposition of NEDD4-1 (PDB ID 2XBF) and the NEDD4-1:1 complex with the protein depicted as a cartoon and the inhibitor as well as the side chain of Cys$^{627}$ shown as sticks.

Figure 24:
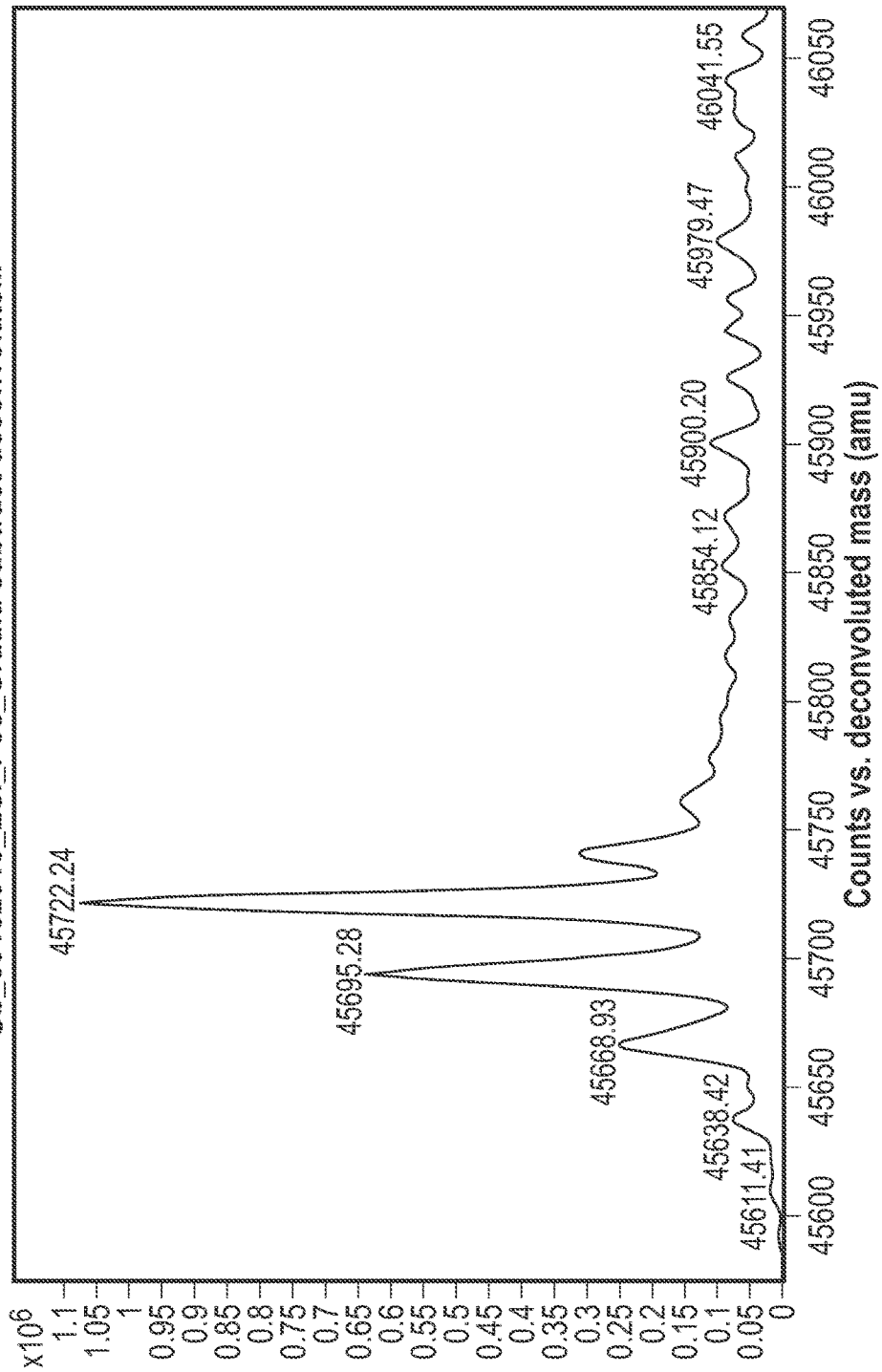
Figure 25A:
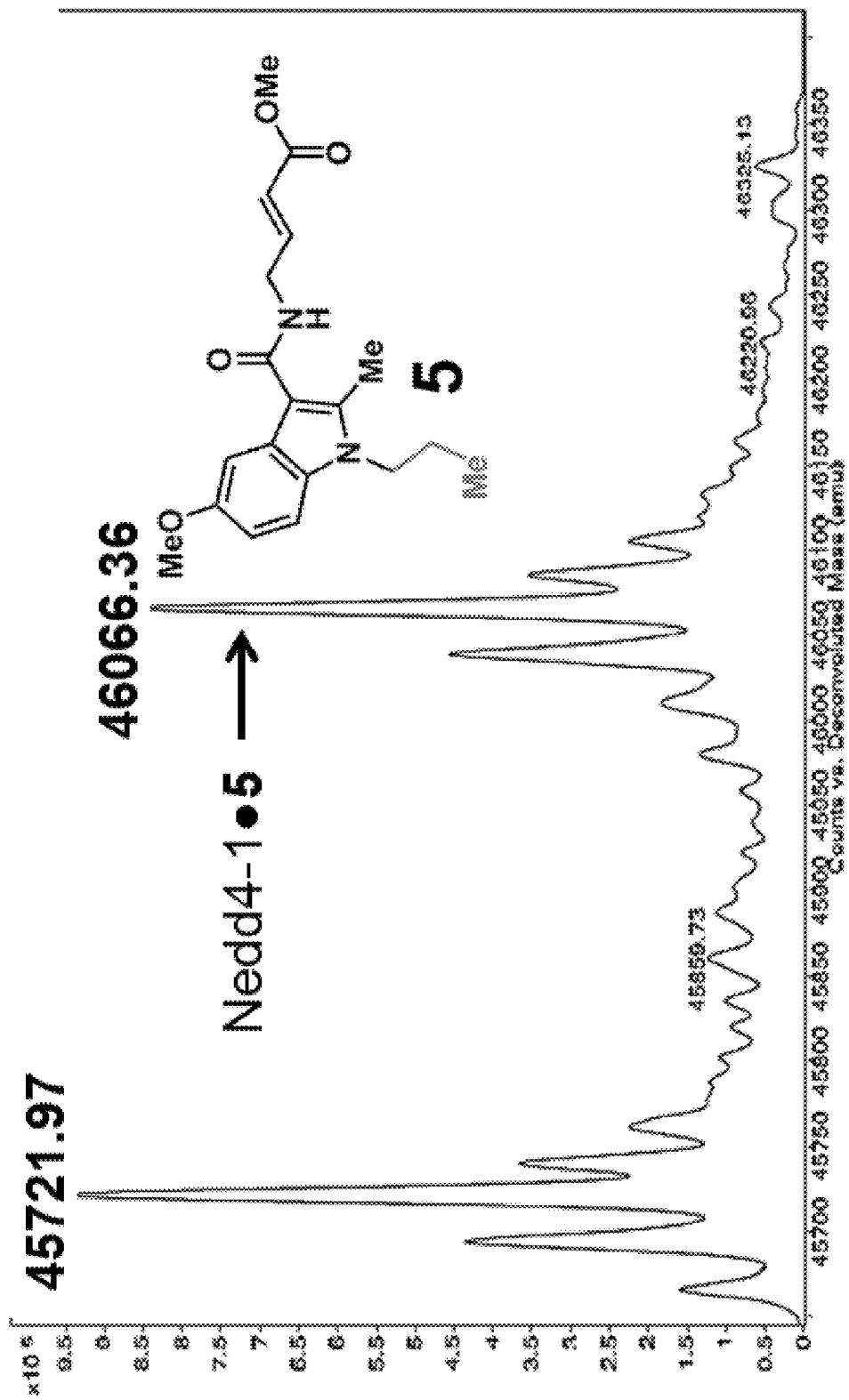
Figure 25B:
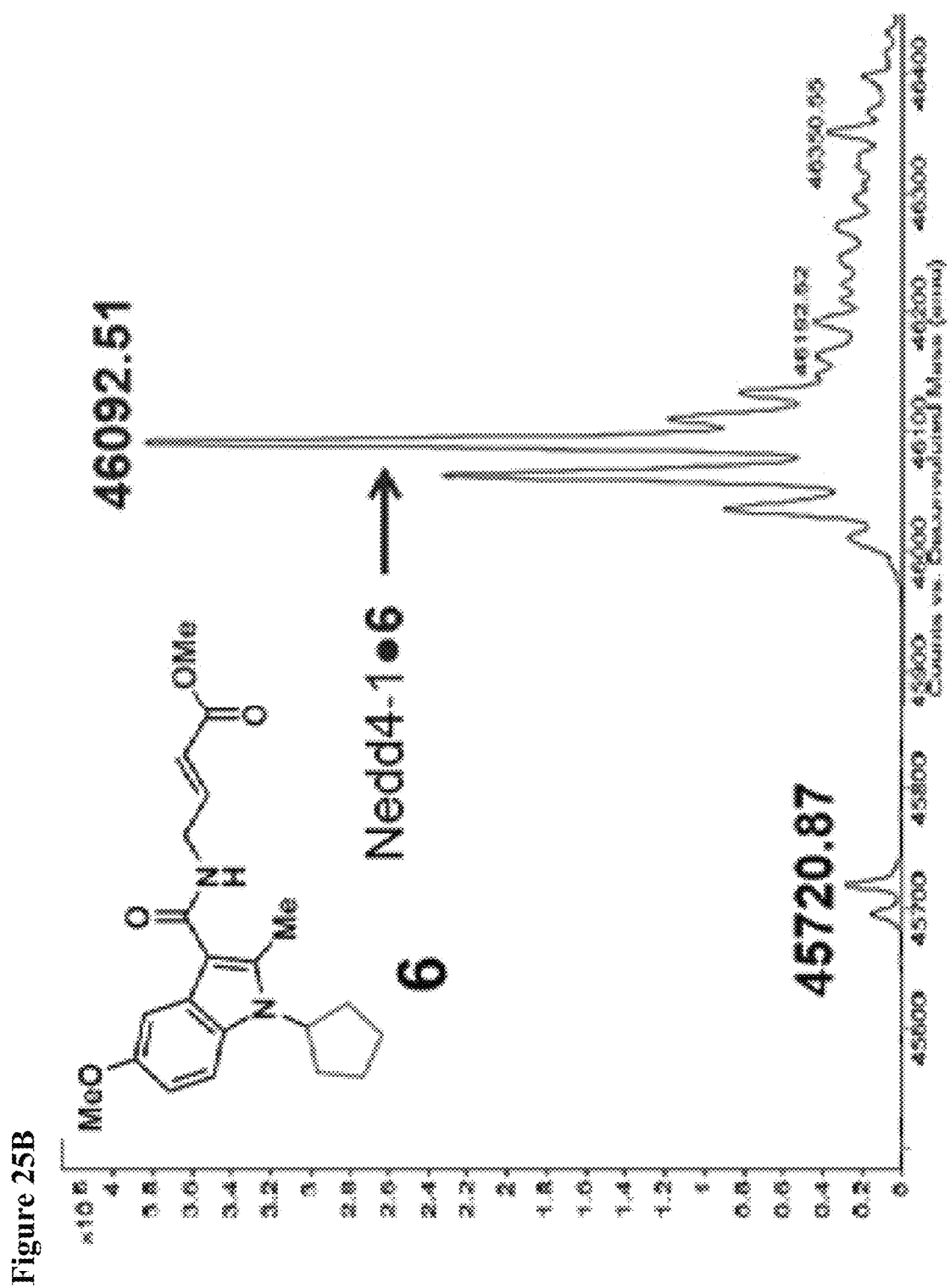
Figure 25C:
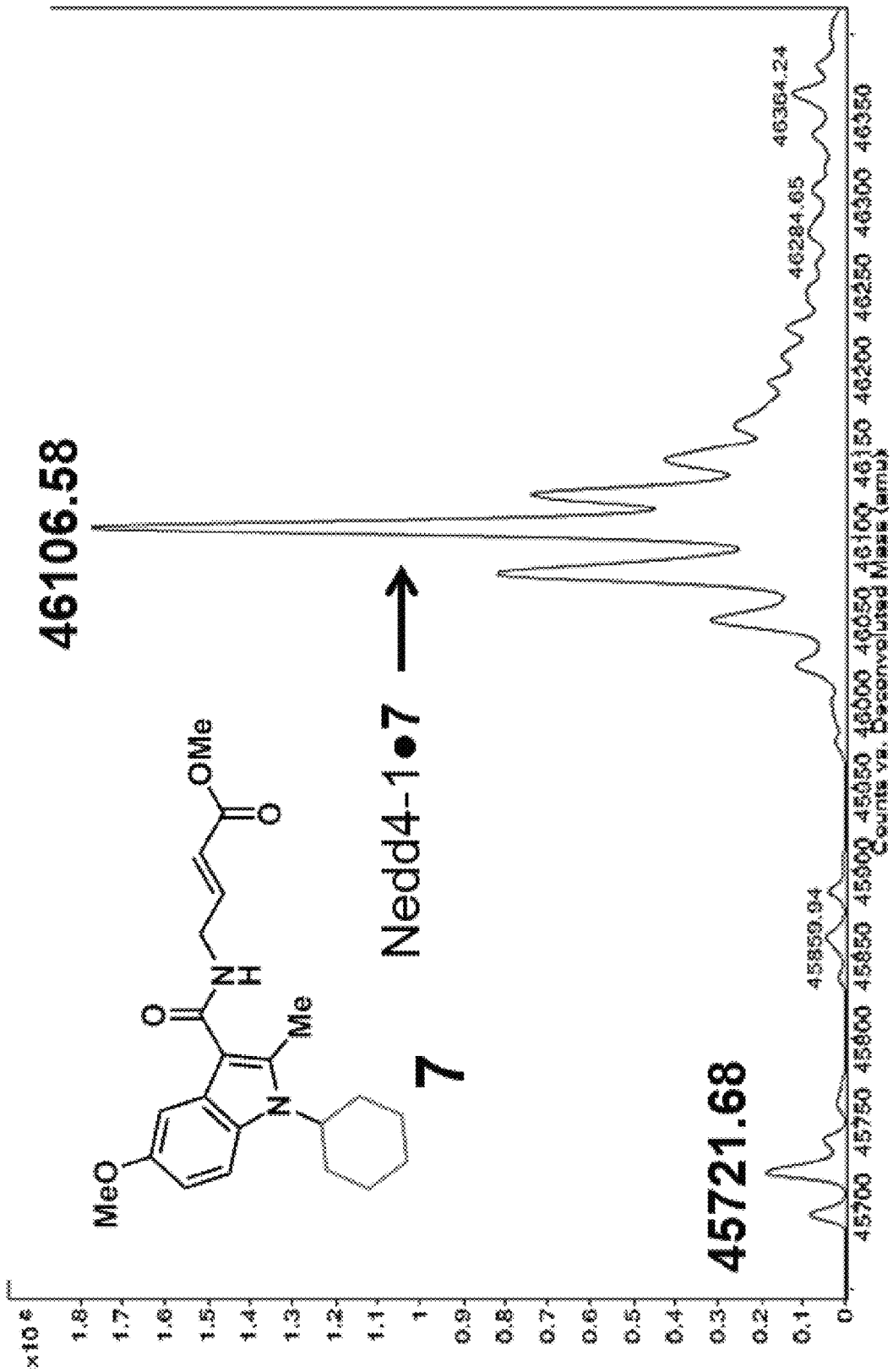
Figure 25D:
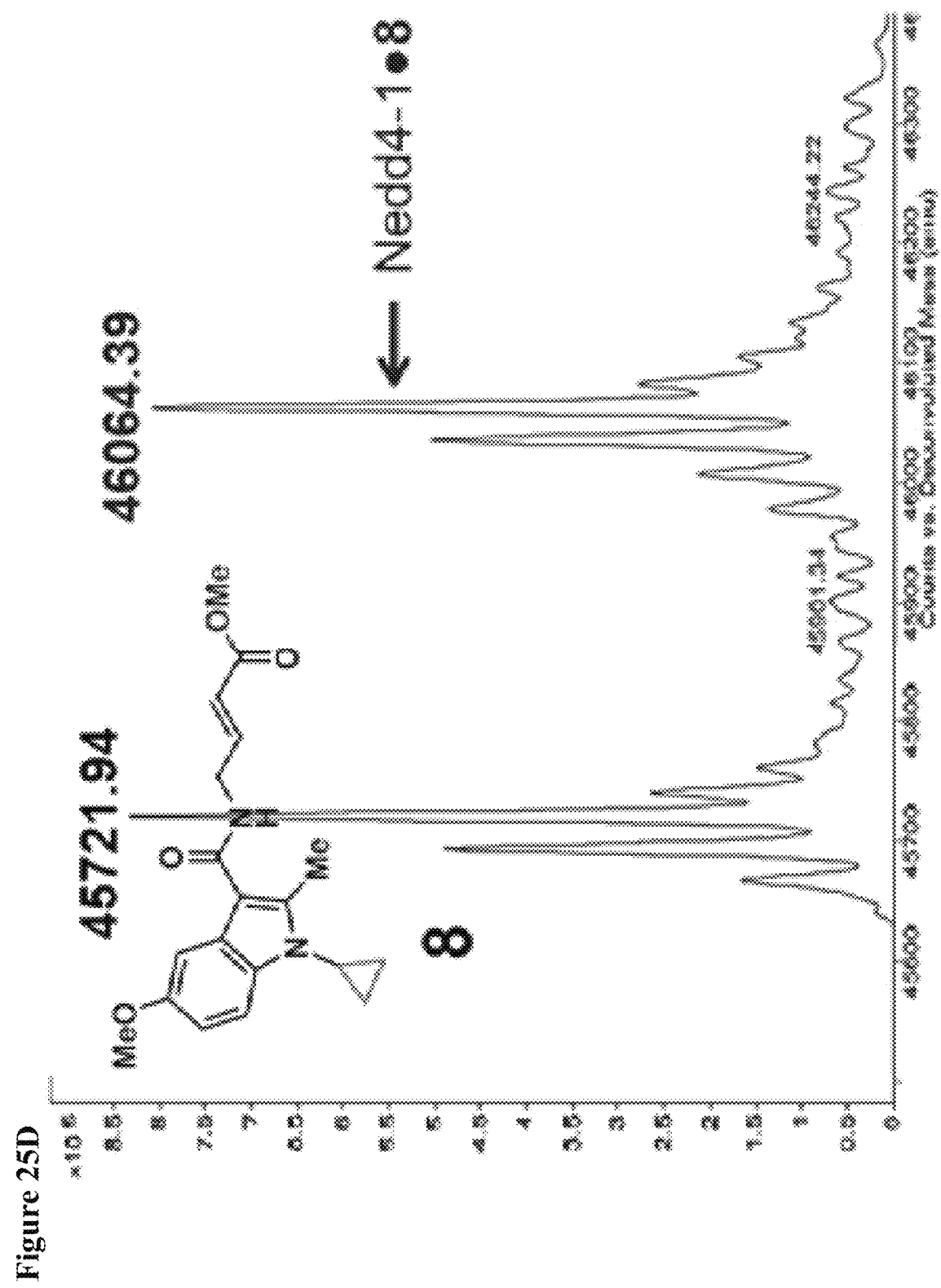
Figure 26A:
Figure 26B:
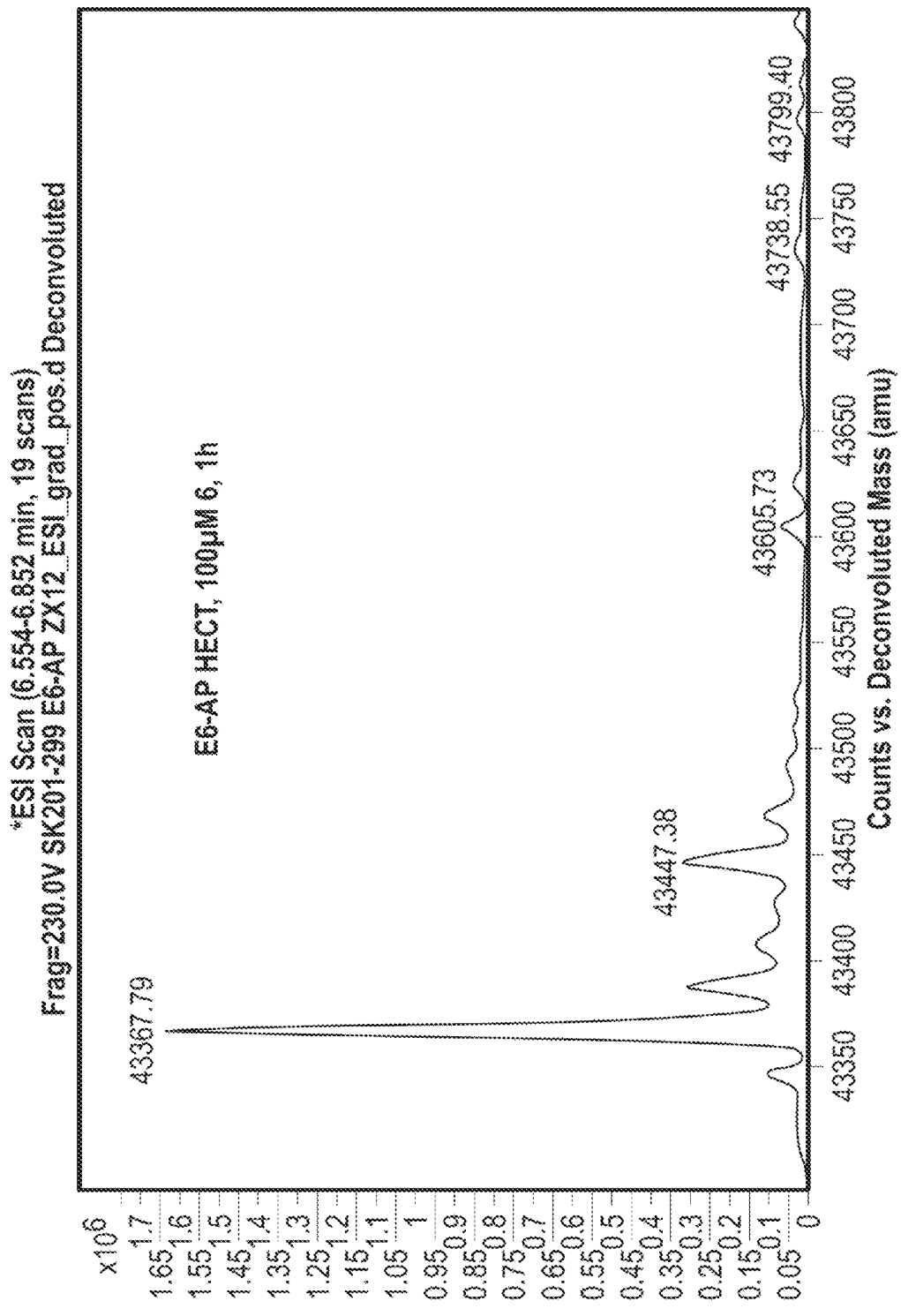
Figure 26C:
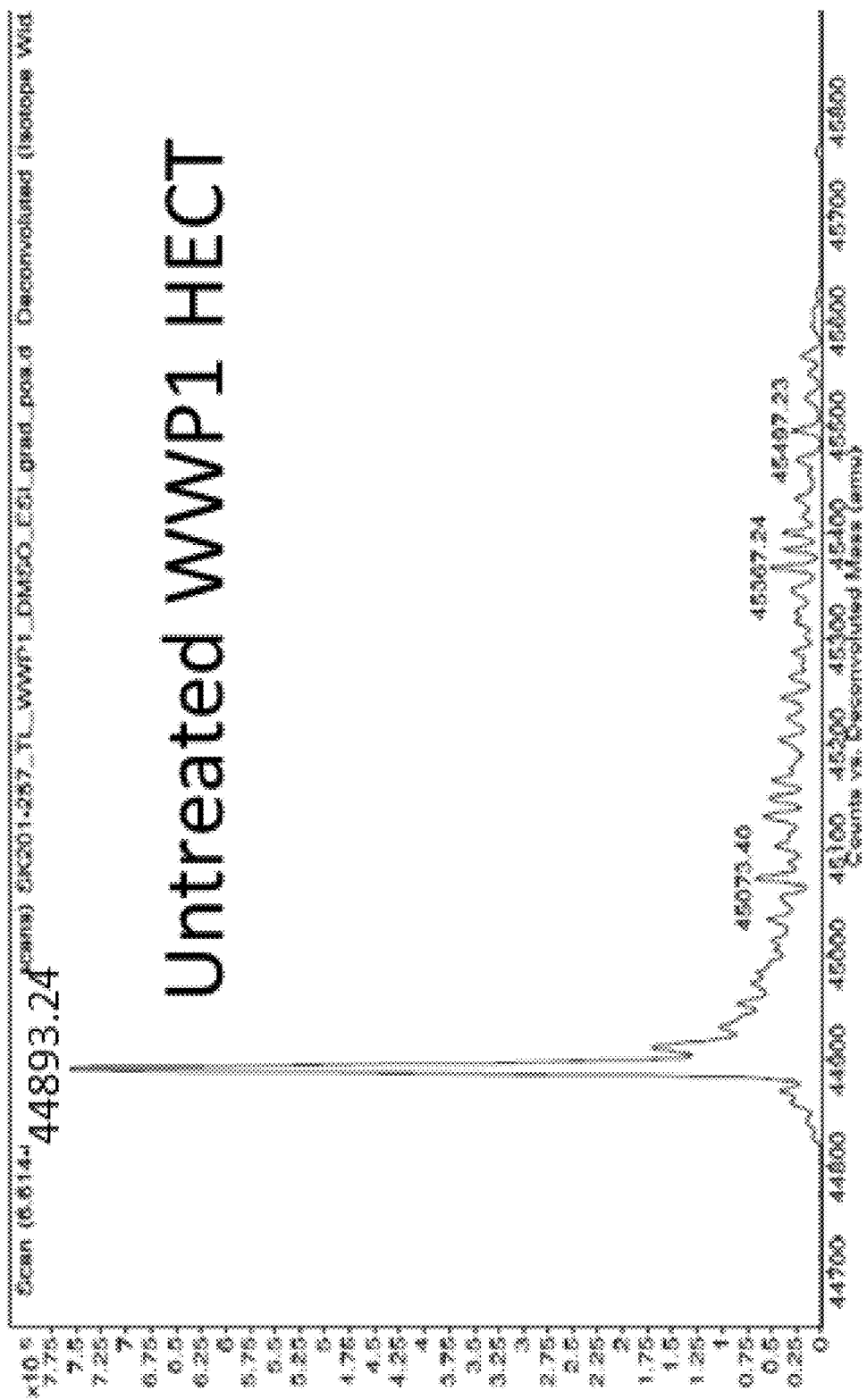
Figure 26D:
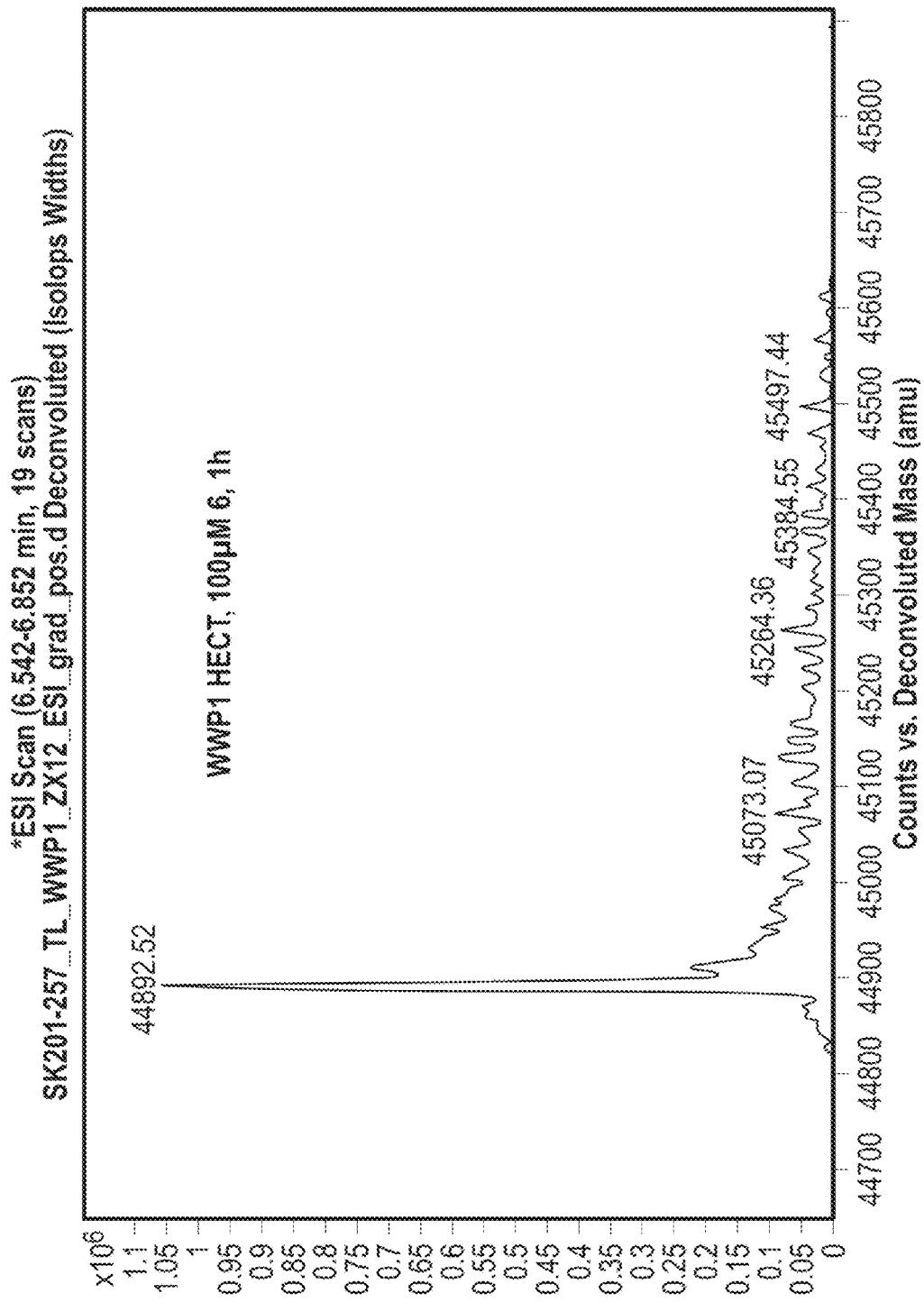
Figure 26E:
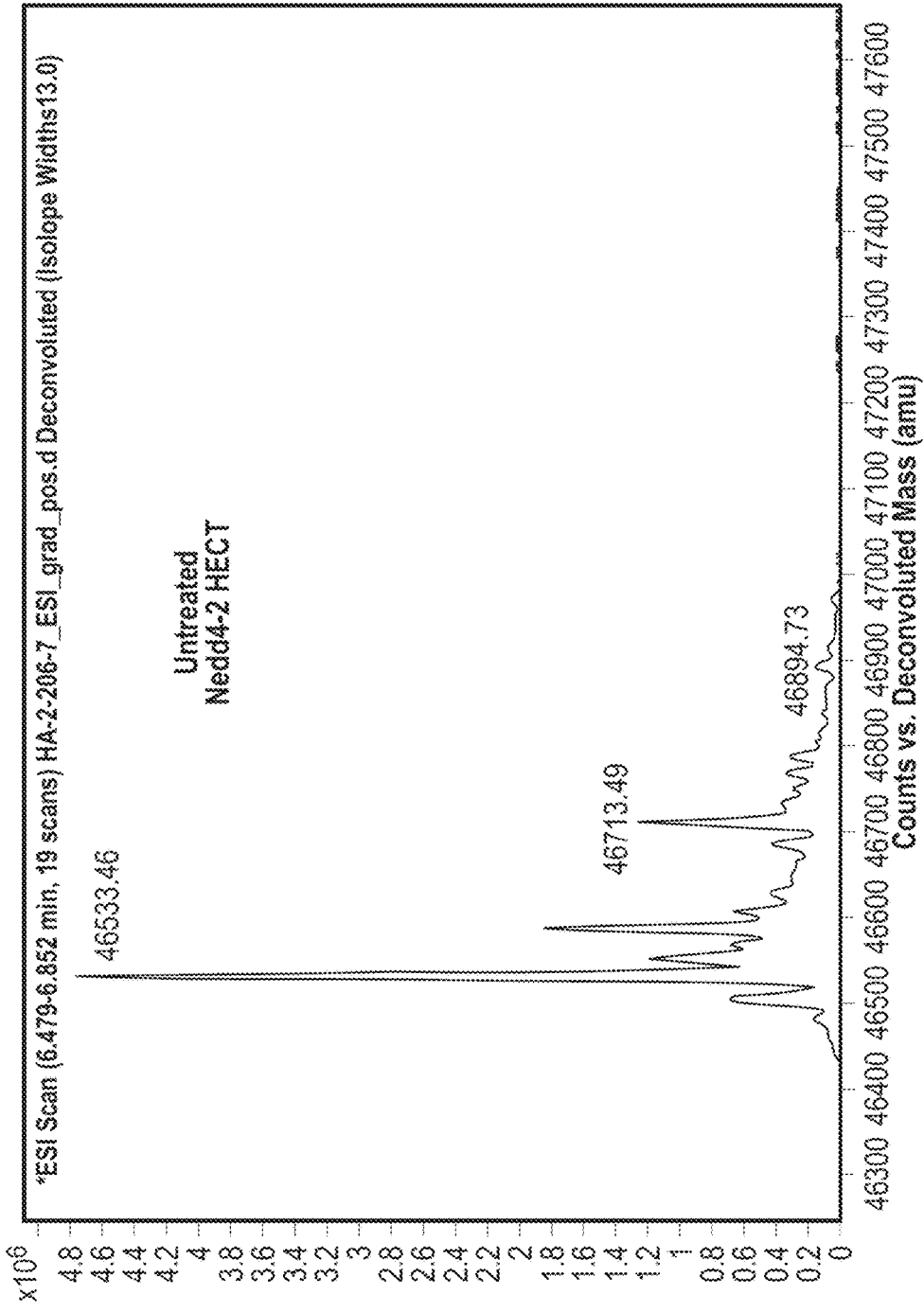
Figure 26F:
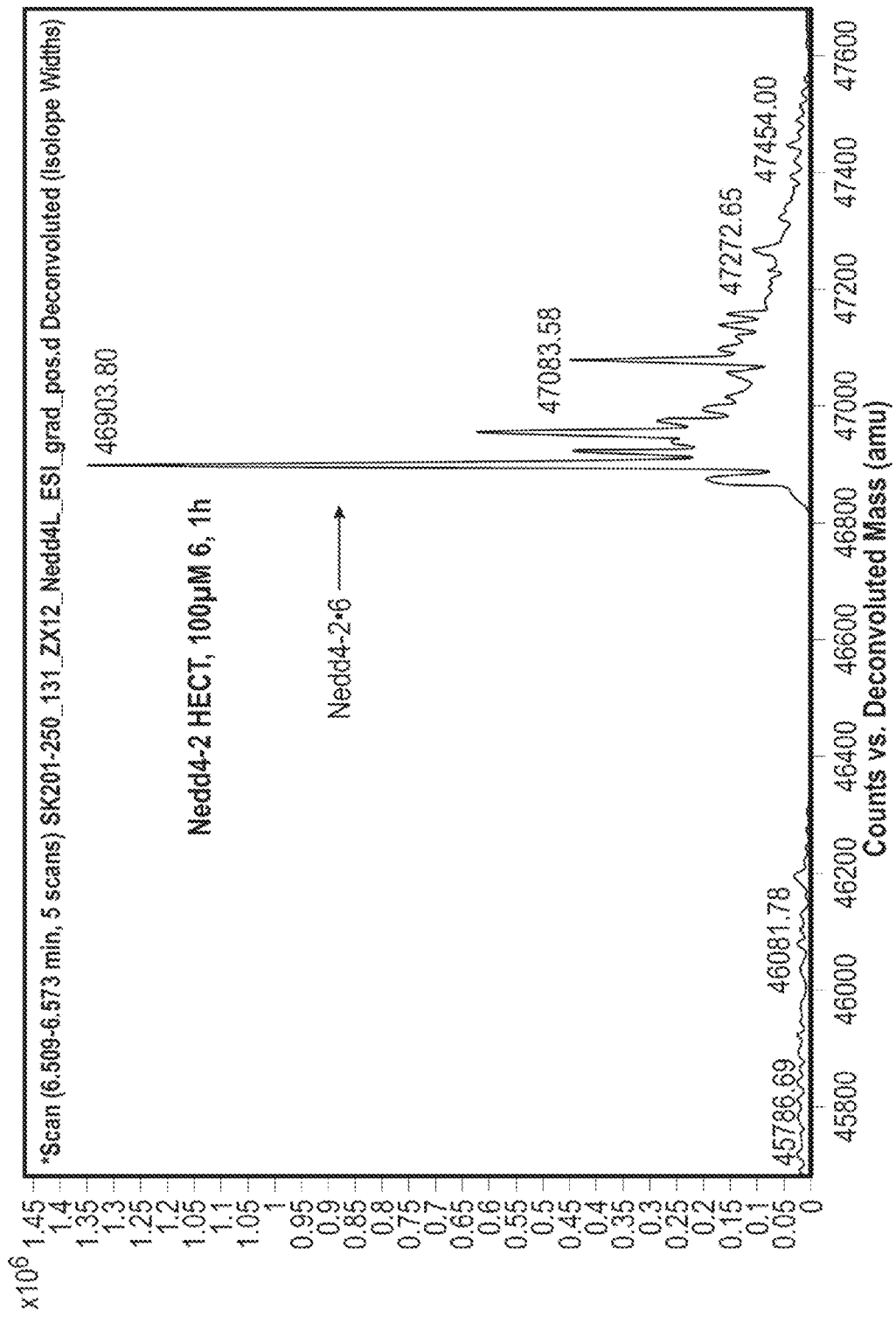

FIG. 24. Inhibition of NEDD4-1 labeling with compound 1 in the presence of 60 μM ubiquitin. Compound 1 (100 μM) in 1% DMSO was incubated with NEDD4-1 HECT domain (10 μM) and ubiquitin (60 μM) for 4 h, followed by gel filtration and whole protein ESI-MS.

FIG. 25A, FIG. 25B, FIG. 25C and FIG. 25D. Structure activity relationship (SAR) studies of N-substituted indole analogs 5-8 to improve the potency of compound 1. NEDD4-1 HECT domain (10 μM) was treated with the indicated compounds in 1% DMSO at 100 μM for 1 h, followed by gel filtration and whole protein ESI-MS.

FIG. 26A, FIG. 26B, FIG. 26C, FIG. 26D, FIG. 26E and FIG. 26F. Counterscreen of compound 6 against catalytic HECT domains of E6-AP, WWP1, and Nedd4-2. Compound 6 at 100 μM in 1% DMSO was incubated with the catalytic domain of the indicated HECT E3 (10 μM) for 1 h, followed by gel filtration and whole protein ESI-MS.

Figure 27:
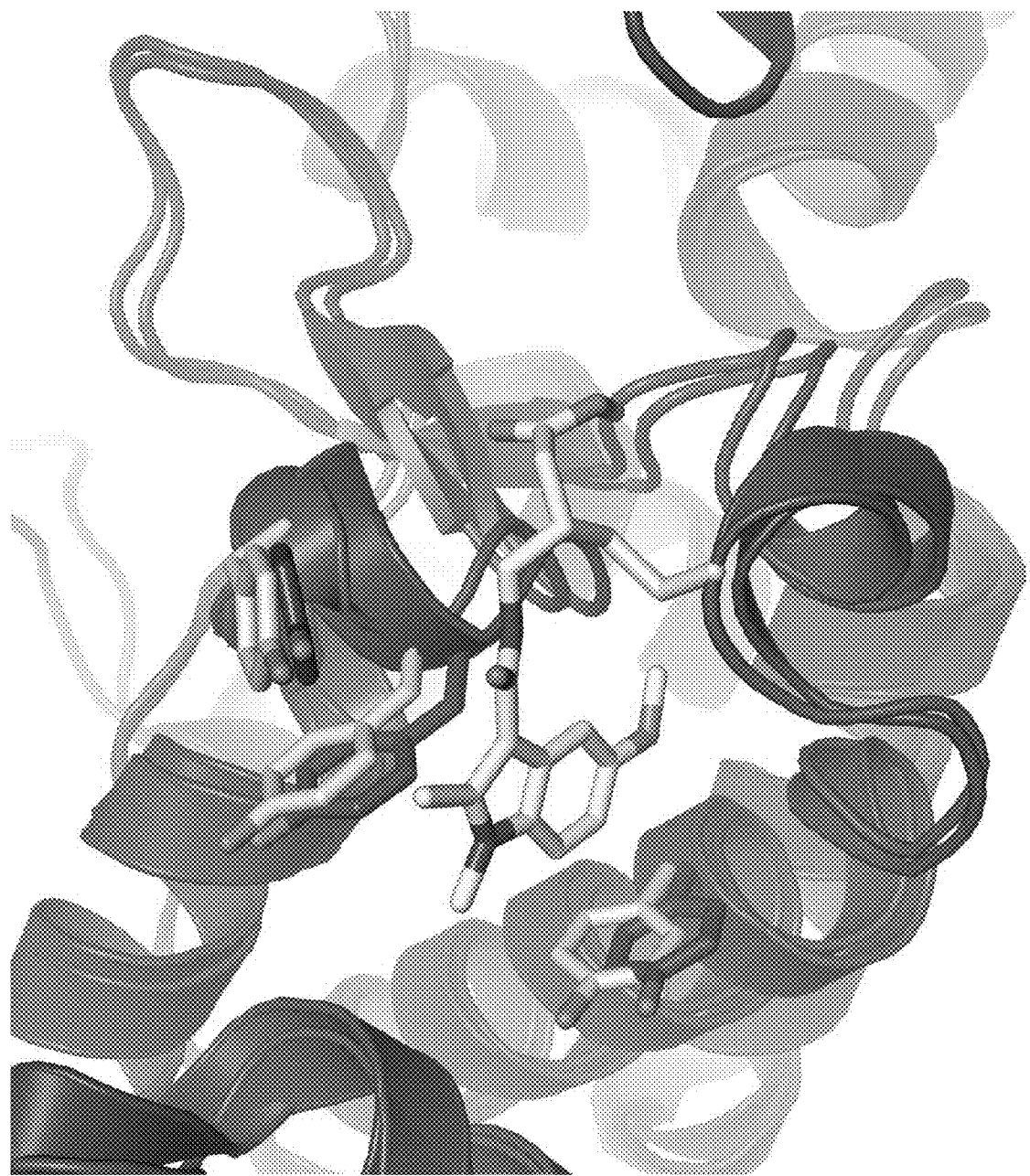
Figure 28A:
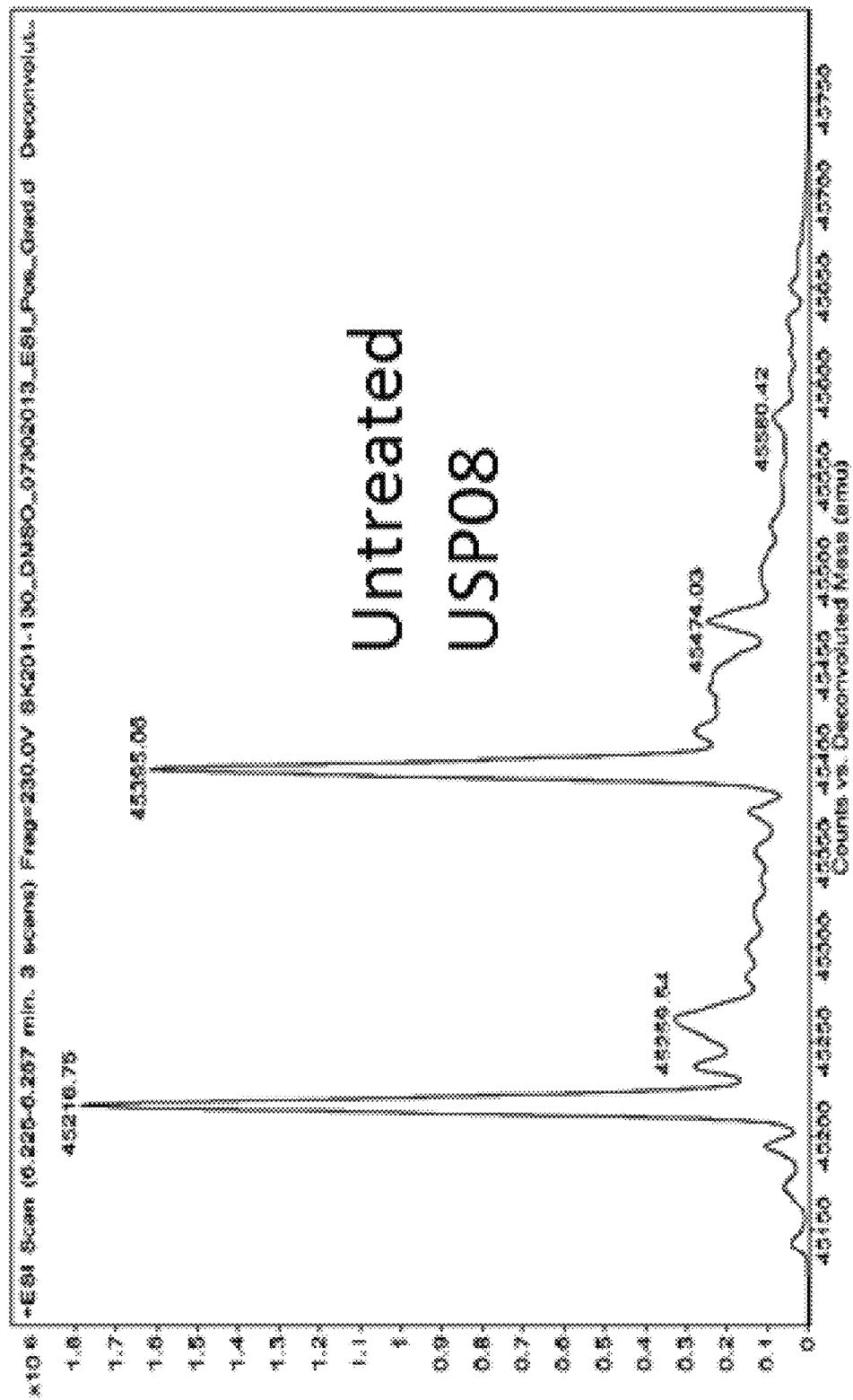
Figure 28B:
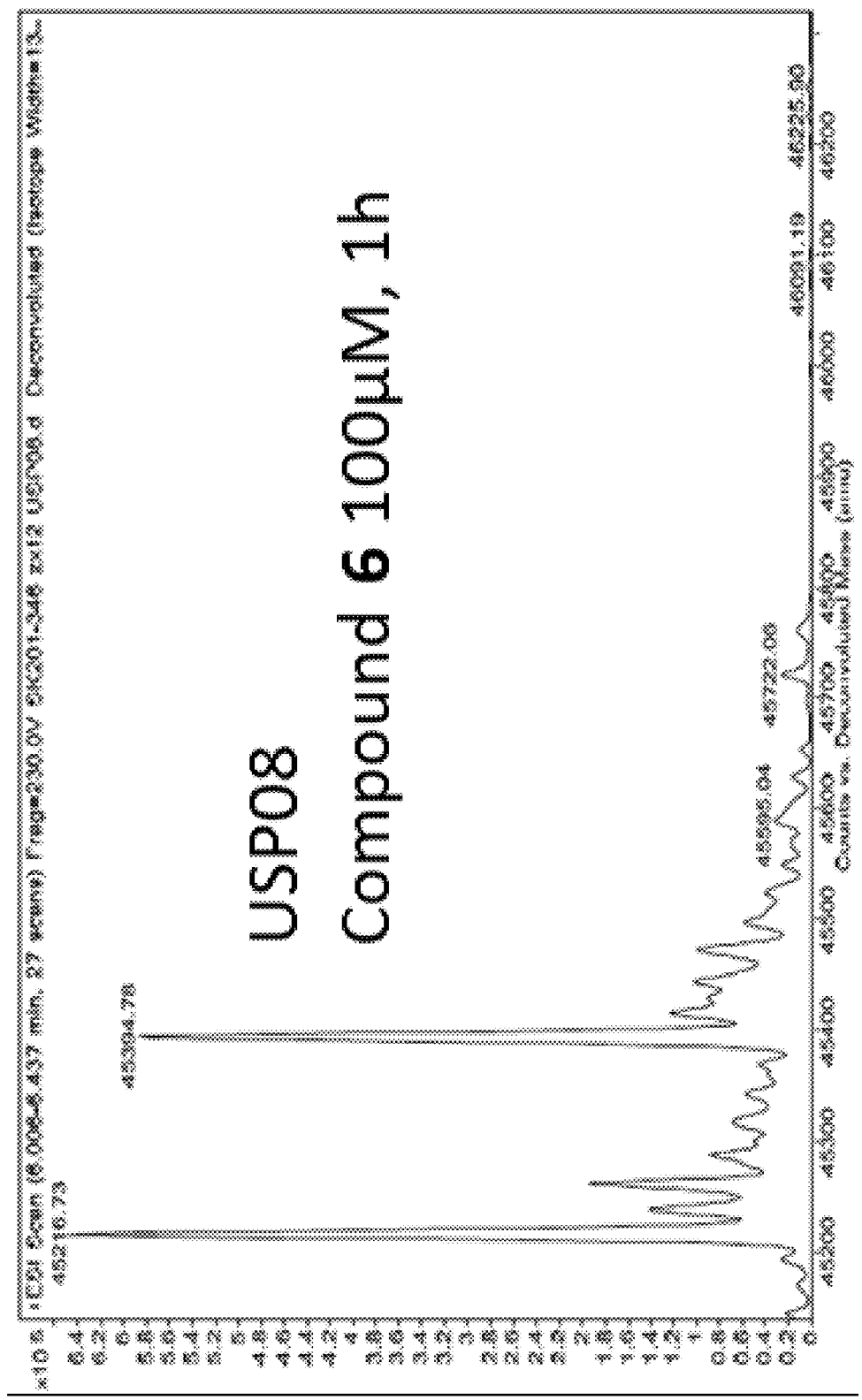
Figure 28C:
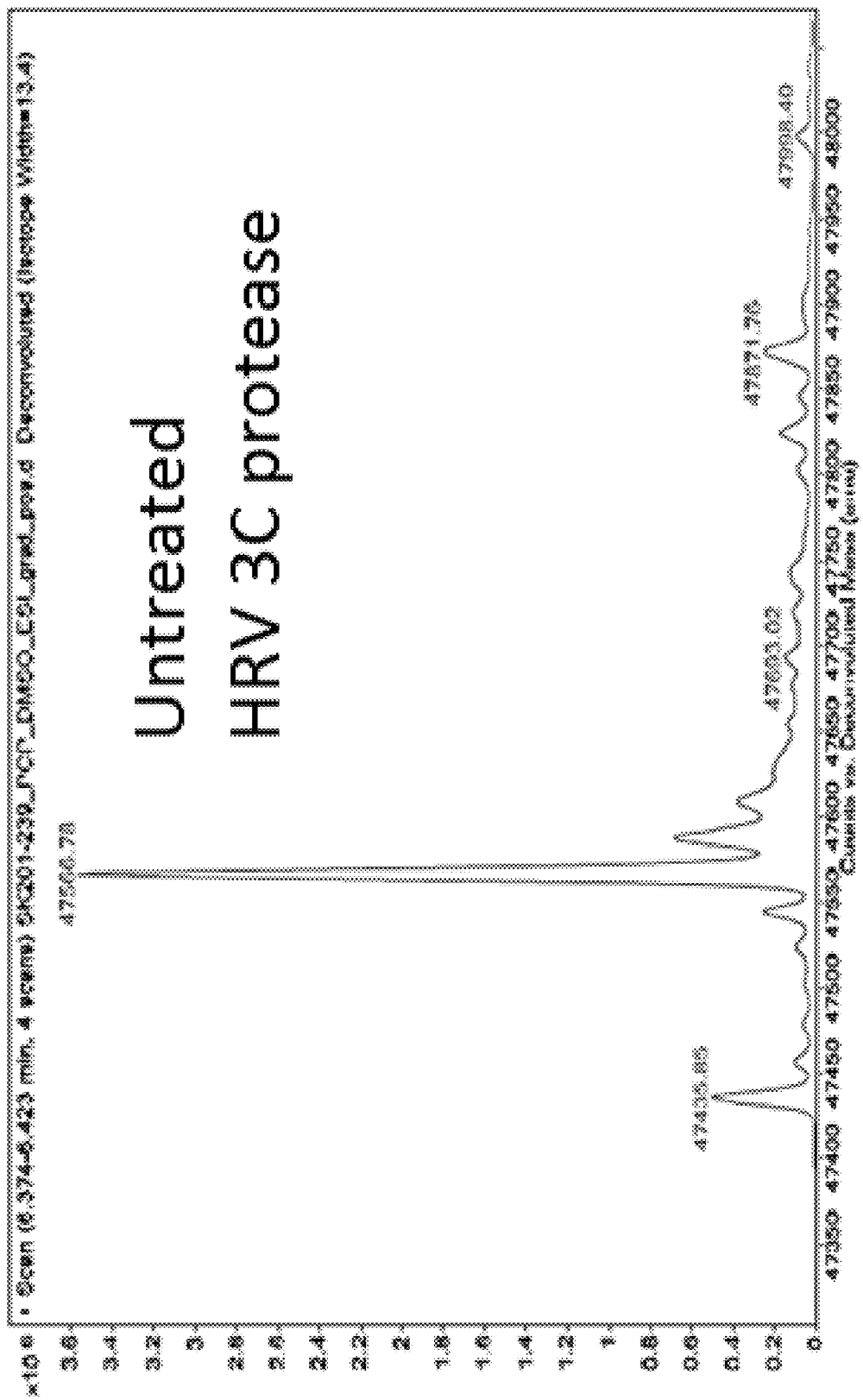
Figure 28D:
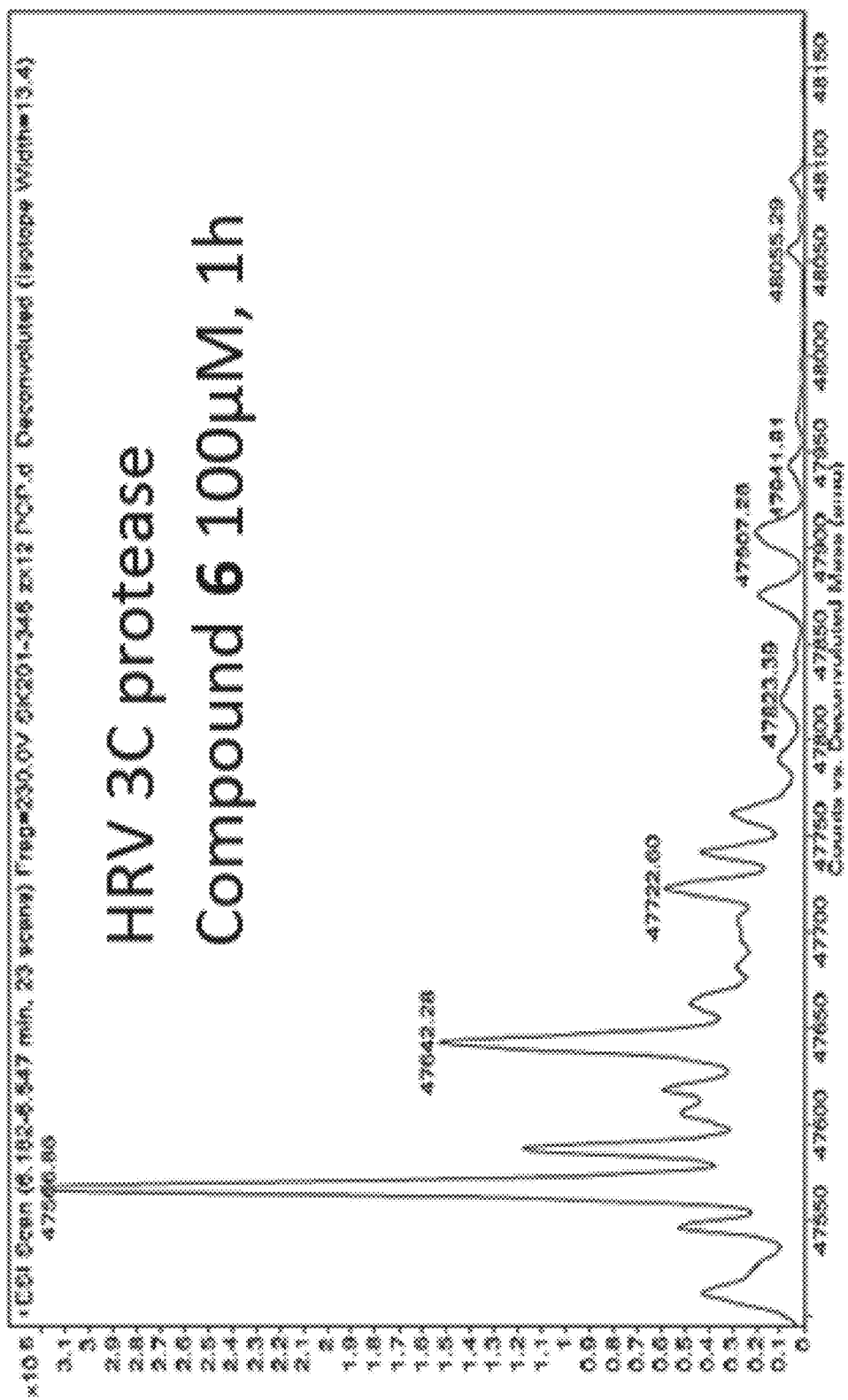

FIG. 27. Superposition of Nedd4-2 (PDB ID 2ONI: blue) and the binding site of 1 in the NEDD4-1:1 complex (red); the protein is depicted as a cartoon, the inhibitor and the side chains of Cys$^{627}$, Tyr$^{604}$, Tyr$^{605}$, Tyr$^{634}$, Tyr$^{659}$ (2ONI), Tyr$^{660}$ (2ONI), Tyr$^{689}$ (2ONI) are shown as sticks.

FIG. 28A, FIG. 28B, FIG. 28C and FIG. 28D. Counter-screen of compound 6 against the deubiquitinase USPO8 and Human Rhinovirus (HRV) 3C protease, both of which have catalytic cysteines. Compound 6 at 100 μM in 1% DMSO was incubated with the catalytic domain of the indicated cysteine protease (10 μM) for 1 h, followed by gel filtration and whole protein ESI-MS.

Figure 29:
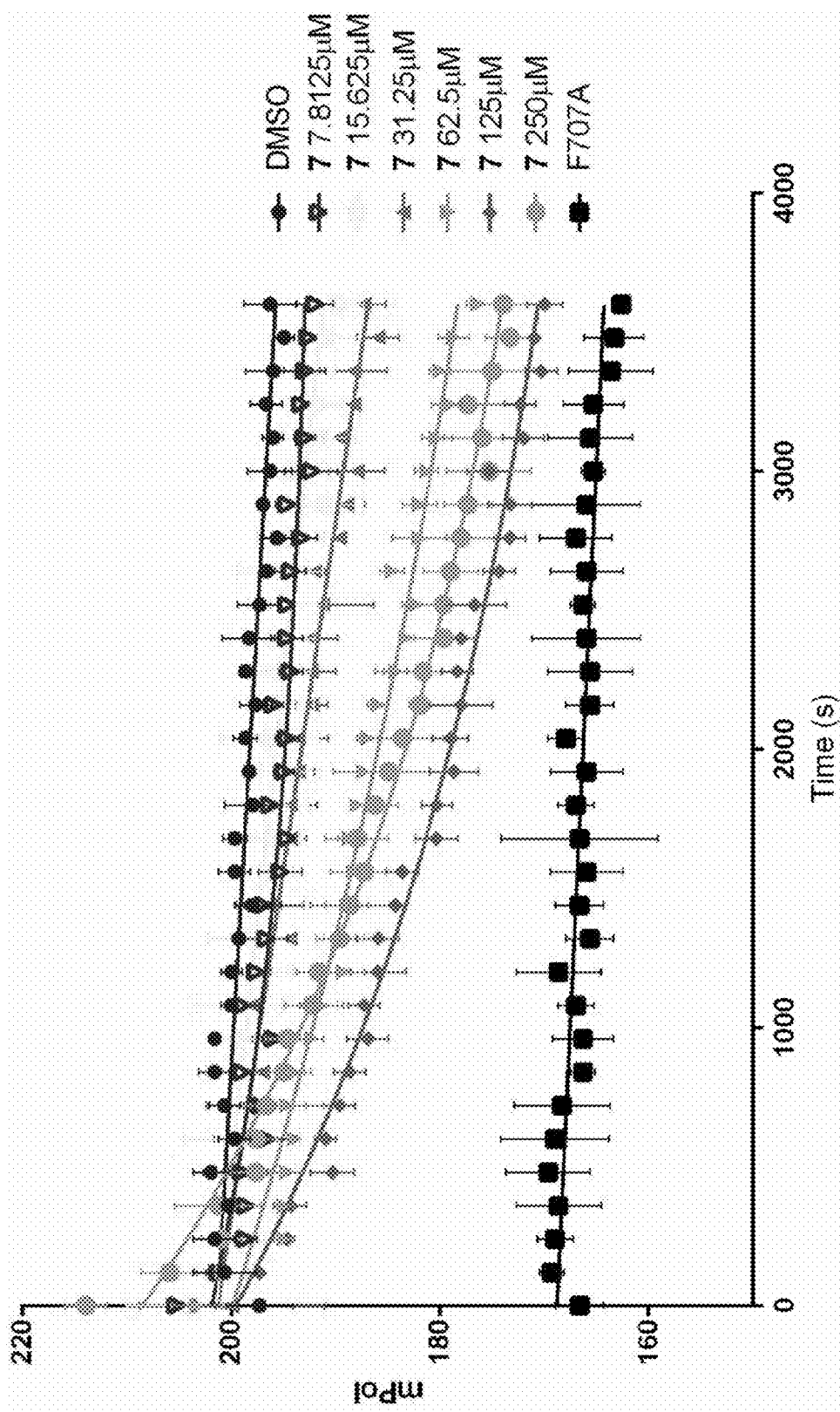

FIG. 29. Potency of cyclohexyl analogue 7 at disrupting NEDD4-1:Ub interactions as assessed by fluorescence polarization. NEDD4-1 HECT and ubiquitin-fluorescein were treated with the indicated concentration of 7 in 1% DMSO. Changes in fluorescence polarization were monitored over 1 h. All reactions were performed in triplicate and plotted as mean±s.e.m.

Figure 30:
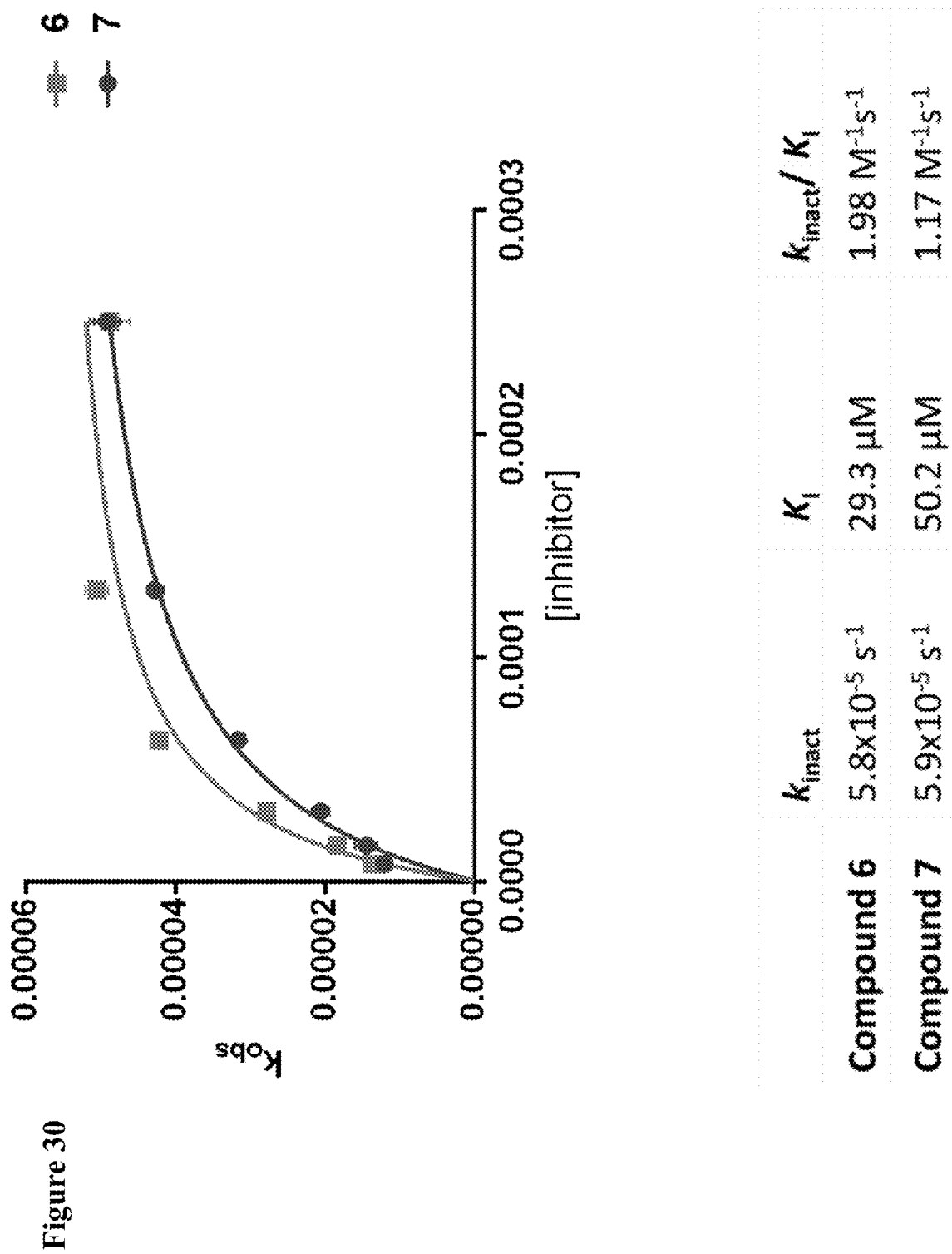

FIG. 30. $k_{obs}$ vs [compound 6] plot showing a two step mechanism for the covalent modification of NEDD4-1, in which the initial non-covalent NEDD4-1:compound 6 complex is formed, followed by the covalent bond formation step. $k_{obs}$ values were determined from the slopes of the log plots of FIG. 15A and FIG. 28. All reactions were performed in triplicate and plotted as mean±s.e.m.

Figure 31:
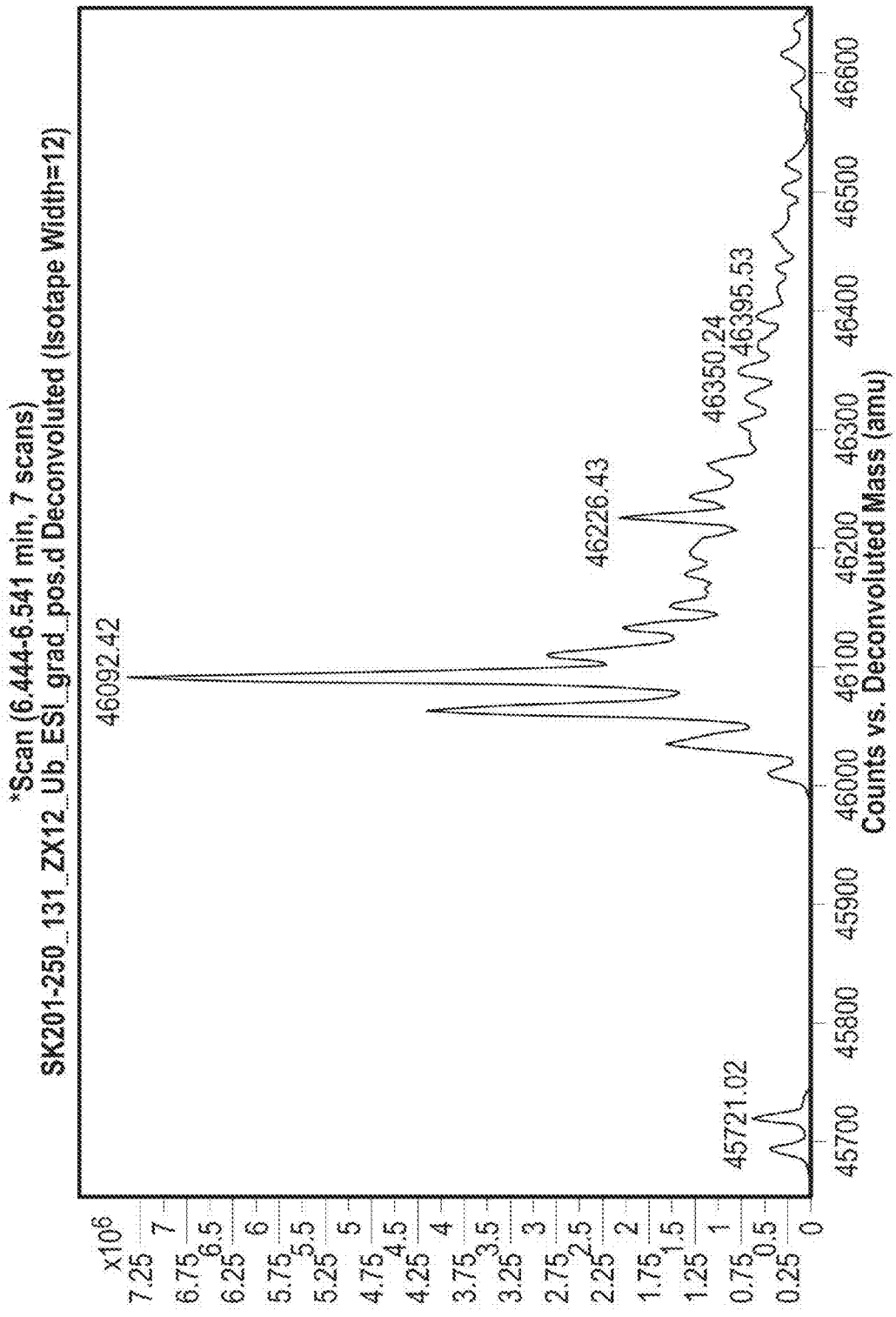

FIG. 31. Compound 6 completely labels NEDD4-1 HECT domain in the presence of 60 μM ubiquitin, which is significantly above the NEDD4-1:Ub $K_d$ value of 11 μM. Compound 6 at 100 μM in 1% DMSO was incubated with NEDD4-1 HECT domain (10 μM) and ubiquitin (60 μM) for 4 h, followed by gel filtration and whole protein ESI-MS.

Figure 32A:
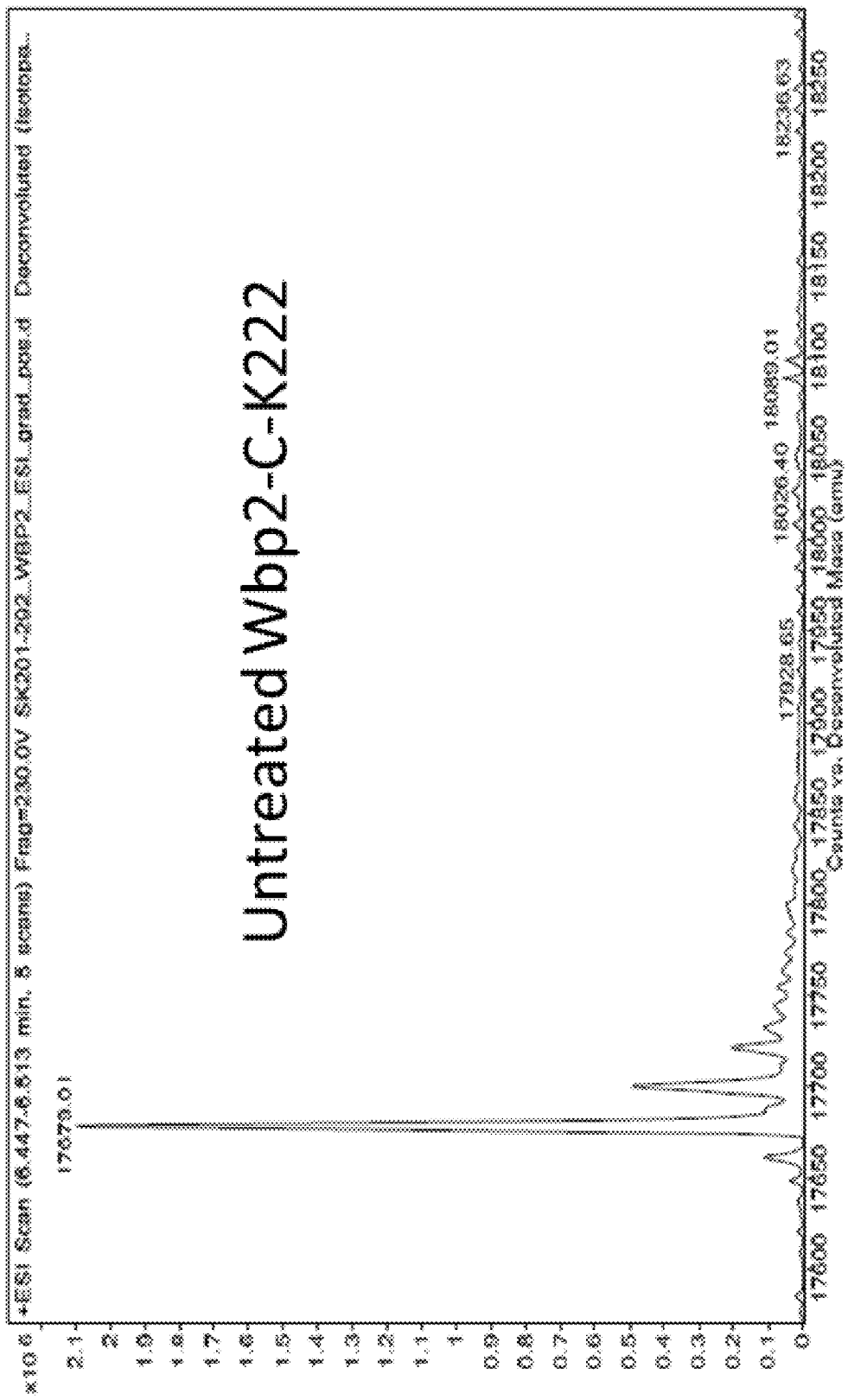
Figure 32B:
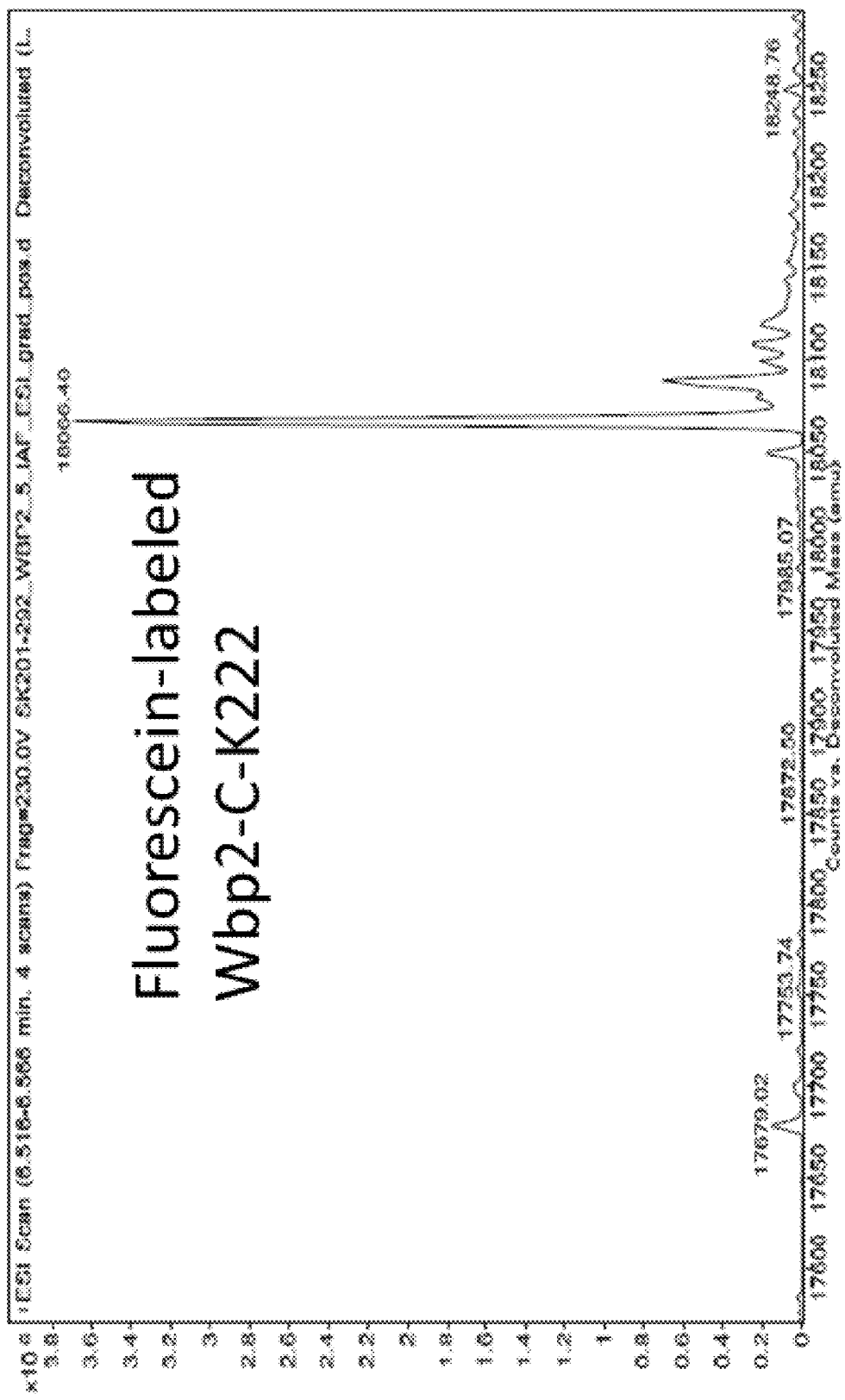

FIG. 32A and FIG. 32B. Covalent labeling of Wbp2-C-K222 with 5-iodoacetamidofluorescein (3 mM, 90 min, 4° C.). Wbp2-C-K222 sequence (SEQ ID NO:6).

Figure 16A:
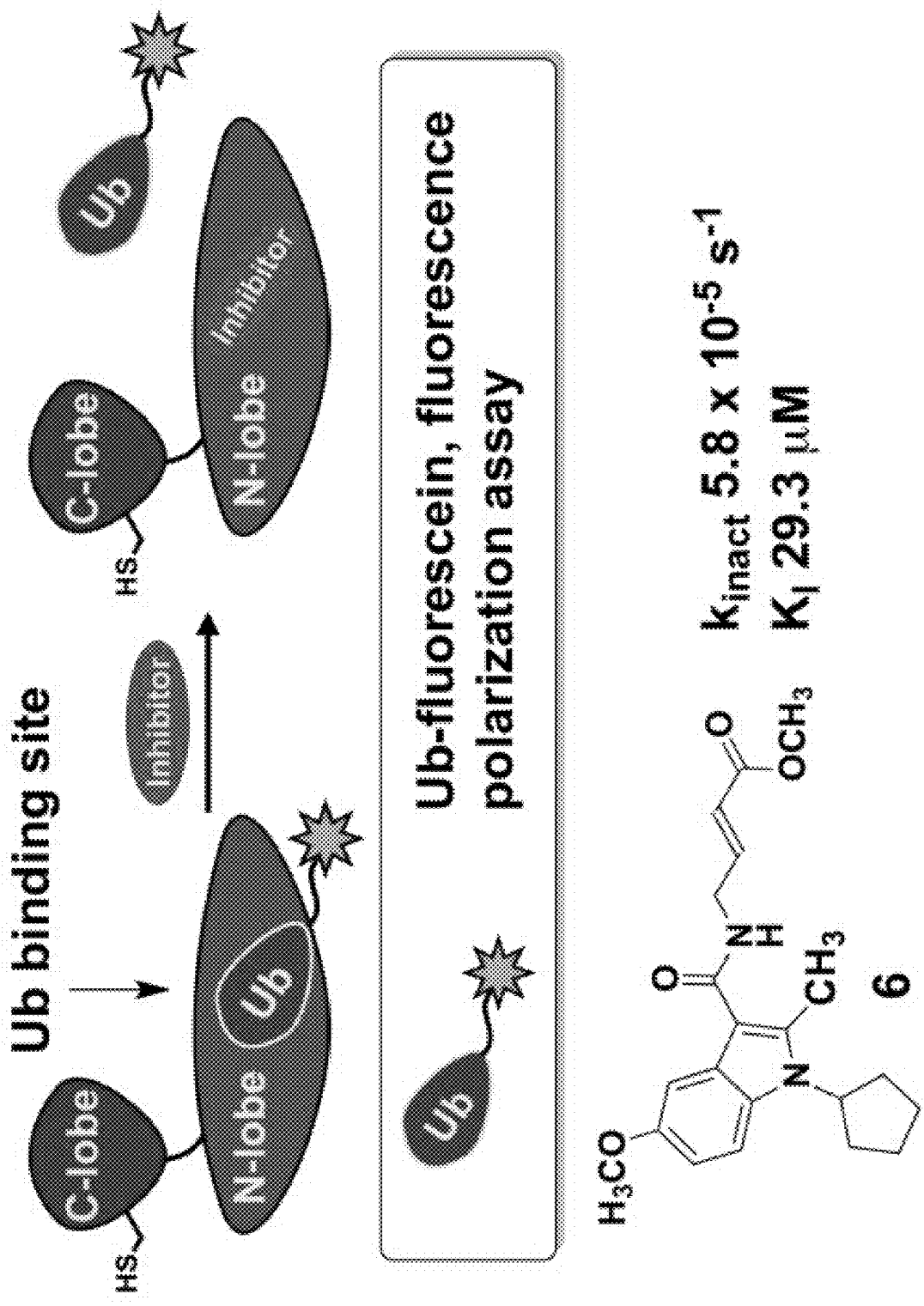
Figure 16B:
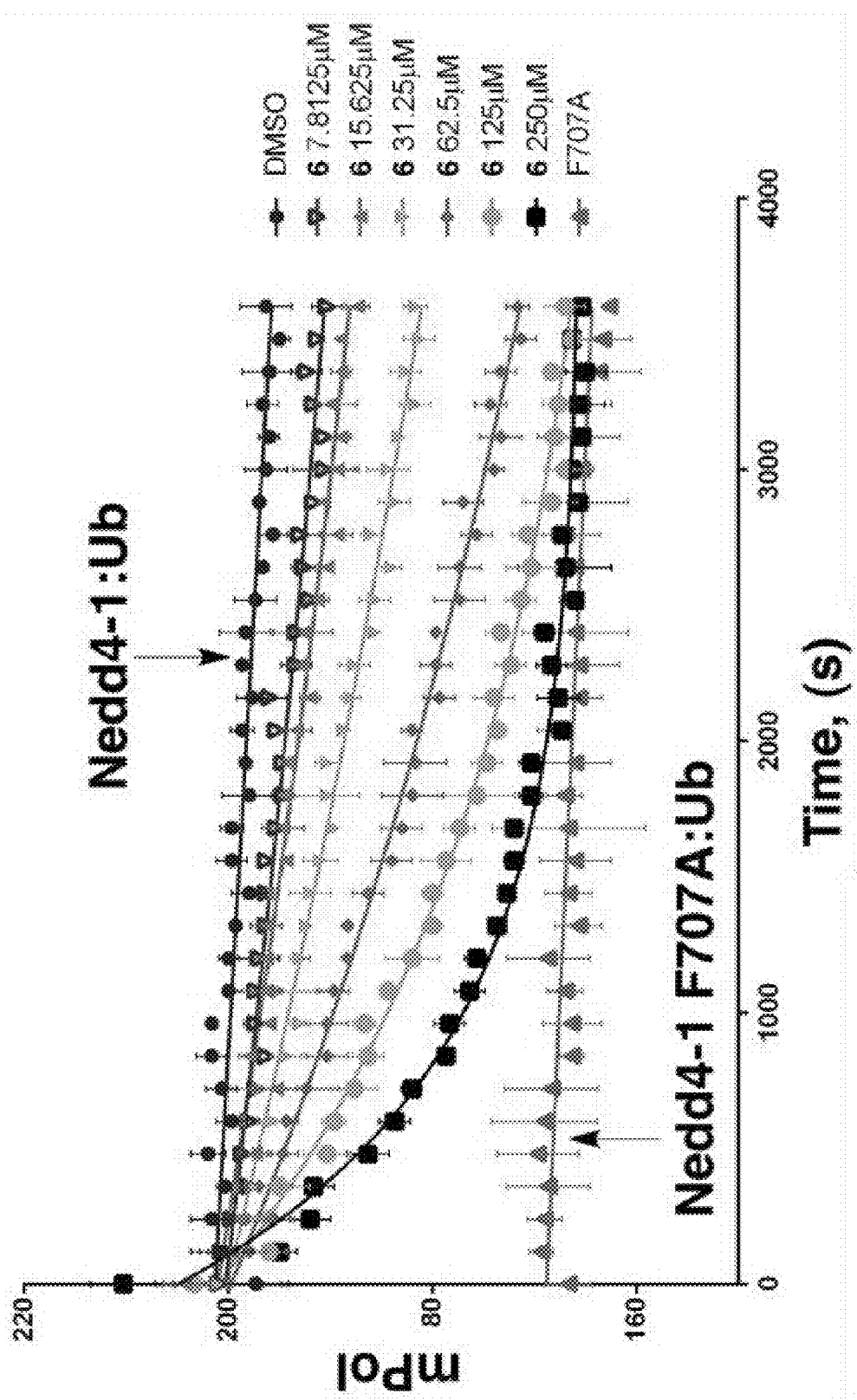
Figure 16C:
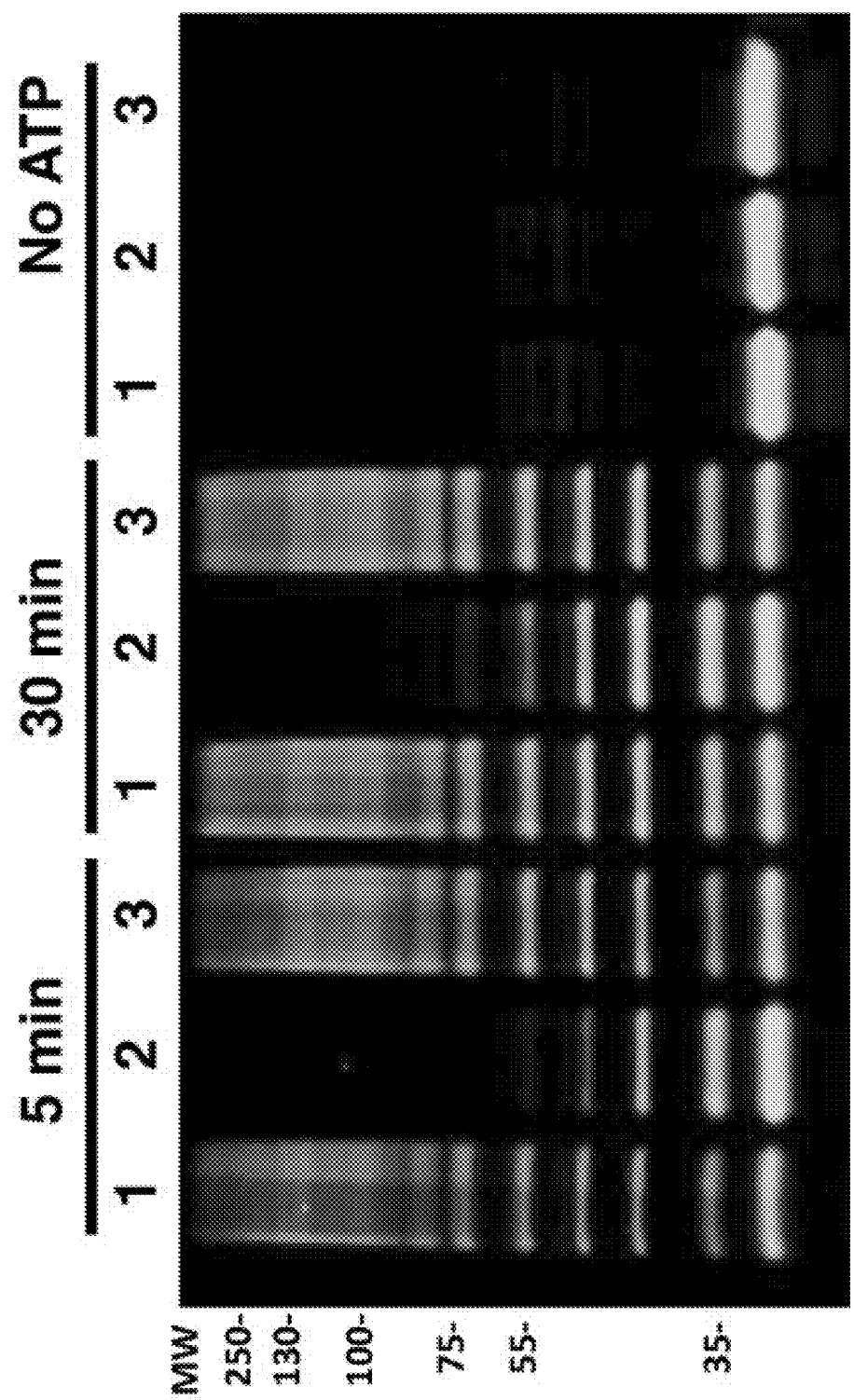
Figure 16D:
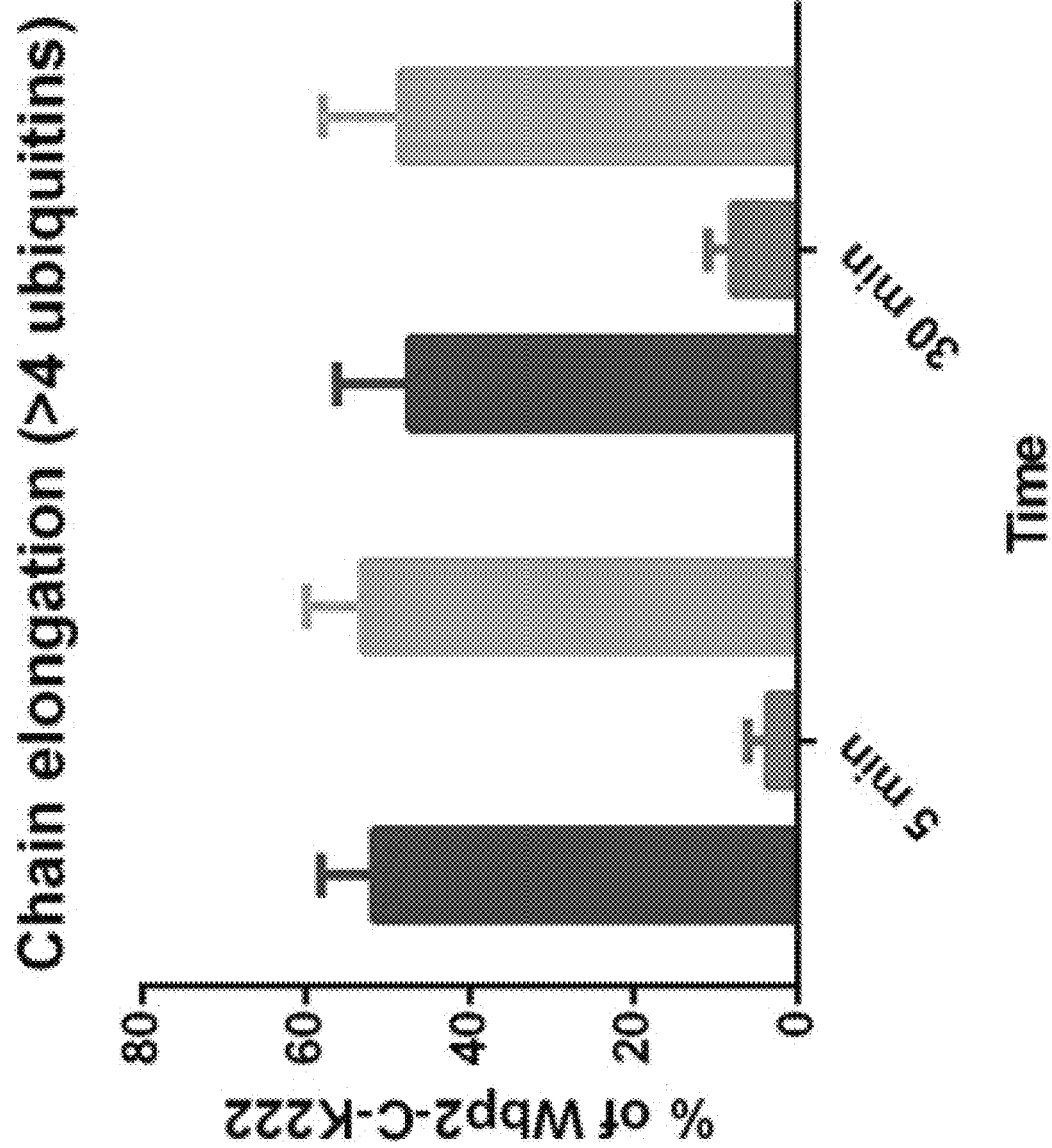
Figure 17A:
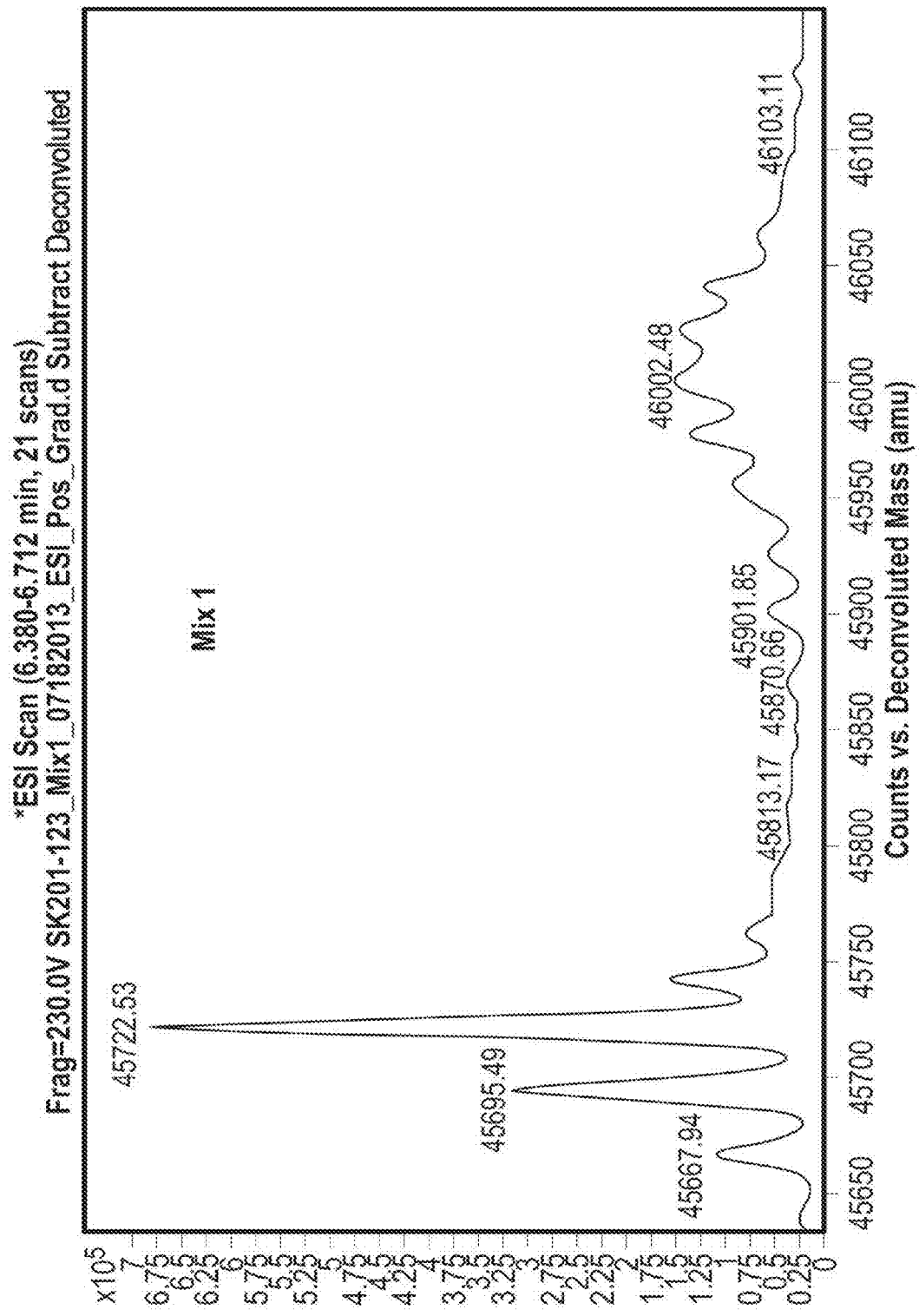
Figure 17B:
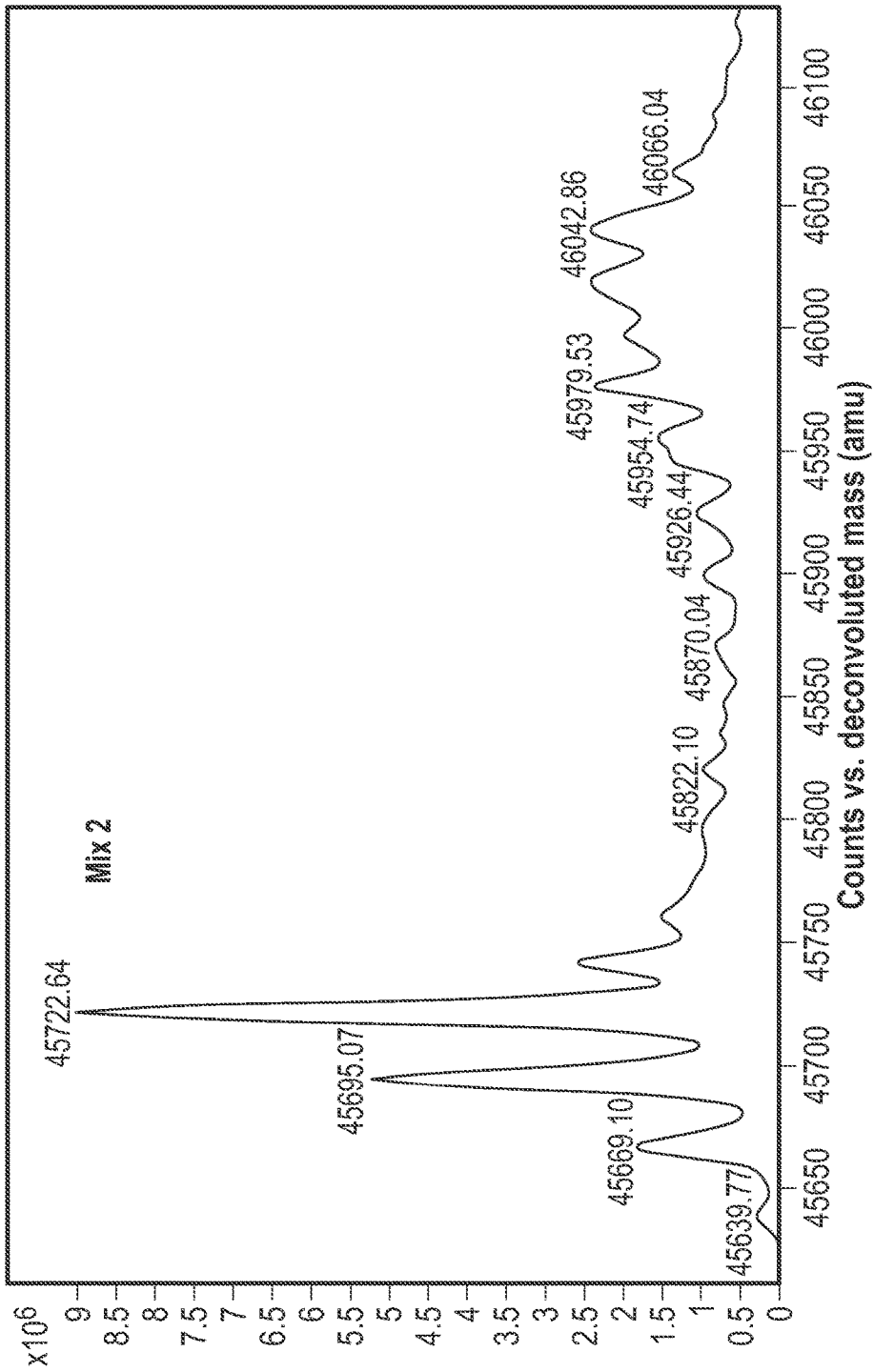
Figure 17C:
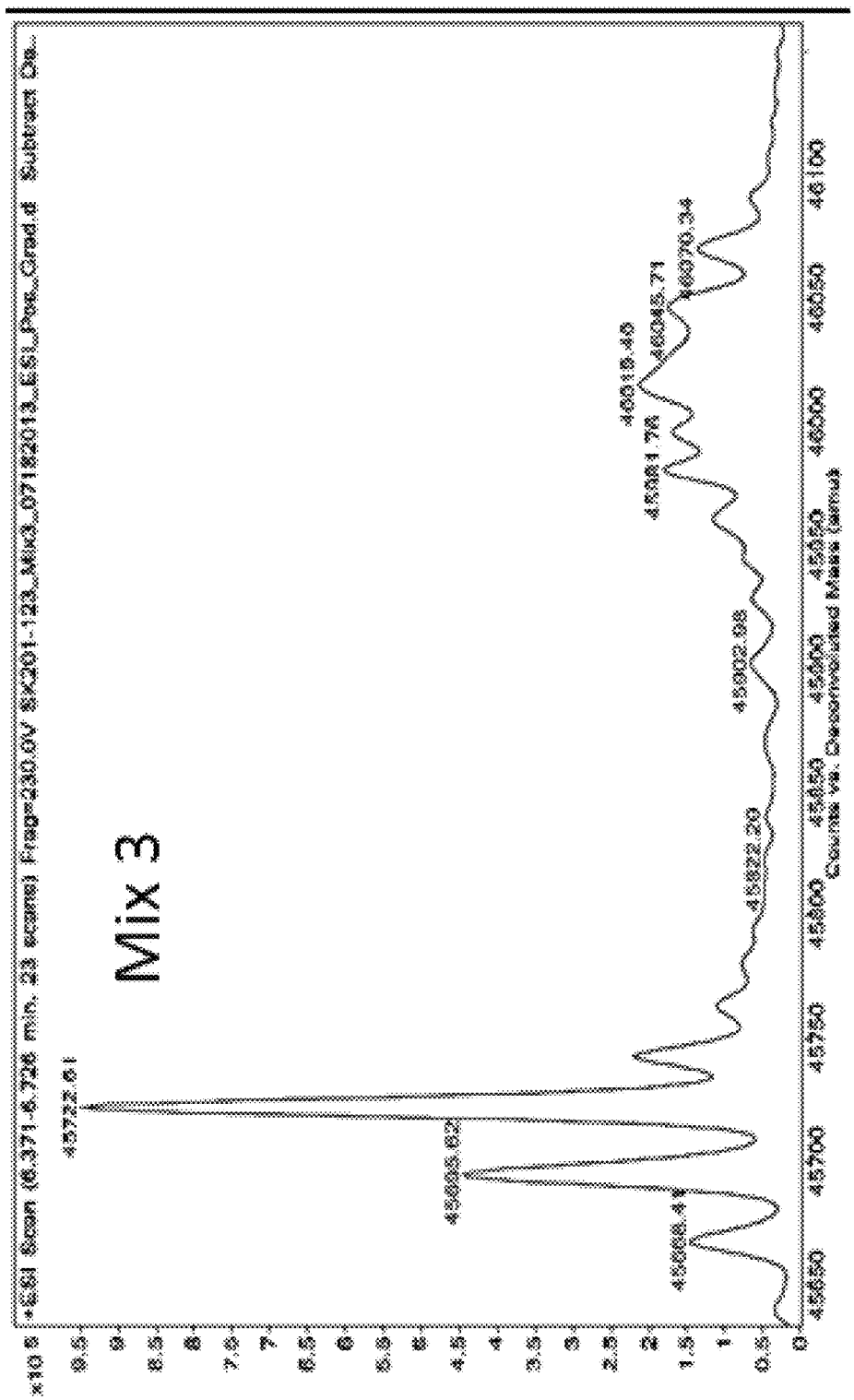
Figure 17D:
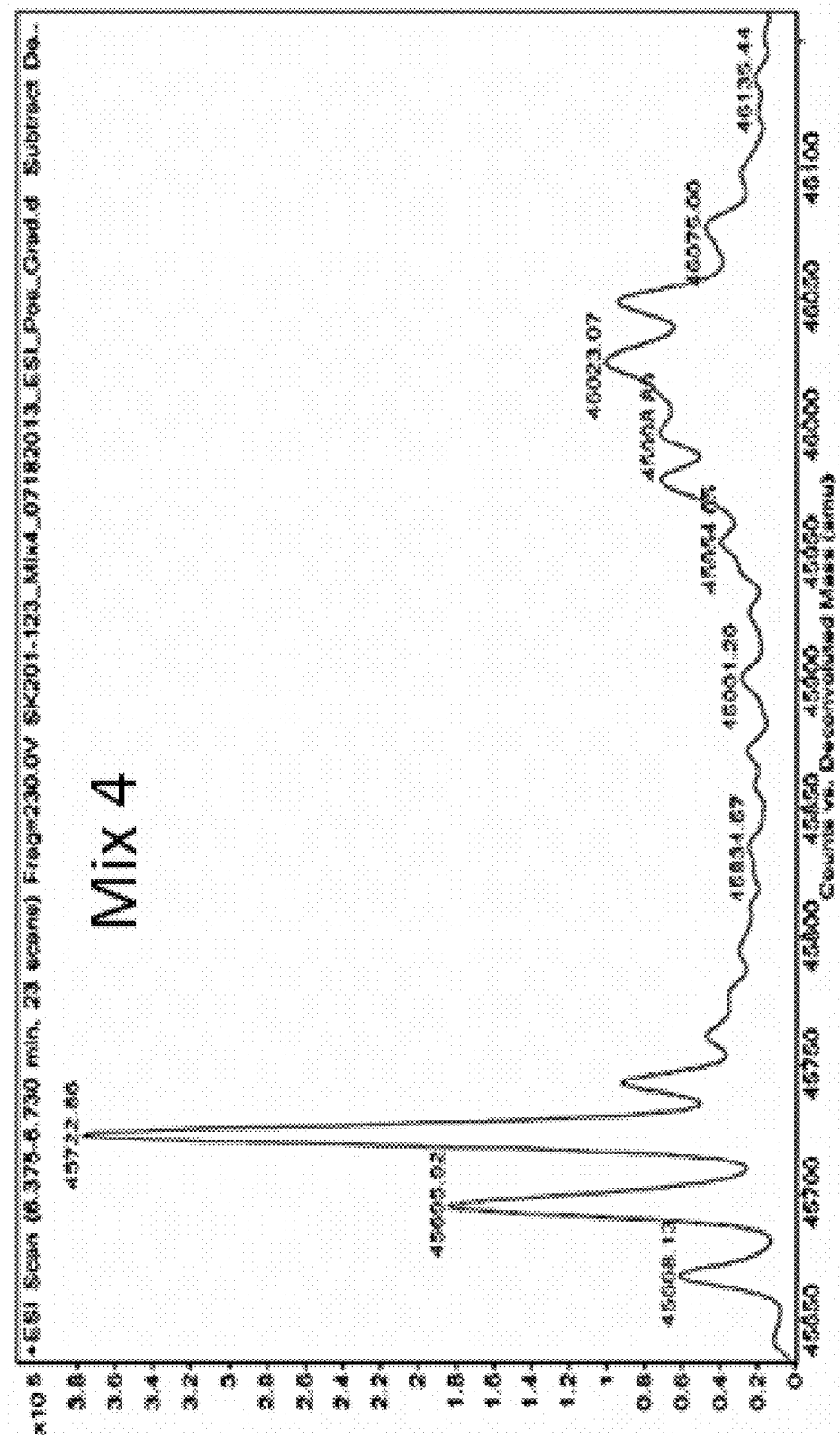
Figure 17E:
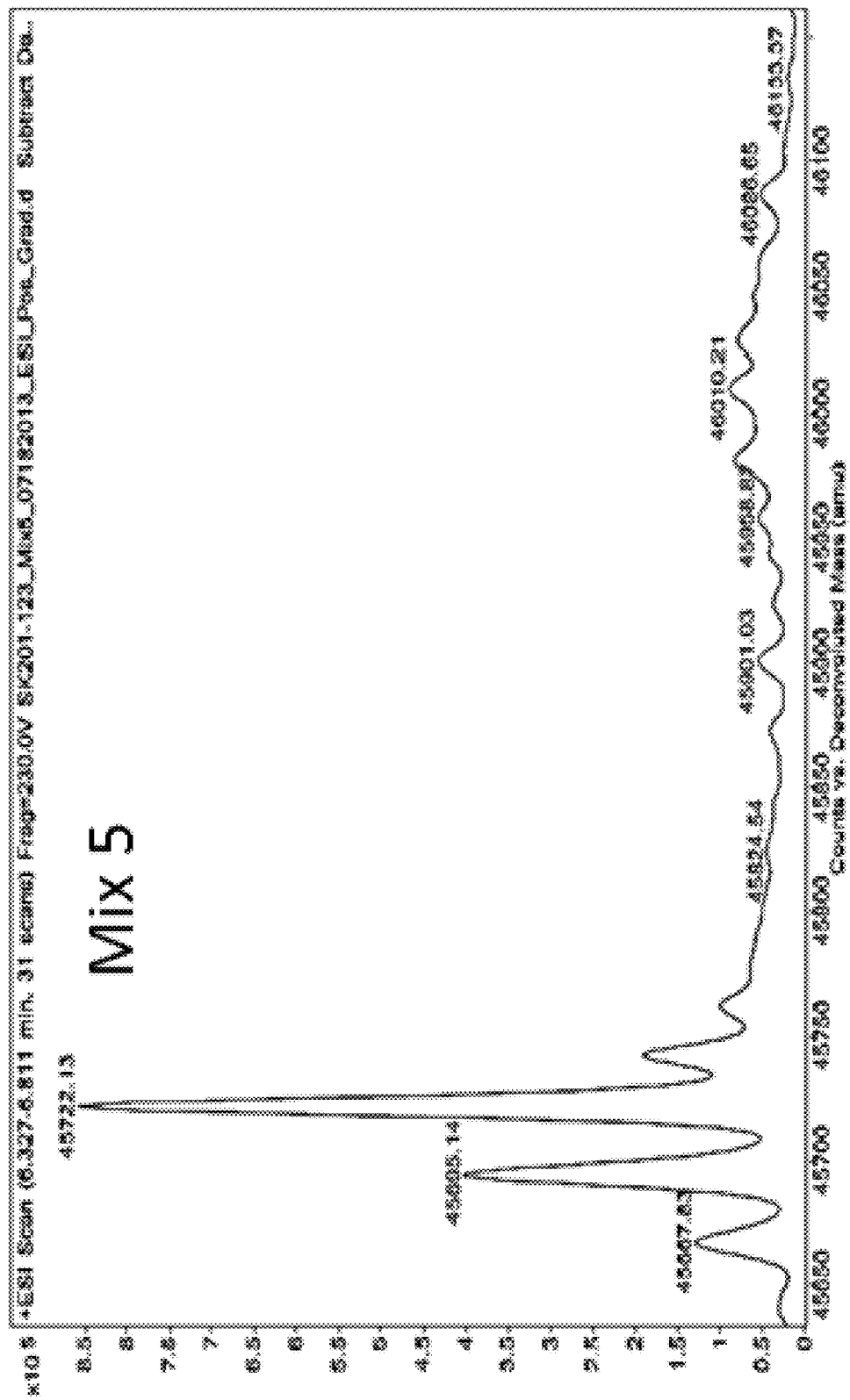
Figure 17F:
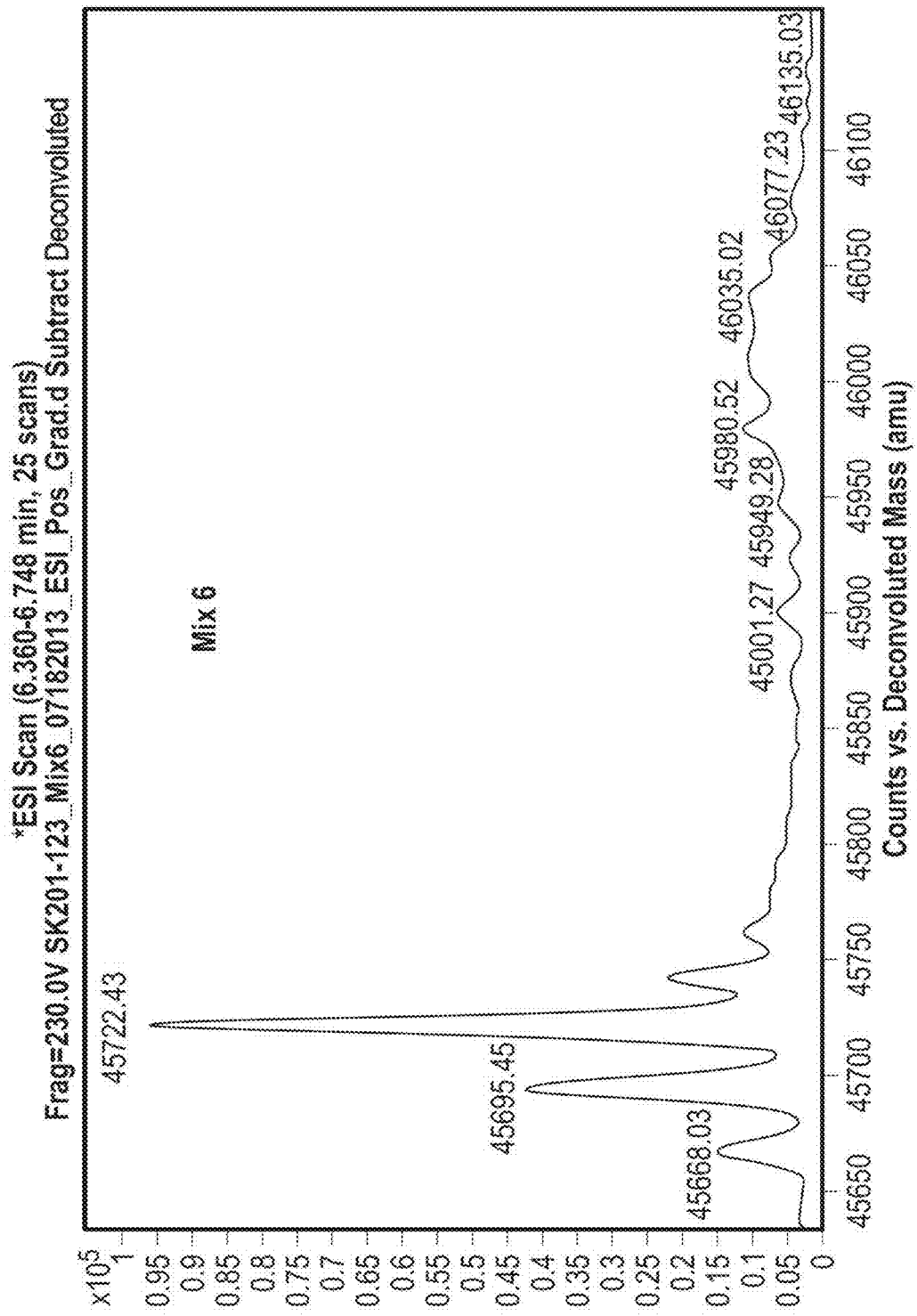
Figure 17G:
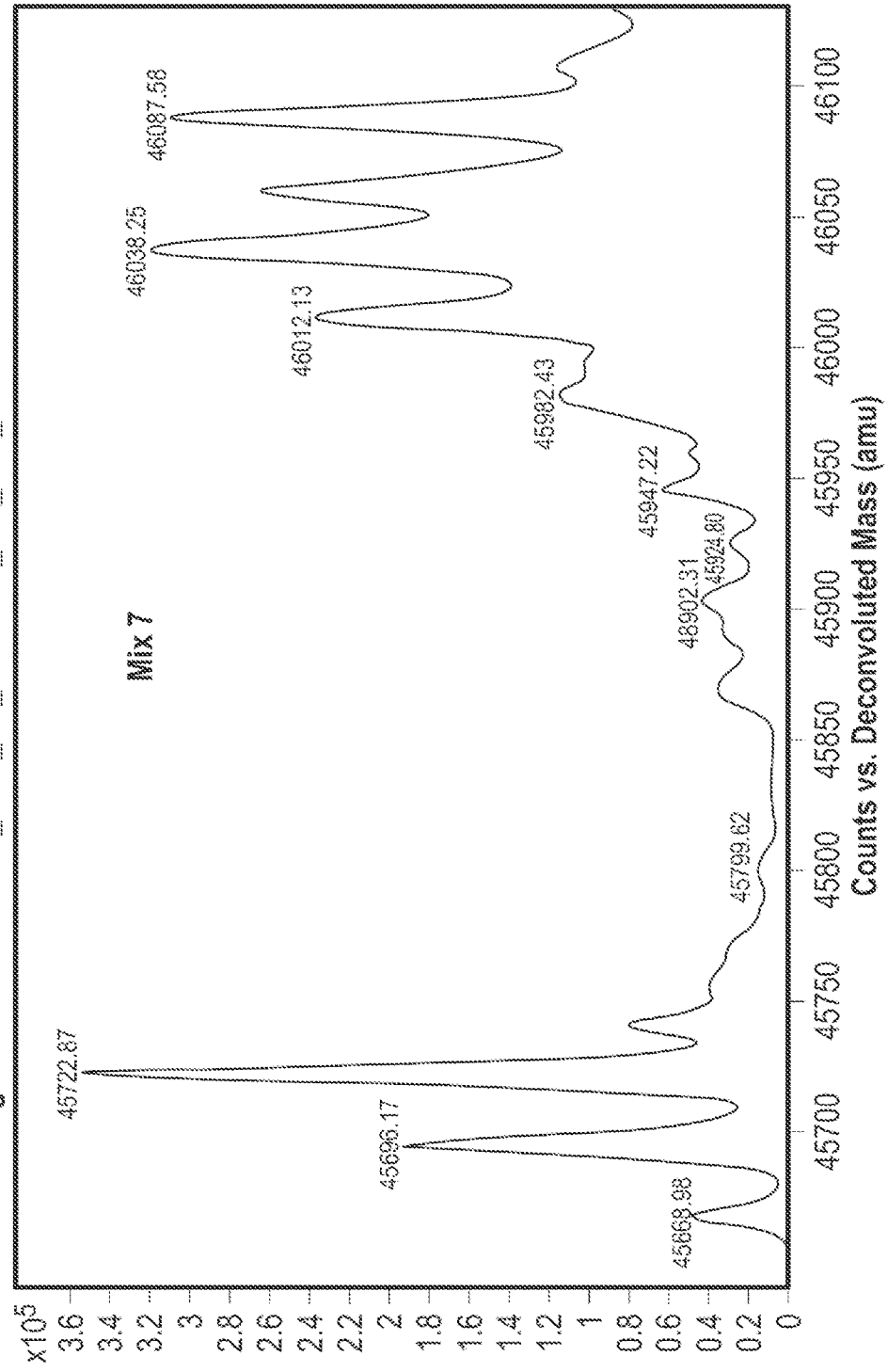
Figure 17H:
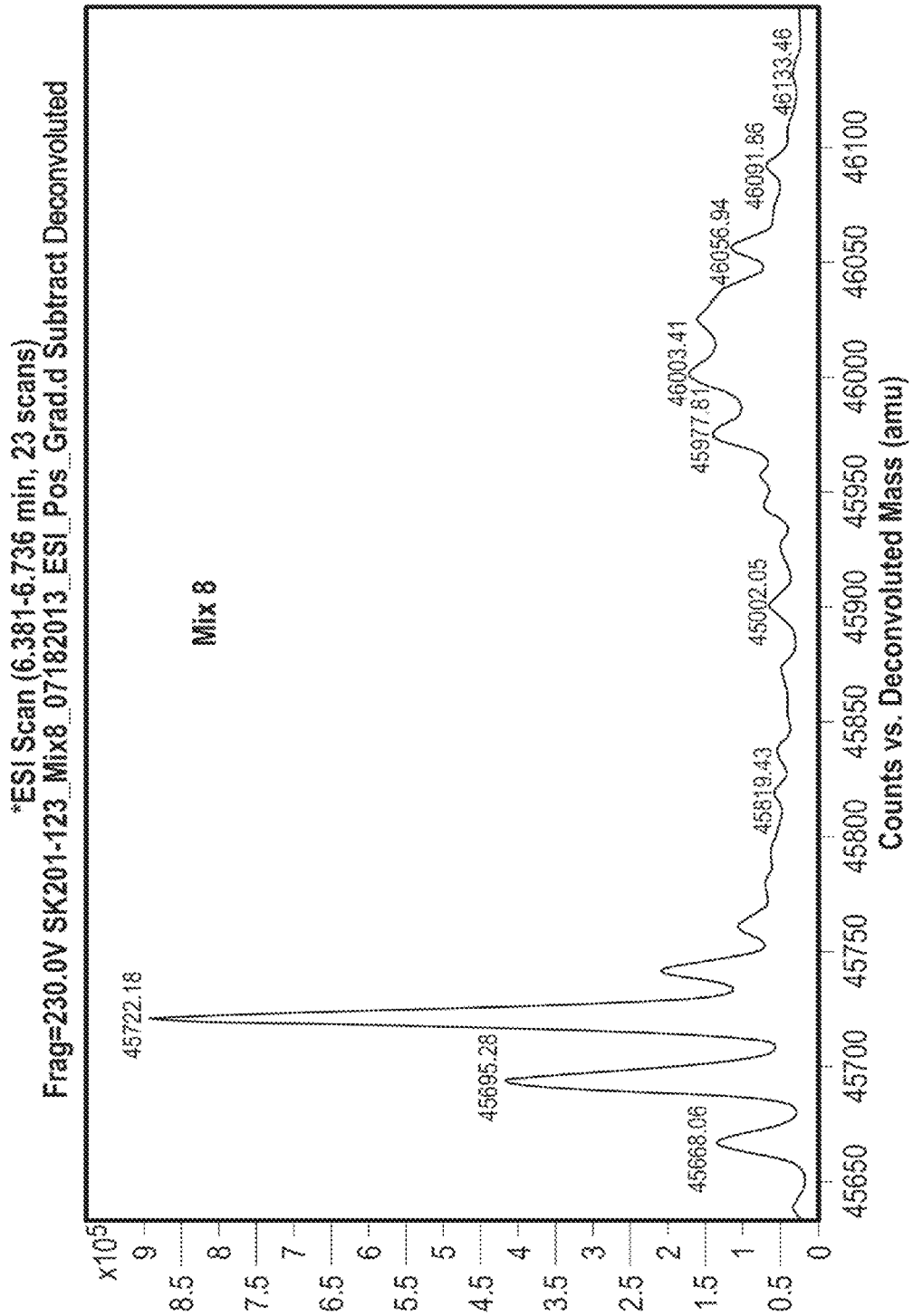
Figure 17I:
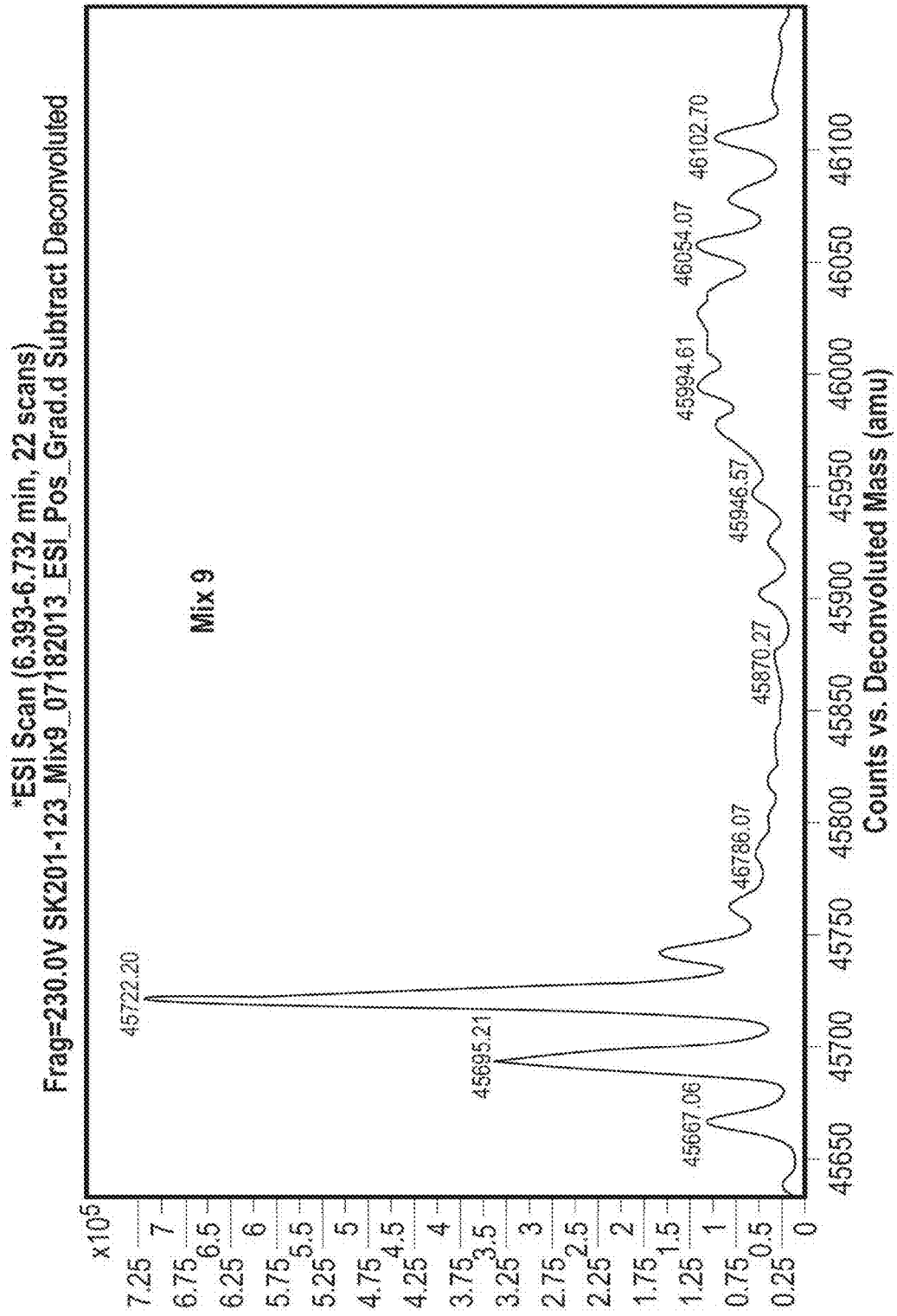
Figure 17J:
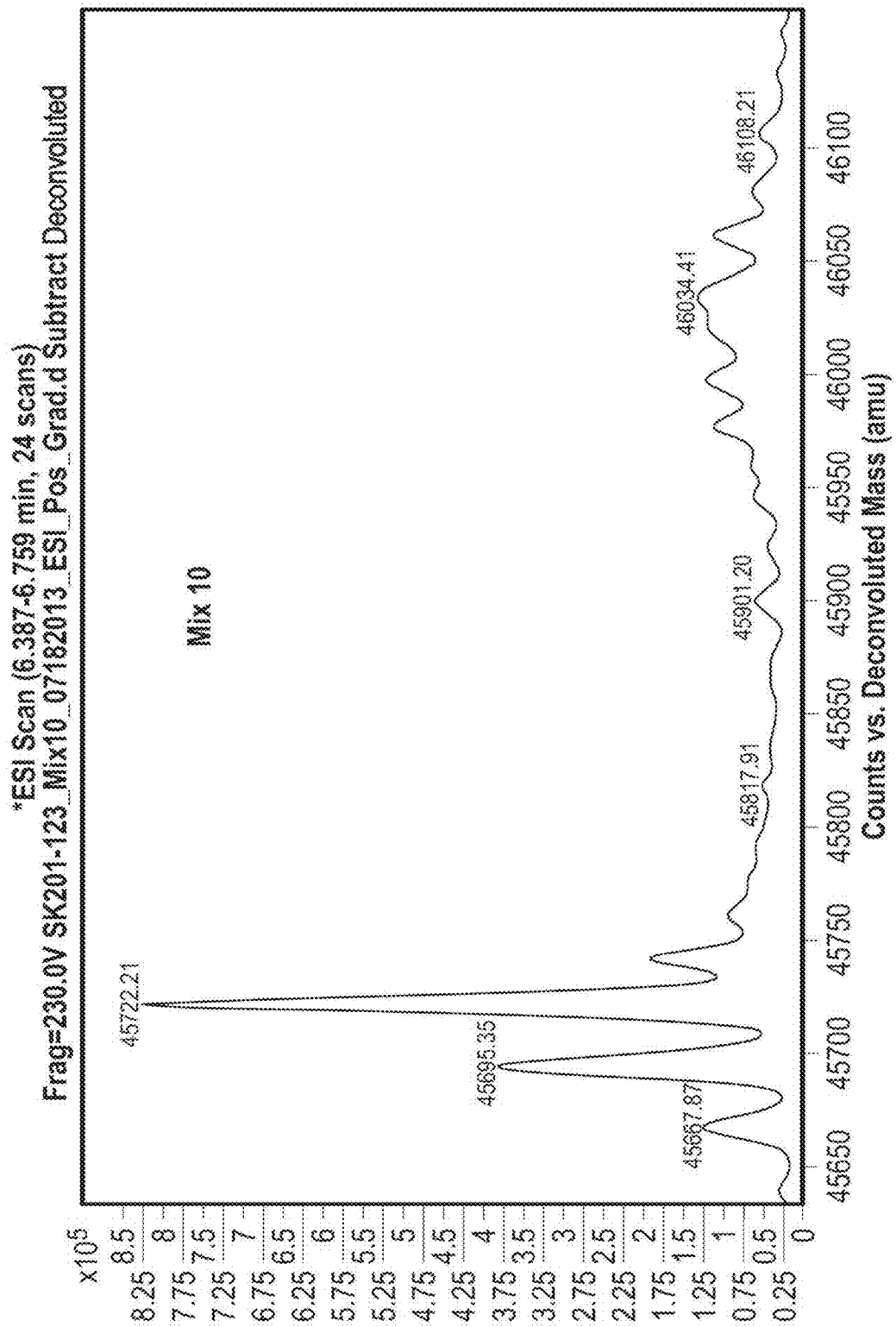
Figure 18A:
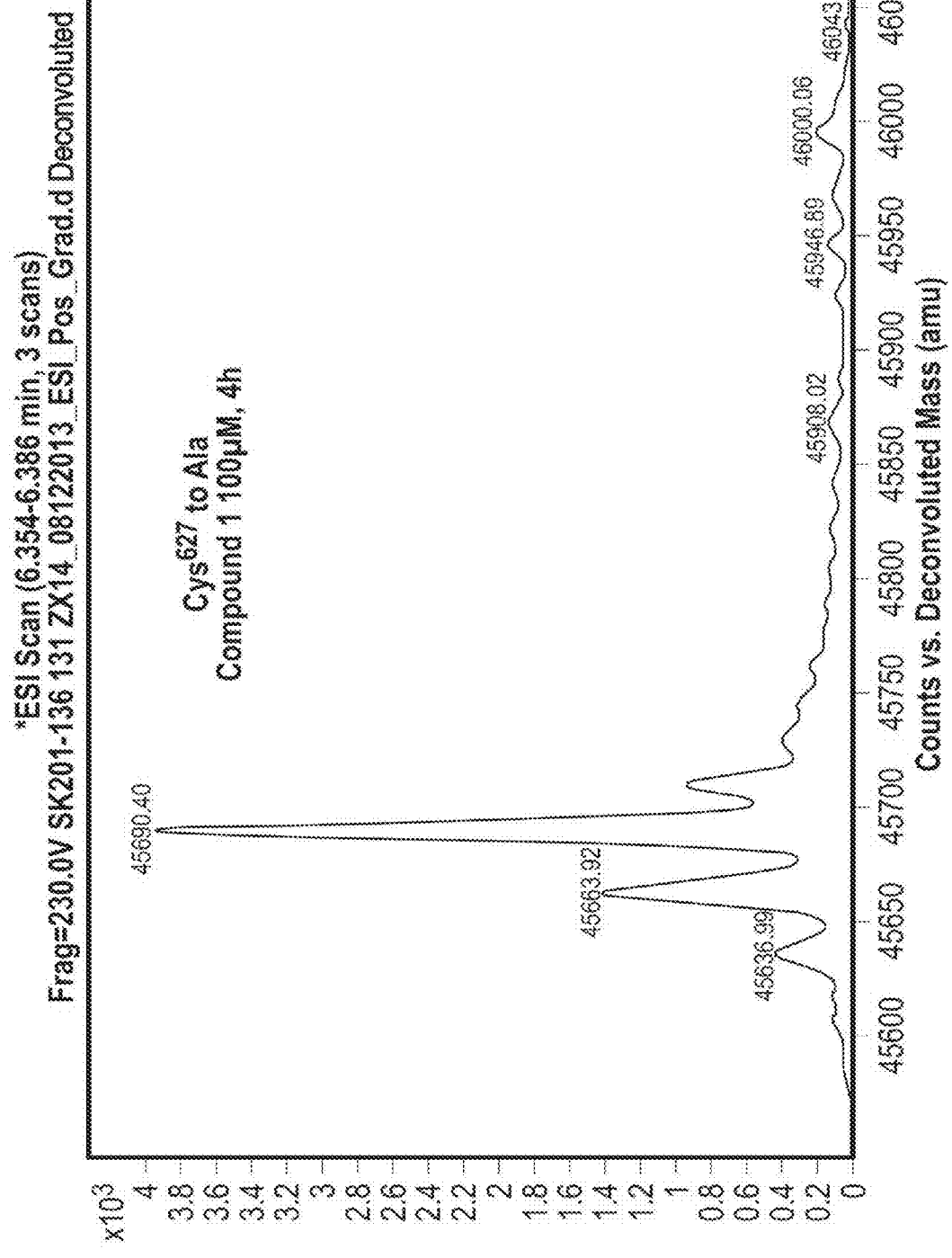
Figure 18B:
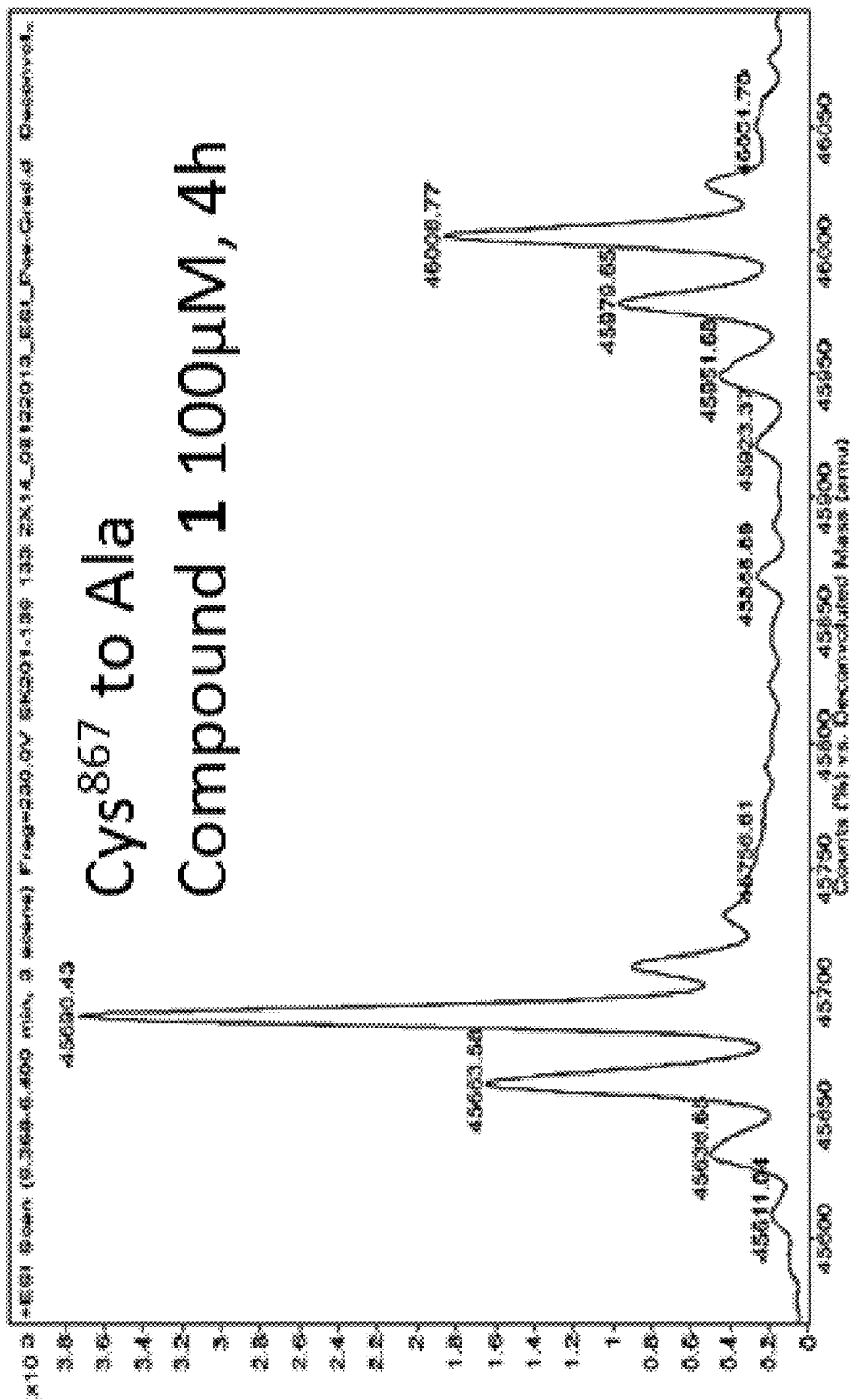
Figure 18C:
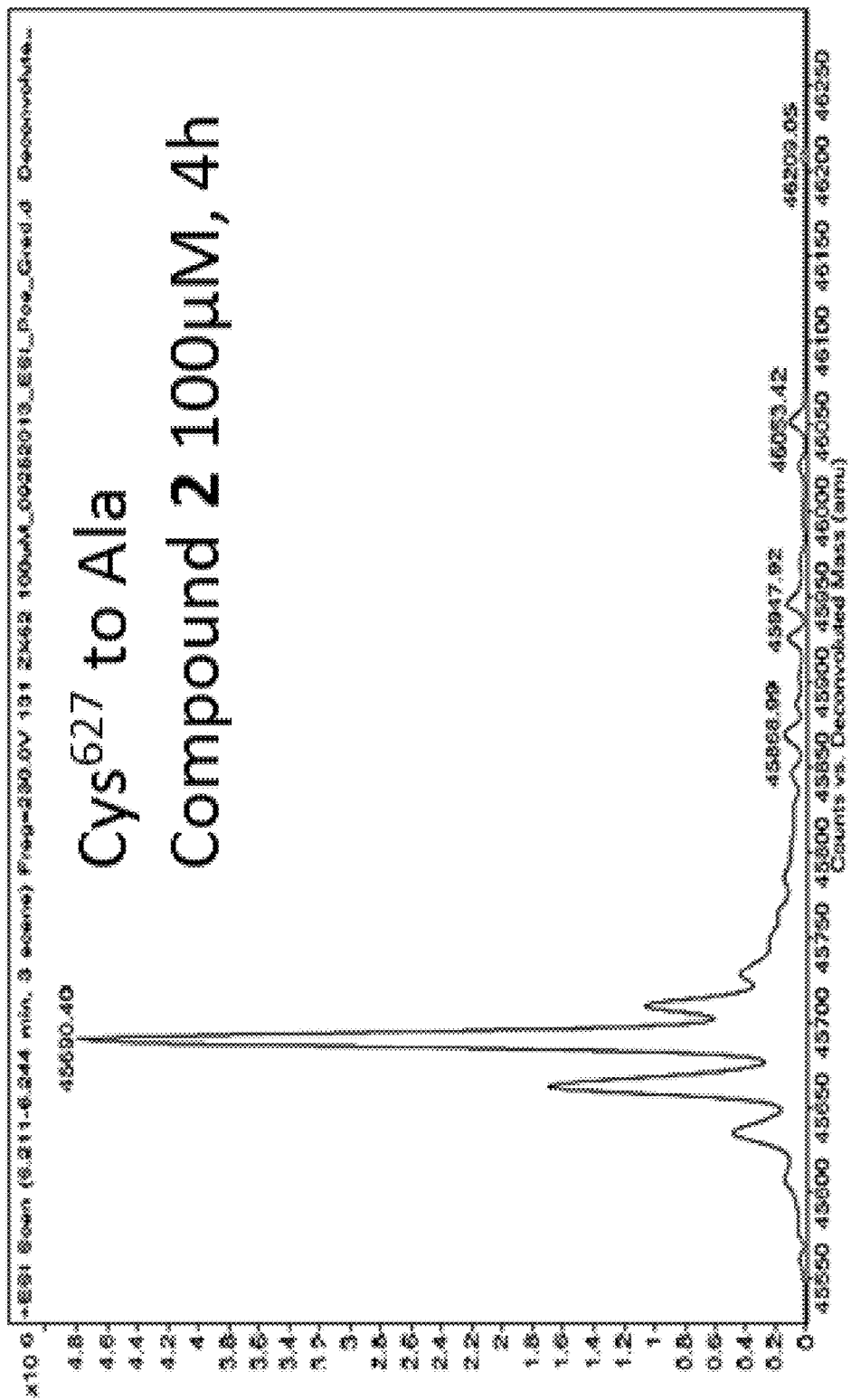
Figure 18D:
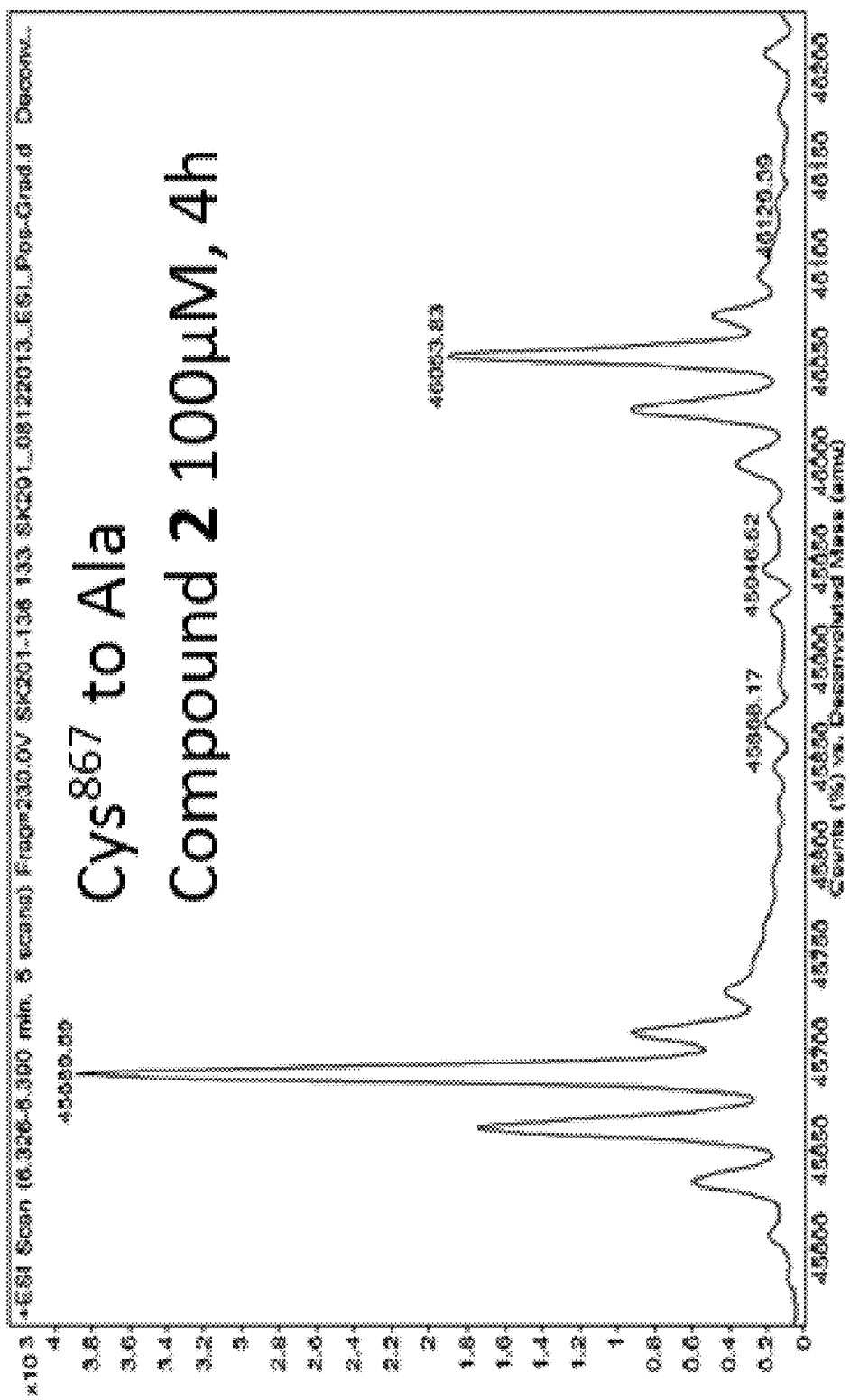
Figure 19A:
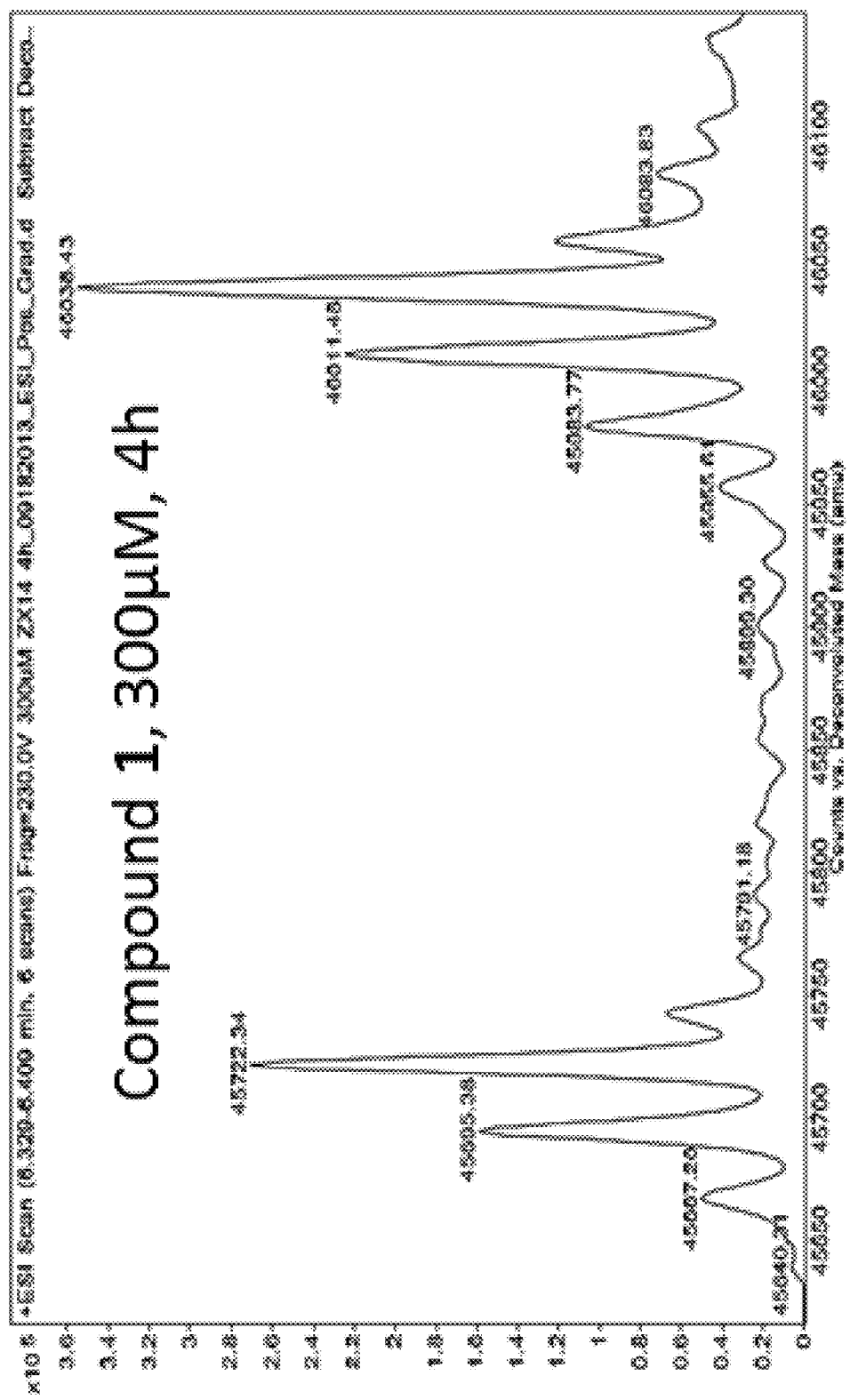
Figure 19B:
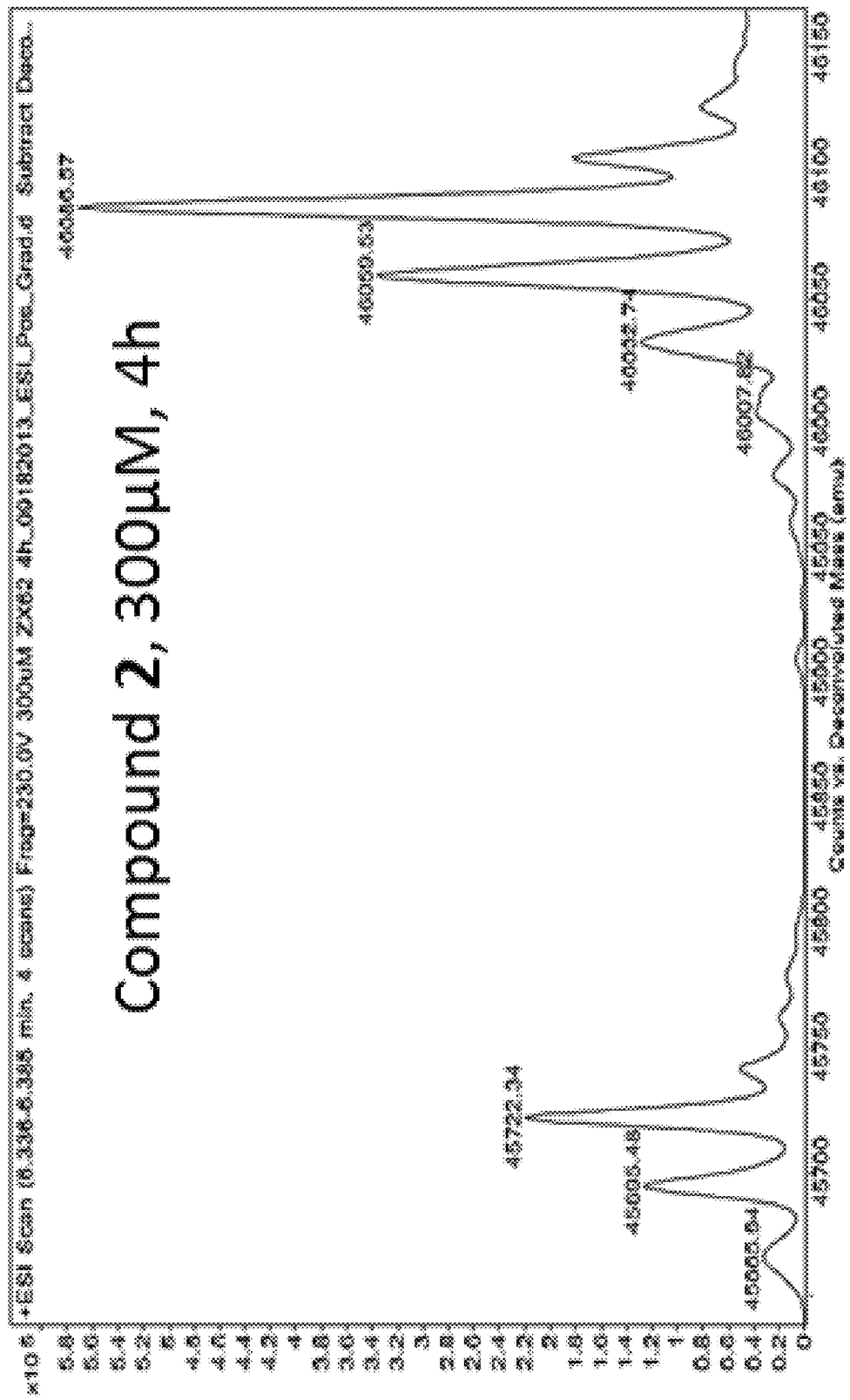
Figure 19C:
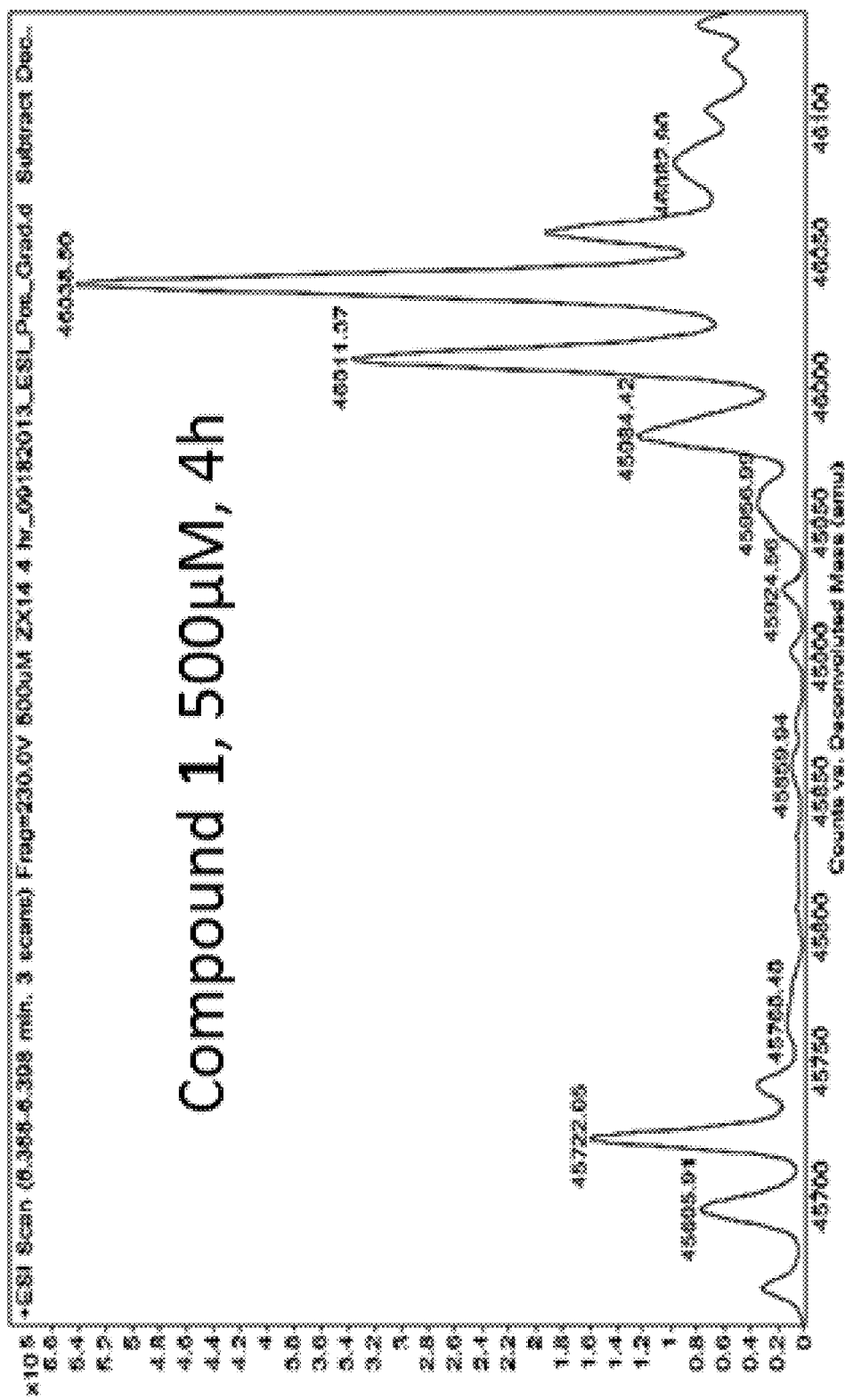
Figure 19D:
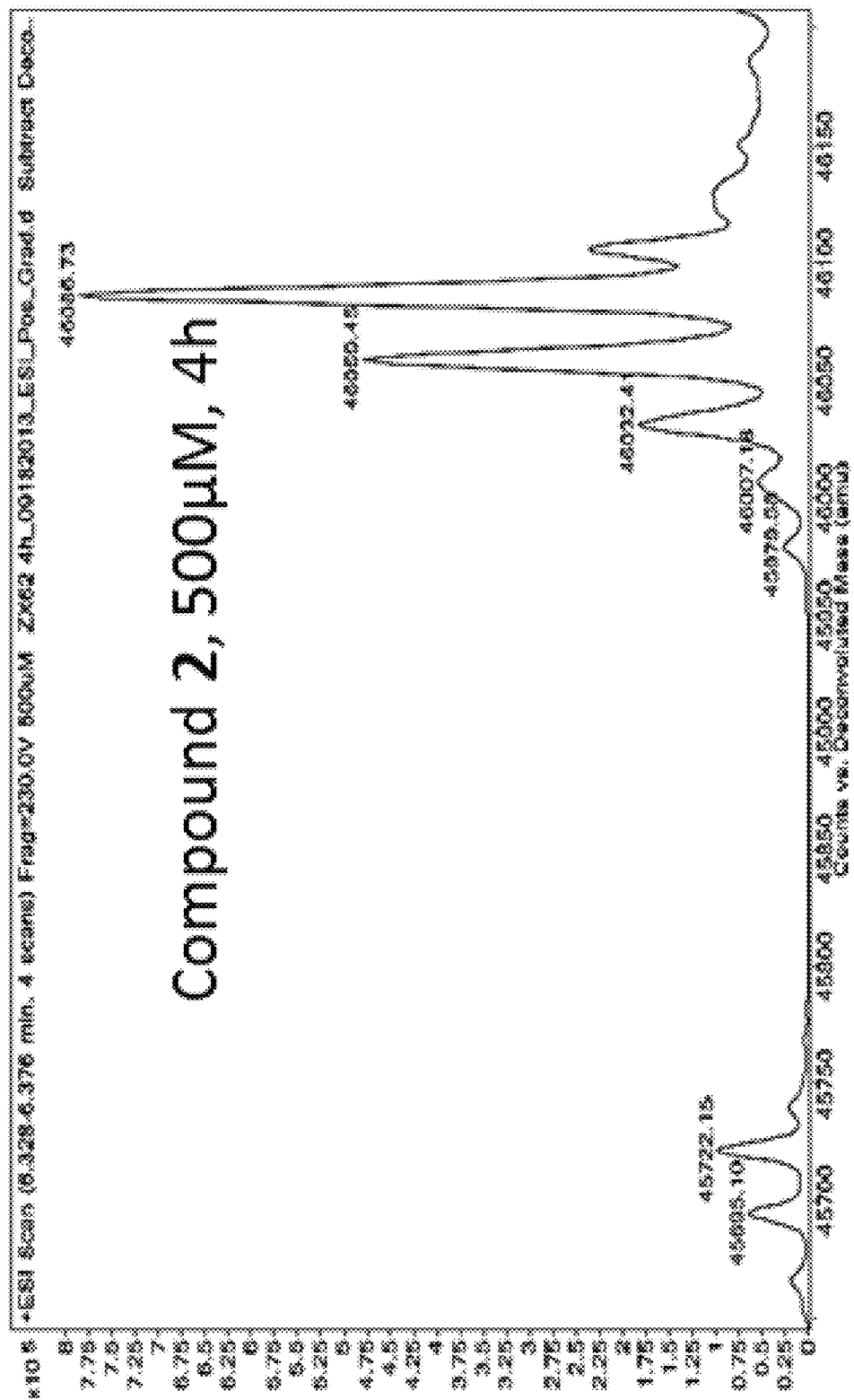
Figure 19E:
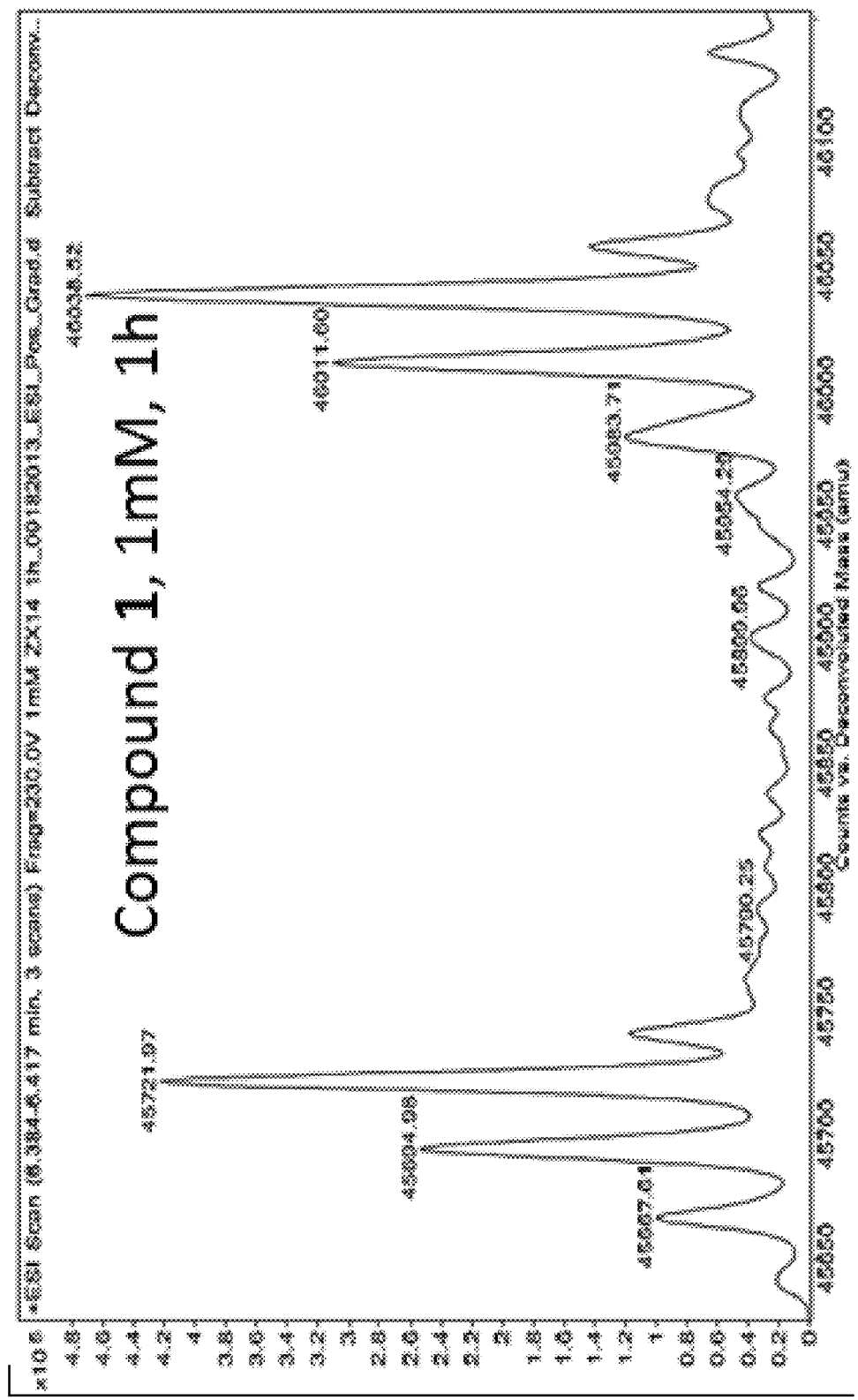
Figure 19F:
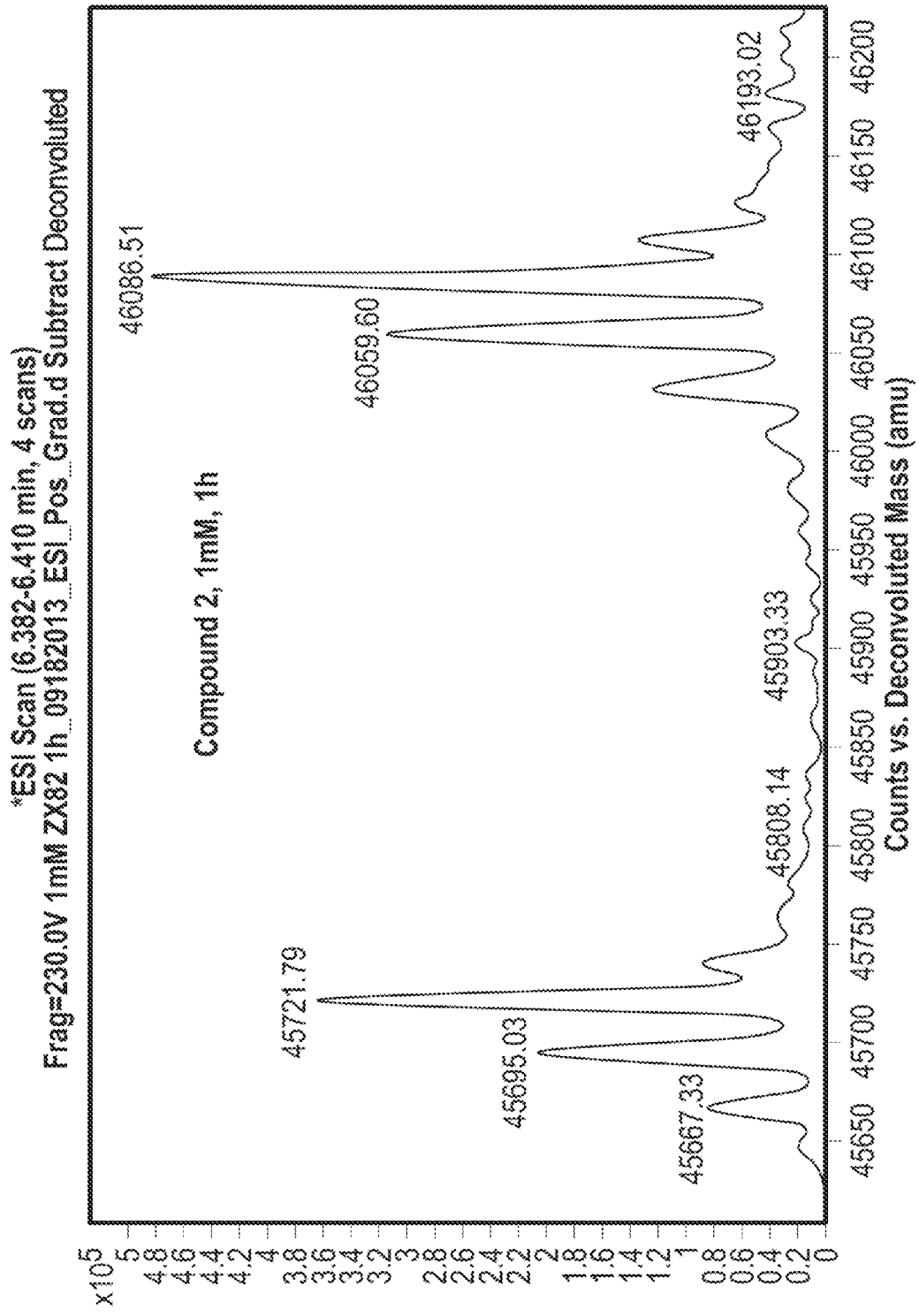
Figure 19G:
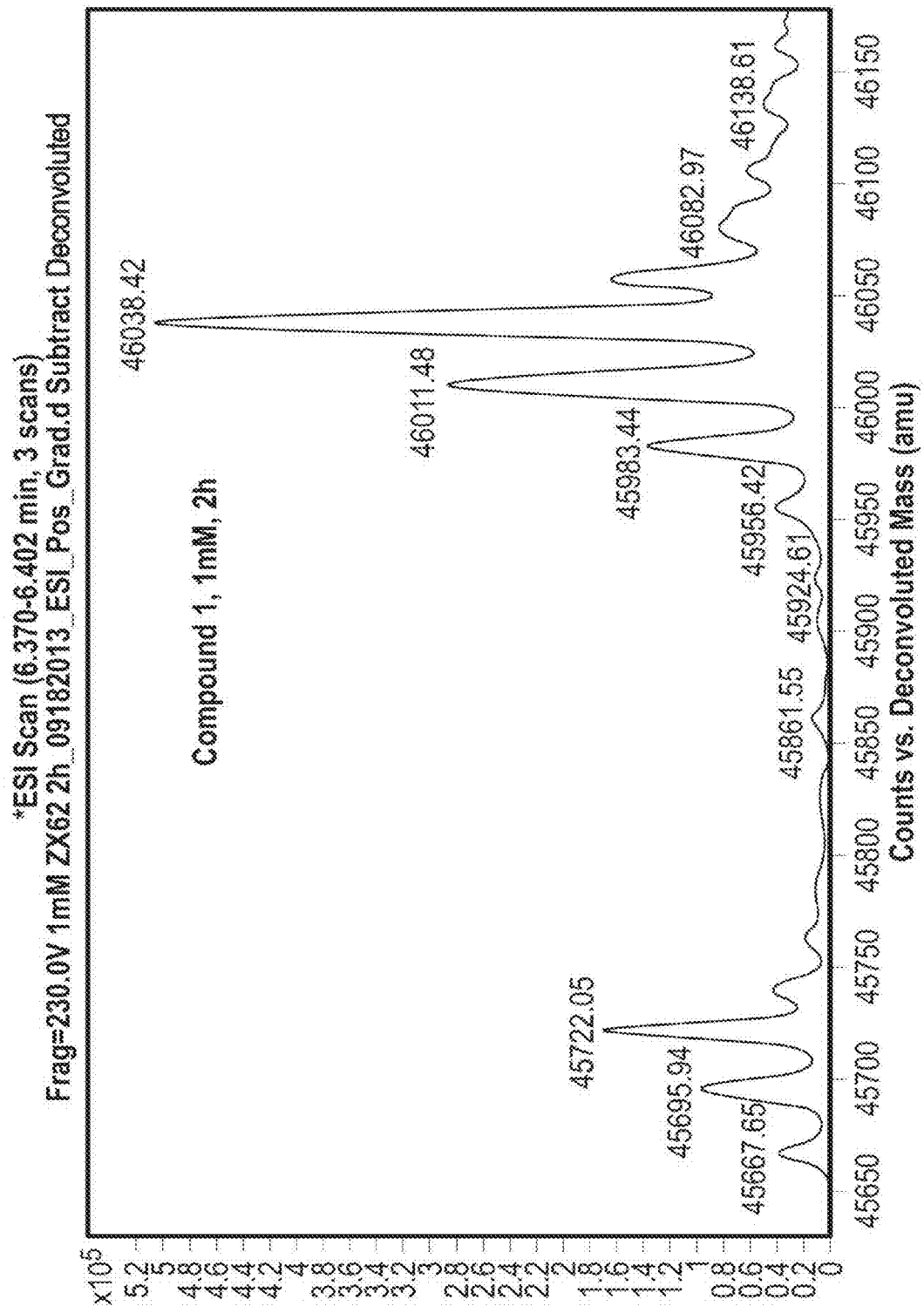
Figure 19H:
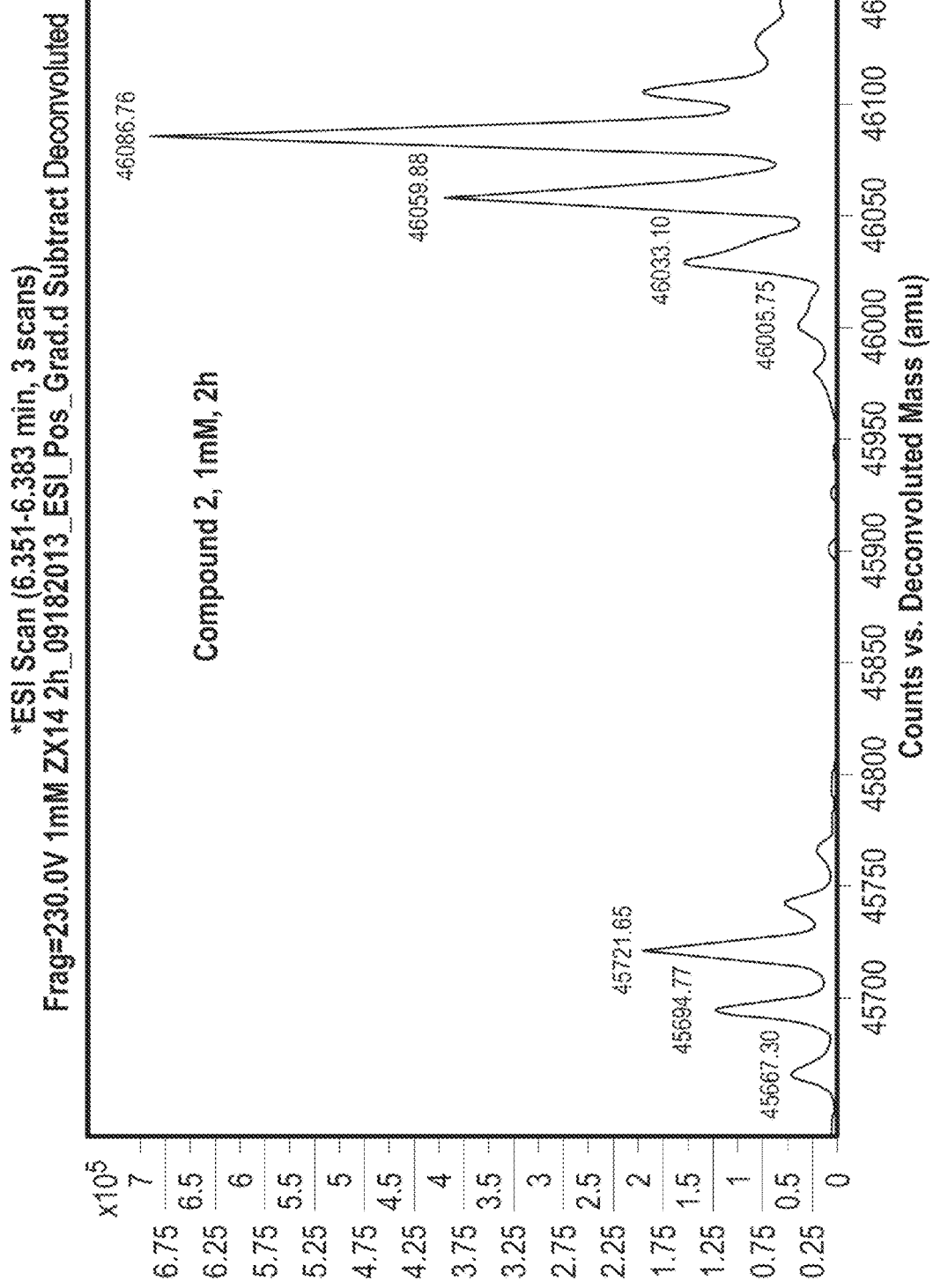
Figure 19I:
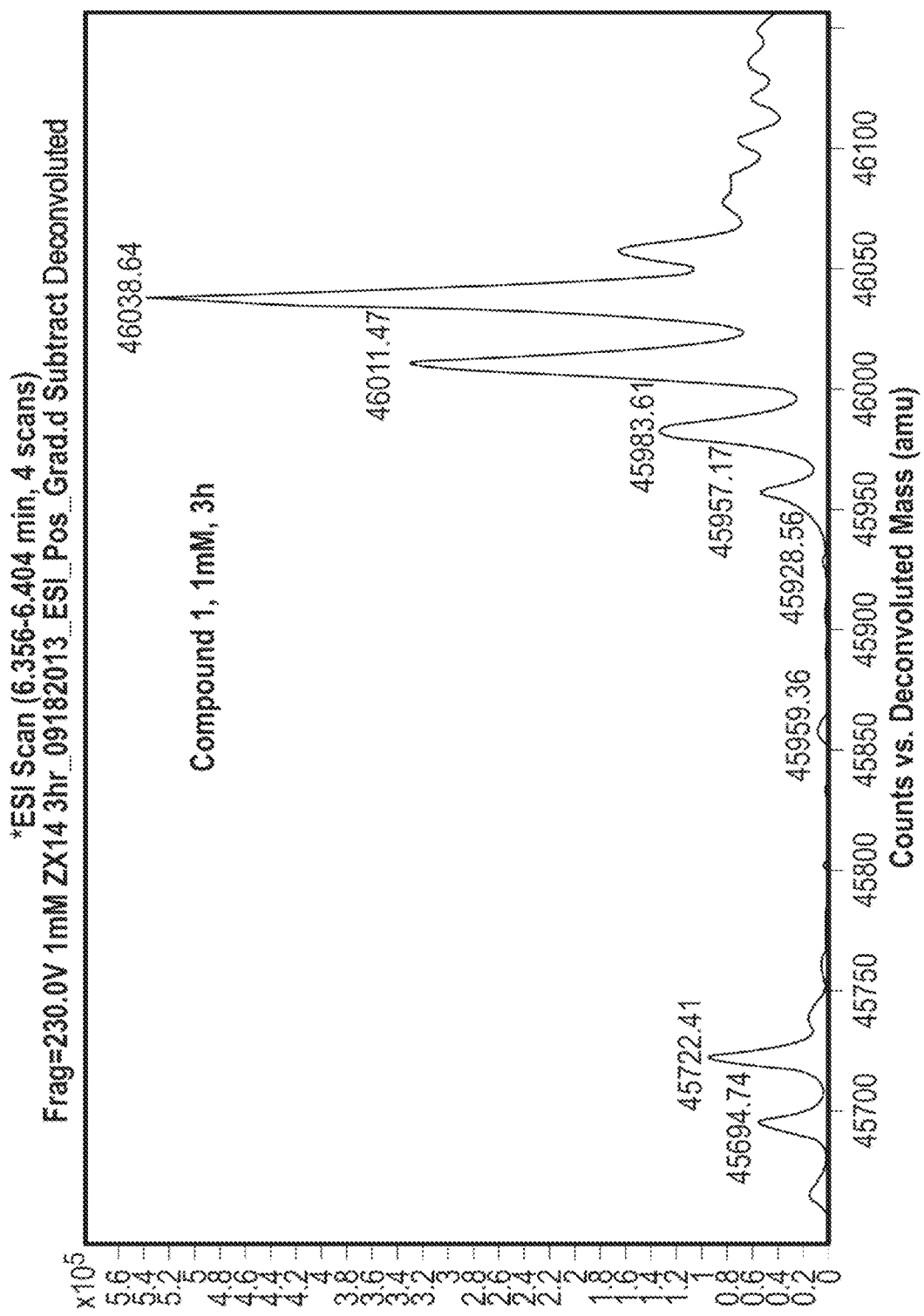
Figure 19J:
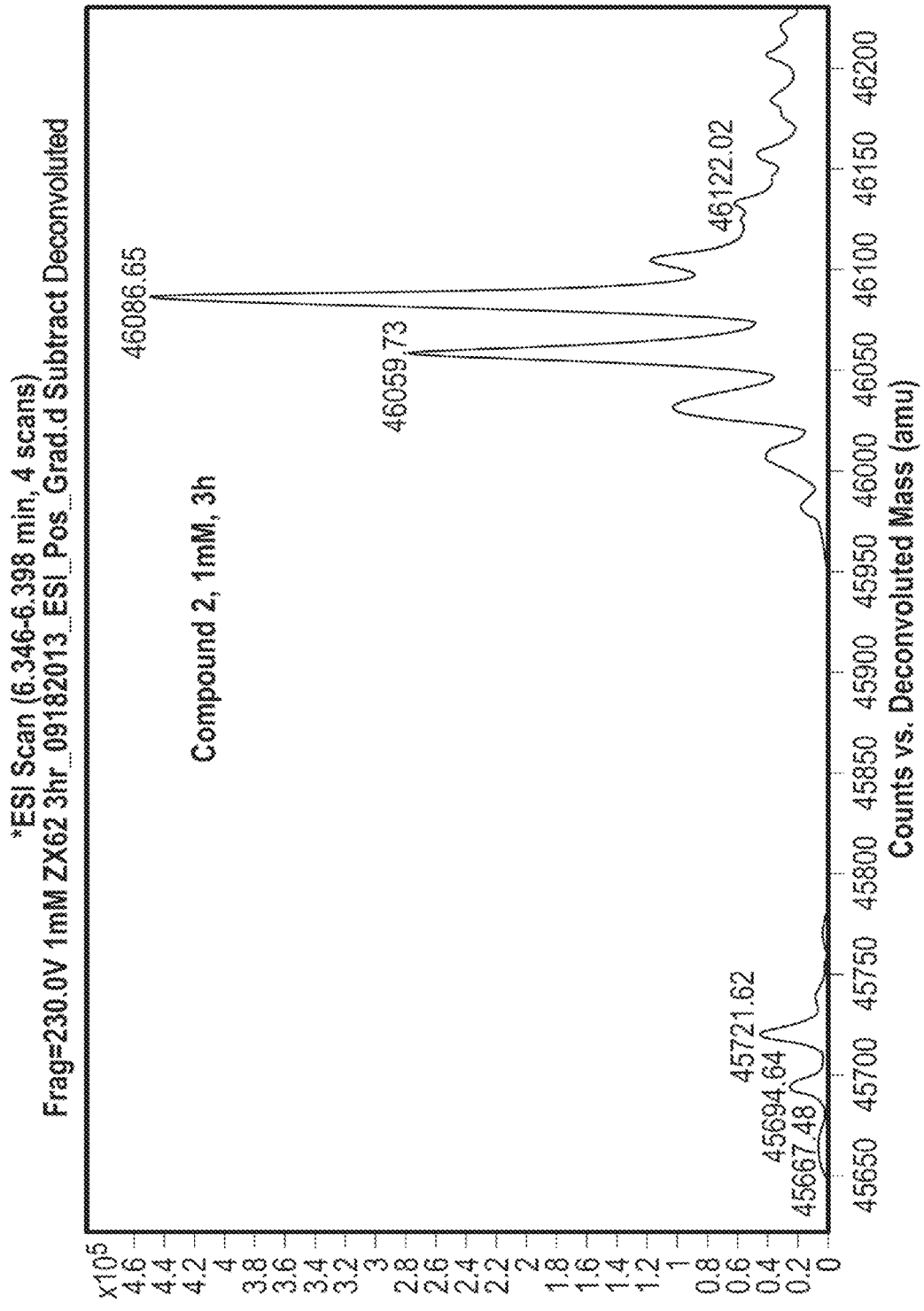
Figure 33A:
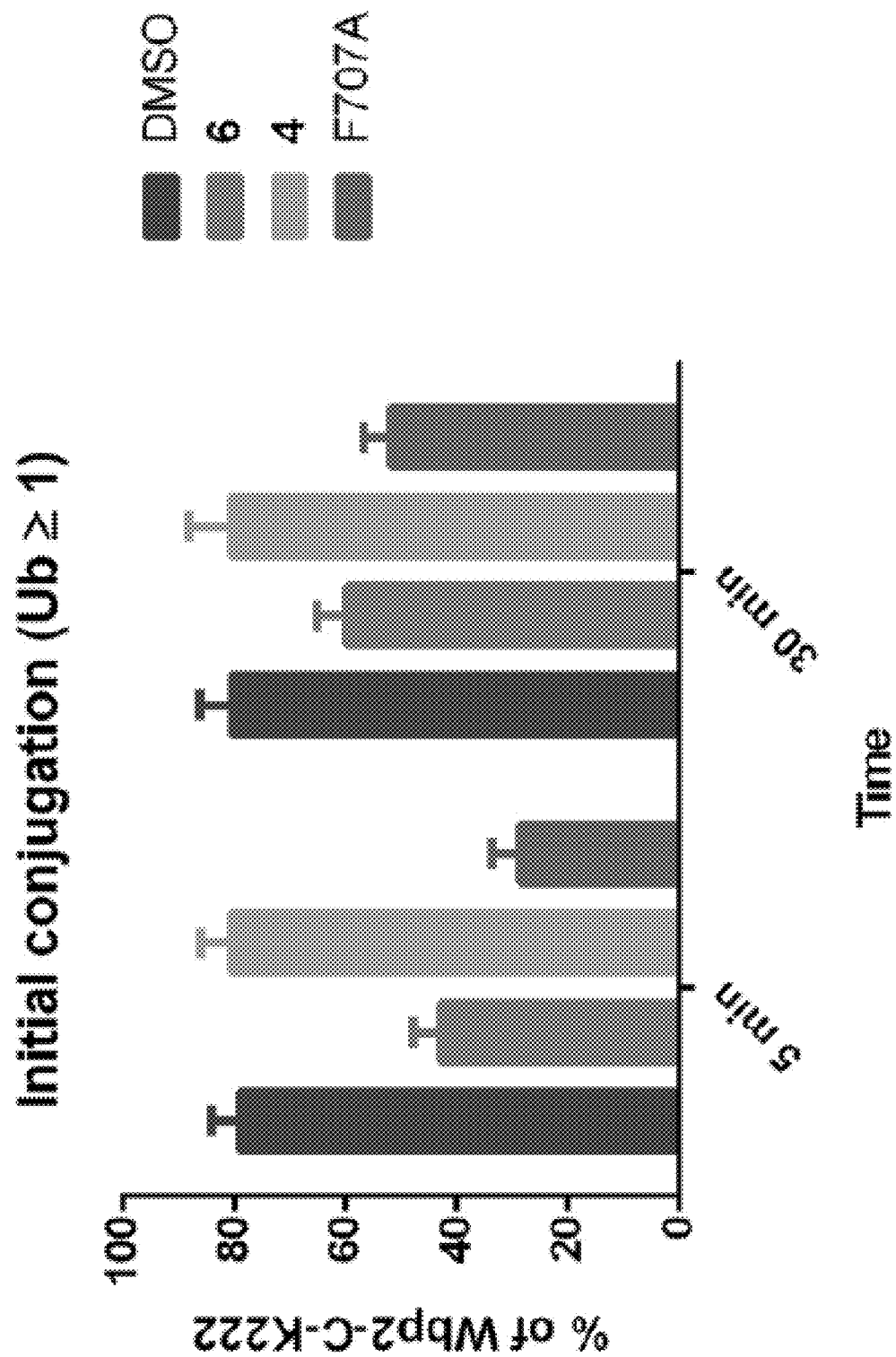
Figure 33B:
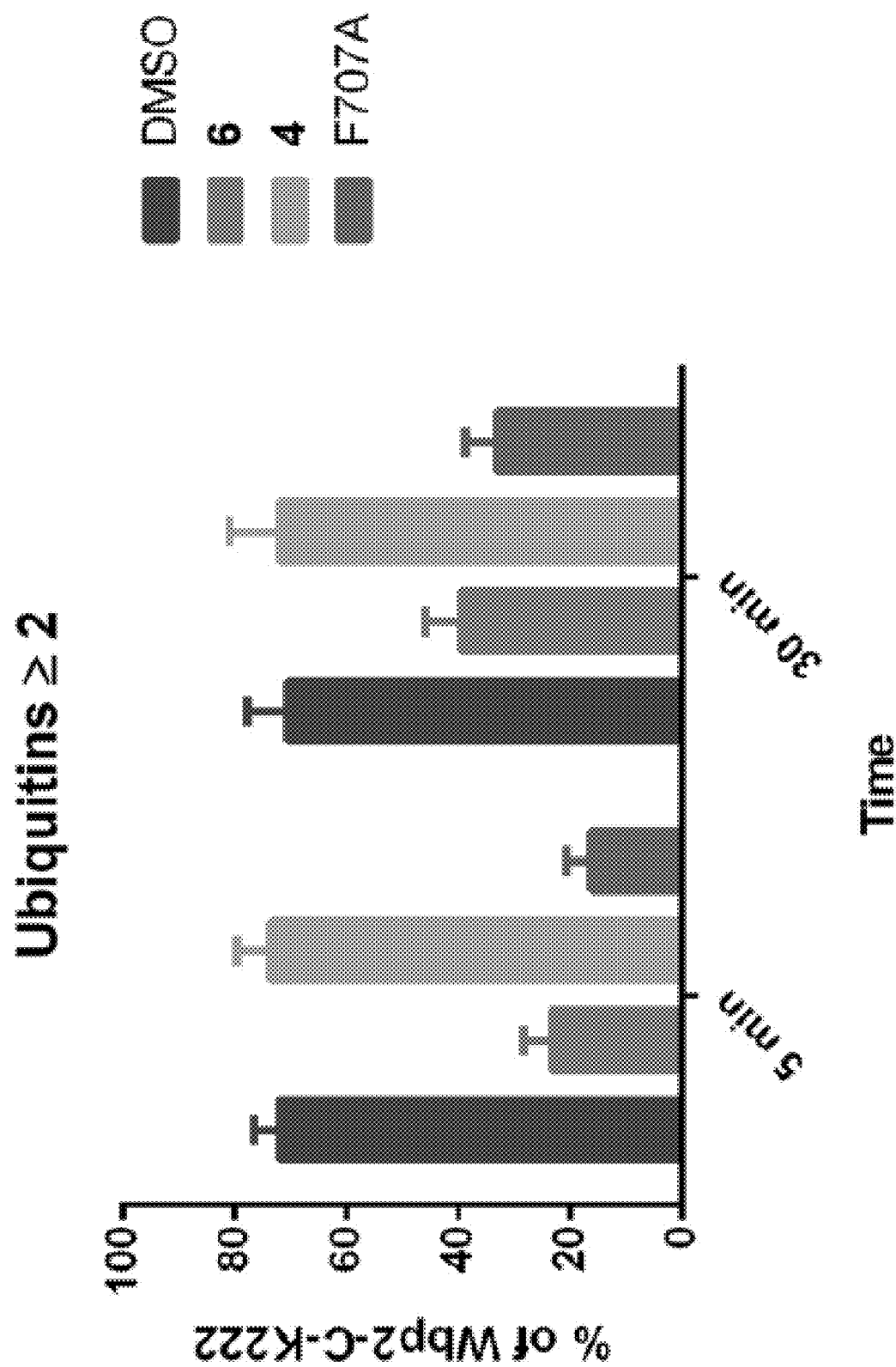
Figure 33C:
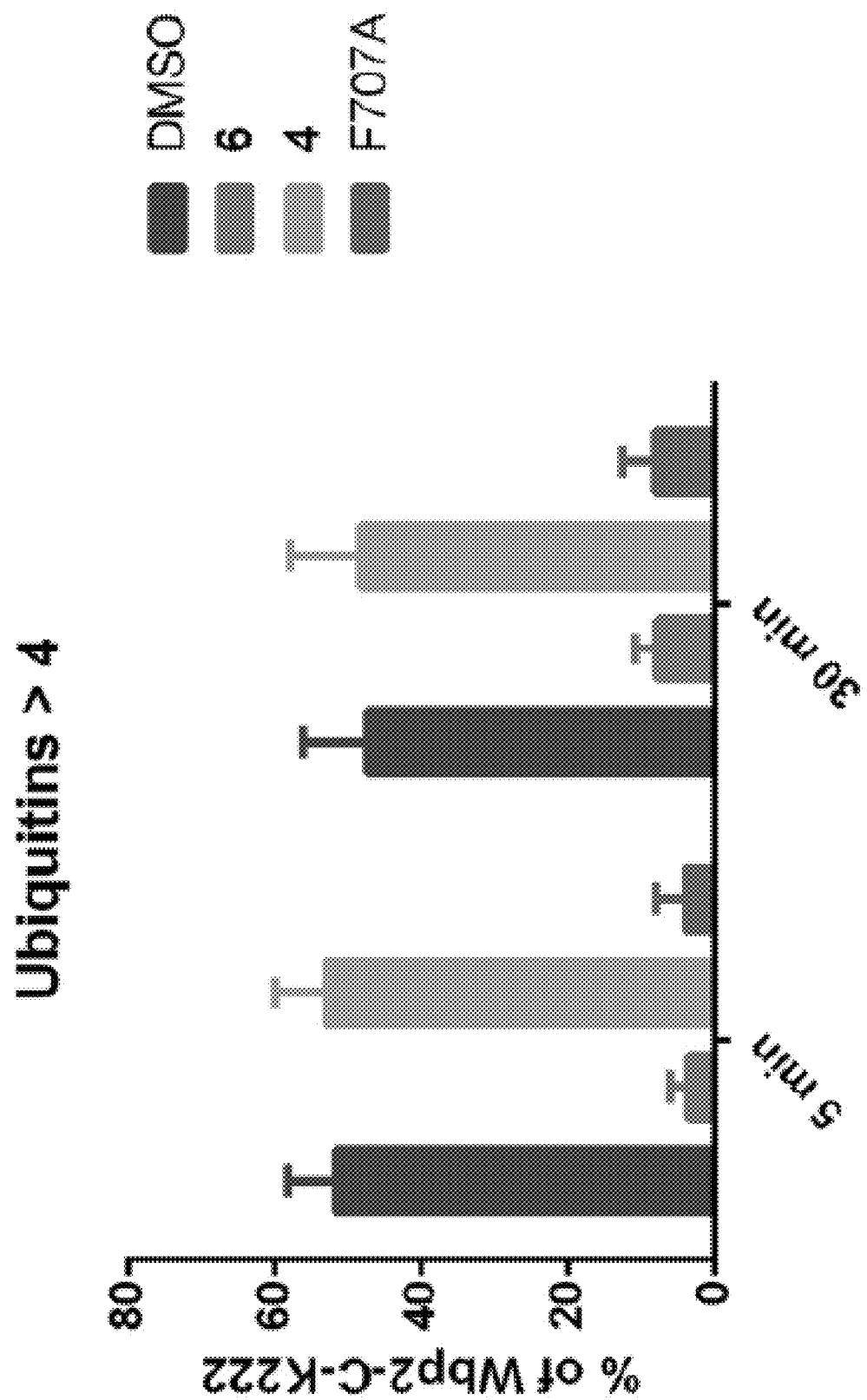

FIG. 33A, FIG. 33B and FIG. 33C. Quantification of fluorescent bands from FIG. 16C and FIG. 23 showing that both initial monoubiquitination and polyubiquitination are disrupted by inhibitor 6, but polyubiquitination is more greatly affected. This effect is comparable to the NEDD4-1 F707A mutation. Fluorescent Wbp2-C-K222 bands with the indicated number of ubiquitins are plotted as percent of total Wbp2-C-K222 bands (non-ubiquitinated+polyubiquitinated). Reactions were performed in duplicate and presented as mean±s.e.m.

Figure 34:
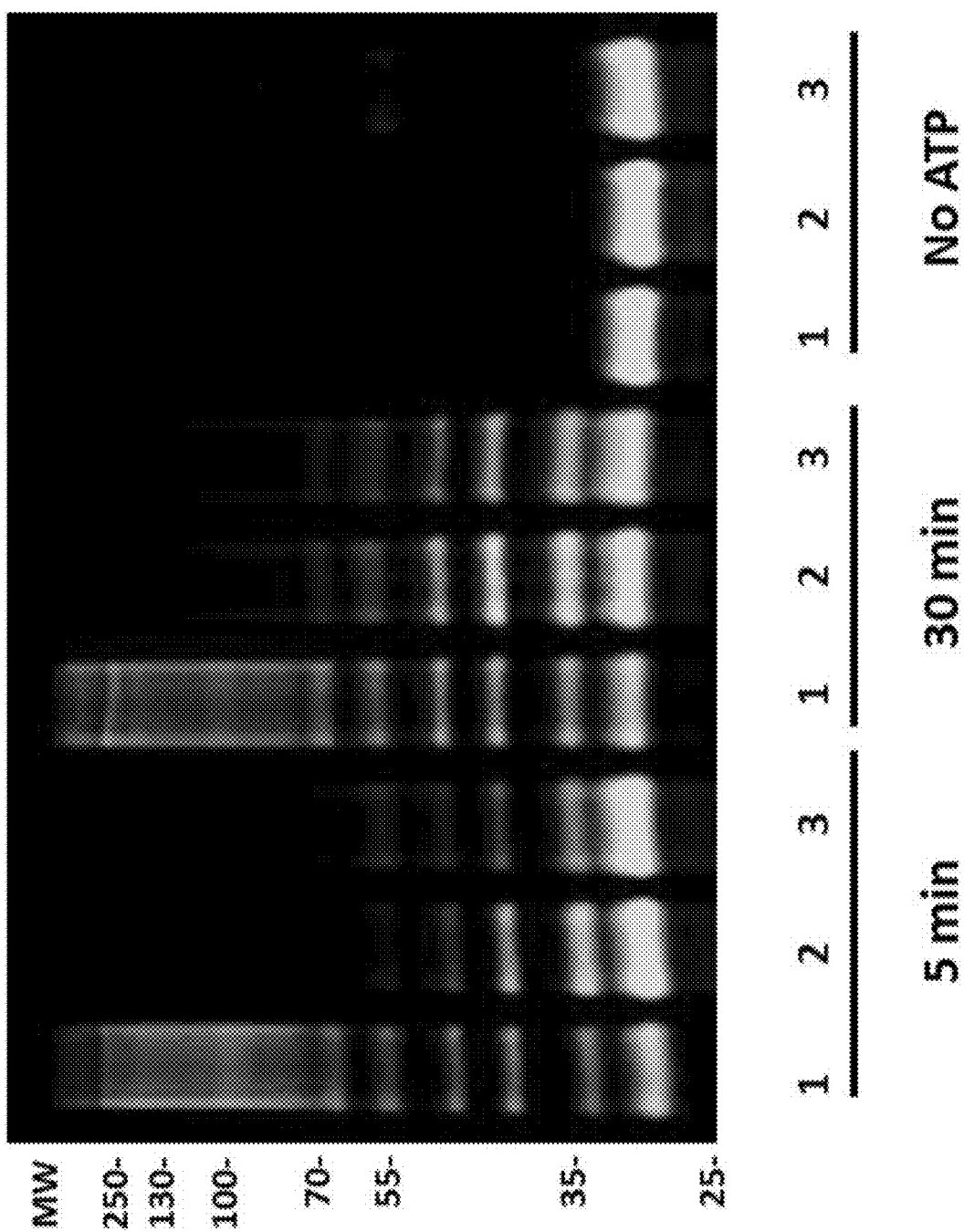

FIG. 34. Ubiquitination of fluorescent Wbp2-C-K222 by the NEDD4-1 F707A mutant is comparable to that of HECT domain of NEDD4-1 treated with inhibitor 6. NEDD4-1 treated with 1% DMSO (lane 1), NEDD4-1•compound 6 covalent complex (lane 2), and NEDD4-1 F707A (lane 3) were incubated with E1 and E2 enzymes, ubiquitin, protein substrate and ATP. Reaction mixtures were quenched at the indicated times and the amount of ubiquitinated Wbp2 was determined using in-gel fluorescence.

Figure 35:
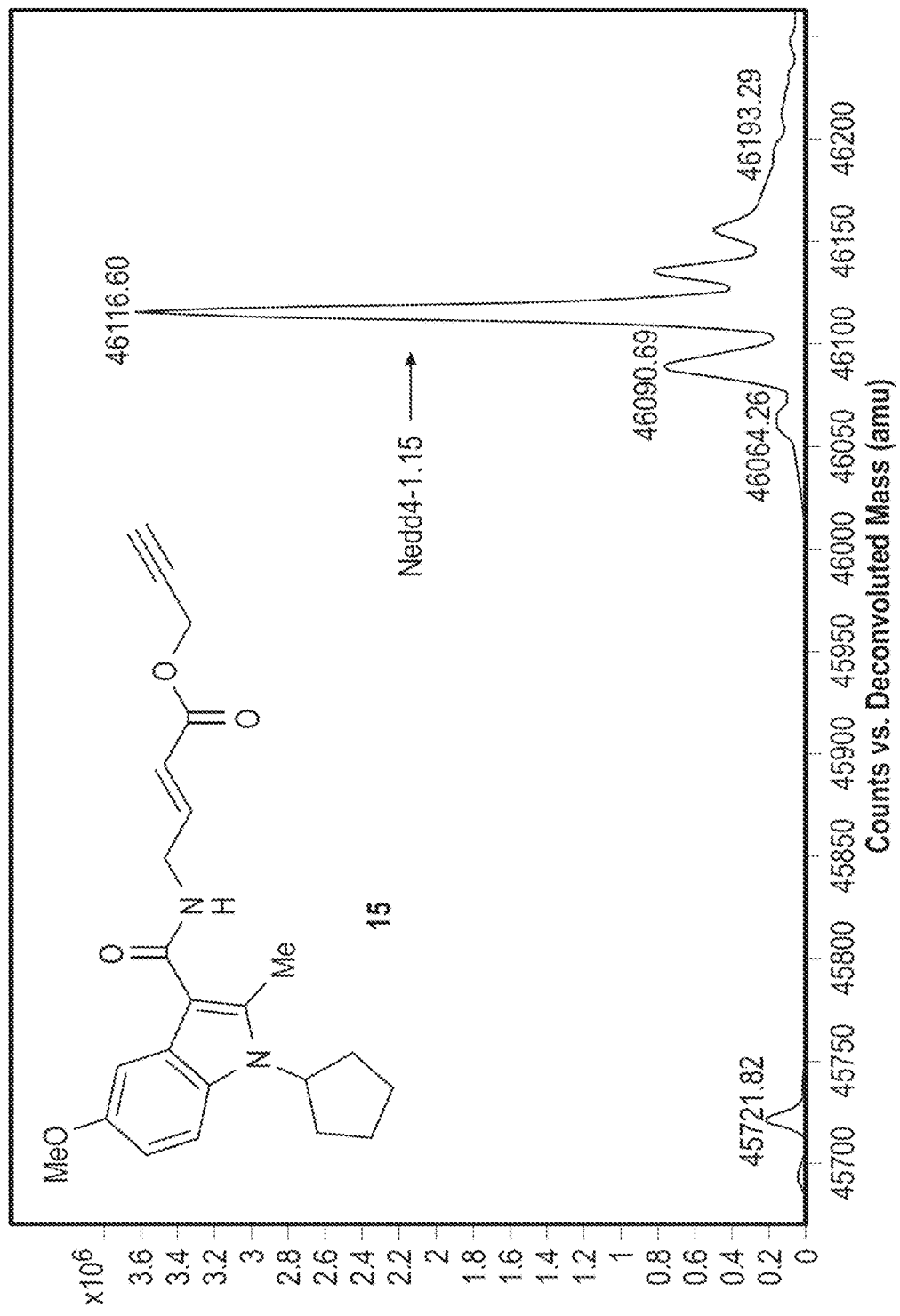

FIG. 35. Probe 15, an alkyne tagged analog of compound 6, is equally effective at labeling NEDD4-1 HECT domain in vitro. NEDD4-1 HECT domain (10 μM) was treated with compound 15 in 1% DMSO at 100 μM for 1 h, followed by gel filtration and whole protein ESI-MS.

Figure 36:
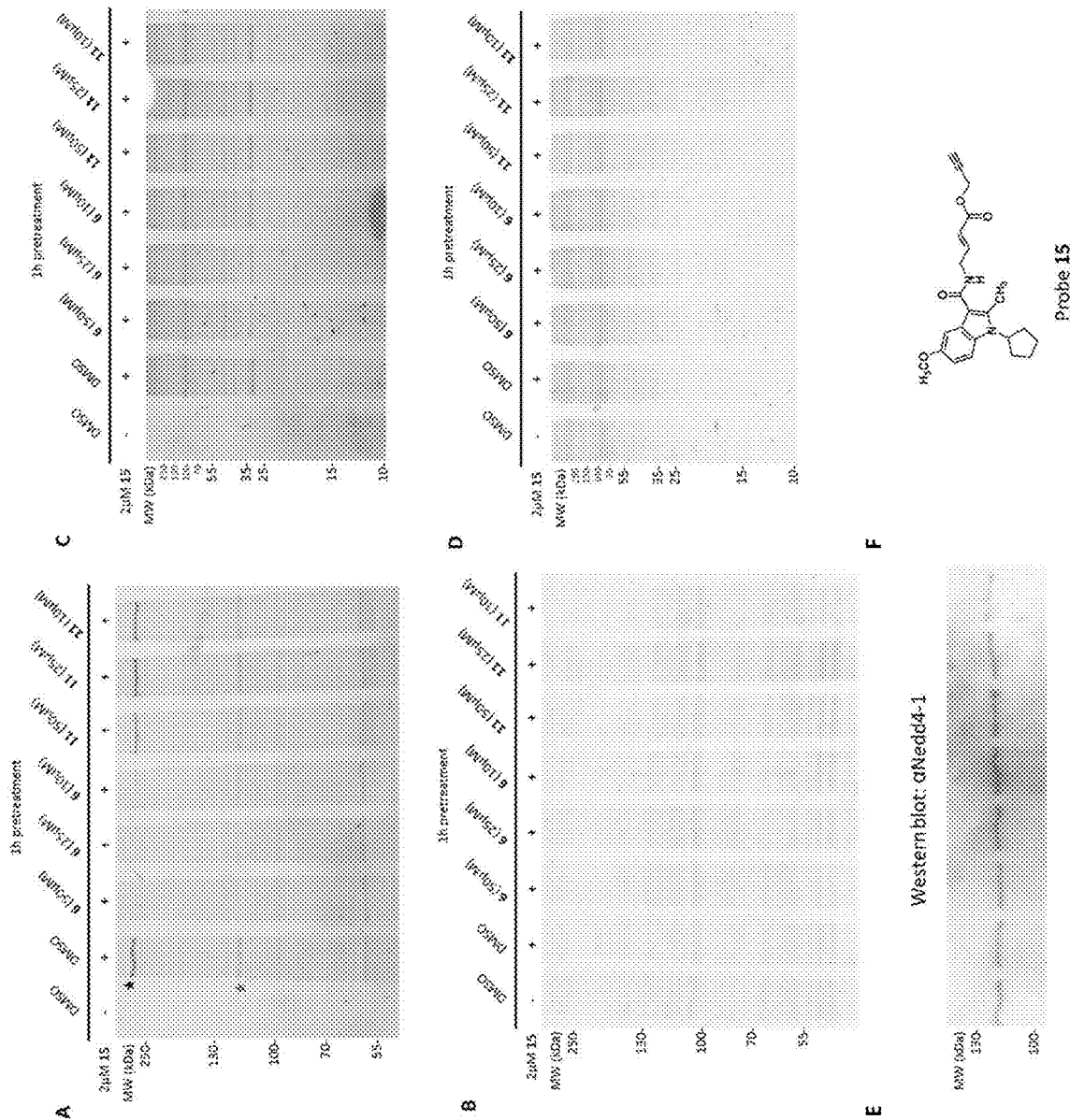

FIG. 36. (A) Click chemistry and in-gel fluorescence with an alkyne-tagged probe 15 demonstrates that compound 6 is cell membrane-permeable and has good selectivity in TC-71 cells. Pretreatment with compound 6 for 1 h, but not the inactive indole 11, abolished labeling of a band at ~120 kDa (star), with a molecular weight corresponding to NEDD4-1. There was also one notable specific off target of 6 at >250 kDa (star). (B) Coomassie stain of the fluorescent SDS-PAGE gel from (A). (C) Same as A, but with a 15% acrylamide SDS-PAGE gel to show proteins below 45 kDa. (D) Coomassie stain of the gel from C. (E) Western blot with NEDD4-1 antibody of the cell lysates from (A) showing that the fluorescent band at ~120 kDa matches NEDD4-1. (F) Probe 15.

DETAILED DESCRIPTION

Disclosed are methods for identifying for screening for the binding affinity of chemical entities to other bioactive molecules. The screened chemical entities may be utilized in pharmaceutical composition or therapeutic methods for treating disease or disorders associated with the bioactive molecules. The methods, compounds, and compositions disclosed herein may be described utilizing terms as defined below.

Unless otherwise specified or indicated by context, the terms "a", "an", and "the" mean "one or more." For example, "an inhibitor of NEDD4-1" should be interpreted to mean "one or more inhibitors of NEDD4-1."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

The disclosed methods may include methods of screening for an inhibitor of an active biological molecule having a catalytic or non-catalytic cysteine residue, including screening for irreversible inhibitors and/or inhibitors that react covalently with the biological molecule. For example, the disclosed methods may include screening for an inhibitor of the neuronal precursor cell-expressed developmentally down-regulated 4-1 ubiquitin ligase (NEDD4-1). The methods may include: (a) selecting an electrophile that is reactive with cysteine residues (which may include but are not limited to electrophiles such as electrophiles selected from the group consisting of acrylamides, vinylsulfonamides, acrylates, methyl acrylates, vinyl sulfones, methyl vinyl sulfones, vinyl ketones, acrylonitriles, and propargyl ketones/esters and amides); (b) preparing a library of candidate inhibitor molecules by reacting the electrophile with a plurality of candidate drug molecules (e.g., by reacting the electrophile with a plurality of candidate drug molecules via an amide-coupling reaction), wherein the library of candidate inhibitor molecules thus prepared is reactive with cysteine residues (and preferably is not reactive with lysine residues and/or histidine residues); (c) contacting the library of molecules of candidate inhibitor molecules with the biological molecule having the catalytic or non-catalytic cysteine residue; (d) measuring binding of the library of candidate inhibitor molecules to the biological molecule comprising having the catalytic or non-catalytic cysteine residue and/or measuring reactivity between the library of candidate inhibitor molecules and the biological molecule, for example, via detecting a reaction product formed between one or more of the candidate molecules and the biological molecule, where binding and or reactivity may be measured via mass spectrometry (MS), specifically electrospray ionization mass spectrometry (ESI-MS); and (e) screening for the inhibitor based on binding affinity of the library of molecules candidate inhibitor molecules to the biological molecule and/or based on reactivity between the library of candidate inhibitor molecules and the biological molecule. The disclosed methods may be used to determine which candidate inhibitor molecules bind to the biological molecule with the greatest affinity, (e.g., where the candidate inhibitor molecules bind to the biological molecule with a $K_d$ of less than about 100, 50, 10, 5, 1, 0.5, 0.1, 0.05, 0.01, 0.005, or 0.001 µM) and/or the disclosed methods may be used to determine which candidate inhibitor molecules bind to the biological molecule with the lowest affinity, e.g., where the candidate inhibitor molecules bind to the biological molecule with a $K_d$ of greater than about 0.001, 0.005, 0.01, 0.05, 0.1, 0.5, 1, 5, 10, 50, or 100 µM).

The methods further may include reacting the library of candidate inhibitor molecules with a molecule comprising a cysteine residue and measuring reaction rates of the library of candidate inhibitor molecules with the molecule comprising the cysteine residue (and optionally determining which candidate inhibitor molecules having the highest reaction rates and/or determining which candidate inhibitor molecules have the lowest reaction rates). Even further, the methods may include measuring inhibitor activity of the library of candidate inhibitor molecules, or a selected molecule from the screened library of candidate inhibitor molecules, against the activity of one or more biological molecules having a catalytic or non-catalytic cysteine residue (e.g., measuring the inhibitor activity of a selected molecule from the screened library of candidate inhibitor molecules against the ubiquitin ligase activity of a molecule such as NEDD4-1 on a substrate, such as PTEN). Optionally, measuring inhibitor activity may include determining which candidate inhibitor molecules have the highest inhibitor activity, (e.g., where the candidate inhibitor molecules have a $K_i$ of less than about 100, 50, 10, 5, 1, 0.5, 0.1, 0.05, 0.01, 0.005, or 0.001 µM) against a biological molecule and/or determining which candidate inhibitor molecules have the lowest inhibitor activity, (e.g., where the candidate inhibitor molecules have a $K_i$ of greater than about 0.001, 0.005, 0.01, 0.05, 0.1, 0.5, 1, 5, 10, 50, or 100 µM) against the same or a different biological molecule.

In the disclosed methods, an inhibitor that reacts covalently and irreversibly with the active biological molecule having a catalytic or non-catalytic cysteine (i.e., an irreversible inhibitor) usually has an affinity much higher than those of reversible inhibitors. By designing irreversible inhibitors, an inhibitor having a weak affinity can be identified from the library of candidate inhibitors in an initial screen and subsequently optimized to enhance its potency as an inhibitor. In some embodiments, the inhibitor may be a combination or conjugation of an electrophilic moiety (i.e., a "warhead") that reacts covalently with a catalytic cysteine residue at an active site through a Michael reaction, and a non-polar ring-based targeting moiety that docks the inhibitor selectively at the catalytic site prior to the electrophilic moiety (i.e., a "warhead") reacting with the catalytic cysteine. Suitable non-polar ring-based targeting moieties may include aryl moieties comprising one or two fused 5-, 6-, or 7-membered rings that optionally include one or more heteroatoms selected from N, O, and S (e.g., phenyl, pyridinyl, pyrimidinyl, and the like).

The following aspects further describe the disclosed methods. In a first aspect, a method to screen for the binding affinity of chemical entities with proteins is disclosed. The method involves providing a chemical-entity, providing a protein, exposing the chemical entity to the protein to create a chemical-entity~protein-complex and measuring the binding affinity of the chemical entity to the protein in the chemical-entity~protein-complex. In this first aspect, the chemical-entity is a cysteine-reactive-electrophilic-fragment. More specifically, the cysteine-reactive-electrophilic-fragment is an irreversible or covalent inhibitor of a kinase, an ubiquitin ligase, cysteine protease, protein-protein interactions or a deubiquitinating enzyme. In a more specific embodiment, the cysteine-reactive-electrophilic-fragment is chosen from the group consisting of acrylate, acrylamide, vinyl sulfone, vinyl ketone, acrylonitrile, and propargyl ketone. In this first aspect, the protein comprises a catalytic or non-catalytic cysteine. More specifically, the chemical entity binds irreversibly or covalently to the protein to form the chemical-entity~protein complex. In this first aspect, the measuring of the binding affinity of the chemical entity to the protein in the chemical-entity~protein-complex occurs by mass spectrometry. The inventors have observed that binding affinity and covalent modification are directly correlated.

In a second aspect, a method to screen for the binding affinity of therapeutic-fragments with cysteine proteases is disclosed. The method includes providing a therapeutic-fragment, providing a cysteine-protease, exposing the therapeutic-fragment to the cysteine-protease to create a therapeutic fragment~cysteine-protease-complex, and measuring the binding affinity of the therapeutic-fragment to the cysteine-protease in the therapeutic-fragment~cysteine-protease-complex. In this second aspect, cysteine-protease comprises a non-catalytic cysteine or a catalytic cysteine. In this second aspect, therapeutic-fragment binds irreversibly or covalently to cysteine-protease to create the therapeutic-fragment~cysteine-protease-complex. Lastly, the measuring of the binding affinity of the therapeutic-fragment to the cysteine-protease in the therapeutic-fragment~cysteine-protease-complex occurs by mass spectrometry.

In a third aspect, a method to screen for the binding affinity of papain-inhibitor with cysteine proteases is disclosed. The method includes providing a papain-inhibitor-fragment, providing a cysteine protease, exposing the papain-inhibitor-fragment to the cysteine-protease to create a papain-inhibitor fragment cysteine-protease-complex, and measuring the binding affinity of the papain-inhibitor fragment to the cysteine-protease in the papain-inhibitor-fragment~cysteine-protease-complex. In this third aspect, measuring the binding affinity of the papain-inhibitor-fragment to the cysteine-protease in the papain-inhibitor-fragment-~cysteine-protease-complex occurs via mass spectrometry.

Additional aspects of the methods that are disclosed and contemplated herein are illustrated in the following publications: Kathman et al., "Covalent Tethering of Fragment for Covalent Probe Discovery," Medchemcomm. 2016 Apr. 1; 7(4):576-585; McShan et al., "Identification of non-peptidic cysteine reactive fragment as inhibitor of cysteine protease rhodesain," Bioorg. Med. Chem. Lett. 2015 Oct. 15; 25(20): 4509-12; and Kathman et al., "A fragment-based method to discover irreversible covalent inhibitors of cysteine proteases," J. Med. Chem. 2014 Jun. 12; 57(11):4969-74; the contents of which are incorporated herein by reference in their entireties.

Inhibitor molecules identified by the disclosed methods may include inhibitors of active biological molecules having a catalytic or non-catalytic cysteine residue, including irreversible inhibitors of active biological molecules having a catalytic or non-catalytic cysteine residue. Inhibitors identified in the disclosed methods may include inhibitors of NEDD4-1, for example, irreversible inhibitors of NEDD4-1.

In some embodiments, the disclosed inhibitors may include a compound having formula I, or a salt, ester, amide, or solvate thereof, which are disclosed as follows:

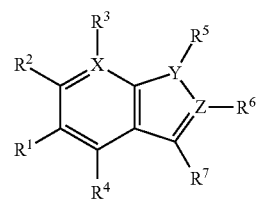

wherein: X is CH or N; Y is N, O, or S; Z is C or N; $R^1$ is selected from hydrogen, hydroxyl, thiol, halogen, alkoxy (e.g., C1-C6 straight chain or branched alkyl-oxy), alkylthio (e.g., C1-C6 straight chain or branched alkyl-thio), amino, alkylamino (e.g., C1-C6 straight chain or branched alkyl-amino), haloalkyl (e.g., C1-C6 straight chain or branched haloalkyl), and haloalkoxy (e.g., C1-C6 straight chain or branched haloalkyl-oxy); $R^2$, $R^3$, and $R^4$ are the same or different and are selected from hydrogen, halogen, and alkoxy (e.g., C1-C6 straight chain or branched alkyl-oxy); $R^5$ and $R^6$ are the same or different and are selected from hydrogen, alkyl (e.g., C1-C6 straight chain or branched alkyl), cycloalkyl, aryl (e.g., phenyl, or naphthyl), and alkylaryl (e.g., benzyl); and $R^7$ has a formula selected from:

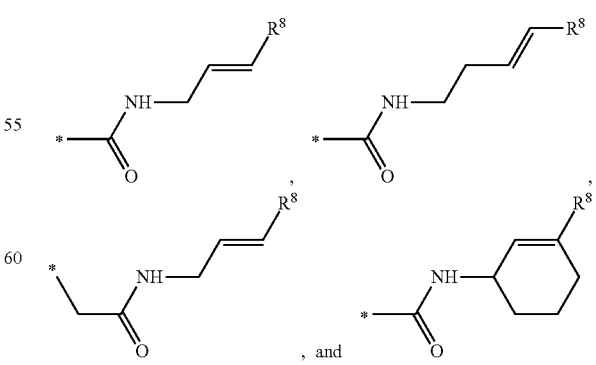

wherein $R^8$ is $COR^9$, COOR, $C(=O)NR_2$, $C(=O)NHR$, $SO_2R^9$ or CN, and $R^9$ is selected from alkyl (e.g., C1-C6 straight chain or branched alkyl), aryl (e.g., phenyl, or naphthyl), alkylaryl (e.g., benzyl), alkoxy (e.g., C1-C6 straight chain or branched alkyl-oxy), amino, alkylamino (e.g., C1-C6 straight chain or branched alkyl-amino), and anilino.

In the disclosed compounds, preferably the compounds contemplated have the formula Ia:

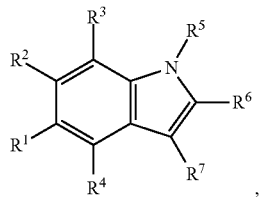

and preferably R¹ is methoxy or ethoxy.

In the disclosed compounds, preferably R⁷ has a formula selected from:

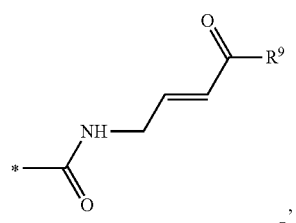

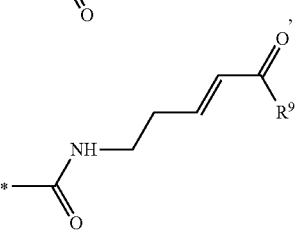

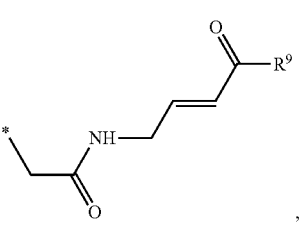

, and

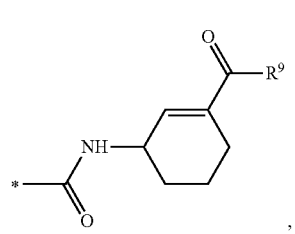

and preferably R⁹ is alkoxy (e.g., C1-C6 straight chain or branched alkyl-oxy, and preferably methoxy or ethoxy).

Specific compounds disclosed herein may include:

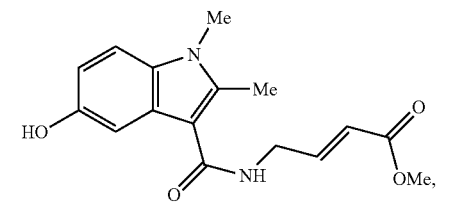

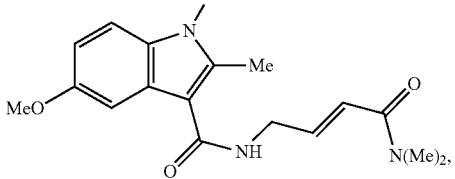

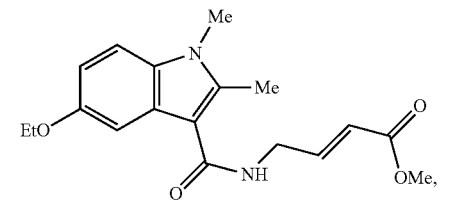

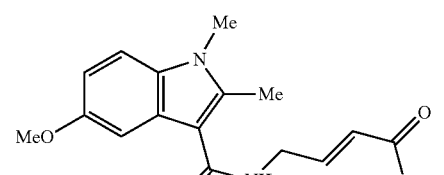

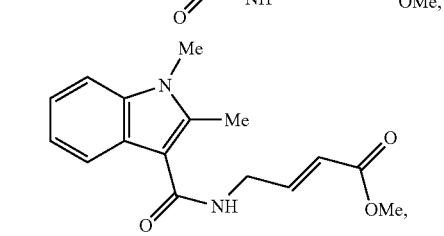

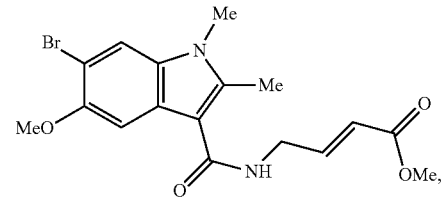

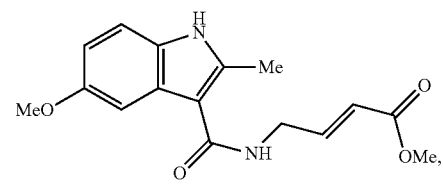

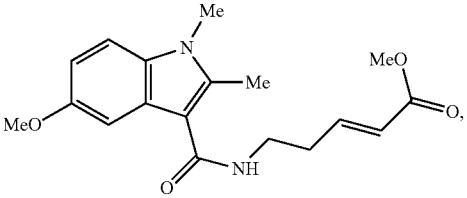

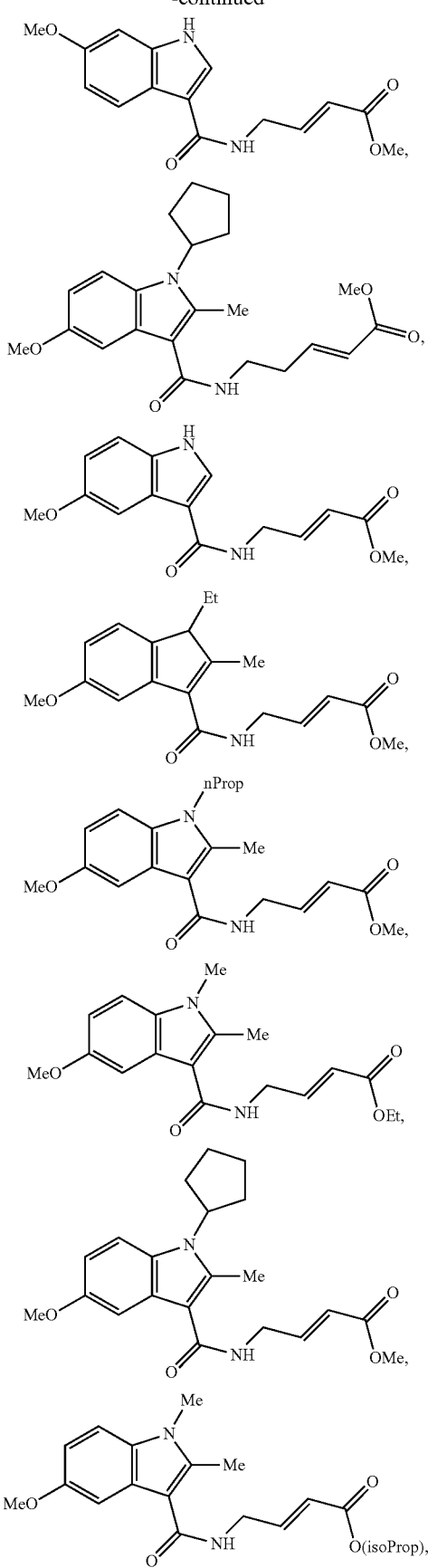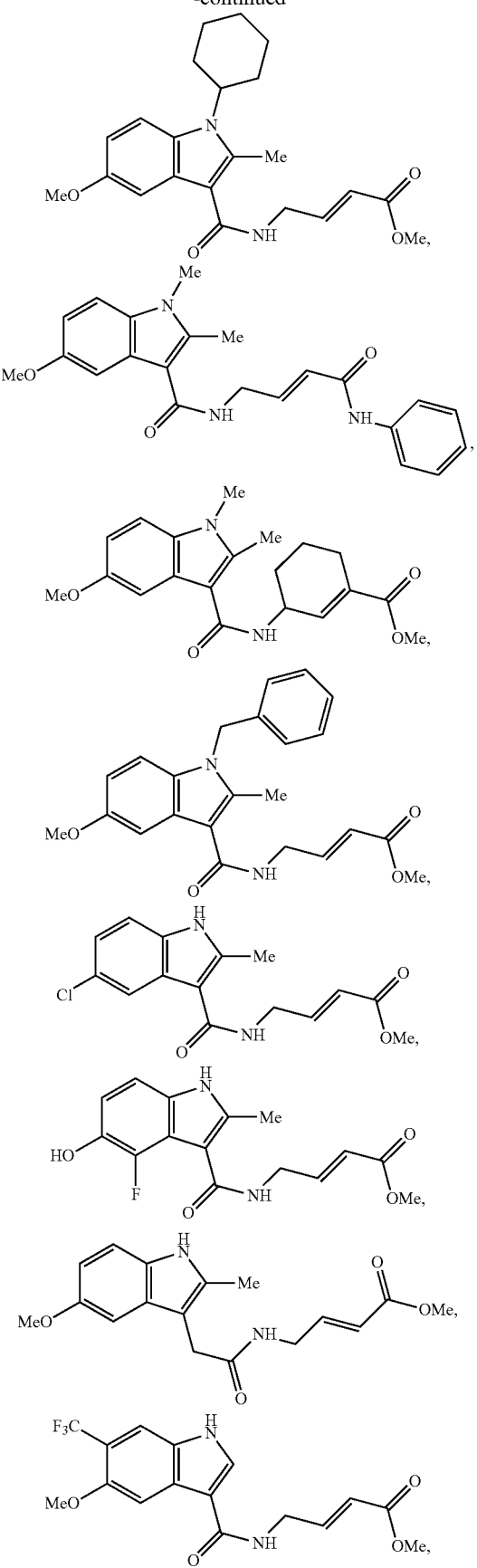

-continued

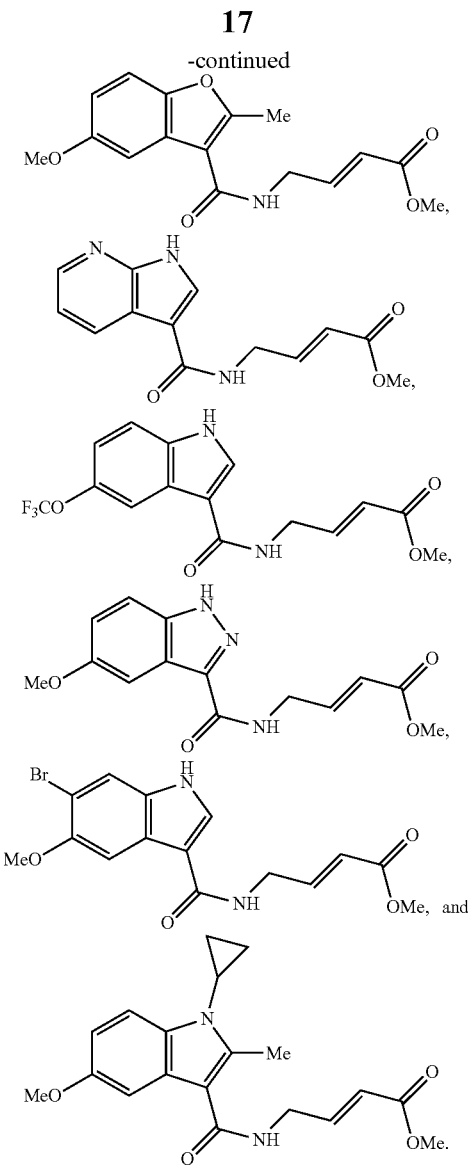

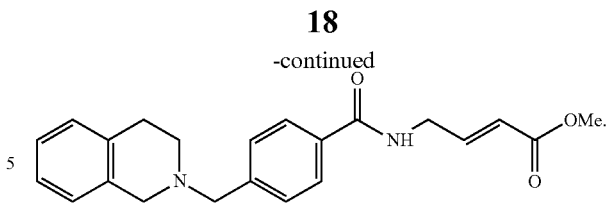

In the compounds above, the abbreviations "MeO," "EtO," "nProp," and "O(isoProp)," refer to a methoxy substituent, an ethoxy substituent, an n-propyl substituent, and an isopropoxy substituent.

Other compounds disclosed herein include the following compounds:

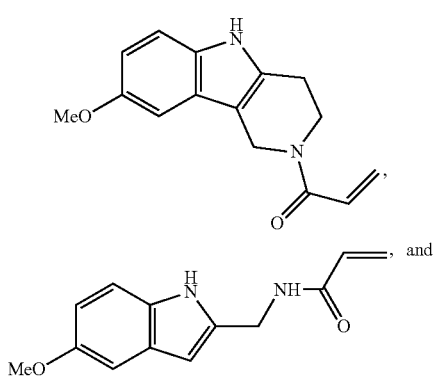

Pharmaceutical compositions comprising the disclosed compounds are also contemplated. The pharmaceutical compositions comprise the disclosed compounds and a pharmaceutical carrier. The disclosed compounds or pharmaceutical compositions comprising the disclosed compounds may be administered to treat and/or prevent a disease or disorder in a subject in need thereof.

The methods contemplated herein include methods for treating a disease or disorder that is associated with an active biological molecule having a catalytic or non-catalytic cysteine residue, where the methods comprise administering to a subject in need thereof an inhibitor of the active biological molecule (e.g., an irreversible inhibitor). The methods of treatment may include methods of treating a disease or disorder that is associated which NEDD4-1 activity in a subject in need thereof, where the methods comprise administering to the subject an inhibitor of NEDD4-1 activity (e.g., an irreversible inhibitor of NEDD4-1 activity).

The terms "subject," "patient," and "individual" may be used interchangeably herein. A subject may be a human subject. A subject may refer to a human subject having or at risk for developing a disease or disorder that is associated with an active biological molecule having a catalytic or non-catalytic cysteine residue. A subject may refer to a human subject having or at risk for developing a disease or disorder that is associated with NEDD4-1 activity, such as aberrant NEDD4-1 activity.

"NEDD4-1" refers to the neuronal precursor cell-expressed developmentally down-regulated 4-1 ubiquitin ligase. The gene for human NEDD4-1 is located on chromosome 15. (See National Center for Biotechnology Information (NCBI), NEDD4 neural precursor cell expressed, developmentally down-regulated 4, E3 ubiquitin protein ligase [*Homo sapiens* (human)], Gene ID: 4734, updated on 4 May 2015, Assembly GRCh38p2 (GCF_000001405.28), Location NC_000015.10 (55826917..55993746, complement)). NEDD4-1 belongs to a family of ubiquitin ligases that are conserved among eukaryotes. Many substrates of NEDD4-1 have been identified and include the tumor suppressor phosphatase and tensin homolog (PTEN, aka "Phosphatidylinositol 3,4,5-trisphosphate 3-phosphatase and dual-specificity protein phosphatase"), membrane receptors utilized by viruses for cell entry and infection, cell components involved in endocytosis. (See e.g., Boase et al. "NEDD4: The founding member of a family of ubiquitin-protein ligases," Gene. 2015 Fe25; 557(2):113-22, Epub 2014 Dec. 17, the contents of which is incorporated by reference herein in its entirety). NEDD4-1 and its family members have been shown to play a role in cancer. (See Bernasolla et al., "The HECT Family of E3 Ubiquitin Ligases: Multiple Players in Cancer Development," Cancer Cell, Volume 14, Issue 1, 8 Jul. 2008, Pages 10-21; and Wang et al., "NEDD4-1 is a Proto-Oncogenic Ubiquitin Ligase for PTEN, Cell Volume 128, Issue 1, 12 Jan. 2007, Pages 129-139; Chen et al., "The Nedd4-like family of E3 ubiquitin ligases and cancer," Cancer Metastasis Rev. 2007 December; 26(3-4):587-604; and Ye et al., "NEDD4: a promising target for cancer therapy," Curr Cancer Drug Targets. 2014; 14(6):549-56; the contents of which are incorporated herein by reference in their entireties).

As used herein, the term "aberrant" means higher or lower expression or activity, typically higher expression or activity, relative to a normal healthy subject. A subject may refer to a human subject having or at risk for developing a disease or disorder that is associated with elevated expression or activity of an active biological molecule having a catalytic or non-catalytic cysteine residue (e.g., NEDD4-1). In some embodiments of the methods disclosed herein, a subject may be treated by inhibiting activity of NEDD4-1 by administering the presently disclosed inhibitors of NEDD4-1. In specific embodiments, a subject may refer to a human subject having or at risk for developing a cell proliferative disease or disorder, including cancers that are associated with NEDD4-1 activity, which may include but are not limited to colorectal cancer, gastric cancer, bladder cancer, prostate cancer, lung cancer (e.g., non-small-cell lung cancer), breast cancer, ovarian cancer, pancreatic cancer, esophageal cancer, and squamous cell cancer. In other specific embodiments, a subject may refer to a human subject having or at risk for developing a neurological disease or disorder, which may include but are not limited to Parkinson's disease, Alzheimer's disease, obesity, IGF-1 driven cancers, and viral infections. (See e.g., Kwak et al., "Upregulation of the E3 ligase NEDD4-1 by Oxidative Stress Degrades IGF-1 Receptor Protein in Neurodegeneration," J Neurosci. 2012 Aug. 8; 32(32): 10971-10981, the content of which is incorporated herein by reference in its entirety). In other specific embodiments, a subject may refer to a human subject having or at risk for developing infection by human immunodeficiency virus 1 (HIV-1). (See Weiss et al., "Rescue of HIV-1 Release by Targeting Widely Divergent NEDD4-Type Ubiquitin Ligases and Isolated Catalytic HECT Domains to Gag," PLos Pathog. 2010 September; 6(9): e1001107, the content of which is incorporated herein by reference in its entirety).

The compounds disclosed herein preferably inhibit activity of an active biological molecule having a catalytic or non-catalytic cysteine molecule, such as NEDD4-1. Inhibition of activity of NEDD4-1 may be assessed utilizing methods known in the art, including ubiquitization assays known in the art. In some embodiments, the compounds inhibit activity of NEDD4-1 relative to a control (e.g., by at least about 10%, 20%, 30%, 40%, 50%, 60%, 70%, 80%, 90%, or more). In other embodiments, an $IC_{50}$ value for the compound in regard to inhibition of NEDD4-1 activity may be determined and preferably the compound has an $IC_{50}$ value of less than about 10 µM, 5 µM, 1 µM, 0.5 µM, 0.1 µM, 0.05 µM, 0.01 µM, 0.005 µM, or 0.001 µM.

The compounds disclosed herein (e.g., compounds of formula I and Ia) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.) As used herein, formulae which do not specify the orientation at one or more chiral centers are meant to encompass all orientations and mixtures thereof.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that inhibits NEDD4-1 activity may be administered as a single compound or in combination with another compound that inhibits NEDD4-1 activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with NEDD4-1 activity, including administering an effective amount of a compound that inhibits NEDD4-1 activity.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1
Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

|  | Weight % |
|---|---|
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

|  |  |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules, each containing 80 mg medicament, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8
An intravenous formulation containing 100 mg of medicament per 5 ml dose can be prepared as follows:

| | |
|---|---|
| Active Ingredient | 100 mg |
| Mannitol | 100 mg |
| 5N Sodium hydroxide | 200 ml |
| Purified water to total | 5 ml |

EXAMPLES

The followings Examples are illustrative only and are not intended to limit the scope of the claimed subject matter.

Example 1—Methods to Screen for the Binding of Chemical Entities

Reference is made to Kathman, et al., "A fragment-based method to discover irreversible covalent inhibitors of cysteine proteases," J. Med. Chem. 2014, Jun. 12:57(11):4969-74, the content of which is incorporated herein by reference in its entirety.

Abstract

We have developed a novel fragment-based drug discovery method, irreversible tethering, which employs the irreversible covalent trapping of drug-like fragments at active site cysteines. We rationally designed a chemical system to attach a cysteine reactive electrophile, (E)-methyl 4-aminobut-2-enoate, to 100 drug-like fragments without significant alterations in the thiol reactivity of the attached electrophile, ensuring that specific binding and not reactivity will produce candidate inhibitors. We employed a simple and high throughput mass spectrometry based assay to screen our library in mixtures of ten fragments and have discovered three non-peptidic inhibitors of the cysteine protease papain and two unique inhibitors of a non-catalytic cysteine of the HECT E3 ubiquitin ligase NEDD4-1, an enzyme which is undruggable. This is the first example of a successful screen of an unbiased library of electrophilic compounds under irreversible conditions which lead to the discovery of specific and novel inhibitor structures for the enzyme of interest. The identified compounds inhibit papain and NEDD4-1 ubiquitin ligases in in vitro enzymatic assays, displaying the characteristics of irreversible inhibitors. The developed irreversible tethering system also displays specificity: under identical reaction conditions, the identified papain and NEDD4-1 inhibitors did not covalently react with UbcH7 or USP08, enzymes which have catalytic and non-catalytic surface cysteines. The developed platform is widely applicable to discover covalent modulators of catalytic and non-catalytic cysteines in the human proteome.

Background and Introduction

Disclosed is a general method to discover covalent inhibitors of catalytic and noncatalytic cysteines using fragment based drug discovery. NMR rate studies were used to compare several electrophiles in order to identify one which is moderately reactive with cysteine and which demonstrates similar reactivity regardless of the structure of the fragment it is attached to (E)-methyl-4-aminobut-2-enoate was identified as an electrophile which meets these criteria. This amine handle of this electrophile was then coupled to a library of fragments containing a carboxylic acid group using amide bond formation reaction. This library was selected on the basis of meeting the "rule of three" drug-like criteria as well as maximizing structural diversity. Pseudo first-order NMR kinetics studies with N-acetyl cysteine methyl ester have confirmed that all members of this library have rate constants within a factor of 2 of each other. The electrophilic fragments can then be screened in batches of ten against the enzyme of interest, and any binders can be identified by mass spectrometry. Whole protein ESI-MS is used to identify any hits based on the mass shift of the protein peak. Selectivity for the catalytic cysteine is confirmed by tryptic digestion and MALDI-TOF MS of the tryptic peptides, or point mutation studies in the protein. Our choice of electrophile ensures that any hits will be selected based on their ability to bind to the active site of the enzyme and not simply due to their greater reactivity. Unique hits have been found against the cysteine protease papain and the HECT E3 ubiquitin ligase NEDD4-1, and their inhibitory activity was confirmed with enzymatic assays. The developed assays are moderately high throughput, and allow the screening of ~100 compounds by one person/per day without the use of specialized robotic equipment.

Results

1. Selecting the Electrophile

To find an electrophile which is suitable for irreversible tethering, we explored the cysteine_reactivity profiles of four Michael acceptors: acrylamides 1 and vinylsulfonamides 2, and aminomethyl methyl acrylates 3 and methyl vinylsulfones 4. (See FIGS. 1A-B).

To test how the cysteine reactivity of these electrophiles would be affected by the structure of attached drug-like fragments, we installed acrylamide and vinylsulfonamide electrophiles on aniline, p-MeO-aniline, and p-NO$_2$-aniline to yield electrophiles 1a-c and 2a-c. The methyl acrylate and vinylsulfone electrophiles in 3 and 4 were covalently attached to derivatives of benzoic acid: benzoic acid, p-MeO-benzoic acid, and p-NO$_2$-benzoic acid to yield 3a-c and 4a-c. We envisioned that the different mesomeric and inductive effects of the —OCH$_3$, —H, and —NO$_2$ moieties would cause changes in the reactivity of electrophiles 1-4 towards cysteine, and these changes would be representative of fluctuations in the reactivity of drug-like fragments toward cysteines. The electrophile that displayed the least fluctuation in reactivity towards cysteine would be the most optimal electrophile to use for irreversible tethering.

We therefore measured the pseudo first order reaction rates for each of the compounds 1-4 with N-acetylcysteine methyl ester using NMR spectroscopy (FIG. 1B).[11] Interestingly, we found that acrylamides 1a-c displayed a ~2044 fold difference in reactivity, with the —NO$_2$ derivative being the most reactive. Since many drug-like fragments contain an amino group attached directly to electron-deficient aromatic rings, we envisioned that similar to compounds 1a-c there could be large fluctuations in the reactivity of such an acrylamide library towards thiols, which would make this library problematic to use. Indeed, as we mentioned previously, in the first publication detailing irreversible tethering method using acrylamides one fragment had to be discarded due to its hyper-reactivity.[9]

Vinylsulfonamides 2a-c displayed only an ~8 fold difference in reactivity toward N-acetylcysteine methyl ester. This result was encouraging, yet we sought electrophiles with an even more reactivity toward cysteine, with only 1.6 and 1.4 fold differences, respectively, in the reactivity between the least reactive and the most reactive electrophiles. We chose acrylates 3 for further studies because they were tenfold less reactive than vinylsulfones 4, and therefore less prone to non-specific covalent modifications of nucleophilic amino acid side chains in proteins.[12]

In addition, acrylates are established electrophiles present in irreversible inhibitors of cysteine proteases with activities in in vitro biochemical and cell based assays.[13] Importantly, in vitro kinact/Ki values of acrylate cysteine protease inhibitors vary dramatically (up to 170 fold in the case of falcipain inhibitors) with changes in the structure of the peptide-derived directing group.[13] This indicates that useful levels of kinetic discrimination can be achieved upon structural changes of the directing group, despite the high reactivity of the catalytic cysteine in cysteine proteases. Moreover, the acrylate functionality has been shown to have good pharmacokinetic properties, and is present in an orally bioavailable inhibitor of human rhinovirus 3C protease.[14] These considerations further confirmed to us that acrylate 3 is a good starting point for validating irreversible tethering. Since known acrylate inhibitors are mostly peptidic in nature, we sought to discover novel non-peptidic inhibitors with irreversible tethering.

2. Building and Characterizing the Library

Figure 2:
FIG. 2. (A) Design and synthesis of the fragment library. (B). Pseudo-first order NMR rate plots of the reaction of compounds 6-55 with N-acetyl cysteine methyl ester. Different colors represent different fragments.

We further validated the utility of electrophile 3 as a thiol-reactive tether by making a library of one hundred structurally diverse drug-like fragments 6-105 containing this electrophile. The library was constructed with an HBTU amide coupling with commercially available carboxylic acid fragments (FIG. 2A). The acids were selected with "rule of three" criteria[15] and a subsequent diversity analysis. We measured the reaction rates for the first fifty fragments to confirm that this library would have balanced cysteine reactivity and could be used for irreversible tethering (FIG. 2B). As we expected, these fifty fragments displayed a narrow range of chemical reactivities similar to 3a-c. Overall we observed only a 2.4 fold difference in the reactivity between the least reactive ($k_1$ 3.327×10-4 s-1) and the most reactive ($k_1$ 7.951×10-4 s-1) fragment (FIG. 2B, Table 1).

TABLE 1

Pseudo-first order rate constants of fragments 6-55.

| Compound | k pseudo-first order |
|---|---|
| 6 | 0.0007951 s$^{-1}$ |
| 7 | 0.0006978 s$^{-1}$ |
| 8 | 0.0004232 s$^{-1}$ |
| 9 | 0.0006824 s$^{-1}$ |
| 10 | 0.0004656 s$^{-1}$ |
| 11 | 0.0007414 s$^{-1}$ |
| 12 | 0.000654 s$^{-1}$ |
| 13 | 0.0003582 s$^{-1}$ |
| 14 | 0.0005016 s$^{-1}$ |
| 15 | 0.0007733 s$^{-1}$ |
| 16 | 0.0006414 s$^{-1}$ |
| 17 | 0.0006156 s$^{-1}$ |
| 18 | 0.0006093 s$^{-1}$ |
| 19 | 0.0004396 s$^{-1}$ |
| 20 | 0.0005603 s$^{-1}$ |
| 21 | 0.0003327 s$^{-1}$ |
| 22 | 0.0007605 s$^{-1}$ |
| 23 | 0.0004979 s$^{-1}$ |
| 24 | 0.0005202 s$^{-1}$ |
| 25 | 0.0005202 s$^{-1}$ |
| 26 | 0.0006107 s$^{-1}$ |
| 27 | 0.0006665 s$^{-1}$ |
| 28 | 0.0004200 s$^{-1}$ |
| 29 | 0.0004038 s$^{-1}$ |
| 30 | 0.0006579 s$^{-1}$ |
| 31 | 0.0005193 s$^{-1}$ |
| 32 | 0.0006296 s$^{-1}$ |
| 33 | 0.0006348 s$^{-1}$ |
| 34 | 0.0007717 s$^{-1}$ |
| 35 | 0.0005755 s$^{-1}$ |
| 36 | 0.0003400 s$^{-1}$ |
| 37 | 0.0004493 s$^{-1}$ |
| 38 | 0.0007728 s$^{-1}$ |
| 39 | 0.000651 s$^{-1}$ |
| 40 | 0.0004793 s$^{-1}$ |
| 41 | 0.0005635 s$^{-1}$ |
| 42 | 0.0005281 s$^{-1}$ |
| 43 | 0.0007616 s$^{-1}$ |
| 44 | 0.0006746 s$^{-1}$ |
| 45 | 0.0003961 s$^{-1}$ |
| 46 | 0.0007806 s$^{-1}$ |
| 47 | 0.0006539 s$^{-1}$ |
| 48 | 0.0004680 s$^{-1}$ |
| 49 | 0.0004975 s$^{-1}$ |
| 50 | 0.0006514 s$^{-1}$ |
| 51 | 0.0005048 s$^{-1}$ |
| 52 | 0.0005984 s$^{-1}$ |
| 53 | 0.0005521 s$^{-1}$ |
| 54 | 0.0005048 s$^{-1}$ |
| 55 | 0.0004520 s$^{-1}$ |
| Average: | 0.000575841 s$^{-1}$ |
| Std Dev: | 0.000127064 s$^{-1}$ |

3. Screening Against the Cysteine Protease Papain

Encouraged by these findings, we asked if we could use this library to discover specific covalent enzyme inhibitors with novel structures. As a model protein we chose the cysteine protease papain. Papain has a molecular weight of 23,422.29 Da and the following amino acid sequence:

(SEQ ID NO: 1)
IPEYVDWRQKGAVTPVKNQGSC*GSC$^{25}$WAFSAVVTIEGIIKIRTGNLNE

YSEQELLDC*DRRSYGC*NGGYPWSALQLVAQYGIHYRNTYPYEGVQRYC

*RSREKGPYAAKTDGVRQVQPYNEGALLYSIANQPVSVVLEAAGKDFQLY

RGGIFVGPC*GNKVDHAVAAVGYGPNYILIKNSWGTGWGENGYI RIKRG

TGNSYGVC*GLYTSSFYPVKN.

The starred cysteines are internal disulfides and Cys25 is a catalytic cysteine.

We reasoned that the presence of a highly reactive active site cysteine in papain would serve as a stringent specificity test for the proposed irreversible tethering method. We hypothesized that if the designed chemical system displays specificity in the presence of the highly reactive catalytic cysteine of papain, this system could also be used to discover ligands for less reactive non-catalytic cysteines. In addition, papain is the founding member of a large family of cysteine proteases, so if the developed system produced inhibitors of papain it could serve as an entry point to discover inhibitors of other medically relevant cysteine proteases.[16] For our initial screening, we used a simple MS assay similar to the original disulfide tethering screening conditions.

Papain (10 µM) was incubated for one hour with ten reaction mixtures that each contained ten electrophilic fragments (100 µM each) (Table S2).

TABLE 2

Composition of reaction mixes used for irreversible tethering.

| Mix 1 | MW | Mix 2 | MW | Mix 3 | MW | Mix 4 | MW |
|---|---|---|---|---|---|---|---|
| 25 | 234.1004 | 29 | 234.1004 | 76 | 239.1521 | 103 | 223.0957 |
| 53 | 254.0458 | 20 | 254.163 | 73 | 257.0567 | 28 | 249.1001 |
| 56 | 272.1161 | 68 | 273.1113 | 21 | 273.1113 | 59 | 259.0768 |
| 17 | 282.1038 | 60 | 283.0611 | 92 | 285.1113 | 67 | 276.1474 |
| 16 | 288.1474 | 91 | 288.1474 | 41 | 290.1267 | 50 | 286.9906 |
| 95 | 298.1317 | 27 | 298.1317 | 89 | 299.0969 | 44 | 290.1267 |
| 47 | 303.1019 | 86 | 303.1107 | 72 | 304.0882 | 23 | 299.1158 |
| 8 | 310.1893 | 35 | 312.011 | 55 | 314.1267 | 11 | 315.0219 |
| 102 | 320.1736 | 98 | 323.0561 | 79 | 326.1267 | 88 | 326.163 |
| 51 | 342.1216 | 90 | 342.9878 | 69 | 347.1037 | 54 | 354.0215 |

| Mix 5 | MW | Mix 6 | MW | Mix 7 | MW | Mix8 | MW |
|---|---|---|---|---|---|---|---|
| 66 | 249.1113 | 57 | 250.0954 | 37 | 251.127 | 39 | 251.127 |
| 36 | 263.1158 | 40 | 266.1267 | 104 | 268.0882 | 64 | 268.1423 |
| 100 | 277.0773 | 61 | 277.1426 | 62 | 277.1426 | 46 | 279.1583 |
| 84 | 287.1158 | 12 | 287.127 | 45 | 287.127 | 48 | 287.127 |
| 101 | 290.1267 | 99 | 291.0831 | 10 | 293.1086 | 19 | 295.0878 |
| 85 | 299.1158 | 49 | 299.127 | 7 | 300.111 | 71 | 302.0878 |
| 26 | 305.1263 | 14 | 306.1016 | 22 | 308.0289 | 63 | 308.1736 |
| 24 | 315.1219 | 18 | 316.1423 | 43 | 316.1423 | 58 | 316.1423 |
| 38 | 327.0106 | 42 | 327.1583 | 87 | 330.158 | 65 | 334.072 |
| 80 | 357.0688 | 74 | 364.119 | 30 | 364.1787 | 83 | 370.1893 |

| Mix 9 | MW | Mix 10 | MW |
|---|---|---|---|
| 96 | 251.127 | 104 | 240.1474 |
| 32 | 270.1004 | 33 | 254.0458 |
| 70 | 280.1059 | 31 | 280.1423 |
| 94 | 287.127 | 97 | 288.1222 |
| 77 | 296.1736 | 34 | 297.0001 |
| 13 | 302.1267 | 15 | 302.1267 |
| 78 | 310.072 | 52 | 310.1317 |
| 81 | 316.1423 | 75 | 320.1736 |
| 6 | 334.0787 | 93 | 340.0423 |
| 82 | 380.0372 | 9 | 387.0986 |

Figure 3A:
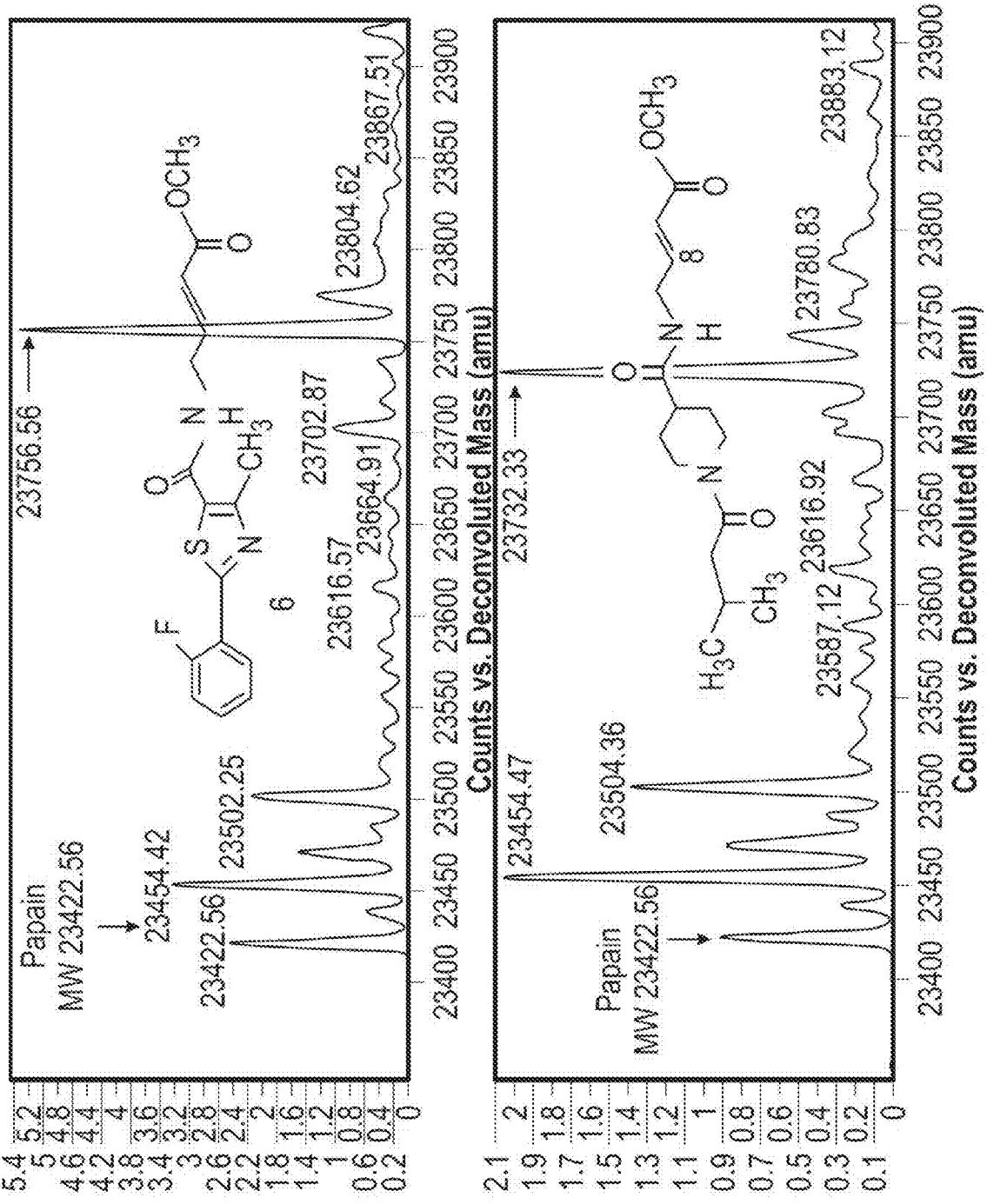
FIG. 3A and FIG. 3B. Representative MS spectra of 4 reaction mixtures containing 10 electrophilic fragments each screened against papain. Papain (10 μM) was incubated with a mixture of 10 electrophilic fragments (100 μM each) for 1 h, followed by gel filtration and ESI-MS of the intact protein.
Figure 3B:
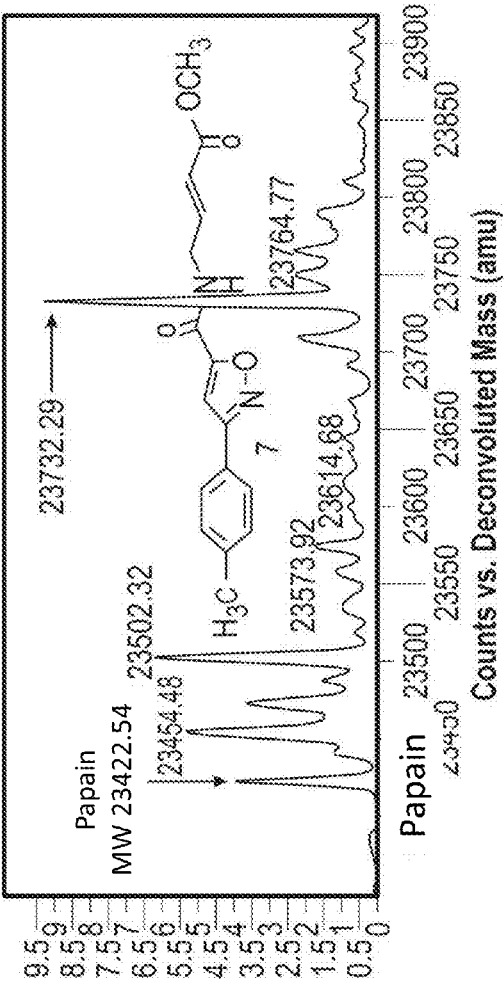
Figure 3B:
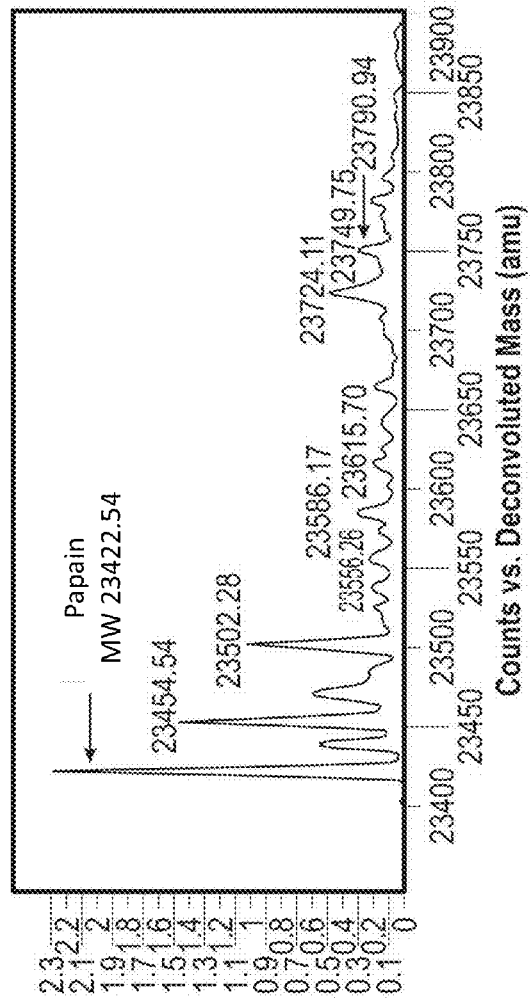

Each fragment in the reaction mixture had a unique molecular weight (at least 5 Da difference from the closest fragment) to ensure that whole protein ESI-MS could identify candidate hits unambiguously. Hits were defined as any compounds which labeled papain more than 50%. Remarkably, under these reaction conditions we observed strong mono-labeling of papain by three electrophilic fragments in three separate reaction mixtures: 6, 7, and 8 (FIGS. 3A and 3B). Such selectivity is impressive, given a 9-fold excess of other cysteine reactive electrophiles over compounds 6, 7, and 8. Moreover, we did not detect significant covalent modification of papain with the other seven reaction mixtures (FIG. 5). This is despite the fact that these reaction mixtures contain a 100-fold excess of cysteine reactive electrophiles relative to the highly reactive catalytic cysteine of papain. Furthermore, compounds 6, 7, and 8 labeled papain even though the corresponding reaction mixtures contained fragments that were equally or even more reactive toward N-acetylcysteine methyl ester. This observation further suggests that in our system the chemical structure of the drug-like fragment rather than its reactivity determines the covalent labeling of papain.

Figure 6A:
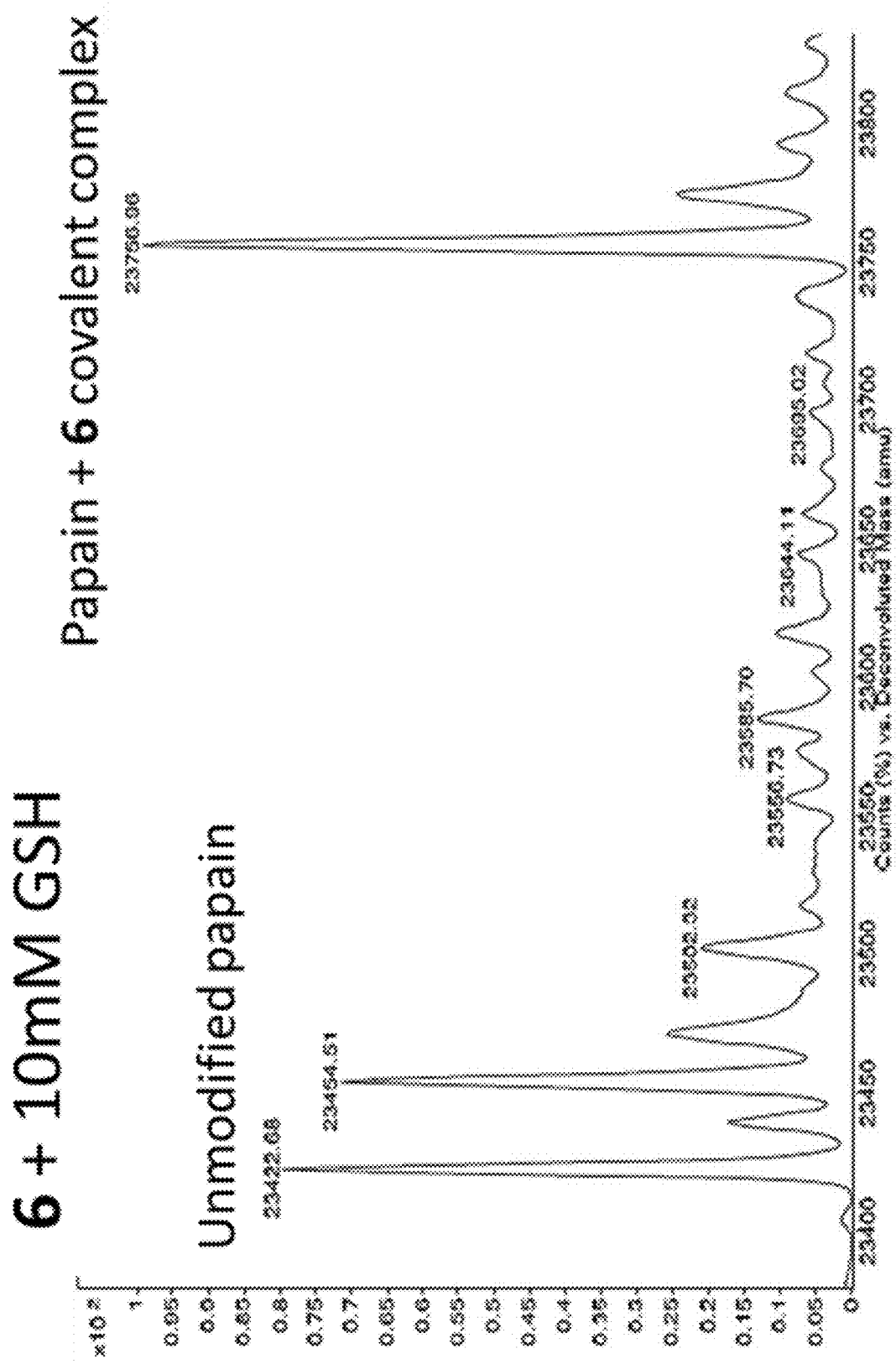
FIG. 6A, FIG. 6B and FIG. 6C. ESI-MS of the labeling of papain (10 μM) by 6 (FIG. 6A), 7 (FIG. 6B), or 8 (C) (100 μM each, 1 h) in the presence of 10 mM glutathione (GSH).
Figure 6B:
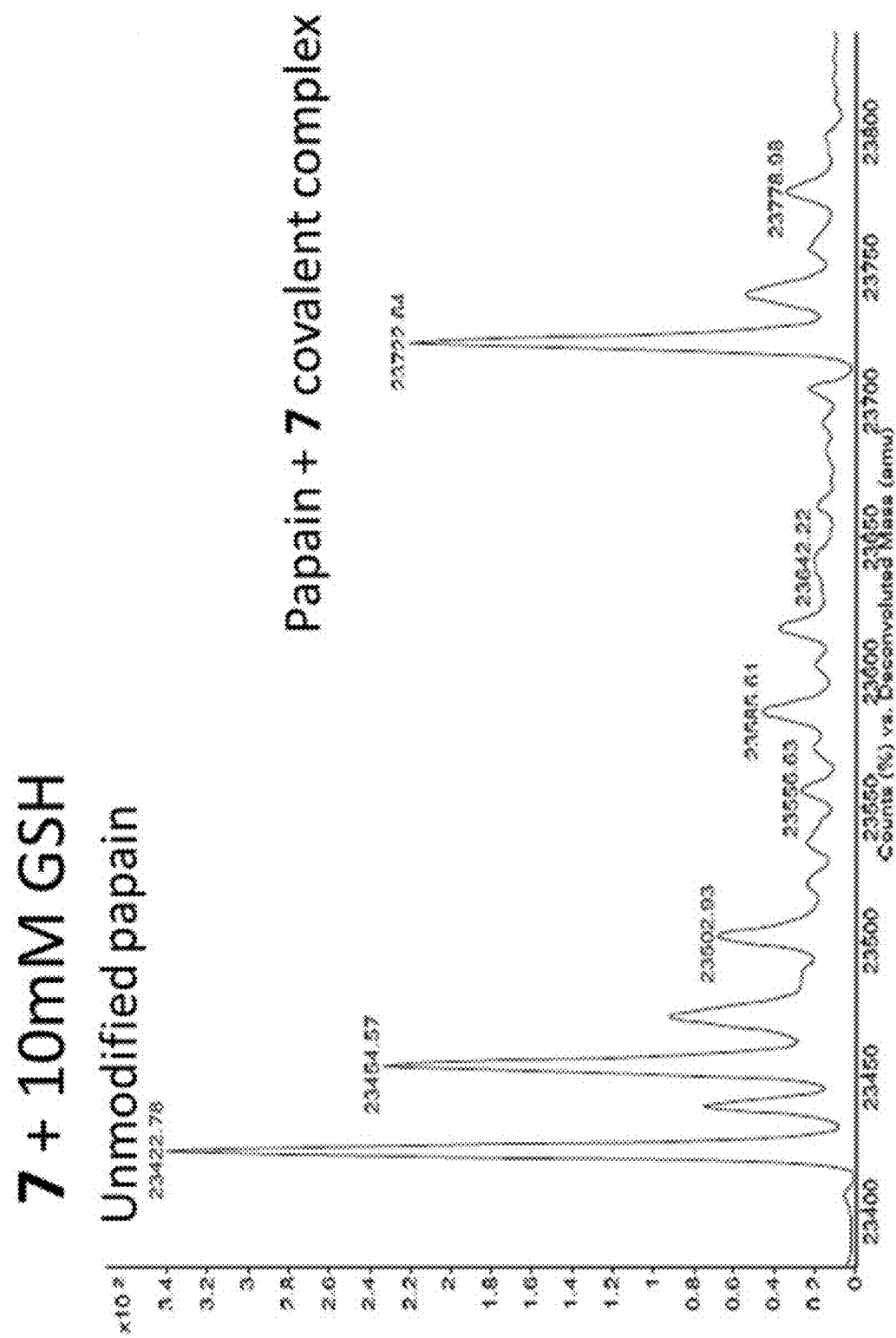
Figure 6C:
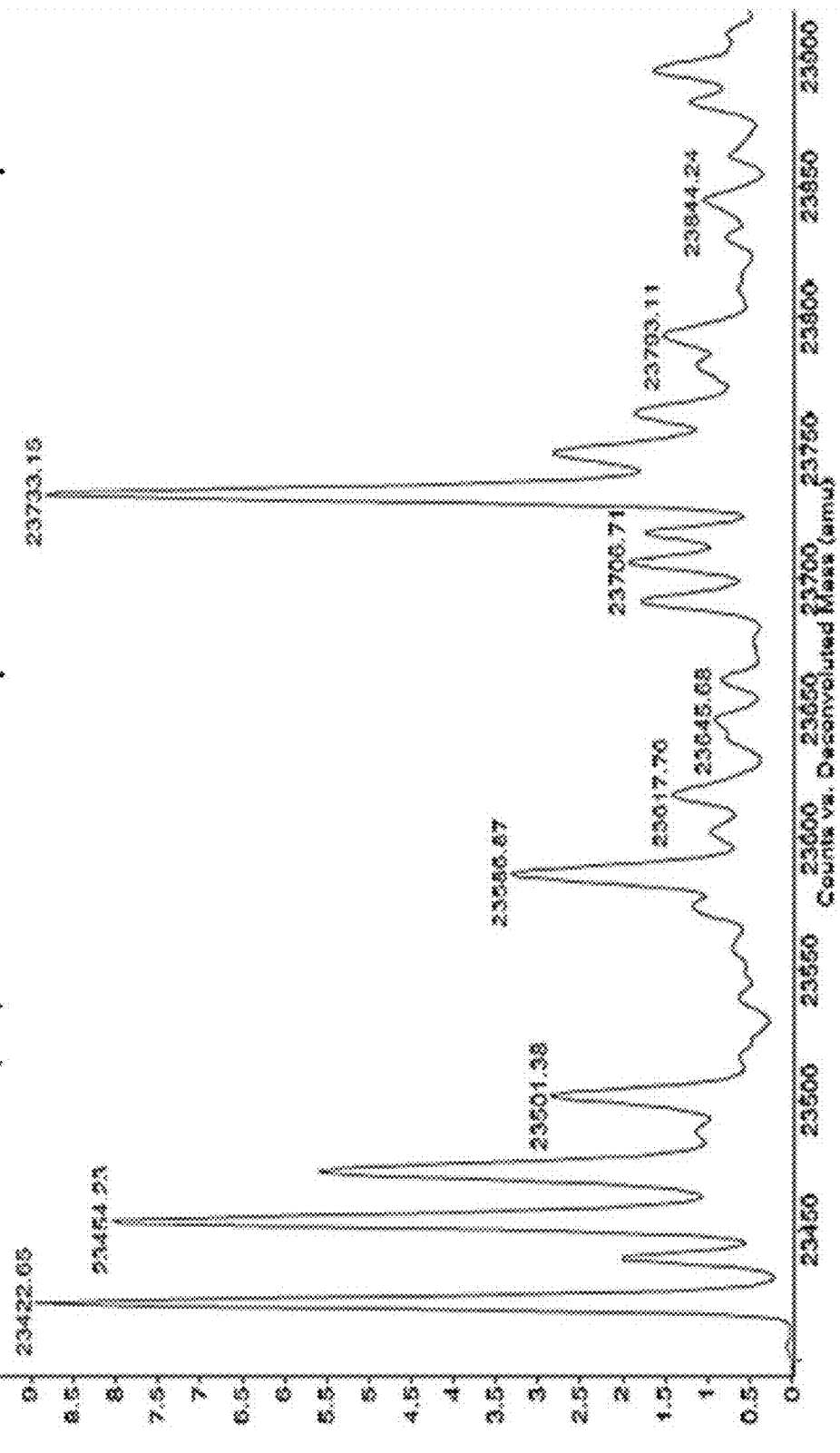

Additionally, compounds 6-8 demonstrated robust labeling of papain in the presence of 10 mM glutathione (1000 fold excess relative to papain), confirming that compounds 6-8 covalently label papain due to their specific binding to papain and not simply due to their greater thiol reactivity (FIG. 6).

Figure 7A:
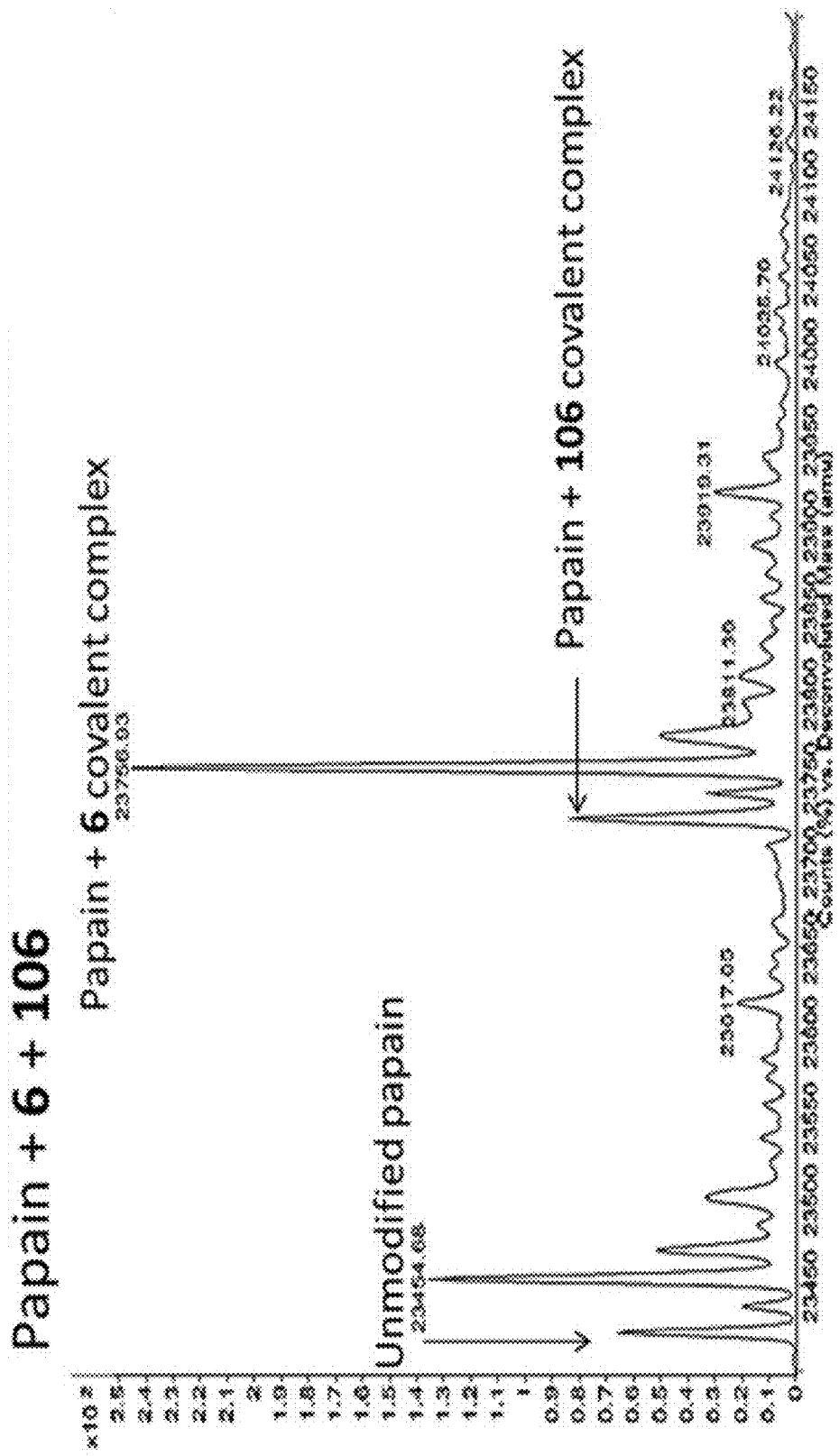
FIG. 7A, FIG. 7B, FIG. 7C, FIG. 7D, FIG. 7E, FIG. 7F and FIG. 7G. ESI-MS of papain treated with 100 μM of 6 (FIG. 7A), 7 (FIG. 7B), or 8 (FIG. 7C) for 1 h followed by addition of 106 (100 μM) and incubation for 1 h. Treatment of papain with 100 μM of 106 alone is shown for comparison. The 7+106 and 8+106 spectra do not show separation between the peaks because inhibitors 7 and 8 are too close in MW to 106, but the peak is instead a weighted average of the two peaks. However, in no case did treatment with 6-8 followed by 106 result in dilabeling of papain. ESI-MS of papain treated with 100 μM of 106 for 1 h (FIG. 7D), followed by addition of 100 μM of 6 (FIG. 7E), 7 (FIG. 7F) or 8 (FIG. 7G). In no case did treatment with 106 followed by 6-8 result in dilabeling of papain.
Figure 7B:
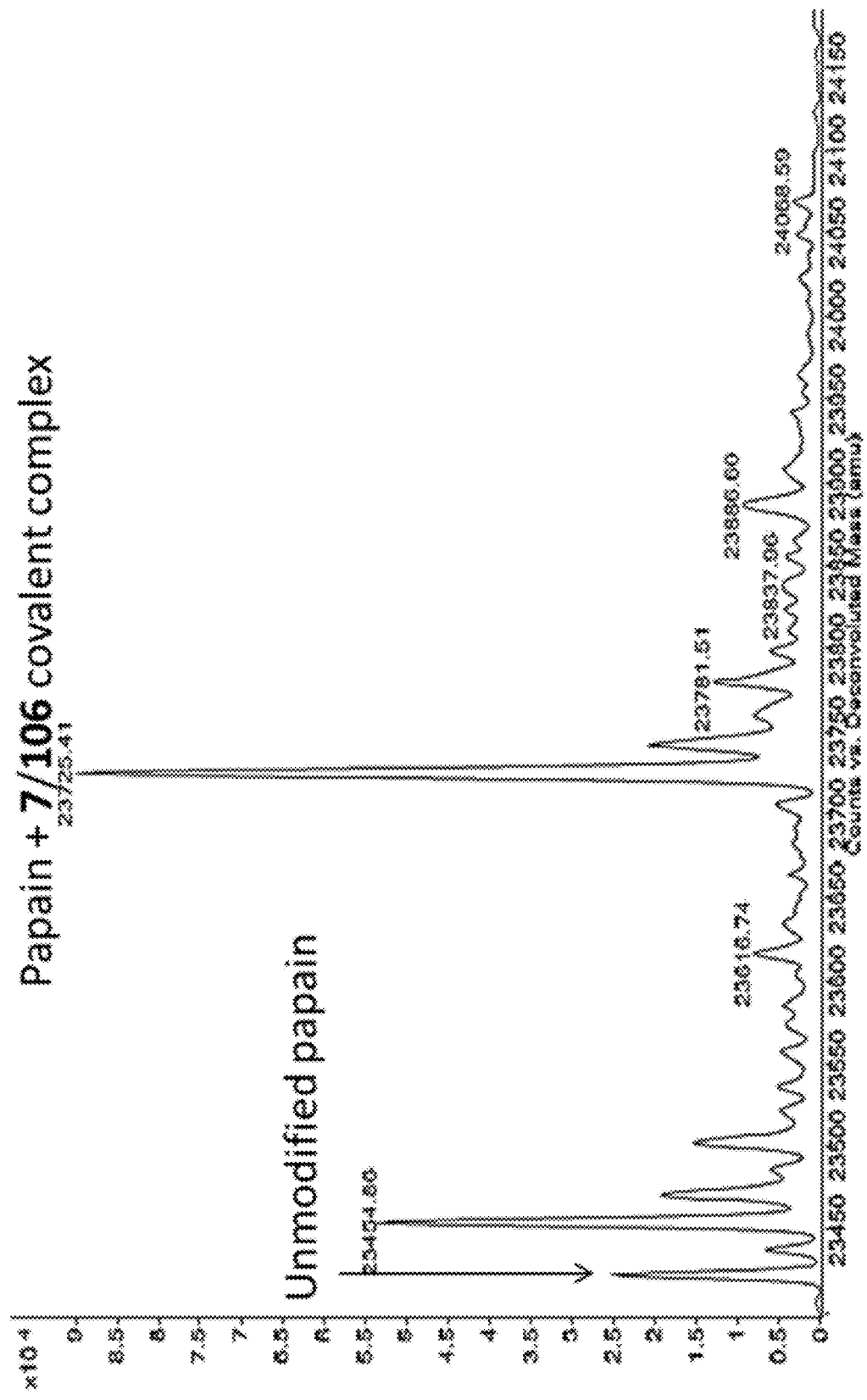
Figure 7C:
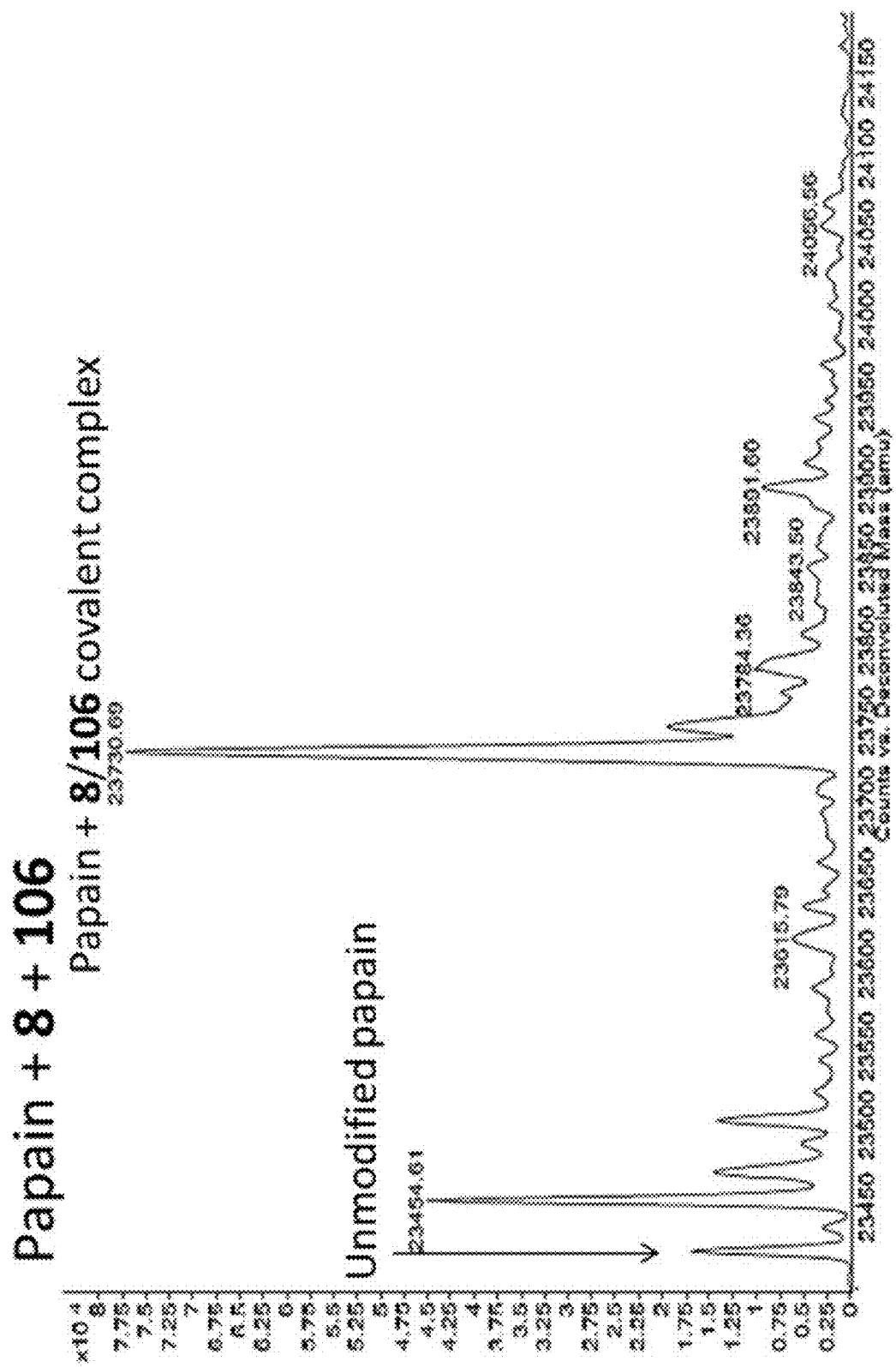
Figure 7D:
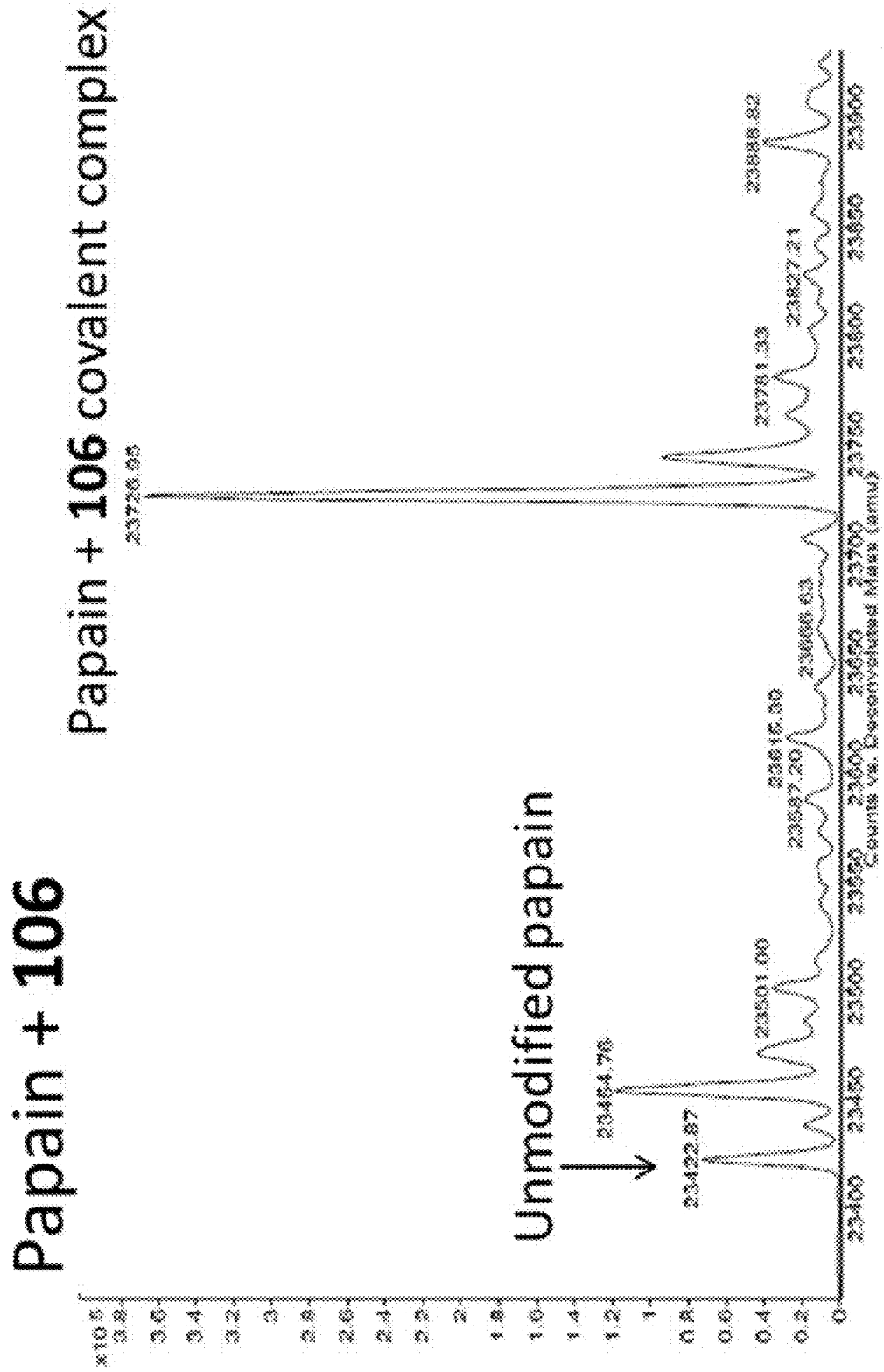
Figure 7E:
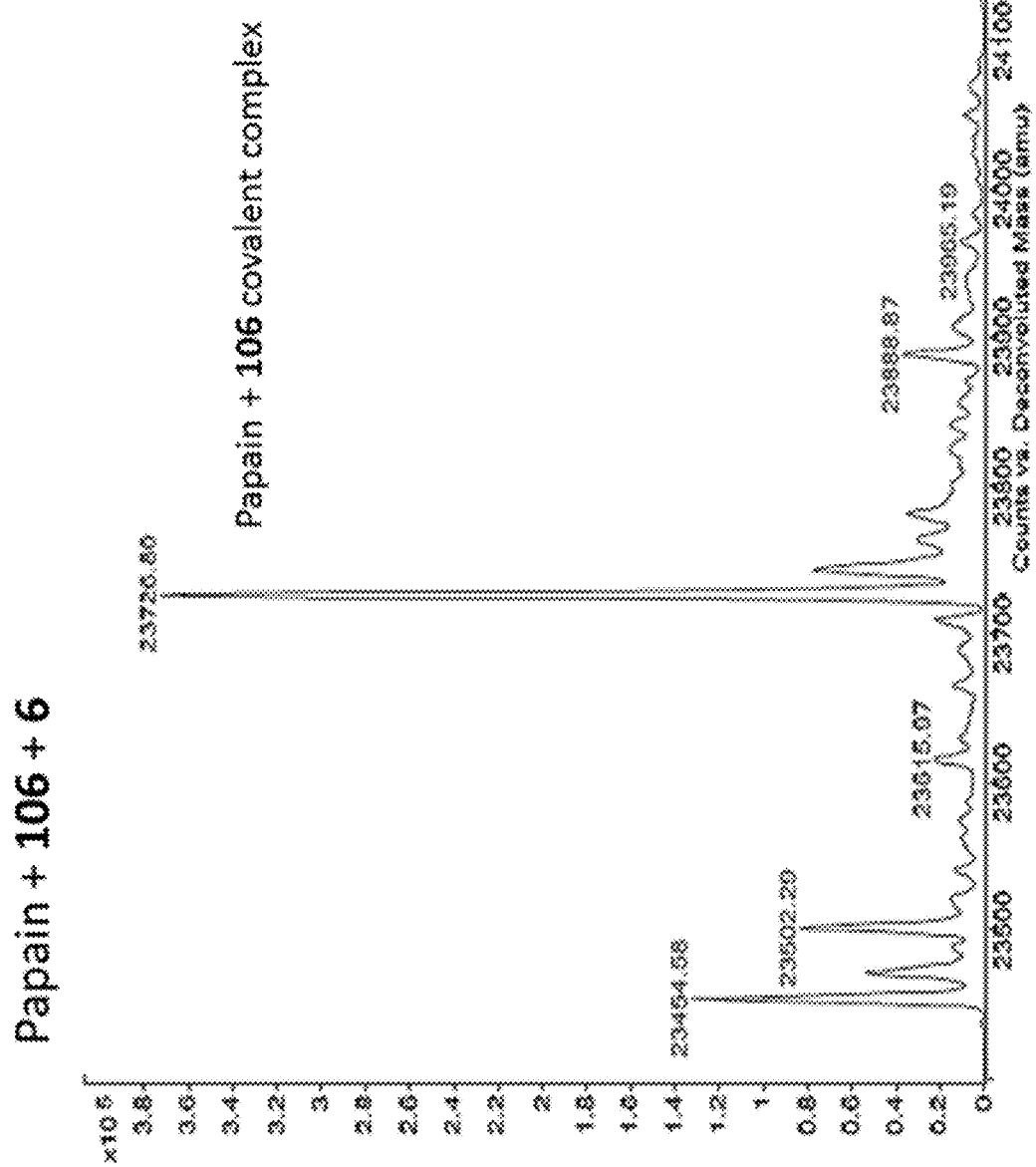
Figure 7F:
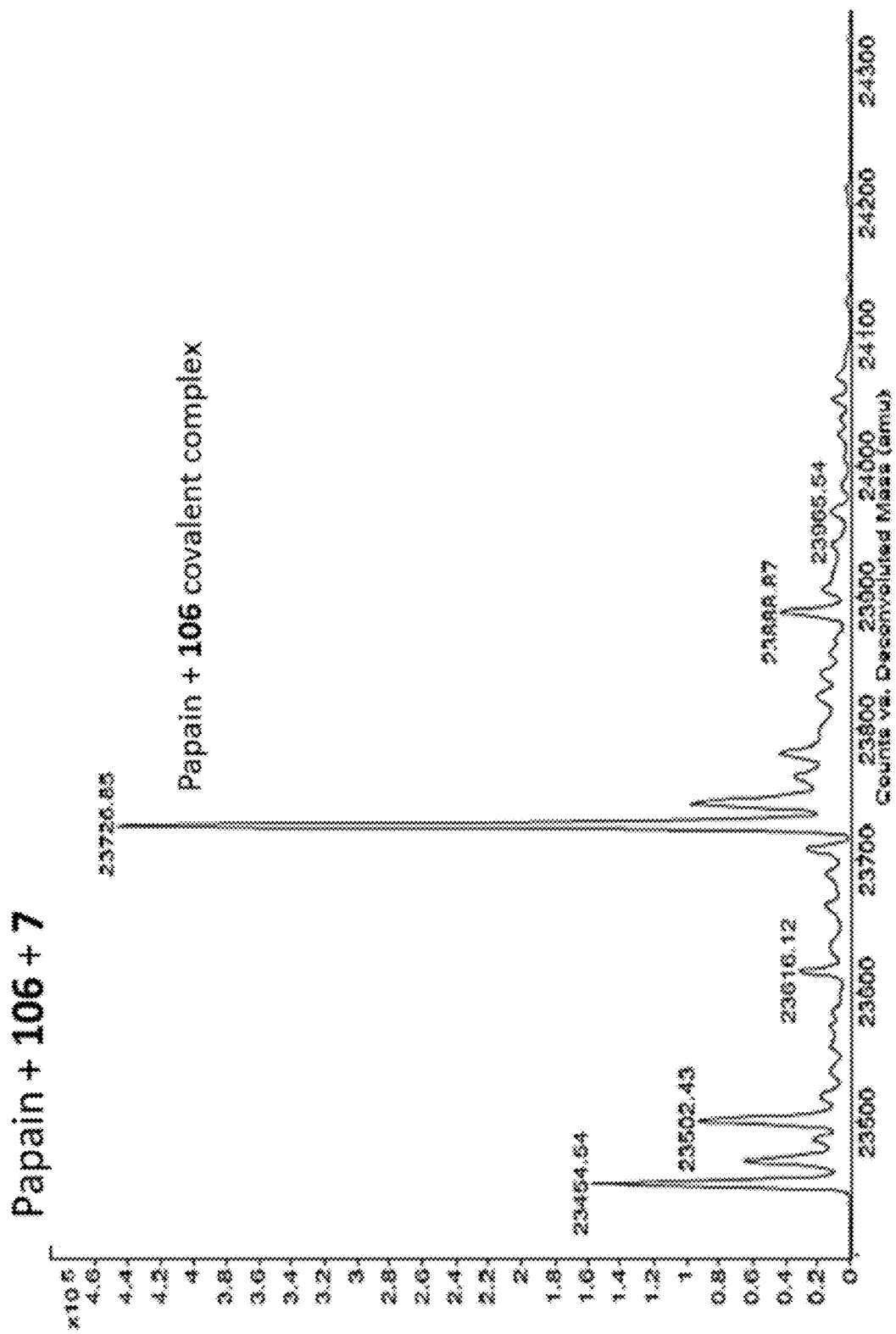
Figure 7G:
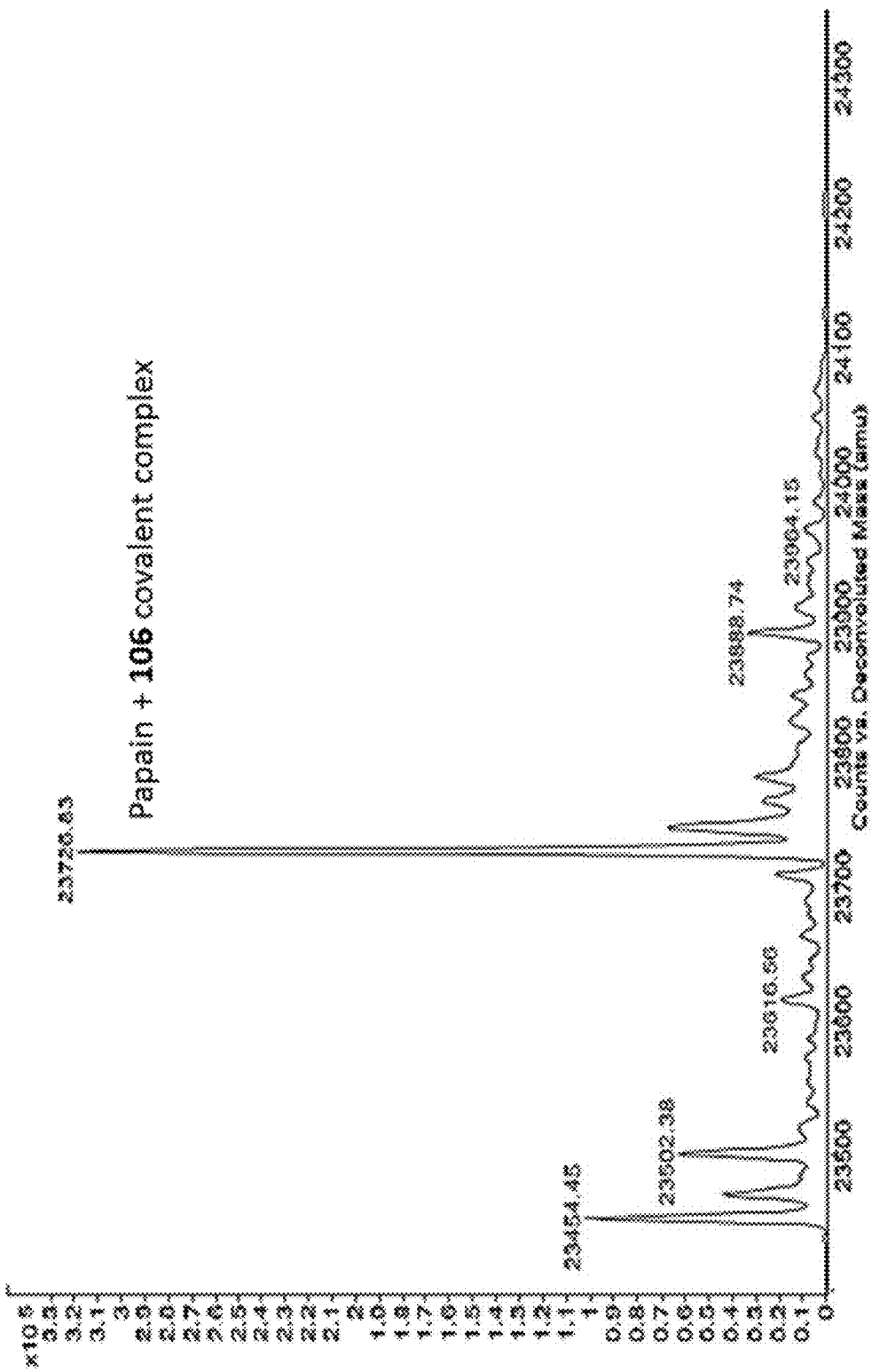
Figure 8A:
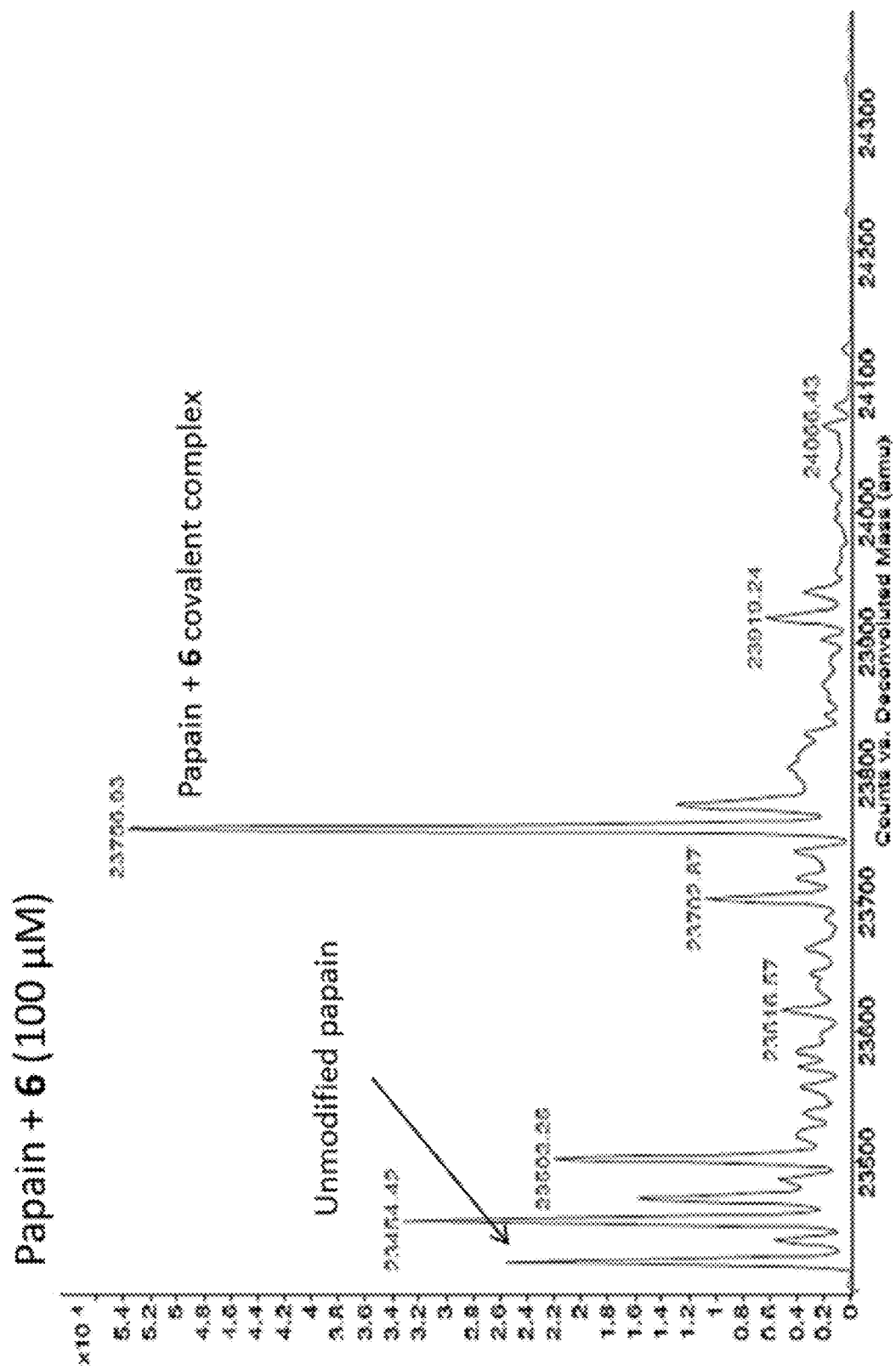
FIG. 8A, FIG. 8B, FIG. 8C, FIG. 8D, FIG. 8E and FIG. 8F. ESI-MS of the labeling of papain (10 μM) by 100 μM each, 1 h of 6 (FIG. 8A), 7 (FIG. 8B), or 8 (FIG. 8C) or 1 mM each, 1 h, of 6 (FIG. 8D), 7 (FIG. 8E), or 8 (FIG. 8F), zoomed out to show no dilabeling.
Figure 8B:
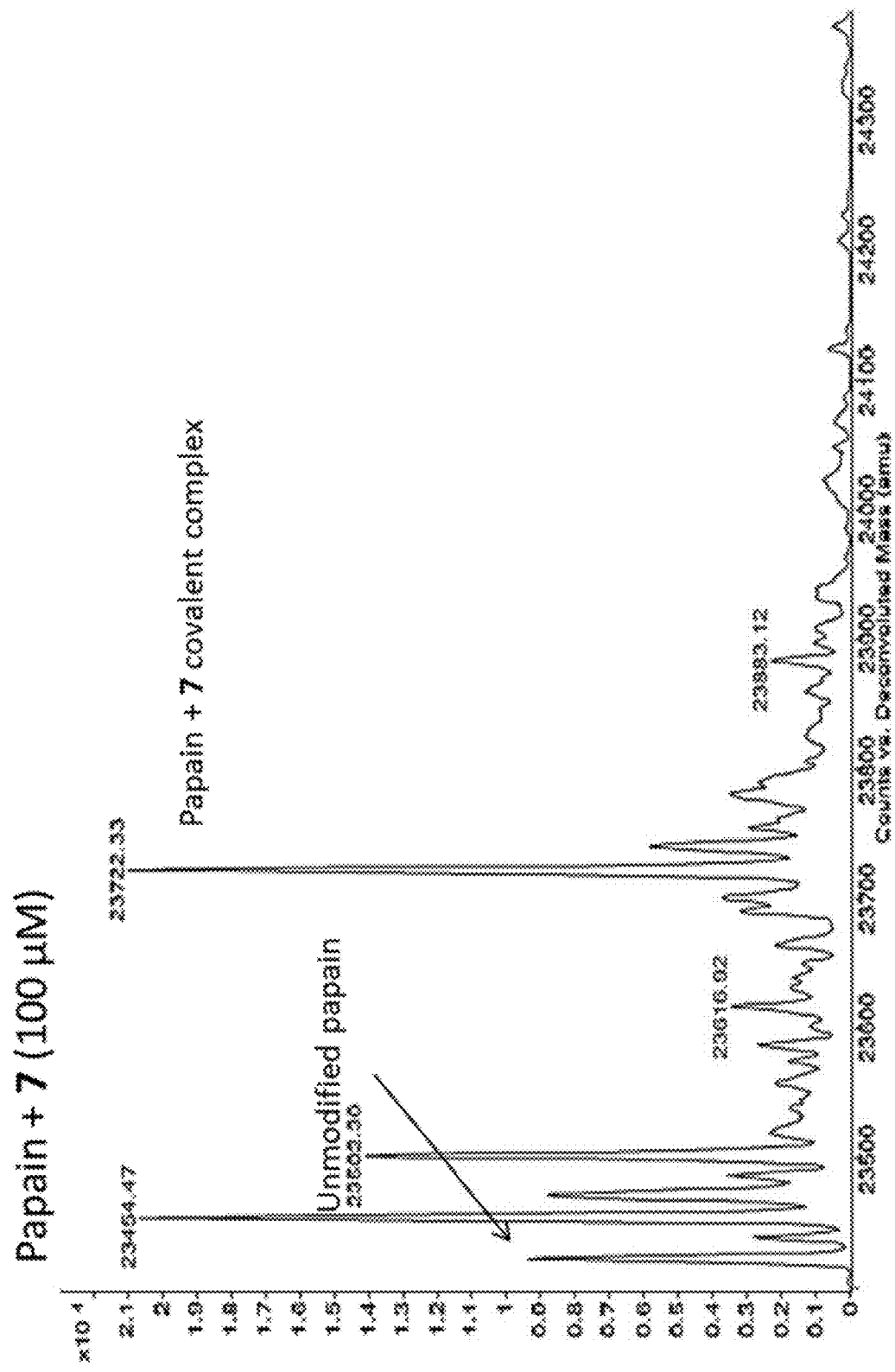
Figure 8C:
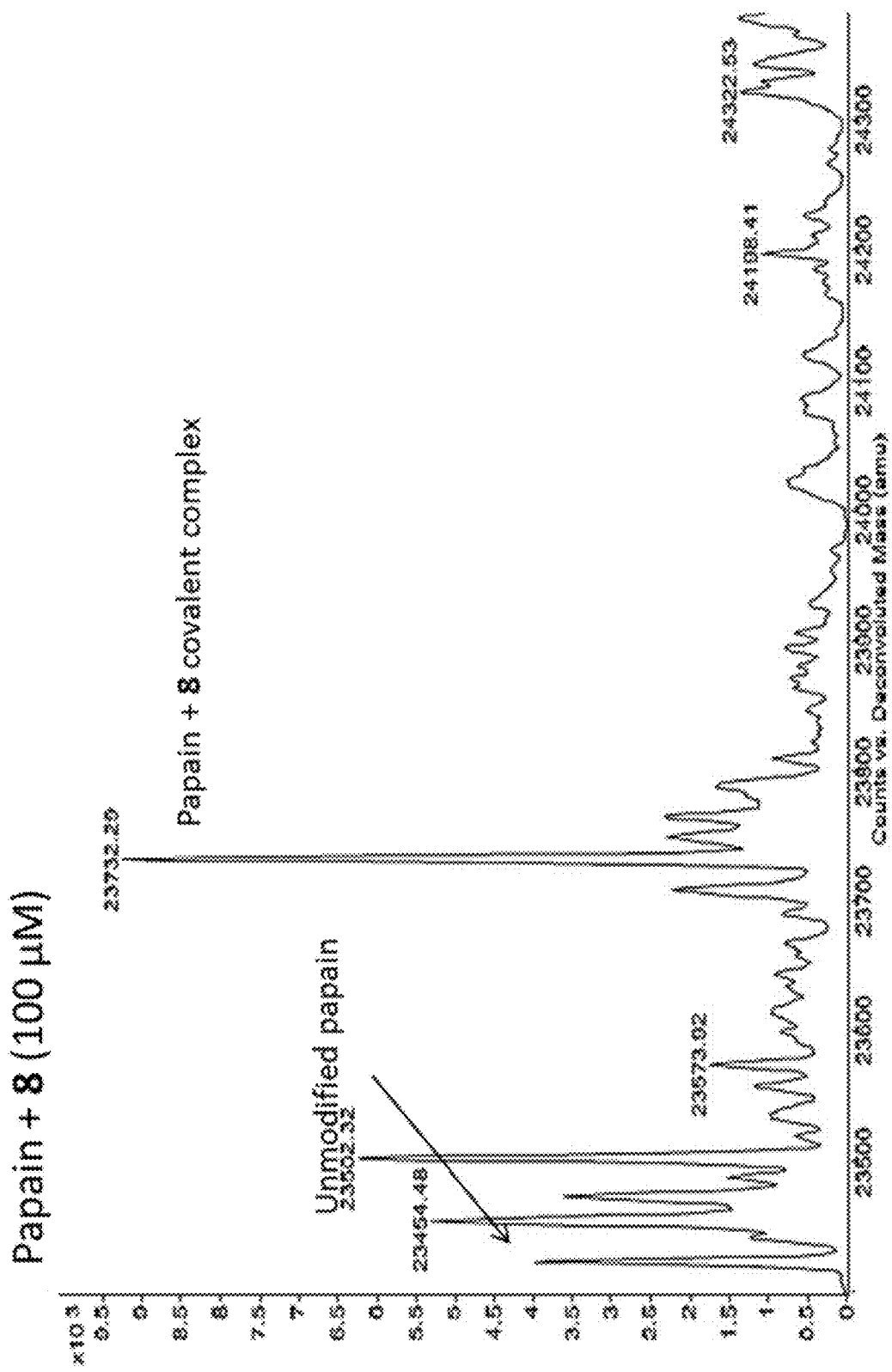
Figure 8D:
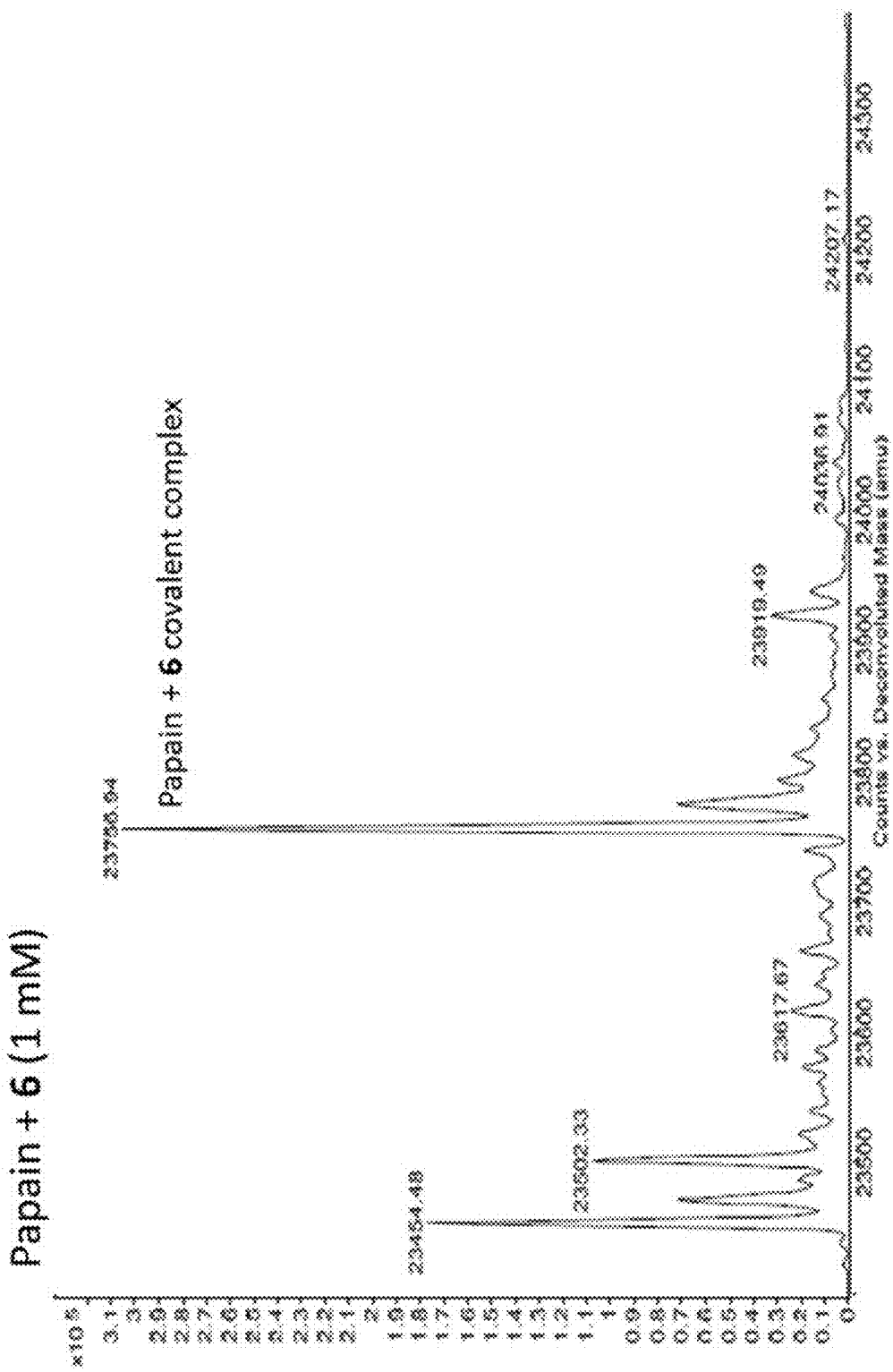
Figure 8E:
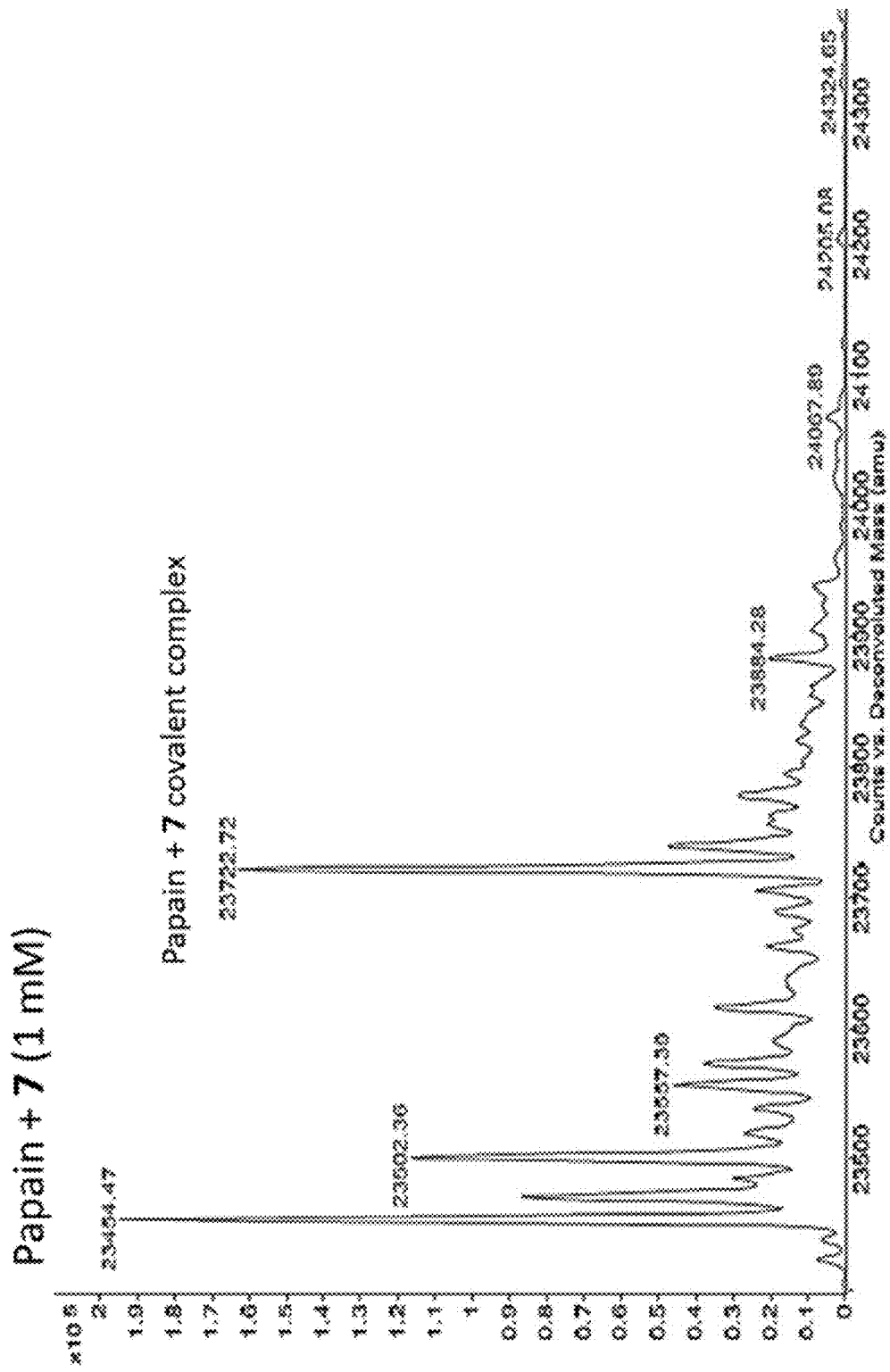
Figure 8F:
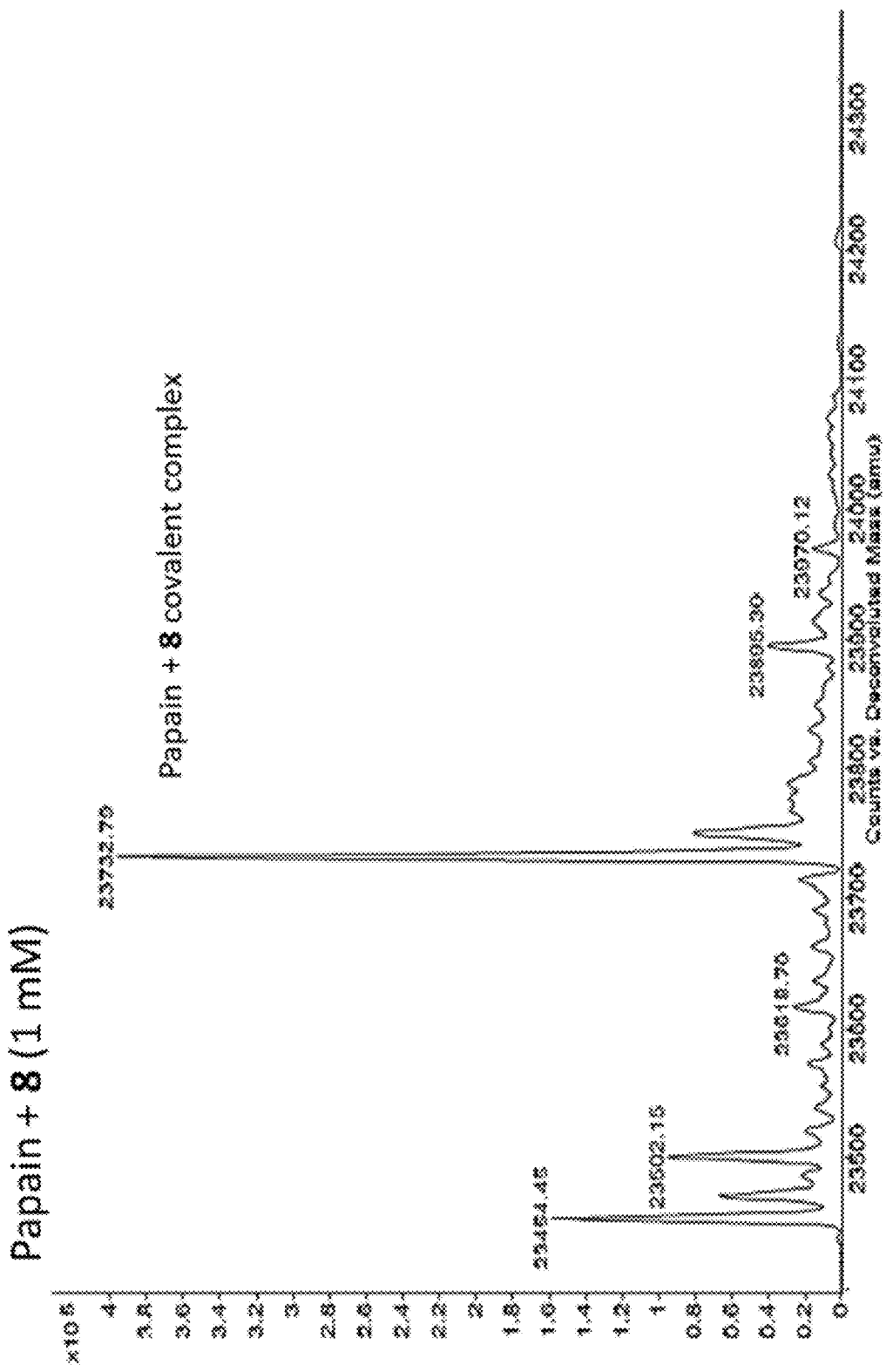
Figure 9A:
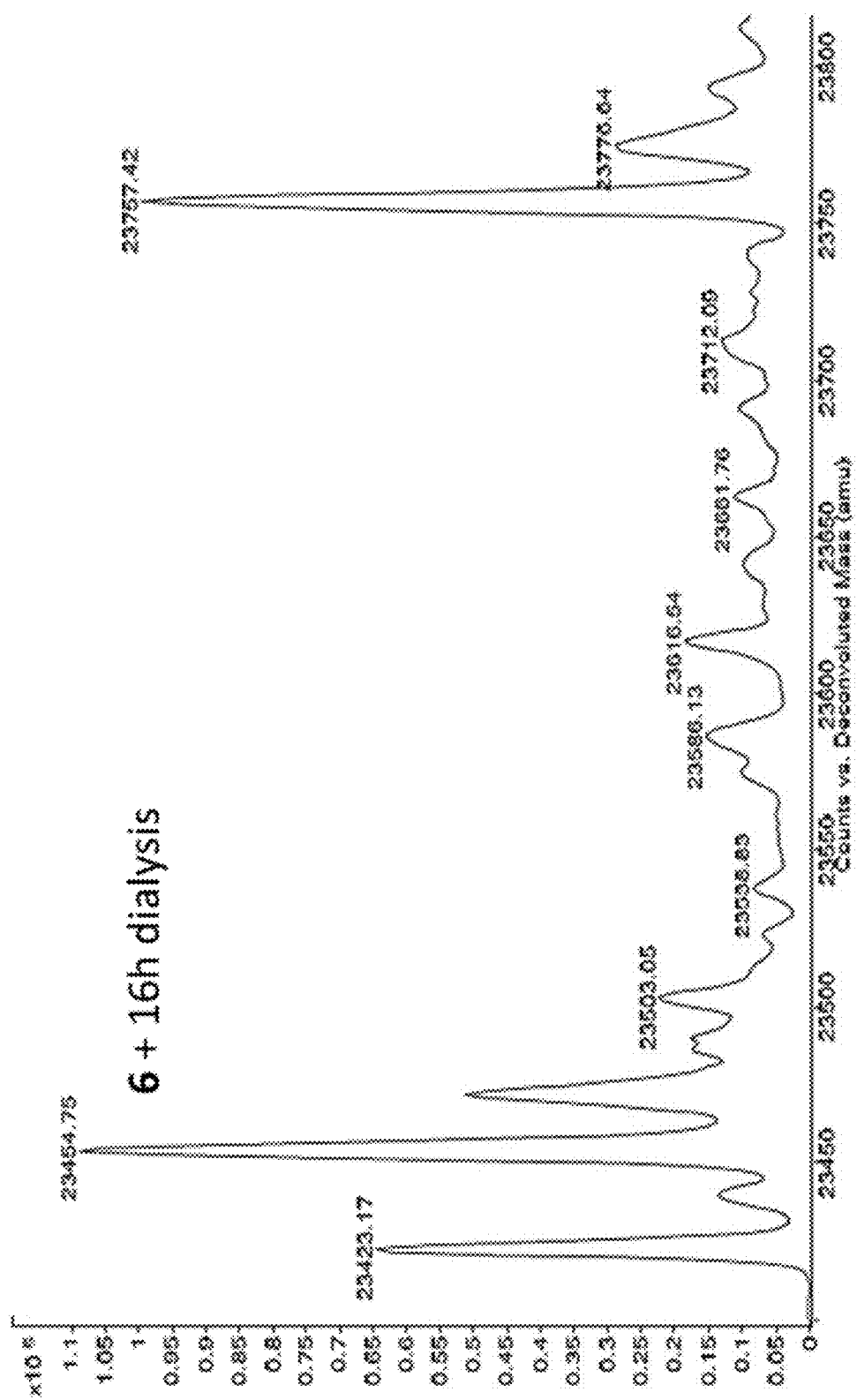
FIG. 9A, FIG. 9B, FIG. 9C, FIG. 9D, FIG. 9E, FIG. 9F, FIG. 9G and FIG. 9H. Papain+compound 6 (FIG. 9A), FIG. 9(B), and (FIG. 9C), Papain+compound 7 (FIG. 9D), (FIG. 9E), and (FIG. 9F), Papain+compound 8 (FIG. 9G) and (FIG. 9H) covalent adducts after 16 h, 40 h, and 64 h of dialysis as described in the experimental section.
Figure 9B:
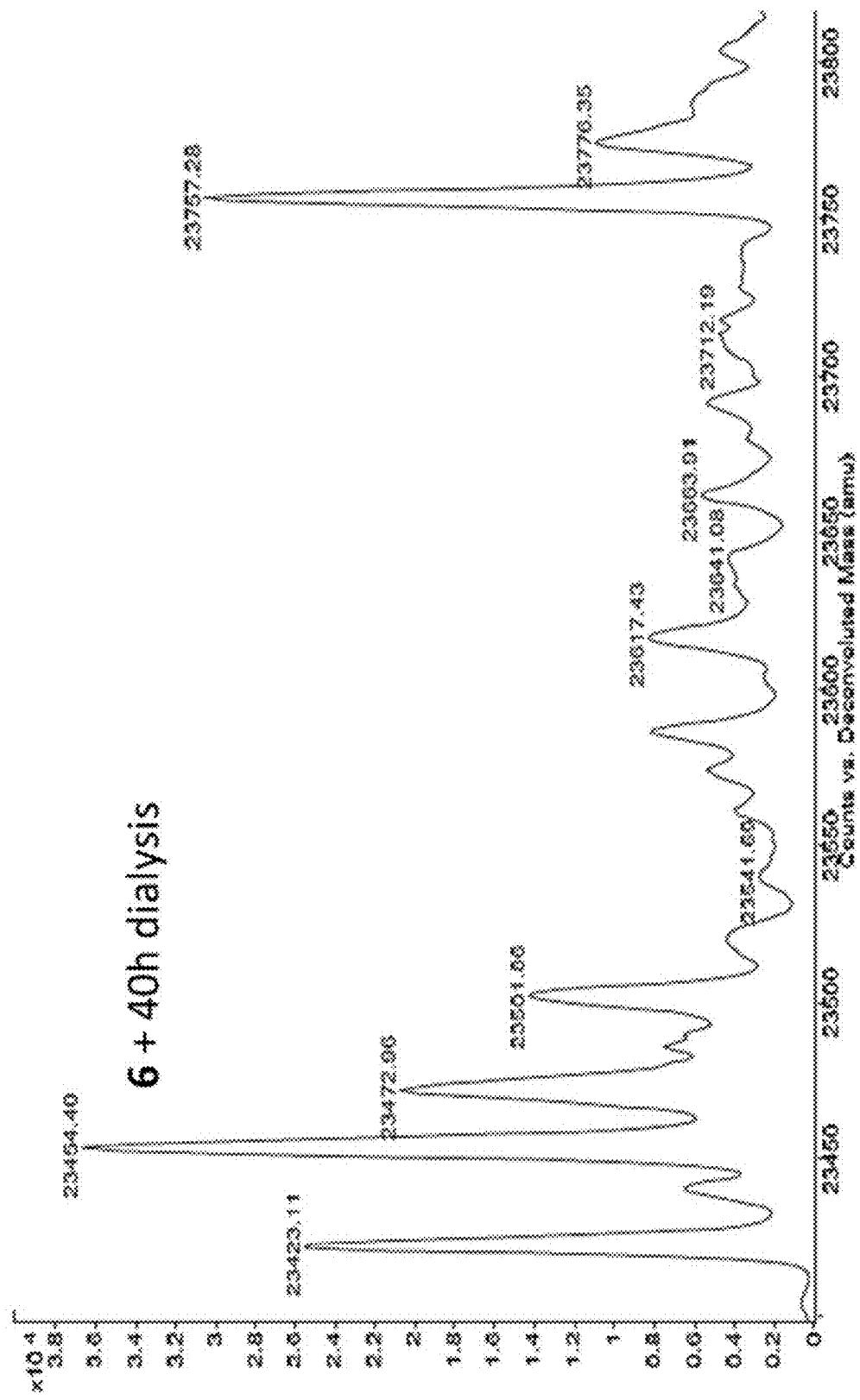
Figure 9C:
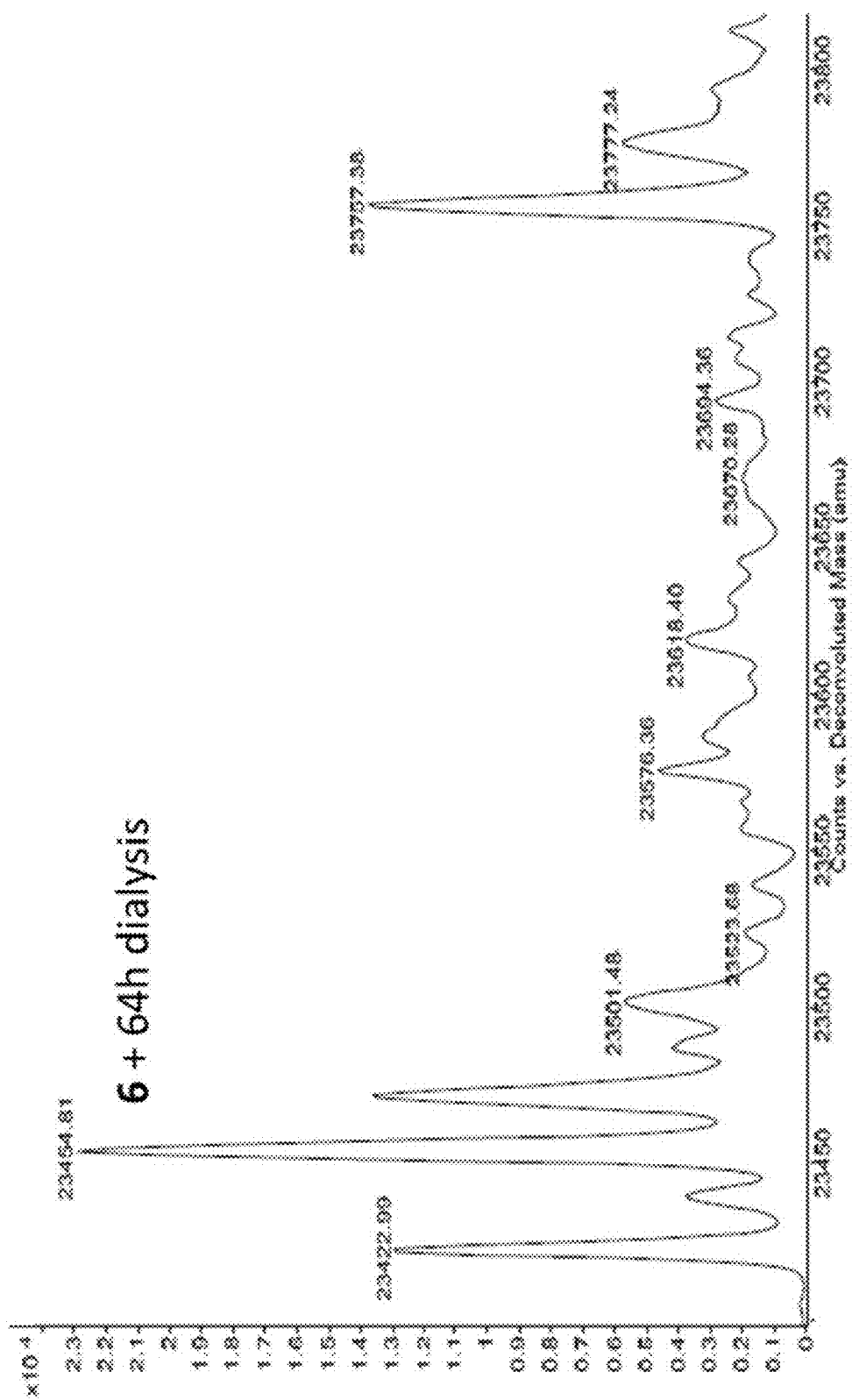
Figure 9D:
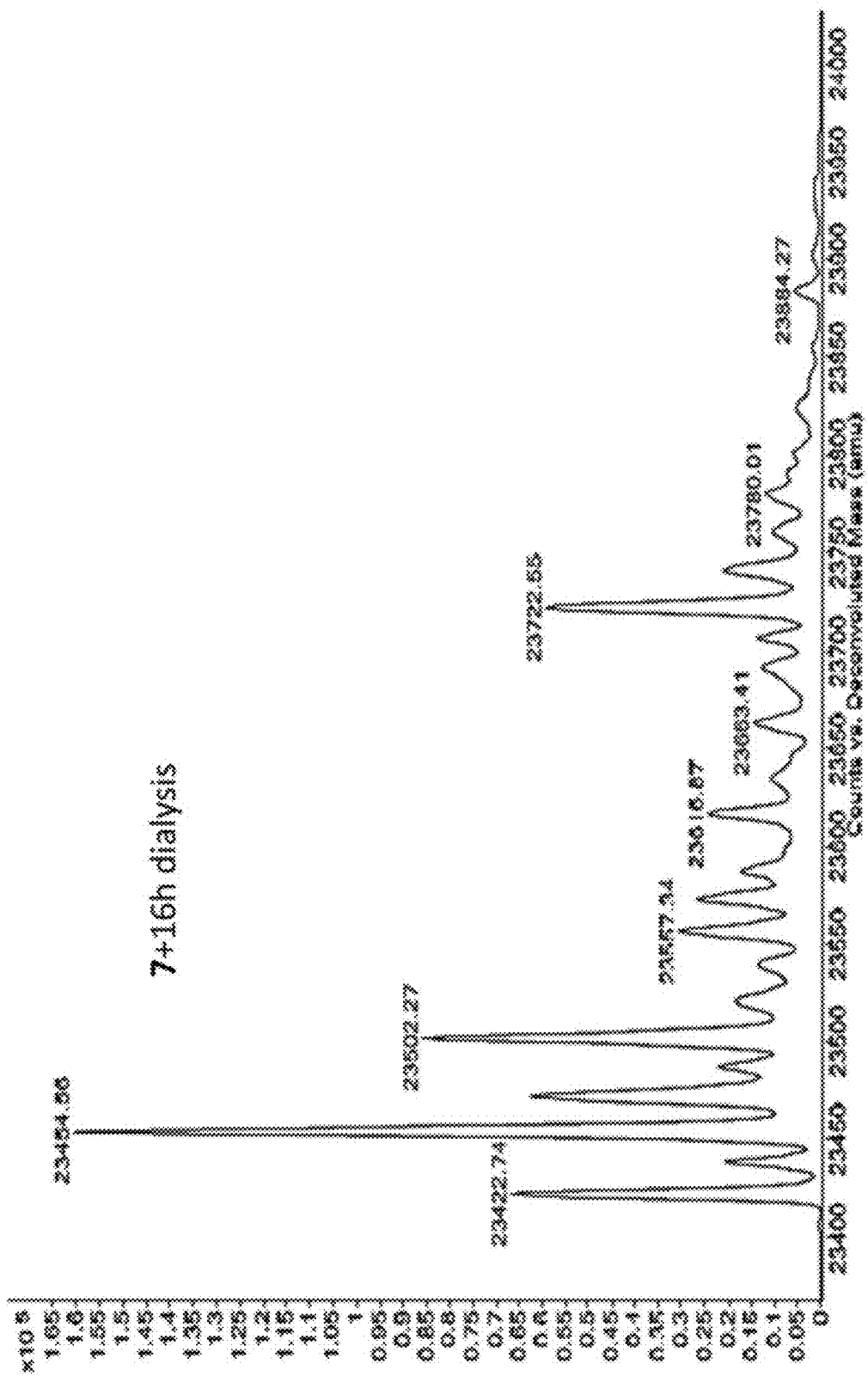
Figure 9E:
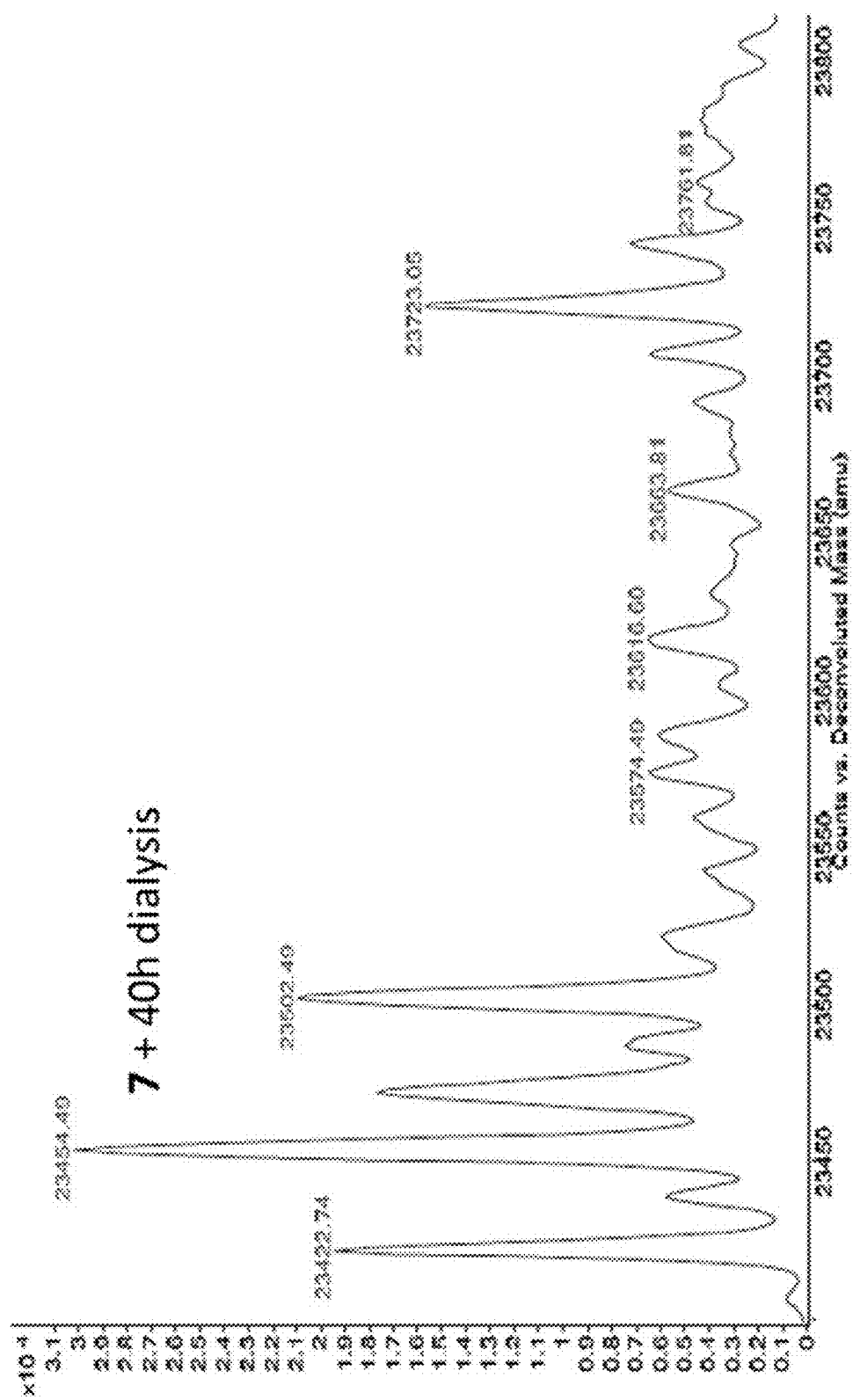
Figure 9F:
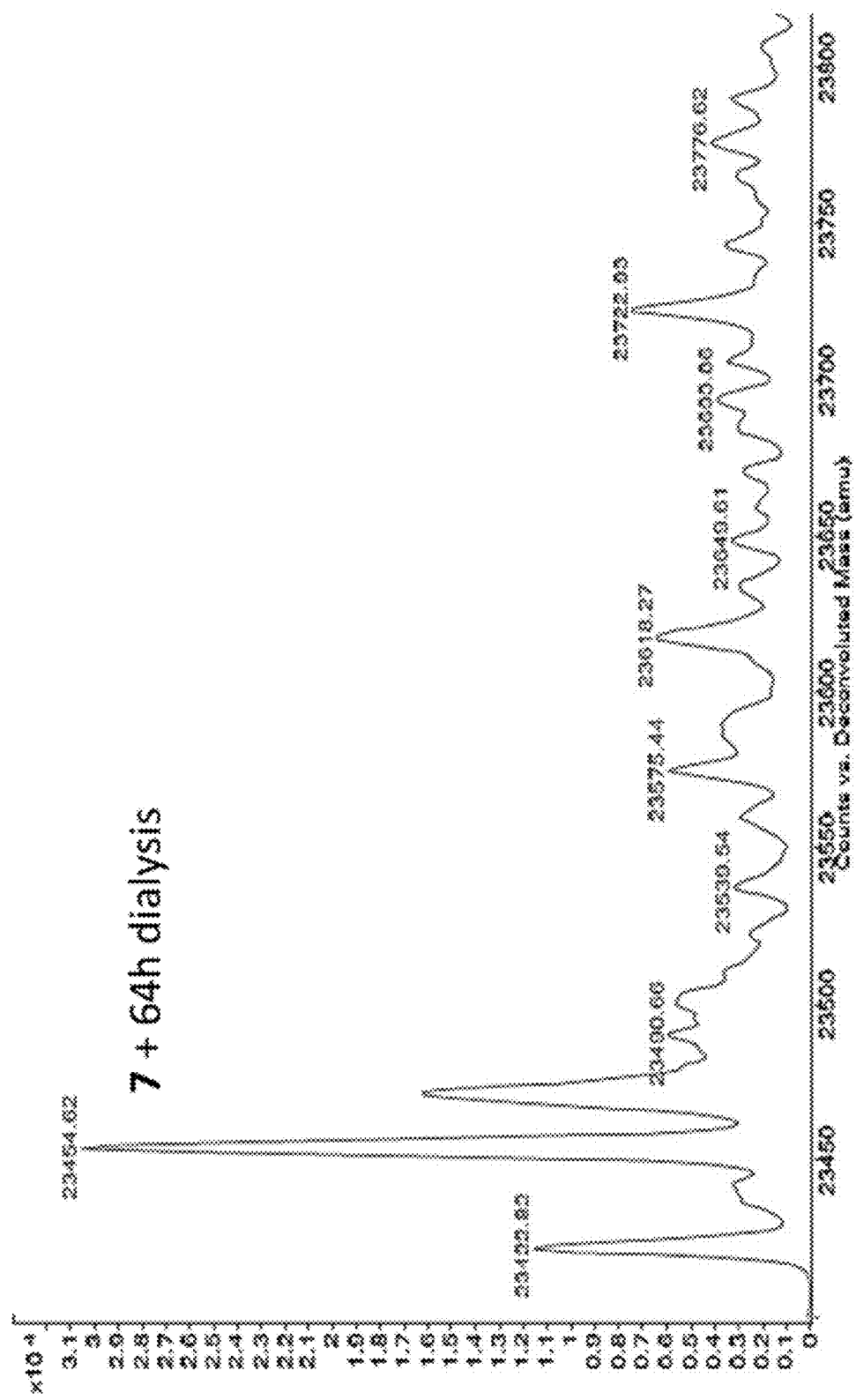
Figure 9G:
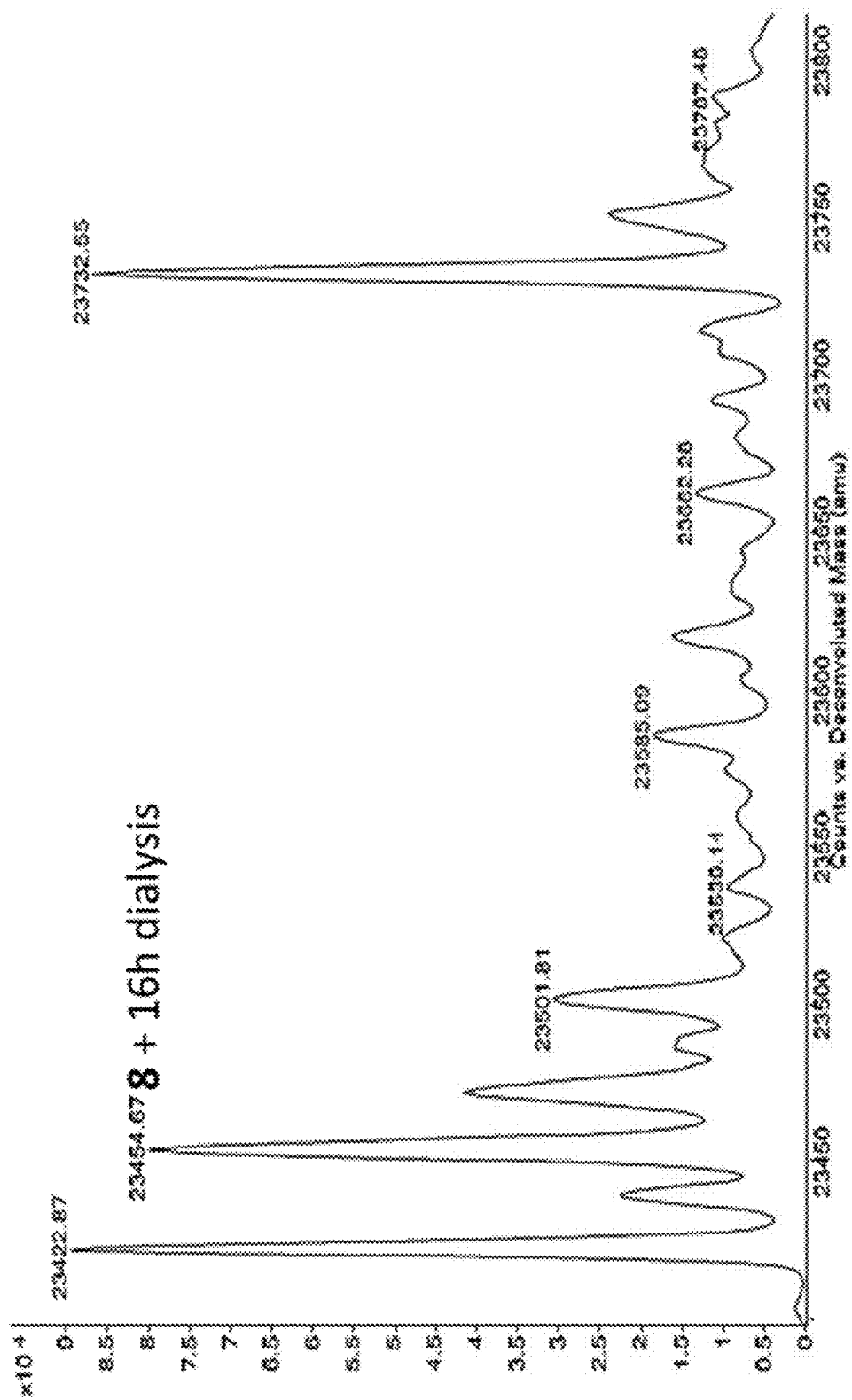
Figure 9H:
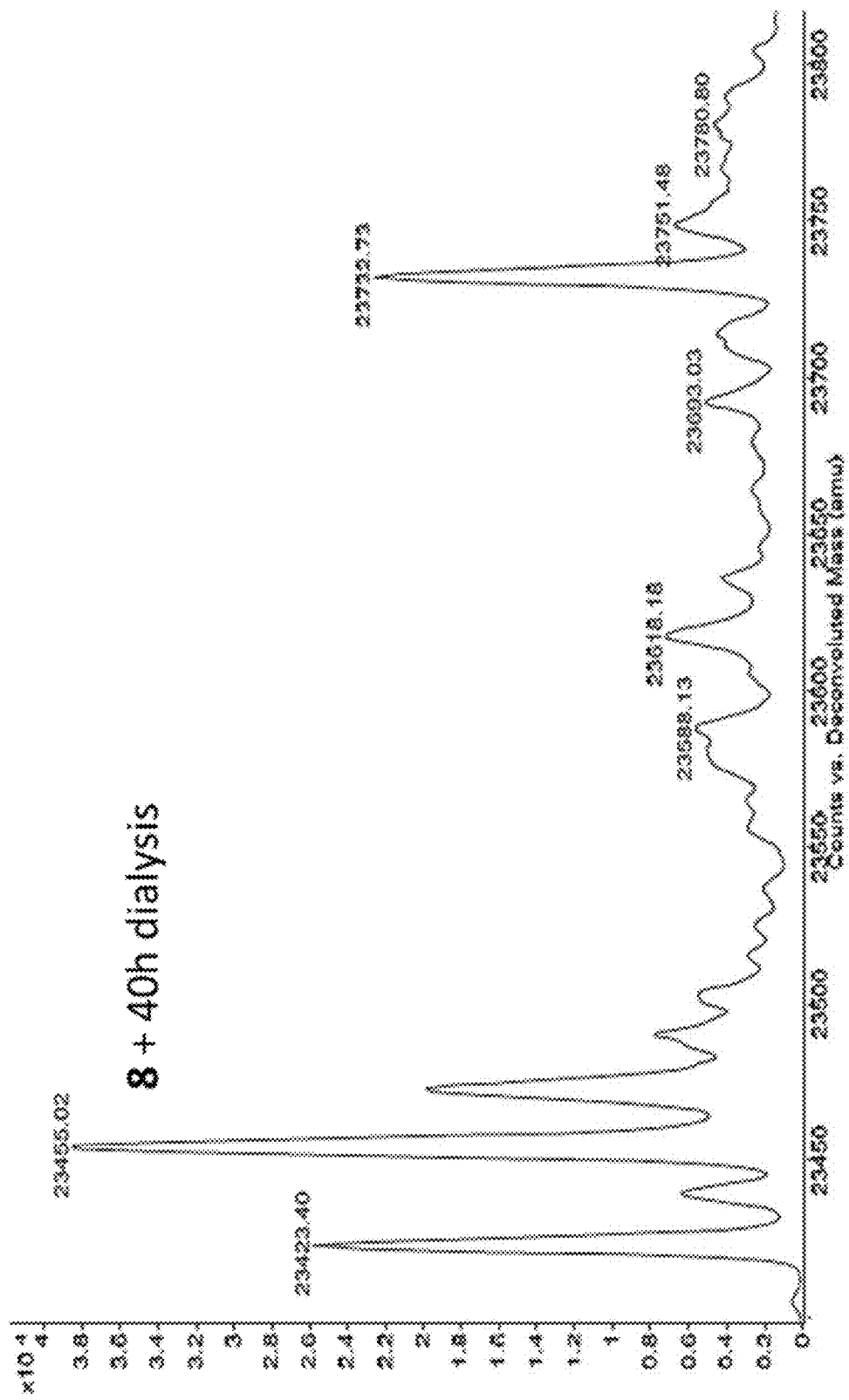
Figure 10A:
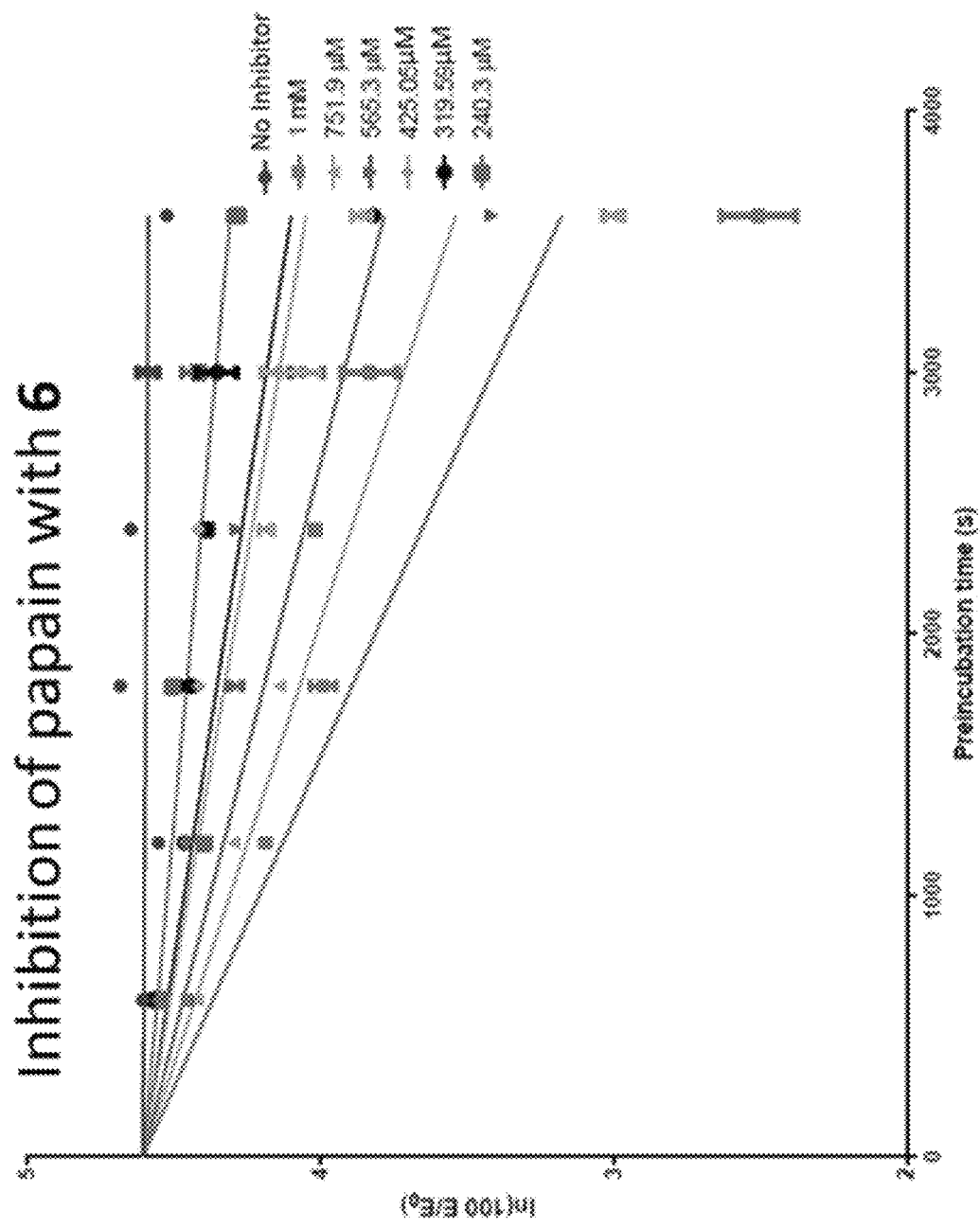
FIG. 10A, FIG. 10B, FIG. 10C, FIG. 10D, FIG. 10E and FIG. 10F. Pseudo-first order papain inhibition plots at different concentrations of 6 (FIG. 10A), 7 (FIG. 10B), 8 (FIG. 10C), 19 (FIG. 10D), 106 (FIG. 10E), and 107 (FIG. 10F).
Figure 10B:
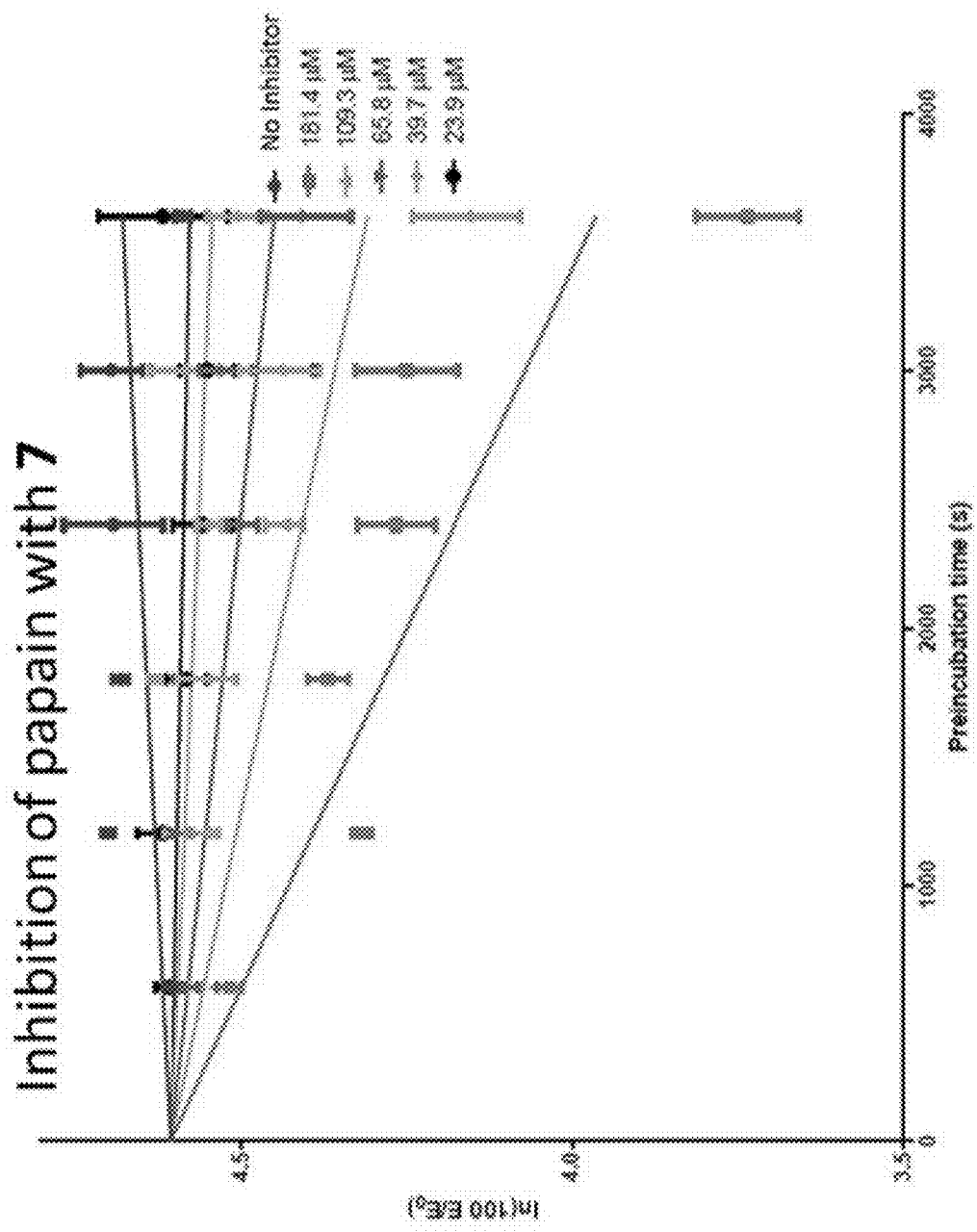
Figure 10C:
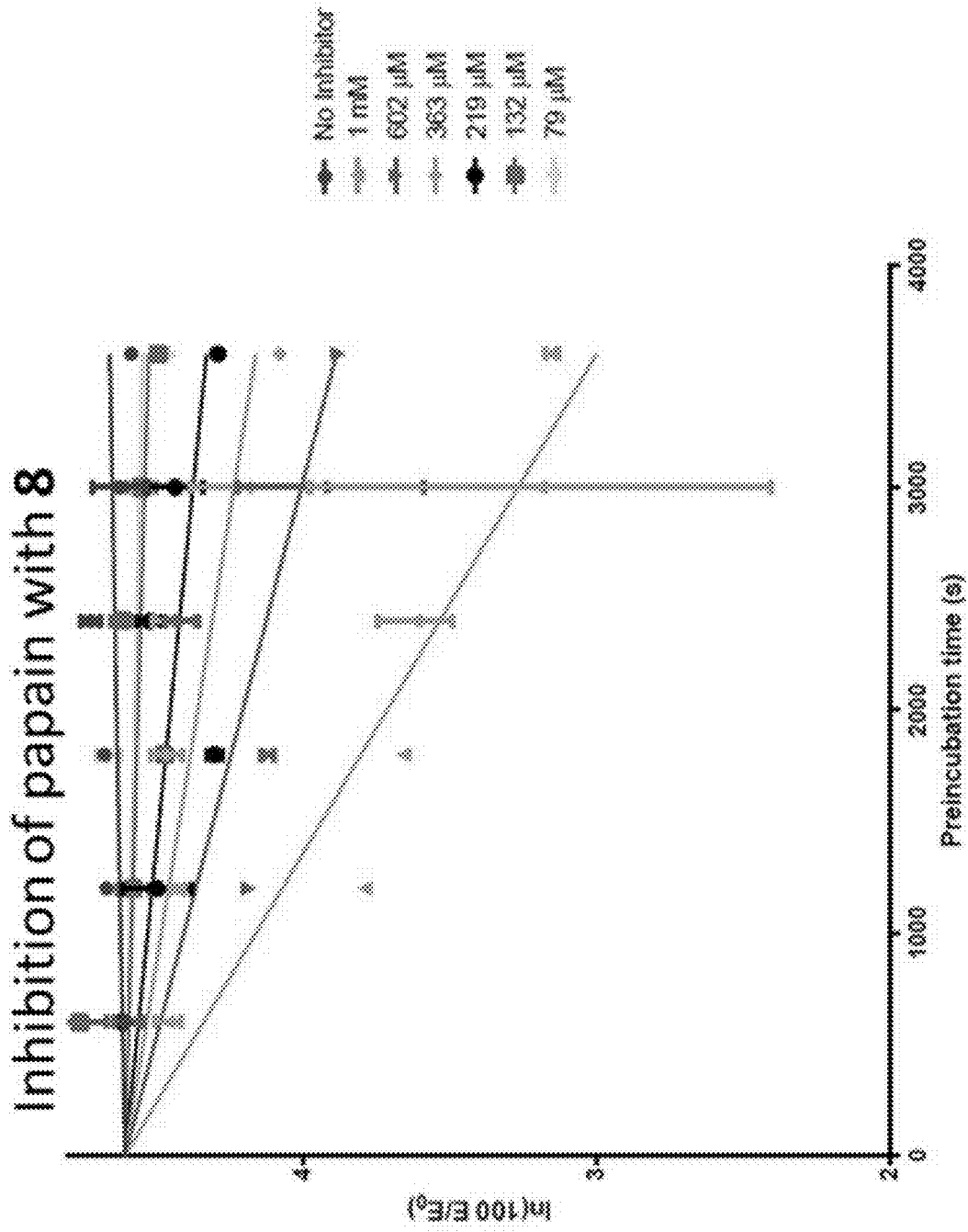
Figure 10D:
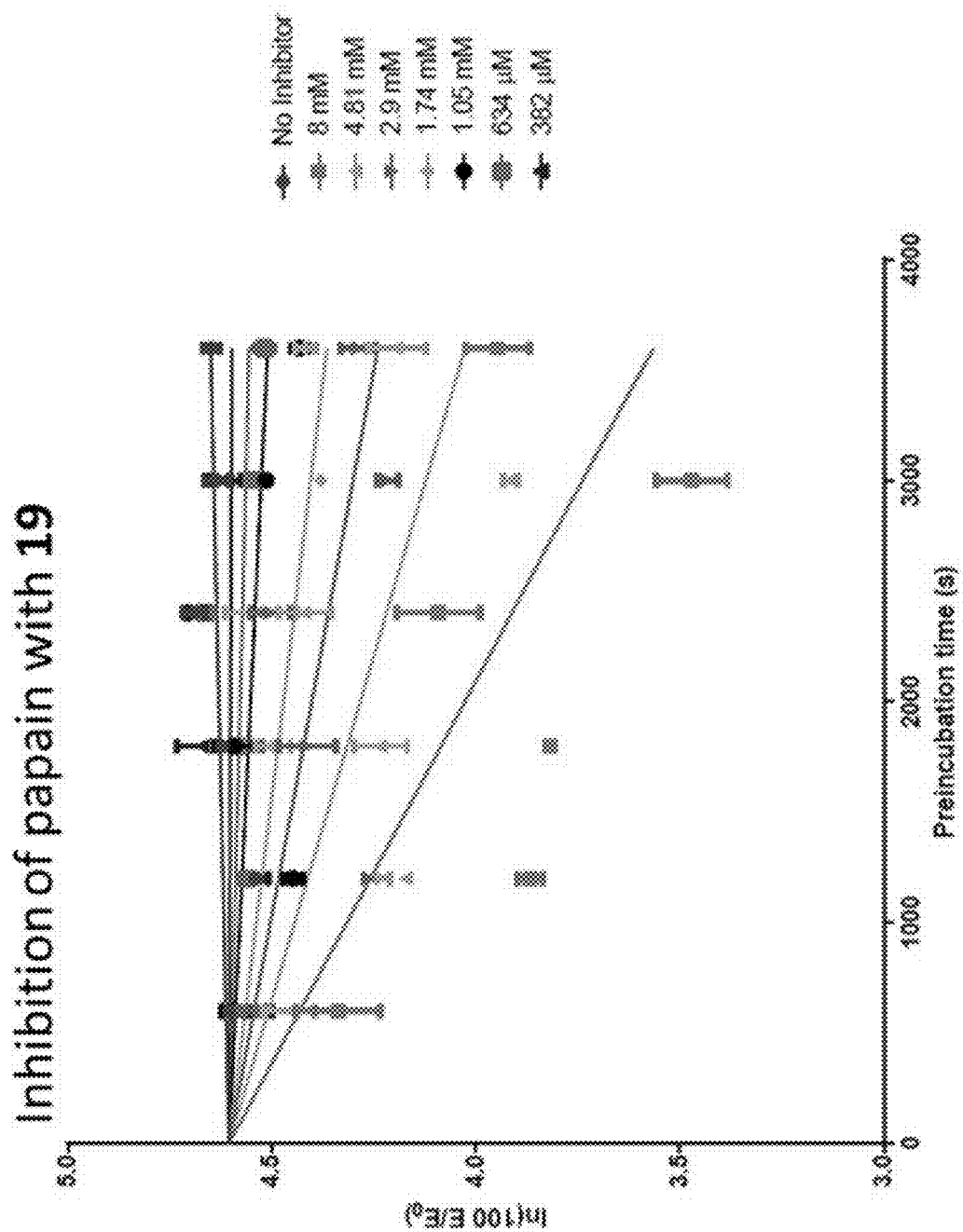
Figure 10E:
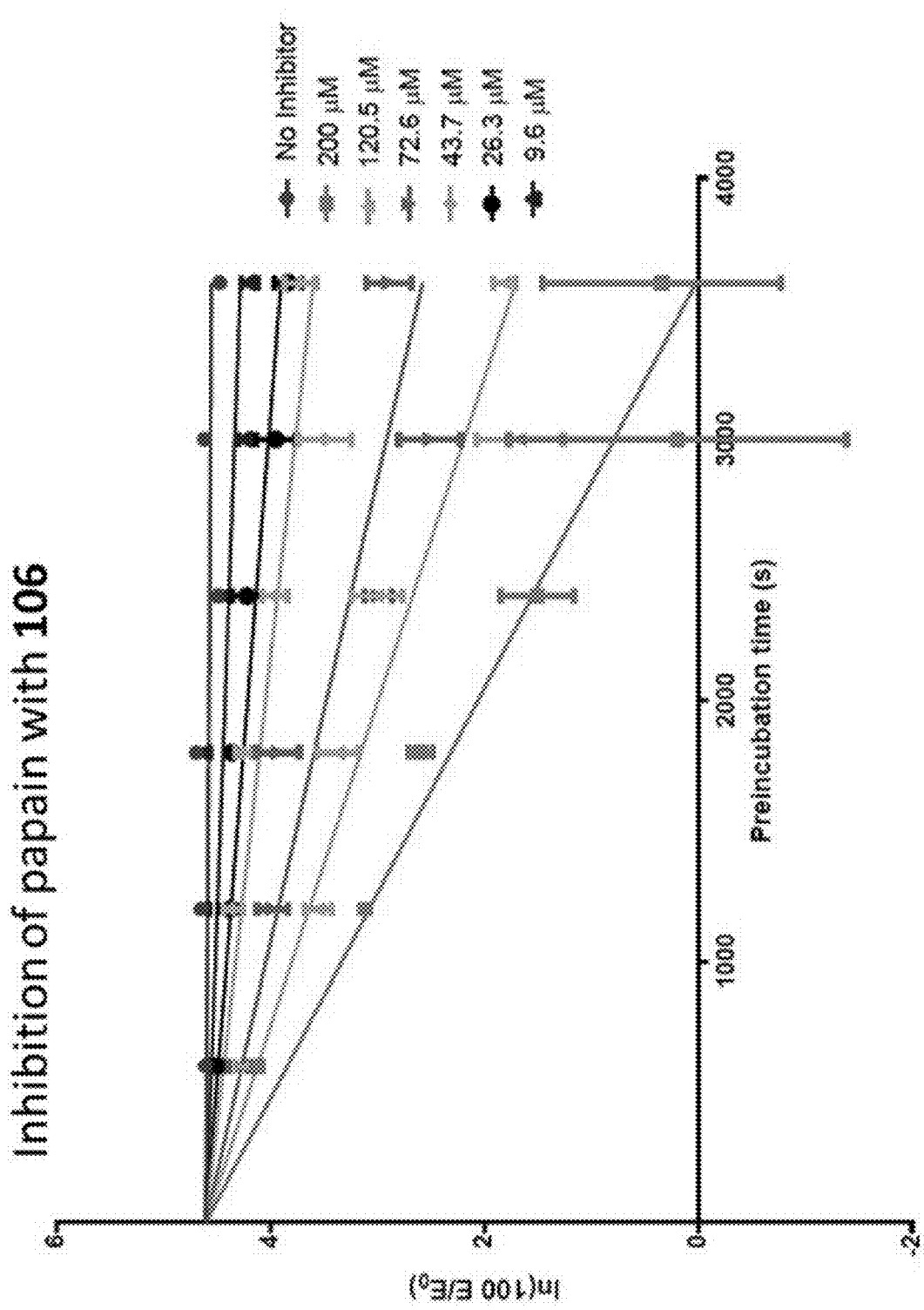
Figure 10F:
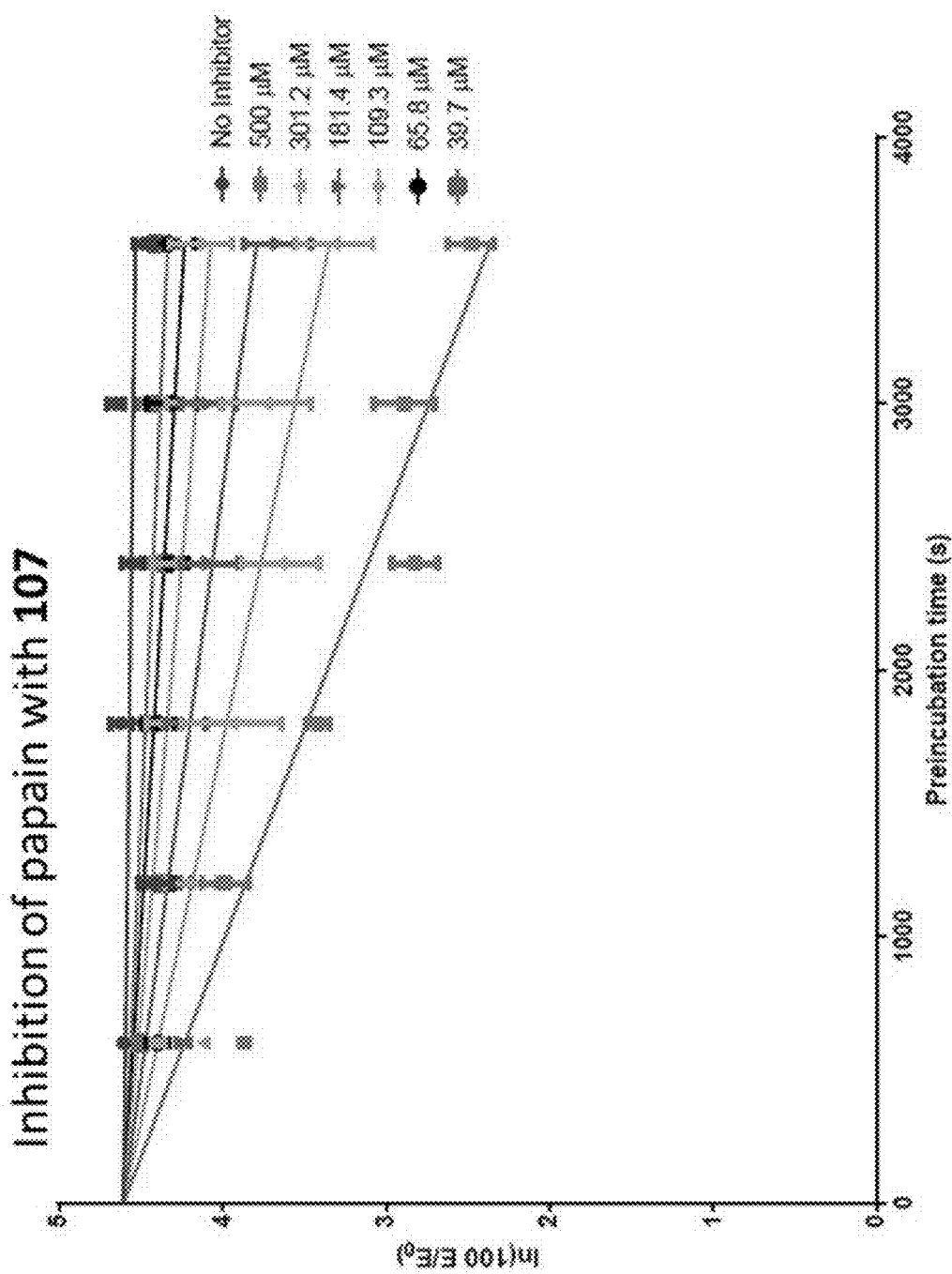

We were unable to directly confirm labeling of the catalytic cysteine because the catalytic cysteine peptide was not detectable by ESI-MS or MALDI-TOF upon digestion with trypsin, chymotrypsin, or Glu-C proteases. However, preincubation of papain with compounds 6-8, followed by treatment with 106, a known papain inhibitor which reacts with its catalytic cysteine,[17] did not cause dilabeling of papain (FIGS. 7A, 7B, and 7C). Additionally, pretreatment of papain with 106 also blocked subsequent labeling by compounds 6-8 (FIGS. 7D, E, and F). These results suggest that compounds 6-8 and inhibitor 106 most likely react with the same nucleophilic residue of papain. Compounds 6-8 labeled papain in a 1:1 stoichiometry at both 100 μM and 1 mM concentrations, confirming the specificity of these electrophiles for cysteine (FIG. 8). Moreover, the observed covalent labeling of papain was irreversible, since the covalent adducts were stable to dialysis (FIG. 9).

4. Papain Inhibition Assay

Figure 4A:
FIG. 4A and FIG. 4B. Second order inhibition plots and kinact/Ki values for papain inhibitor compounds 6-8 and known papain inhibitors 106-108. Note: testing of compound 7 at higher concentrations was limited by poor solubility.
Figure 4B:
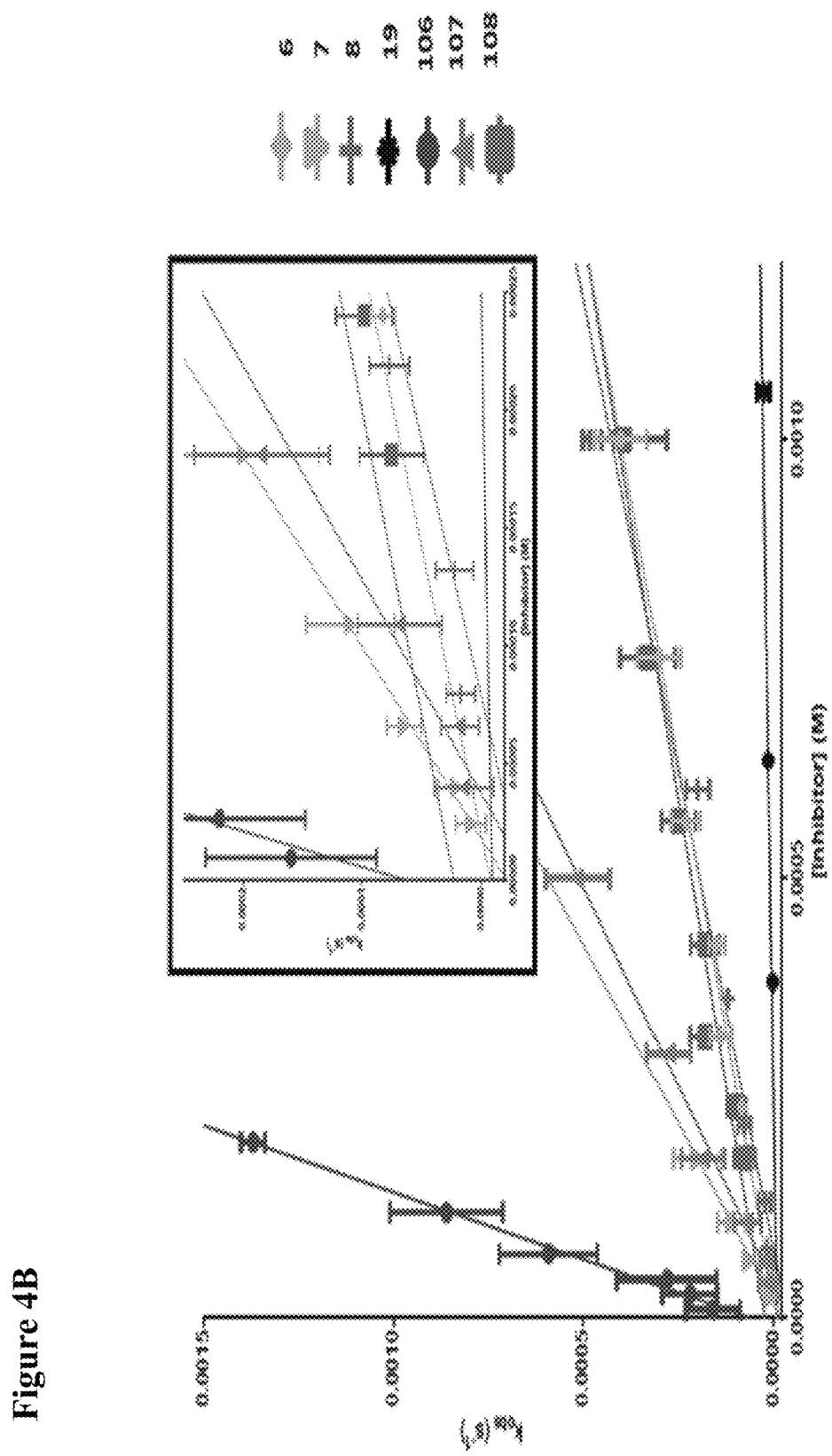
Figure 5A:
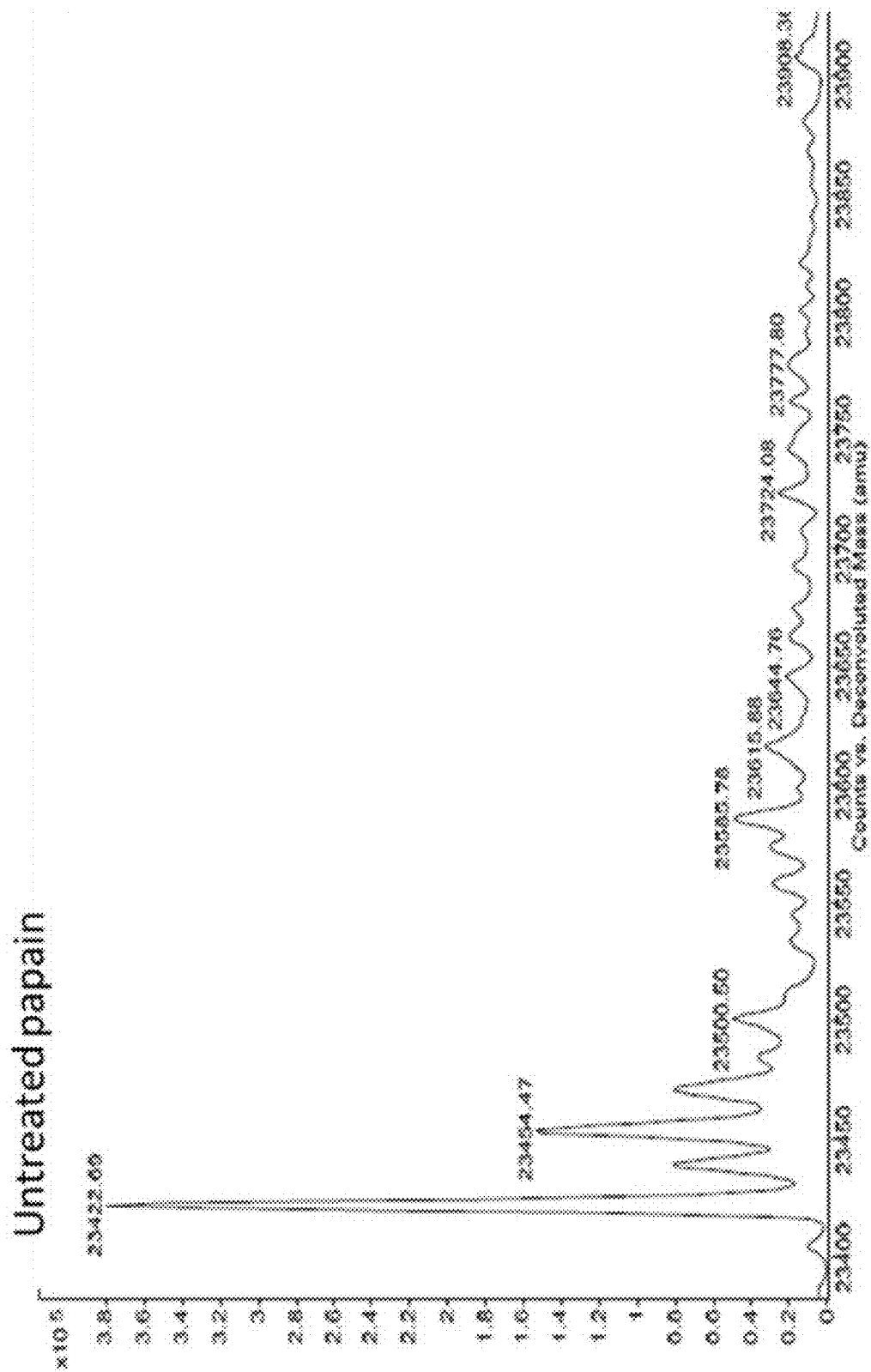
Figure 5B:
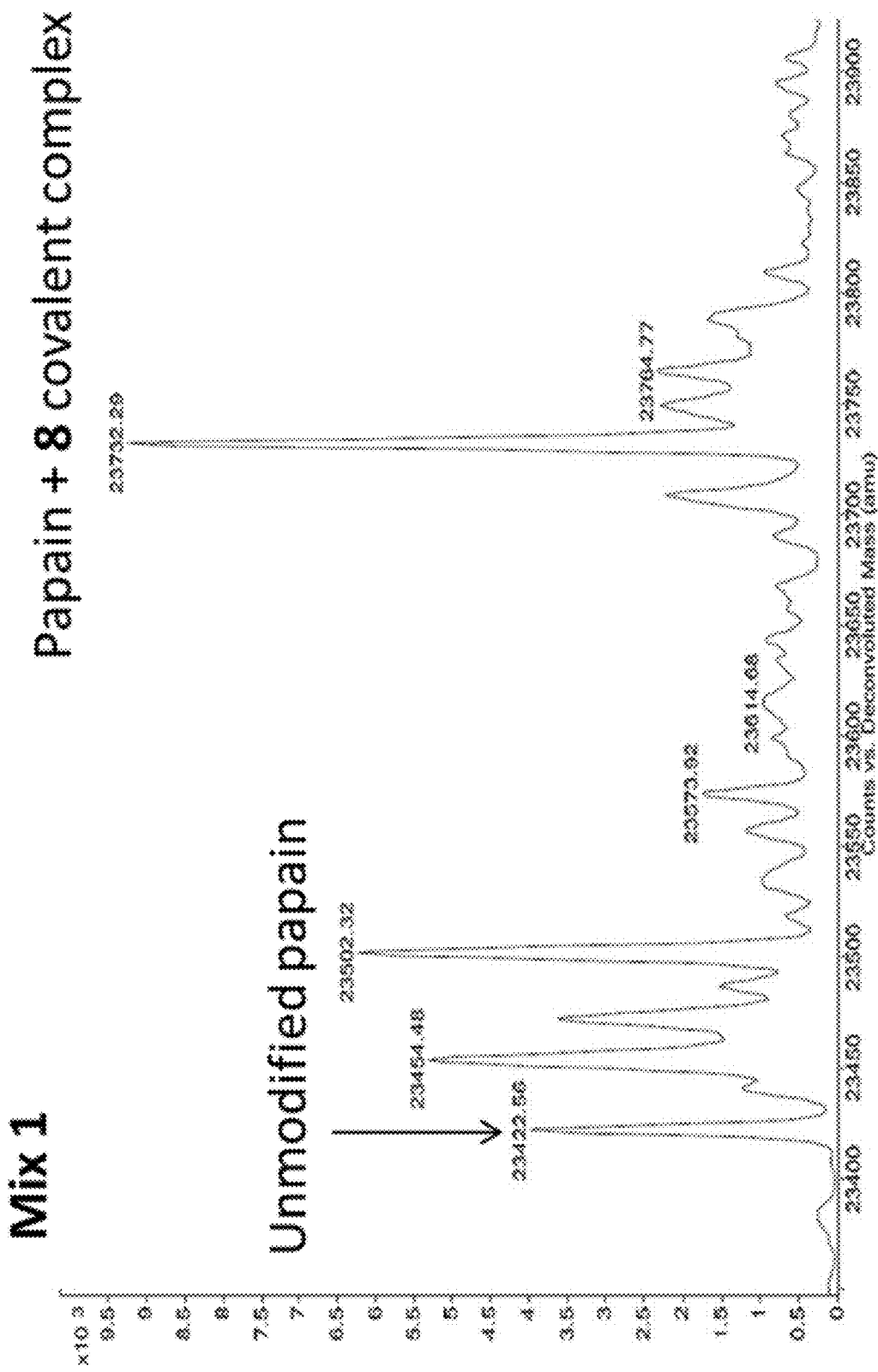
Figure 5D:
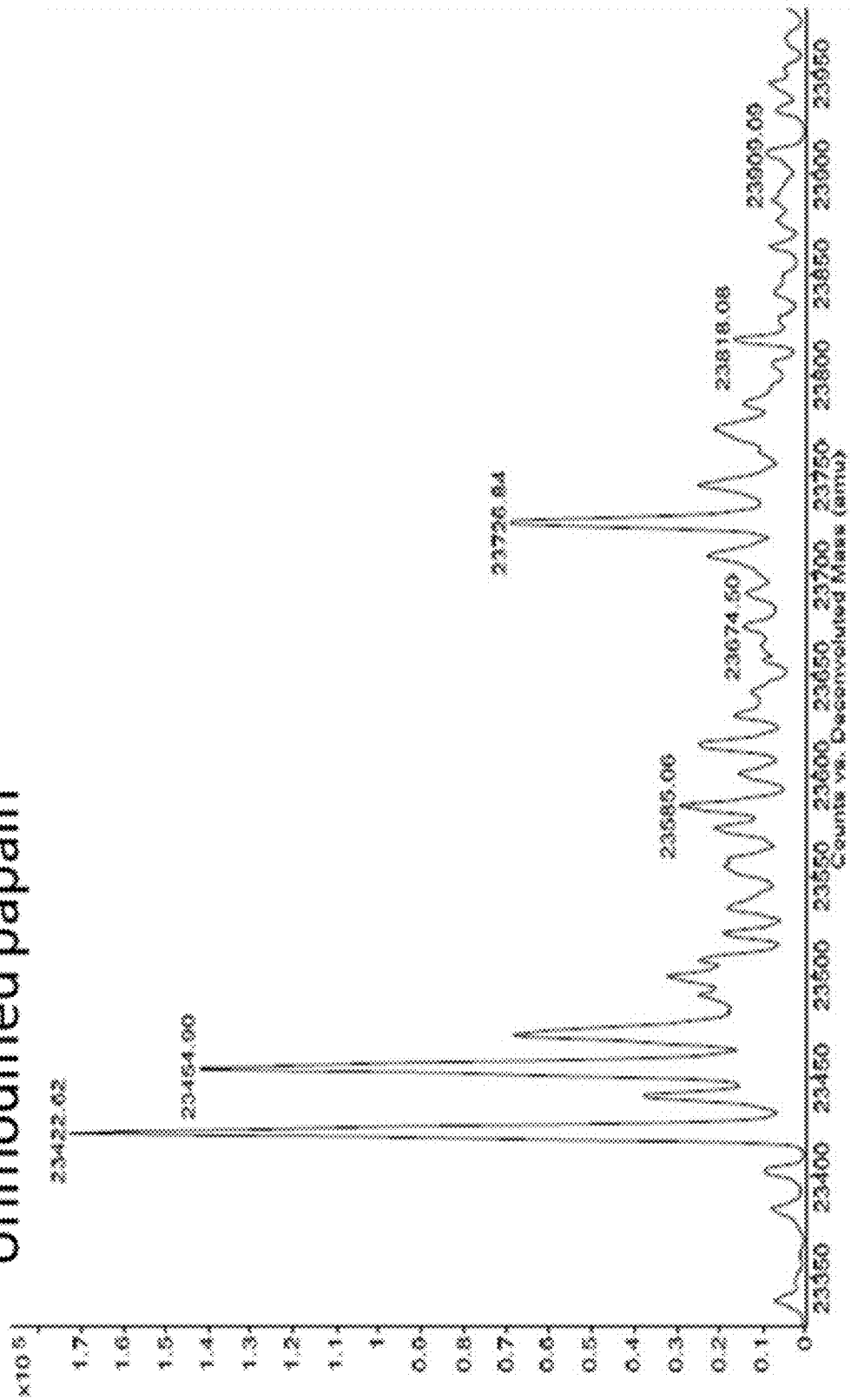
Figure 5F:
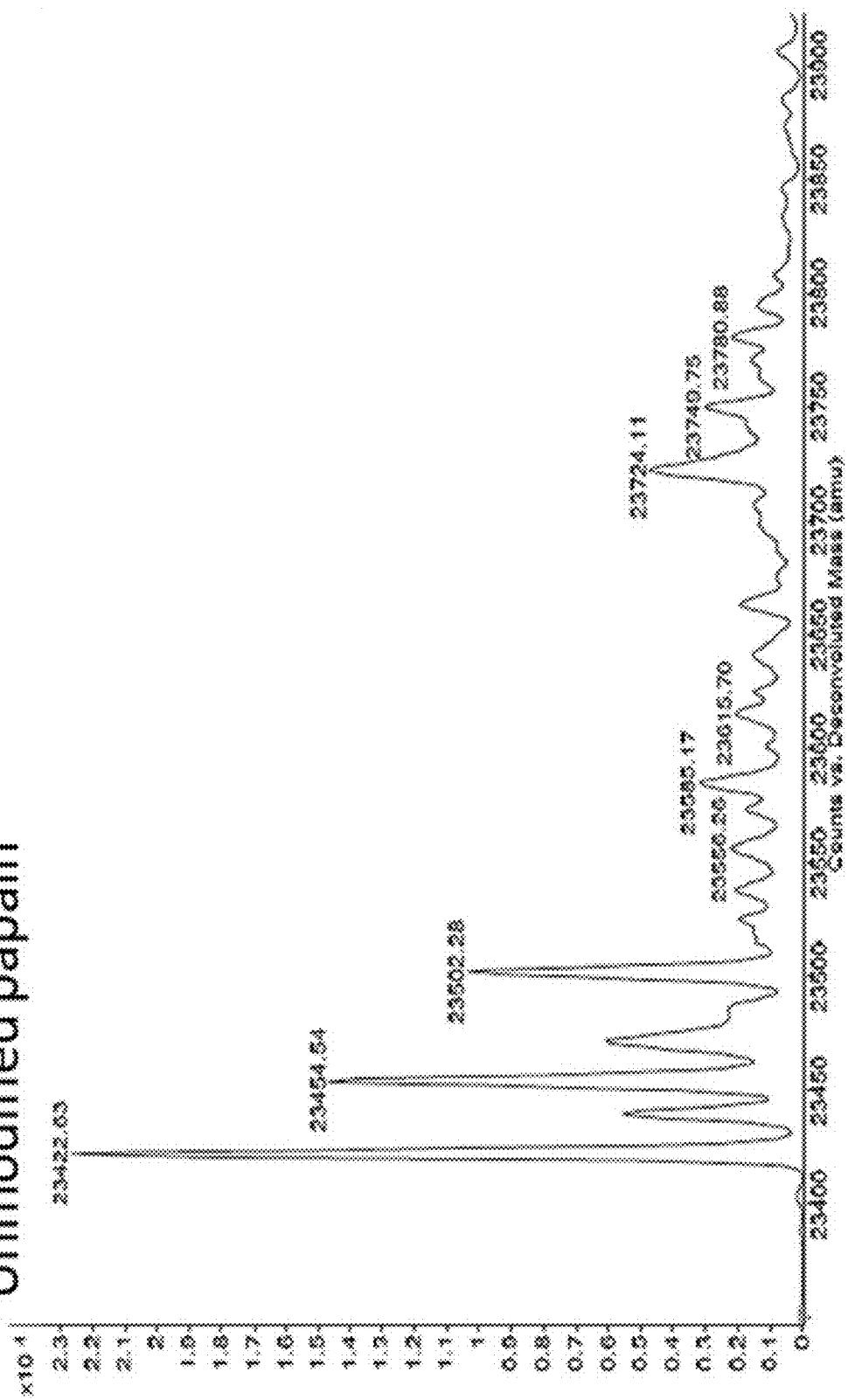
Figure 5G:
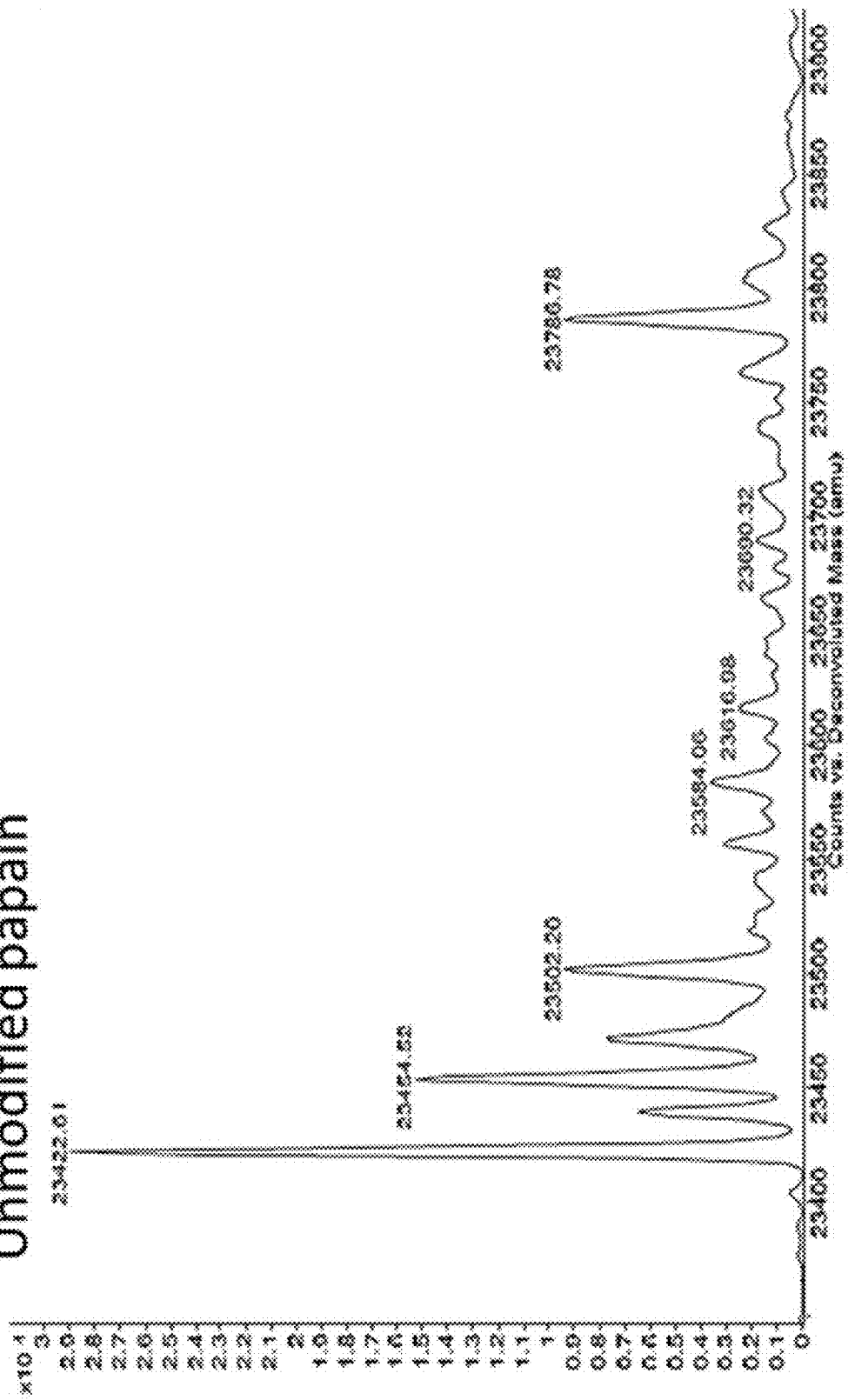
Figure 5H:
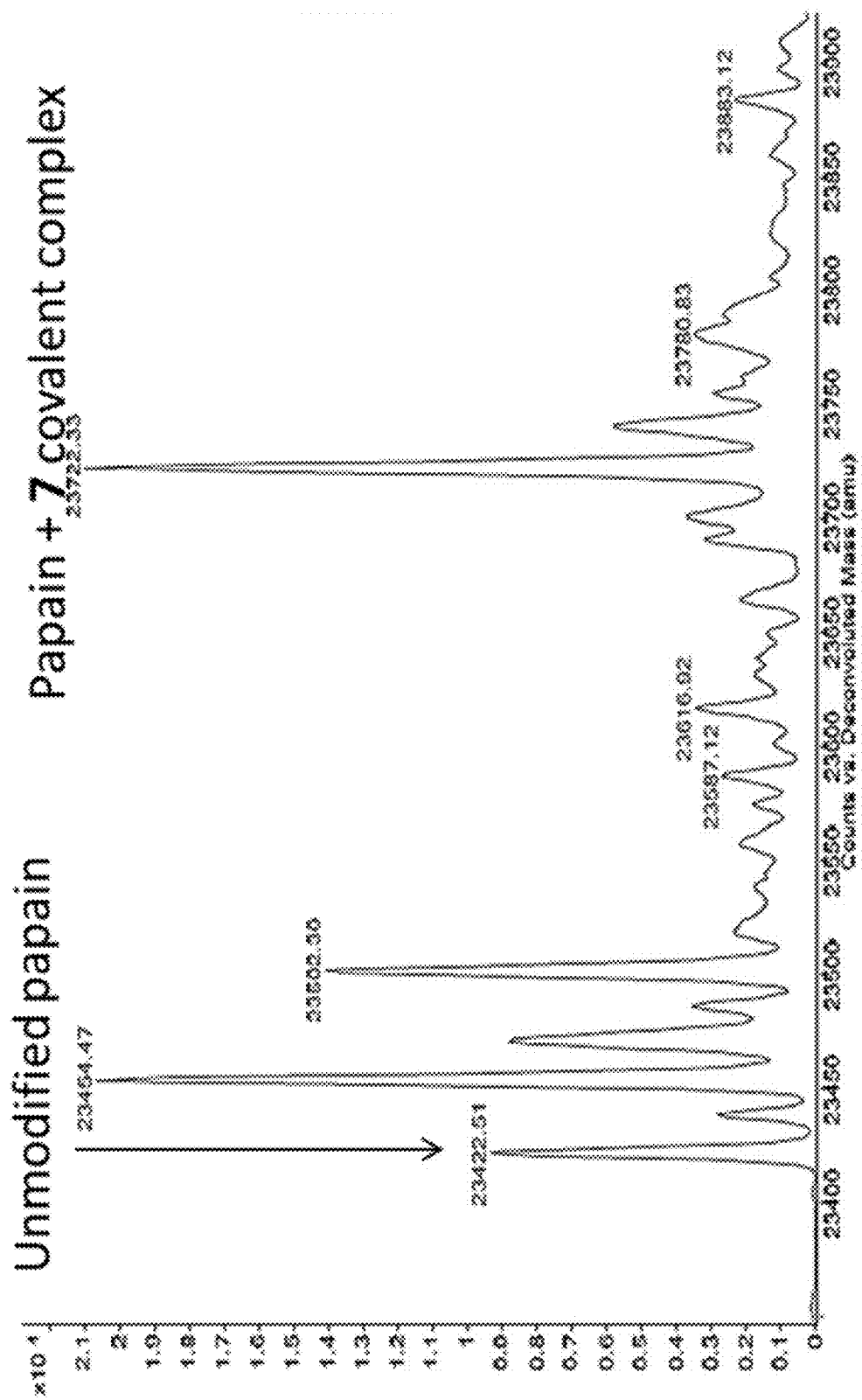
Figure 5I:
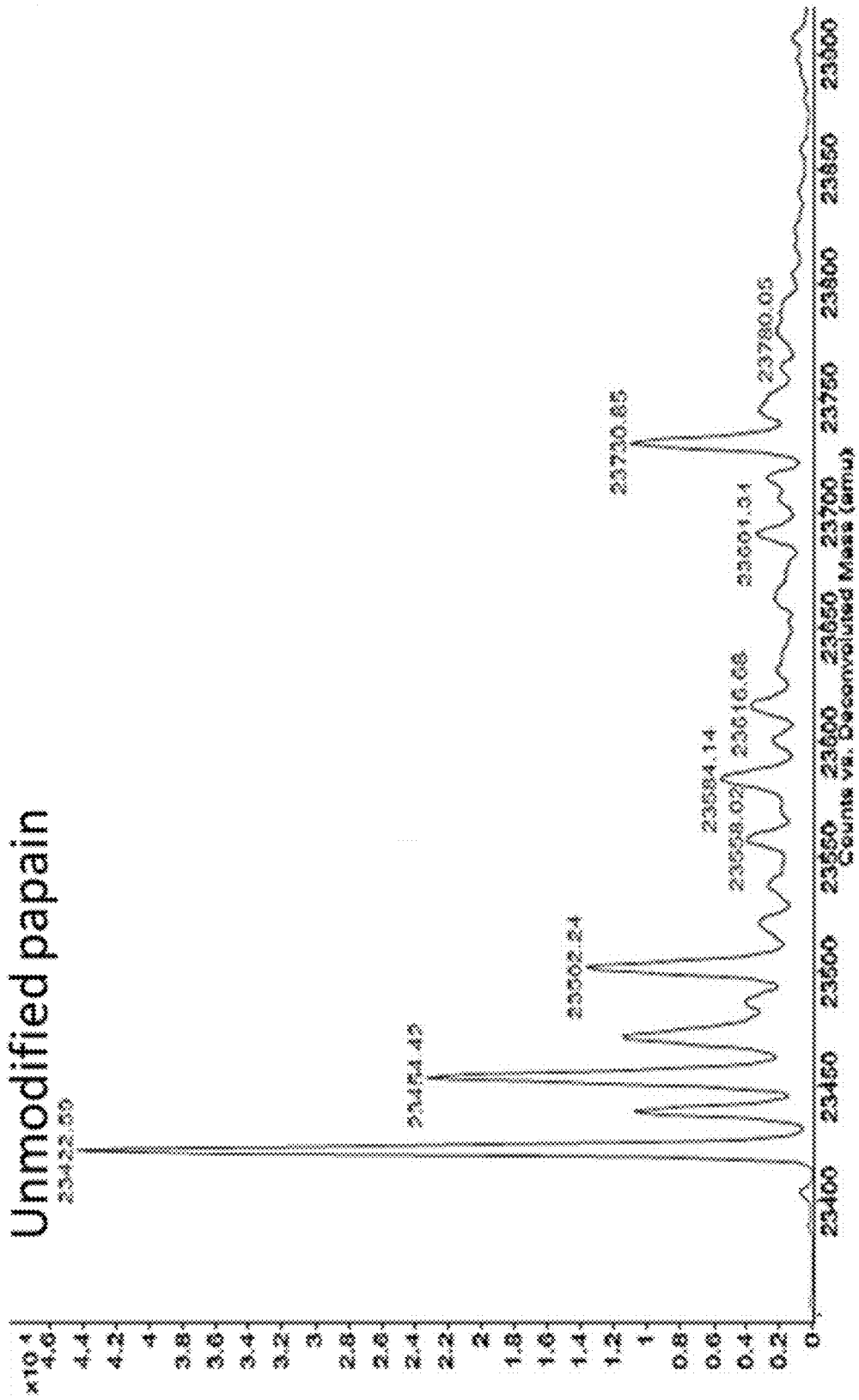
Figure 5J:
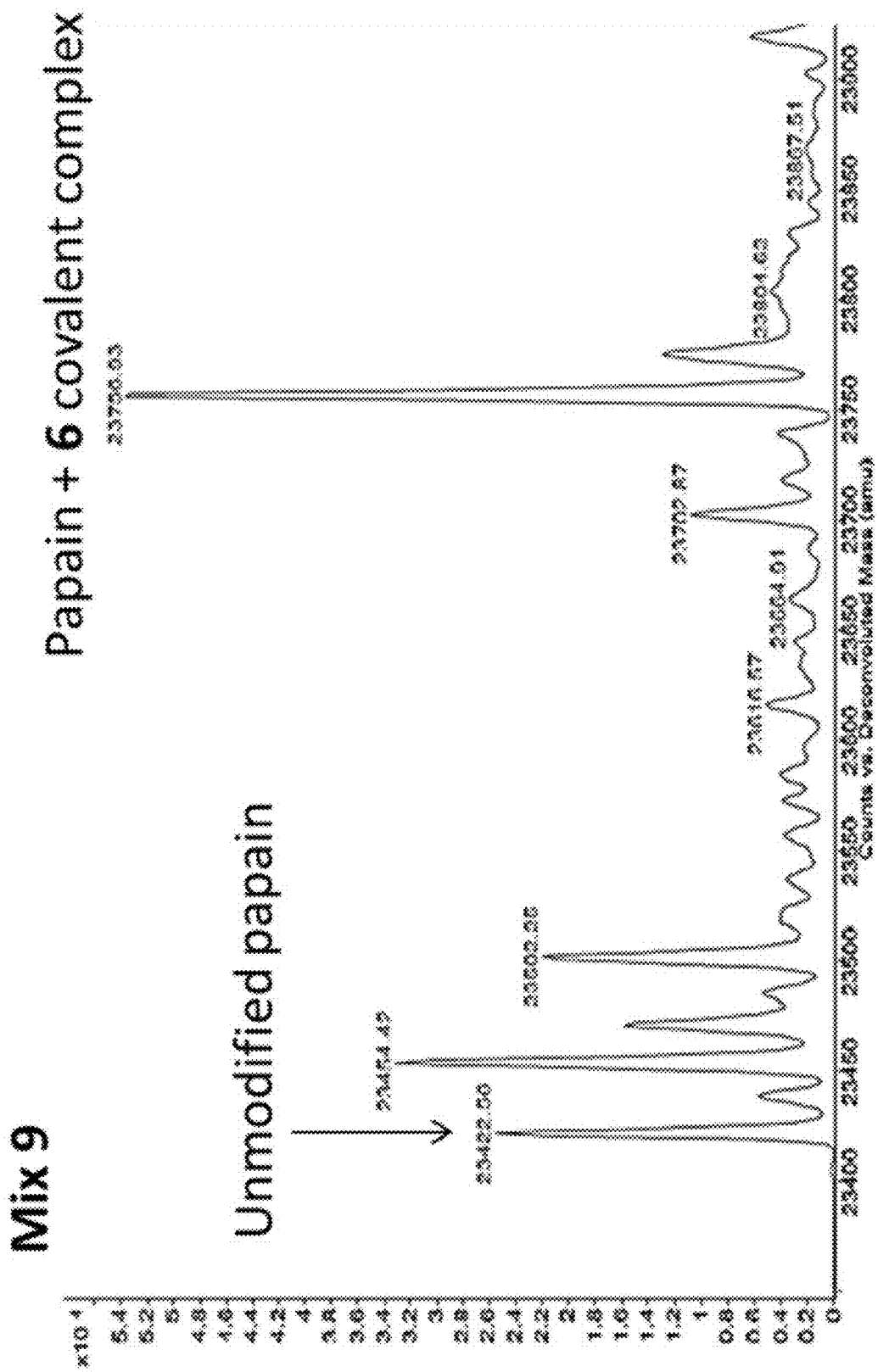
Figure 5K:
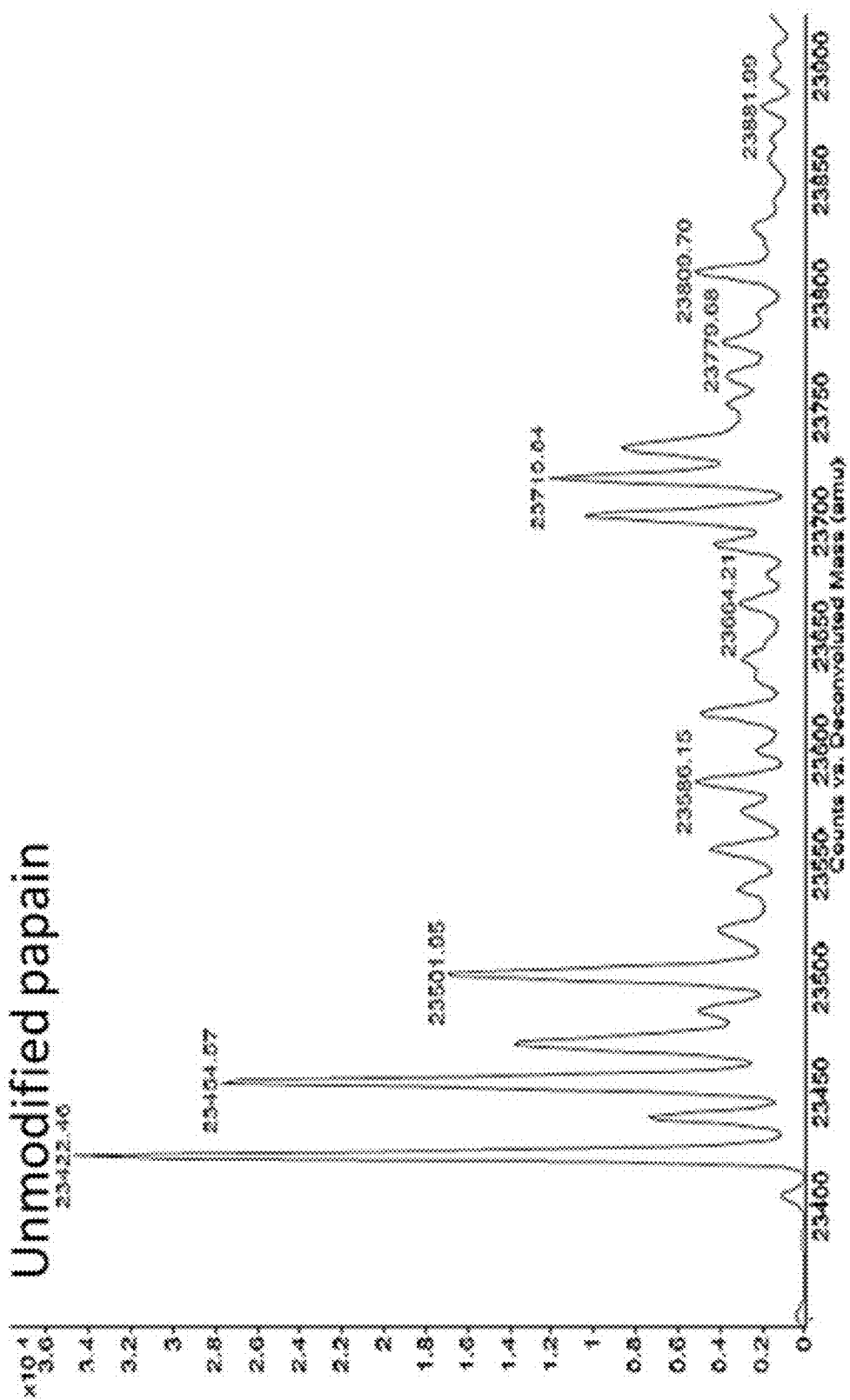

We subsequently tested compounds 6-8 in an enzymatic assay to confirm that they inhibited papain in the concentration and time dependent manner that is characteristic of irreversible inhibitors.[18] Using assay conditions previously described for papain,[17] we determined kinact/$K_1$ values for compounds 6-8 (FIGS. 4 and 10). Notably, compound 7 was as potent at inhibiting papain as a known moderate peptidic inhibitor 107,[17] but compounds 6-8 were less potent inhibitors than the known strong peptidic papain inhibitor 106. This result is expected, since irreversible tethering is designed to detect weak binding interactions between the drug-like fragments and the protein target to identify initial hits. Compounds 6-8 were all more potent inhibitors than the weak peptidic papain inhibitor 108.[17] A negative control molecule 19, which did not label papain in our screen, was ~10 fold less potent at inhibiting papain than the least potent inhibitor 6 and ~33 fold less potent than the most potent inhibitor 7. Remarkably, compounds 6-8 do not have a peptidic character in comparison to traditional cysteine protease inhibitors, including known papain inhibitors (FIG. 4).[19] This result is significant since the proposed method can serve as an entry point to discover other types of non-peptidic inhibitors for medically relevant cysteine proteases, avoiding the known undesirable pharmacological properties of peptidic inhibitors.[20]

5. Counter-Screen Against Human Rhinovirus 3C Protease (HRV3C), USP08, and UbcH7

To further test the specificity of the developed irreversible tethering system, we conducted a counter-screen of the same set of 100 compounds (10 mixtures of 10 compounds each) against three other enzymes: human rhinovirus 3C protease, the deubiquitinase USP08, and the E2 ubiquitin-conjugating enzyme UbcH7. Human rhinovirus 3C protease is a cysteine protease, an antiviral drug-target, and there are known orally bioavailable acrylate inhibitors for this protease.[14] Recent reports have indicated that targeting USPO8 is a promising approach to overcome gefitinib resistance in lung cancer,[21] while UbcH7 on the other hand regulates the entrance into and progression through the S-phase of the cell cycle.[22] As a source of HRV3C protease we used PreScission protease, which is a GST-fused HRV3C protease routinely used for protein purification purposes. The molecular weight of GST-HRV3C protease is 47566.72 Da and its amino acid sequence is provided as (SEQ ID NO:2).

We have found that HRV3C protease was labeled by compound 22 (~35% labeling) as well as compounds 32 and 98 (~20% labeling) under the same reaction conditions (data not shown). None of the three papain hits, and remaining electrophilic fragments reacted with HRV3C protease under these reaction conditions, indicating that these hits are selective binders. Although the three HRV3C hits did not label their target as strongly as the papain hits did, they could eventually be optimized into potent inhibitors of this clinically important cysteine protease. For UbcH7 (SEQ ID NO:3) and USPO8 (SEQ ID NO:4), we found that none of compounds 6-105 covalently modified these enzymes under the same reaction conditions (data not shown). When we increased the incubation time with USPO8 to 4 h, we found two compounds that weakly labeled ~30% of USP08. One was compound 6, while another was a unique compound (9) (data not shown). The other two papain inhibitors 7 and 8 did not label USPO8 even after 4 h, showing that our system is well behaved and can identify selective binders.

Discussion and Conclusion

In summary, we have rationally designed a chemical system for screening mixtures of electrophilic fragments against the catalytic cysteine of a protein of interest, which eliminates the concern that such an approach would only select the most reactive fragment, or otherwise be nonspecific due to the high reactivity of the catalytic cysteine. Using this method, we identified specific, non-peptidic covalent inhibitors of the cysteine protease papain, which contain novel chemical scaffolds. This is the first example of a successful screen of an unbiased library of electrophilic compounds under irreversible conditions, which led to the discovery of specific and novel inhibitor structures for the enzyme of interest.

The key advantage of the reported method is its simplicity. For example, electrophilic fragments 6-105 are prepared in one step from commercially available materials using a robust amide bond formation reaction. Moreover, the synthesized electrophilic fragments elicit a predictable and narrow range of chemical reactivities toward thiols and do not react with other nucleophilic residues such as histidine or lysine. The developed screening protocol is simple, and is moderately high-throughput. Hundreds of compounds can be screened in one day without the use of special robotic equipment. Moreover, mixtures of electrophilic fragments can be stored as DMSO stocks, transported, and used to screen fragments against novel protein targets. The developed irreversible tethering method displays a high hit rate (3% for papain and HRV3C protease), and the discovered papain inhibitors have weak potency in enzymatic assays. These are typical characteristics of fragment based drug discovery methods. Our failure to discover strong inhibitors of USPO8 and UbcH7 is most likely not due to the limitations of the method, but rather due to the limited sampling of chemical space since only ~100 fragments were prepared and tested. Since USPO8 and UbcH7 do not have classical hydrophobic binding pockets like the P2 substrate pocket of papain, it is likely that a larger library will be required to find adequate binders.

While the developed approach can be used to tether weakly bound fragments to the highly reactive catalytic cysteine of papain, it remains to be seen whether the same approach can be used to tether weakly bound fragments to non-catalytic cysteines on protein surfaces. We are currently exploring that particular aspect of this technology. Further investigations and applications of the developed method to discover enzyme and protein-protein interaction inhibitors by targeting catalytic and non-catalytic cysteines will be reported in the near future.

Experimental Section

1. Fragment Library Design

Using the Discovery Studio Package with Pipeline Pilot from Accelrys, 94,275 commercially available carboxylic acids were identified from the ChemBridge, ChemDiv, May-Bridge, NCI and Sigma-Aldrich libraries using SMARTS query strings. 62,000 of these were removed because they contained reactive functional groups (e.g. acyl halides) or were unsuitable leads (e.g. nitro compounds). Compounds were then filtered based on "rule of three" criteria which were modified to increase the number of resulting compounds: molecular weight (MW)≤350 Da; AlogP≤3; hydrogen-bond acceptors≤3; hydrogen-bond donors≤3; rotatable bonds≤3; polar surface area≤80. A principal component analysis and neighborhood algorithm was applied to the 1,522 remaining compounds to produce 281 fragments with a 0.75 diversity index. 100 of these compounds were then initially selected based on affordability and the ease of future analog synthesis 2. Synthesis of 6-108

The carboxylic acid fragment (0.2 mmol) was dissolved in dimethylformamide (0.2M, 1 mL), then 5 (46 mg, 0.2 mmol), HBTU (73.8 mg, 0.16 mmol), and HOBt (29.8 mg, 0.22 mmol) were added, followed by EtN(i-Pr)2 (100.7 µL, 0.6 mmol). The reaction was stirred at 23° C. for 16 h. TLC at 16 h showed conversion to product. The reaction was quenched with $H_2O$ (5 mL) and extracted three times with $CH_2Cl_2$ (5 mL). The combined organic layers were washed with 1M HCl (10 mL), saturated aqueous $NaHCO_3$ (10 mL), and saturated aqueous NaCl (10 mL). The organic layer was dried over $MgSO_4$, filtered, and evaporated. Purified by flash column chromatography with a $CH_3OH/CH_2Cl_2$, $CH_3OH$ gradient 0-5% to yield compounds 6-108. Yields ranged from 11% to 100%, with an average yield of 60%. Chemical structures of compounds 6-108 are shown in Supporting Information. For initial library creation, compounds were characterized by $^1H$ NMR and low resolution MS. All compounds tested in enzymatic assays were also characterized by $^{13}C$ NMR and ≥95% purity was confirmed by HPLC.

3. NMR Rate Studies

N-Acetyl cysteine methyl ester was dissolved in 2:1 deuterated PBS:DMSO-d6 (78 mM) with 10 mM $CH_2Cl_2$ as an internal standard. The electrophile (10 mM) was then added immediately prior to acquiring spectra. H1 spectra were taken every 30 s for 30 min (or every 4 s for 5 min for highly reactive compounds 1c and 2a-c). The integrals of the vinyl peaks were used to determine the concentration of the electrophile over time. The natural logarithm of the concentration of the electrophile versus time was then plotted using GraphPad Prism software. The linear slope of this plot was used to determine the pseudofirst order rate constant. Deuterated PBS recipe: 20 mM $Na_3PO_4$, 50 mM NaCl in $D_2O$ was adjusted to pD 8 with DC1 solution.

4. Irreversible Tethering Screening Assay

10 µM of papain (Sigma P4762), UbcH7 (recombinantly expressed) or USPO8 (recombinantly expressed) in 50 mM HEPES 150 mM NaCl 0.1 mM EDTA pH 7.5 was treated with a mixture of ten fragments (Table S2) (10 mM DMSO stock solutions, final concentrations: 100 µM of each fragment, and 1% DMSO). The reaction mixture was incubated for 1 h or 4 h at 23° C. before being passed through Zeba gel filtration columns (Thermo, 7K MWCO) to remove unreacted fragments. The protein solution was then immediately analyzed by whole protein LC/ESI-MS.

5. LC/ESI-MS Protocol

Accurate-mass data were obtained on an Agilent 6210A LC-TOF mass spectrometer in positive ion mode using electrospray ionization. Samples were chromatographed on the LC-TOF instrument using a Poroshell 120 EC-C18 HPLC column (2.1*50 mm, 2.7 micron), an Agilent Series 1200 HPLC binary pump, and an Agilent Series 1200 autoinjector. The HPLC column was held at 45° C. and the autosampler was held at 8° C. Mobile Phase A was a solution of 0.1% formic acid in water:acetonitrile (19:1). Mobile Phase B was a solution of 0.1% formic acid in acetonitrile. The flow rate was set to 250 µL/min. The gradient used was 0% B for 2 minutes, ramping linearly to 90% B from 2 minutes to 5 minutes, holding at 90% B from 5 minutes to 7 minutes, and then returning to 0% B at 7.1 minutes. The column was allowed to equilibrate for 2.7 minutes before the next injection was initiated. The eluent from the column was diverted to waste for the first 2 minutes. The spectra were acquired from 301 to 3200 daltons using a gas temperature of 340° C., a gas flow of 7 liters/min, and the nebulizer gas at 35 psi. The following voltages were used: capillary 4200 V, fragmentor 230V, skimmer 64V, and octapole RF peak 250V. Spectra were acquired at a rate of 1 spectra/sec. The data was processed using MassHunter software version B.02.00. Maximum entropy deconvolutions were performed with a Mass Step of 1, S/N Threshold of 30, Average Mass at 90% of Peak Height, and 5 Charge States Minimum.

6. Papain Activity Assays

Papain (4.8 µM) in 50 mM Na3PO4 2 mM EDTA was preactivated with 1 mM DTT for 30 min. Activated papain (3.84 µM) in 4:1 mixture of 50 mM $Na_3PO_4$, 2 mM EDTA at pH 6.2 and acetonitrile was then preincubated for 1 h with varying concentrations of the electrophilic fragment. Every 10 min, 10 µL of the reaction mixture was added to a well of 96-well plate containing 100 µL of 4:1 50 mM Na3PO4 2 mM EDTA pH 6.2:acetonitrile with 400 µM Cbz-Gly-ONp. p-Nitrophenol product formation was monitored by absorbance at 340 nM (£: 6800 M-1 cm-1) with a Biotek Synergy 4 plate reader. All reactions were performed in duplicate. Product concentration versus time was plotted with GraphPad Prism software and the initial slope was calculated to determine enzymatic activity (E). The values of kinact/KI for each inhibitor were then determined according to the method of Kitz and Wilson.23 Briefly, the slopes of the plots of ln(100*Einhibited/Euninhibited) vs. time were used to determine the pseudo-first order inhibition constant kobs for a given concentration of a given inhibitor. The slope of the plot of kobs vs. [Inhibitor] was then used to determine the second order inhibition constant kinact/KI (since [I]<<KI the plots were linear at the concentrations tested).

Supplemental Information

A. Chemical Synthesis

In general, methanol (ACS grade), ethyl acetate (ACS grade), chloroform (ACS grade), toluene(ACS grade), and diethyl ether (ACS grade), acetonitrile (HPLC grade), and hexanes (ACS grade) were purchased from Fisher Scientific and used without further purification. Dichloromethane, tetrahydrofuran and dimethylformamide were purified by passing over activated alumina. Commercially available reagents were used without further purification. Unless otherwise specified, all reagents were purchased from Sigma-Aldrich. Reactions were monitored by thin-layer chromatography (TLC) on pre-coated glass backed plates (60 Å silica gel, 0.25 mm, Whatman), and components were visualized by UV light (254 and 365 nm) or by treating the plates with anisaldehyde, KMnO₄, and ninhydrin stains followed by heating. Flash column chromatography was performed over ultra pure silica gel (230-400 mesh) from Silicycle. $^1$H and $^{13}$C NMR spectra were obtained on a Bruker AVANCE III 500 MHz spectrometer or an Agilent DDR2 400 MHz spectrometer (Funded by NSF CHE-1048773, 2010). Chemical shifts were reported in ppm relative to the residual solvent peak (CDCl₃ or DMSO-d₆). Multiplicity was indicated as follows: s (singlet); d (doublet); t (triplet); q (quartet); m (multiplet); dd (doublet of doublets); ddd (doublet of doublet of doublets); dt (doublets of triplets); td (triplet of doublets); brs (broad singlet). Coupling constants were reported in Hz. Small molecule ESI-MS was performed on an Agilent 1100 MSD quadropole instrument. For compounds tested in enzymatic assays, purity was confirmed by analytical HPLC on a Shimadzu LC-6AD instrument with a Restek Pinnacle C18 column with UV detection at 220 nm with a 5495% acetonitrile/water gradient, 0.1% trifluoracetic acid.

1. Synthesis of 1a-c

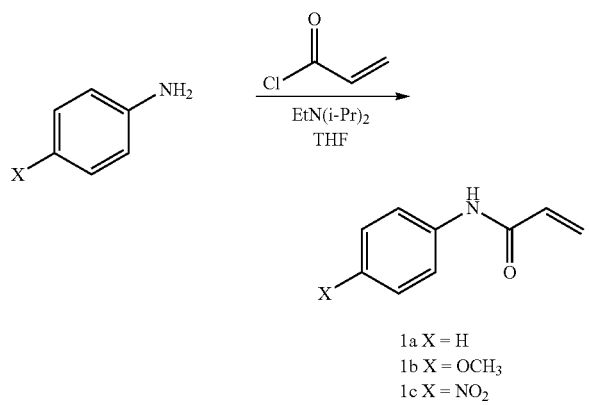

1a X = H
1b X = OCH₃
1c X = NO₂

Aniline, p-methoxyaniline, or p-nitroaniline (1.07 mmol) was dissolved in THF (0.1 M, 10.7 mL) and cooled to 0° C. with stirring. Diisopropylethylamine (1.4 mL, 8.58 mmol) was then added, followed by acryloyl chloride (175 μL, 2.14 mmol). After 5 min., the reaction was warmed to 23° C. and stirred for 1 hour. TLC showed a full conversion to product. THF was evaporated under reduced pressure, and the residue was dissolved in 20 mL dichloromethane and washed with a saturated aqueous solution of NaHCO₃ (2×20 mL). The organic layer was dried with magnesium sulfate, filtered, and evaporated under reduced pressure. The residue was purified by flash chromatography with an ethyl acetate/hexanes gradient 25% EtOAc→100% EtOAc. 1a (108 mg, 68% yield)$^1$H NMR (500 MHz, CDCl₃) δ 7.52 (d, J=7.9 Hz, 2H), 7.35-7.23 (m, 3H), 7.06 (t, J=7.4 Hz, 1H), 6.38 (dd, J=16.9, 1.3 Hz, 1H), 6.19 (dd, J=16.8, 10.2 Hz, 1H), 5.71 (dd, J=10.3, 1.2 Hz, 1H). $^{13}$C NMR (126 MHz, CDCl₃) δ 163.53, 137.71, 131.16, 129.07, 127.90, 124.56, 119.97. 1b (166 mg, 87% yield)$^1$H NMR (500 MHz, CDCl₃) δ 7.52 (d, J=8.9 Hz, 2H), 7.21 (s, 1H), 6.90 (d, J=9.0 Hz, 2H), 6.45 (dd, J=16.8, 1.3 Hz, 1H), 6.26 (dd, J=16.8, 10.2 Hz, 1H), 5.78 (dd, J=10.3, 1.3 Hz, 1H), 3.83 (s, 3H). $^{13}$C NMR (126 MHz, CDCl₃) δ 163.38, 156.55, 131.14, 130.79, 127.50, 121.76, 114.18, 55.49. 1c (44.4 mg, 22% yield)$^1$H NMR (500 MHz, CDCl₃) δ 8.17 (d, J=9.1 Hz, 2H), 7.72 (d, J=9.1 Hz, 2H), 7.43 (s, 1H), 6.45 (dd, J=16.8, 1.0 Hz, 1H), 6.21 (dd, J=16.8, 10.3 Hz, 1H), 5.83 (dd, J=10.4, 1.0 Hz, 1H). $^{13}$C NMR (126 MHz, CDCl₃) δ 164.59, 144.55, 143.20, 130.47, 128.98, 124.92, 119.23.

2. Synthesis of 2a-c

Aniline, p-methoxyaniline, or p-nitroaniline (1.07 mmol) was dissolved in CH₂Cl₂ (0.1M, 10.7 mL), and cooled to 0° C. with stirring. 2-chloroethane sulfonyl chloride (112 μL, 1.07 mmol) was then added, followed by triethylamine (150 μL, 1.07 mmol). After 1 h of reaction time, a second equivalent of triethylamine (150 μL, 1.07 mmol) was added and the reaction was warmed to 23° C. After one hour TLC showed full conversion of the starting material to product, and the reaction was quenched with 20 mL water and extracted 2×20 mL dichloromethane. The combined organic layers were washed with 20 mL 1M HCl and 20 mL saturated aqueous sodium chloride. The organic phase was then dried over magnesium sulfate, filtered, and evaporated under reduced pressure. Purified by flash column chromatography with a CH₃OH/CH₂Cl₂, CH₃OH gradient 0→5%.

2a (107.6 mg, 55% yield)$^1$H NMR (400 MHz, CDCl₃) δ 7.37-7.27 (m, 2H), 7.20-7.06 (m, 3H), 6.56 (s, 1H), 6.55 (dd, J=16.5, 9.9 Hz, 1H), 6.27 (d, J=16.5 Hz, 1H), 5.94 (d, J=9.9 Hz, 1H). $^{13}$C NMR (126 MHz, CDCl₃) δ 136.15, 135.02, 129.53, 128.57, 125.42, 120.97. 2b (160 mg, 70% yield)$^1$H NMR (500 MHz, CDCl₃) δ 7.17 (d, J=8.9 Hz, 2H), 6.88 (d, J=8.9 Hz, 2H), 6.56 (dd, J=16.5, 9.9 Hz, 1H), 6.28 (s, 1H), 6.22 (d, J=16.6 Hz, 1H), 5.96 (d, J=9.9 Hz, 1H), 3.82 (s, 3H). $^{13}$C NMR (126 MHz, CDCl₃) δ 158.03, 134.96, 128.44, 128.27, 125.12, 114.61, 55.50. 2c (64.8 mg, 26% yield)$^1$H NMR (500 MHz, CDCl₃) δ 8.24 (d, J=9.1 Hz, 2H), 7.27 (d, J=9.1 Hz, 2H), 6.64 (dd, J=16.4, 9.8 Hz, 1H), 6.49 (d, J=16.5 Hz, 1H), 6.15 (d, J=9.8 Hz, 1H). $^{13}$C NMR (126 MHz, Chloroform-d) δ 143.55, 143.33, 135.05, 128.84, 125.35, 117.82.

3. Synthesis of 3a-c

General Synthesis Scheme

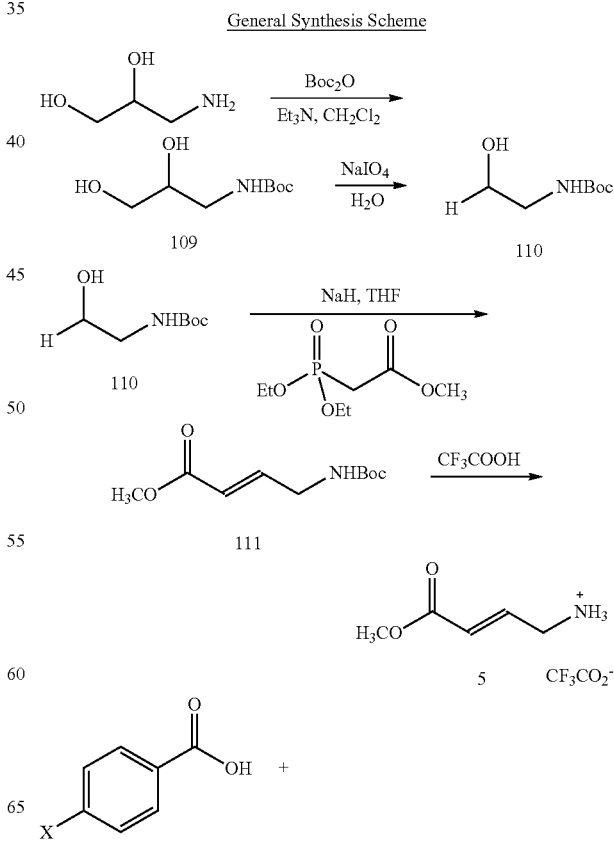

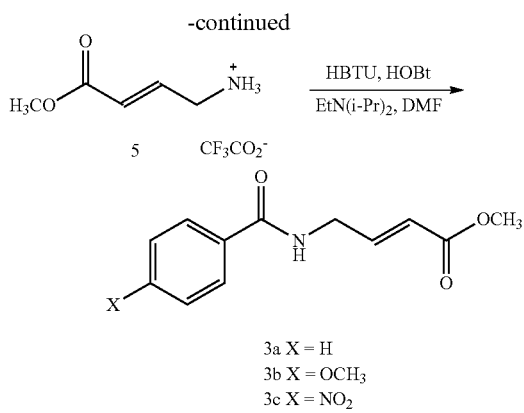

3a X = H
3b X = OCH₃
3c X = NO₂

4. Synthesis of 109

(±)-3-amino-1,2-propanediol (11.29 g, 124 mmol) was dissolved in CH$_2$Cl$_2$:CH$_3$OH (1:5) (1M) and triethylamine (2 mL, 14.7 mmol) was added. Di-tert-butyl dicarbonate (32.5 g, 149 mmol) was dissolved in dichloromethane (0.8M, 186 mL) and added slowly to the reaction mixture. The resulting reaction was stirred at 23° C. for 2 h, followed by TLC analysis that showed a full consumption of the starting material. The reaction mixture was evaporated under reduced pressure, and the residue was purified by column chromatography with EtOAc:Hexanes 1:4, then dried on high vacuum to yield 109 as a white solid (23.7 g, 94% yield). $^1$H NMR (500 MHz, CDCl$_3$) δ 5.28-4.96 (m, 1H), 3.83-3.73 (m, 1H), 3.60 (qd, J=11.7, 4.9 Hz, 2H), 3.44 (s, 1H), 3.27 (dt, J=12.9, 6.0 Hz, 2H), 1.46 (s, 9H). $^{13}$C NMR (126 MHz, Chloroform-d) δ 157.45, 80.13, 71.37, 63.58, 28.35, 27.42.

5. Synthesis of 110

109 (10 g, 52 mmol) was suspended in H$_2$O (0.6M, 87.2 mL) and the flask was covered in foil (to protect NaIO$_4$ from light). NaIO4 (13.4 g, 62.8 mmol) was then added and the reaction was stirred for 1 h. A white precipitate had formed after 1 h, and TLC analysis showed full consumption of the starting material. The precipitate was filtered off, and the aqueous layer was extracted with CHCl$_3$ (8×50 mL). The organic layer was dried with MgSO$_4$, filtered, and evaporated to yield 110 as a yellow oil, which was used immediately without further purification (7.7 g, 93% yield). $^1$H NMR (500 MHz, CDCl3) δ 9.68 (s, 1H), 5.23 (s, 1H), 4.10 (d, J=5.2 Hz, 2H), 1.47 (s, 9H). $^{13}$C NMR (126 MHz, CDCl3) δ 197.21, 155.67, 80.19, 51.39, 28.28.

6. Synthesis of 111

Sodium hydride (60% dispersion in mineral oil) (1.9 g, 46.6 mmol) in tetrahydrofuran (0.17 M, 274 mL) was cooled to 0° C., then triethylphosphonoacetate (8.5 mL, 46.6 mmol) in THF was added dropwise. The reaction was stirred at 0° C. for 20 min, then 110 (7.4 g, 46.6 mmol) in THF was added. The reaction was allowed to warm to 23° C. and was stirred for 1 h. TLC showed a full consumption of the starting materials and conversion to product. THF was removed under reduced pressure, and the residue was then diluted with ethyl acetate (200 mL) and water (200 mL). The layers were separated, followed by the extraction of the aqueous layer with EtOAc (2×100 mL). The organic layer was then dried over MgSO$_4$, filtered, and evaporated. The residue was purified by flash column chromatography with an ethyl acetate/hexanes gradient 25% EtOAc→50% EtOAc to yield 111 (6.6 g, 66% yield). $^1$H NMR (500 MHz, CDCl3) δ 6.94 (dt, J=15.7, 4.8 Hz, 1H), 5.97 (dt, J=15.8, 1.9 Hz, 1H), 4.73 (s, 1H), 3.95 (t, J=5.6 Hz, 2H), 3.76 (s, 3H), 1.48 (s, 9H). $^{13}$C NMR (126 MHz, CDCl3) δ 166.55, 145.26, 120.71, 79.73, 60.37, 51.58, 41.28, 28.30.

7. Synthesis of 5

111 (6.6 g, 30.8 mmol) was dissolved in trifluoroacetic acid (47 mL, 617 mmol) and stirred at 23° C. for 30 min. TLC at 30 min showed conversion to product. TFA was evaporated and azeotroped with toluene (2×100 mL). The residue was then dried on high vacuum for 2 hours, dissolved in 2 mL methanol and dropped into ice cold diethyl ether (200 mL). The ether was then filtered to collect 5 as the TFA salt (6.2 g, 88% yield). $^1$H NMR (500 MHz, DMSO-d6) δ 8.08 (s, 3H), 6.86 (dt, J=15.9, 5.6 Hz, 1H), 6.15 (dt, J=16.0, 1.7 Hz, 1H), 3.70 (s, 3H), 3.70 (d, J=1.8 Hz, 2H). $^{13}$C NMR (126 MHz, DMSO-d6) δ 165.33, 140.61, 123.22, 51.72.

8. Synthesis of 3a-c

Benzoic acid, p-methoxybenzoic acid, or p-nitrobenzoic acid (0.35 mmol) was dissolved in dimethylformamide (0.2M, 1.75 mL), then 5 (42.6 mg, 0.35 mmol), HBTU (128 mg, 0.34 mmol), and HOBT (51.8 mg, 0.38 mmol) were added, followed by diisopropylethylamine (175 µL, 1.047 mmol). The reaction was stirred at 23° C. for 16 h. TLC at 16 h showed conversion to product. The reaction was quenched with H2O (5 mL) and extracted with DCM (3×5 mL). The combined organic layers were washed with 1M HCl (10 mL), saturated aqueous NaHCO$_3$ (10 mL), and saturated aqueous NaCl (10 mL). The organic layer was dried over MgSO$_4$, filtered, and evaporated. Purification with flash column chromatography with CH$_3$OH/CH$_2$Cl$_2$ (CH$_3$OH gradient 0→5%) yielded 3a (65.6 mg, 86% yield) $^1$H NMR (500 MHz, CDCl$_3$) δ 7.93-7.71 (m, 2H), 7.62-7.52 (m, 1H), 7.53-7.37 (m, 2H), 7.03 (dt, J=15.7, 5.1 Hz, 1H), 6.39 (s, 1H), 6.02 (dt, J=15.7, 1.9 Hz, 1H), 4.43-4.18 (m, 2H), 3.76 (s, 3H). $^{13}$C NMR (126 MHz, CDCl3) δ 167.43, 166.42, 144.13, 133.85, 131.87, 128.72, 126.96, 121.61, 51.75, 40.61. 3b (75.7 mg, 87% yield) $^1$H NMR (500 MHz, CDCl$_3$) δ 7.79 (d, J=8.8 Hz, 2H), 7.04 (dt, J=15.7, 5.1 Hz, 1H), 6.97 (d, J=8.8 Hz, 2H), 6.22 (s, 1H), 6.02 (dt, J=15.7, 1.9 Hz, 1H), 4.28 (ddd, J=6.1, 5.1, 1.9 Hz, 2H), 3.89 (s, 3H), 3.76 (s, 3H). $^{13}$C NMR (126 MHz, CDCl$_3$) δ 166.88, 166.46, 162.43, 144.39, 128.79, 126.08, 121.50, 113.87, 55.47, 51.73, 40.57. 3c (59.9 mg, 65% yield) $^1$H NMR (400 MHz, CDCl3) δ 8.30 (d, J=8.7 Hz, 2H), 7.94 (d, J=8.7 Hz, 2H), 6.98 (dt, J=15.7, 5.3 Hz, 1H), 6.31 (s, 1H), 5.99 (d, J=15.7 Hz, 1H), 4.28 (td, J=5.7, 1.9 Hz, 2H), 3.74 (s, 3H). $^{13}$C NMR (126 MHz, CDCl3) δ 166.25, 165.42, 149.78, 143.19, 139.37, 128.24, 123.97, 122.17, 51.86, 40.87.

9. Synthesis of 4

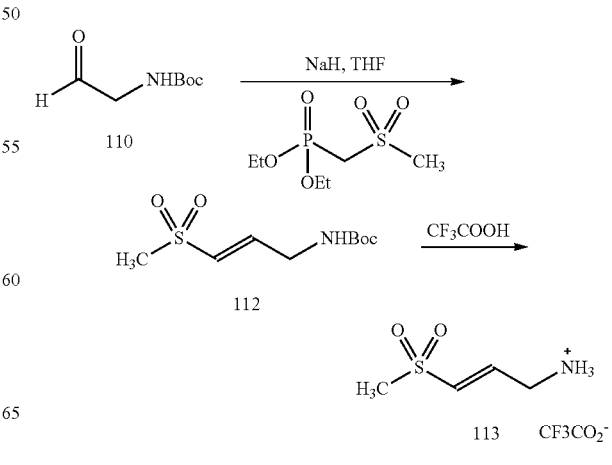

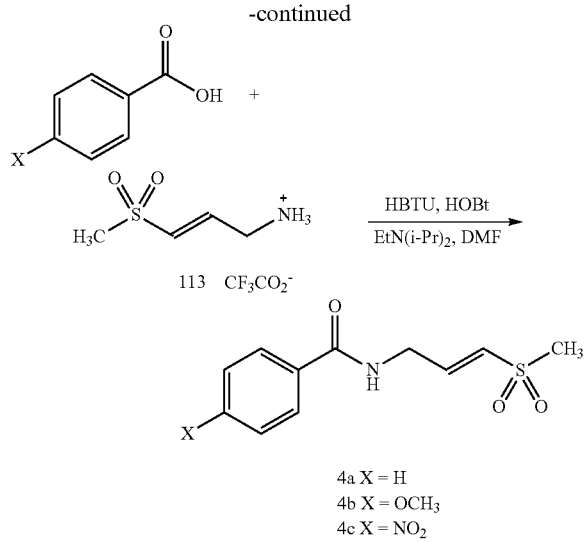

4a X = H
4b X = OCH₃
4c X = NO₂

10. Synthesis of 112

Sodium hydride (60% dispersion in mineral oil) (233.2 mg, 5.83 mmol) in tetrahydrofuran (0.17M, 34.3 mL) was cooled to 0° C. with stirring, followed by the dropwise addition of diethyl(methylsulfonylmethyl)phosphonate (Oakwood) (1342.2 mg, 5.83 mmol) in 5 mL THF. The reaction was stirred at 0° C. for 20 min, then 110 (928 mg, 5.83 mmol) in 5 mL THF was added. The reaction was allowed to warm to 23° C. and was stirred for 1 h. TLC showed conversion to the product. THF was removed under reduced pressure, and the residue was then diluted with ethyl acetate (30 mL) and water (30 mL). The layers were separated, and the aqueous layer was extracted with EtOAc (2×30 mL). The organic layer was then dried over MgSO4, filtered, and evaporated. The residue was purified by flash column chromatography with an ethyl acetate/hexanes gradient 25% EtOAc→50% EtOAc to yield 112 (530.4 mg, 56% yield). $^1$H NMR (400 MHz, CDCl$_3$) δ 6.38 (dd, J=11.7, 5.8 Hz, 1H), 6.28 (dt, J=11.4, 1.7 Hz, 1H), 5.01 (s, 1H), 4.23 (td, J=6.3, 1.7 Hz, 2H), 3.00 (s, 3H), 1.41 (s, 9H).

11. Synthesis of 113

112 (530.4 mg, 2.26 mmol) was dissolved in trifluoroacetic acid (3.45 mL, 45.1 mmol) and stirred at 23° C. for 30 min. TLC at 30 min showed conversion to product. Trifluoroacetic acid was evaporated off and azeotroped with toluene (2×30 mL). The residue was then dried on high vacuum for 2 hours, dissolved in 1 mL methanol and dropped into ice cold diethyl ether (100 mL). The resulting mixture was filtered to collect 113 as the TFA salt (435 mg, 77% yield). $^1$H NMR (500 MHz, DMSO-d6) δ 8.18 (s, 1H), 6.99 (dt, J=15.4, 1.7 Hz, 1H), 6.75 (dt, J=15.4, 5.5 Hz, 1H), 3.76 (dd, J=5.3, 1.7 Hz, 2H), 3.06 (s, 3H). $^{13}$C NMR (126 MHz, DMSO-d6) δ 137.95, 133.13, 48.56, 42.02.

12. Synthesis of 4a-c

Benzoic acid, p-methoxybenzoic acid, or p-nitrobenzoic acid (0.2 mmol) was dissolved in dimethylformamide (0.2M, 1 mL), then 113 (50 mg, 0.2 mmol), HBTU (73.8 mg, 0.16 mmol), and HOBT (29.8 mg, 0.22 mmol) were added, followed by DIPEA (100.7 μL, 0.6 mmol). The reaction was stirred at 23° C. for 16 h. TLC at 16 h showed conversion to product. The reaction was quenched with H$_2$O (5 mL) and extracted with CH$_2$Cl$_2$ (3×5 mL). The combined organic layers were washed with 1M HCl (10 mL), saturated aqueous NaHCO$_3$ (10 mL), and saturated aqueous NaCl (10 mL). The organic layer was dried over MgSO$_4$, filtered, and evaporated. Purified by flash column chromatography with a CH$_3$OH/CH$_2$Cl$_2$, CH$_3$OH gradient 0→5% to yield 4a (30.5 mg, 64% yield). $^1$H NMR (500 MHz, CDCl$_3$) δ 7.83 (dt, J=7.1, 1.4 Hz, 2H), 7.74-7.56 (m, 1H), 7.56-7.44 (m, 2H), 7.04 (dt, J=15.2, 4.5 Hz, 1H), 6.56 (d, J=15.1 Hz, 1H), 6.48 (t, J=5.8 Hz, 1H), 4.37 (ddd, J=6.2, 4.5, 1.9 Hz, 2H), 2.98 (s, 3H). $^{13}$C NMR (126 MHz, CDCl$_3$) δ 167.46, 144.22, 133.31, 132.21, 130.08, 128.84, 126.98, 42.85, 39.88. 4b (31.5 mg, 58% yield) $^1$H NMR (500 MHz, CDCl$_3$) δ 7.80 (d, J=8.8 Hz, 2H), 7.04 (dt, J=15.2, 4.4 Hz, 1H), 6.99 (d, J=8.8 Hz, 2H), 6.55 (dt, J=15.2, 2.0 Hz, 1H), 6.33 (t, J=6.1 Hz, 1H), 4.35 (ddd, J=6.2, 4.5, 1.9 Hz, 2H), 3.90 (s, 3H), 2.98 (s, 3H). $^{13}$C NMR (126 MHz, CDCl3) δ 166.95, 162.67, 144.58, 129.91, 128.87, 125.51, 113.98, 55.51, 42.86, 39.82. 4c (9.2 mg, 16% yield) $^1$H NMR (500 MHz, CDCl$_3$) δ 8.37 (d, J=8.7 Hz, 2H), 8.01 (d, J=8.7 Hz, 2H), 7.03 (dt, J=15.2, 4.8 Hz, 1H), 6.58 (dt, J=15.3, 1.9 Hz, 1H), 6.52 (s, 1H), 4.40 (ddd, J=6.4, 4.8, 1.9 Hz, 2H), 3.00 (s, 3H). $^{13}$C NMR (126 MHz, CDCl$_3$) δ 165.92, 149.72, 144.05, 139.07, 129.84, 128.53, 123.74, 42.63, 39.90.

13. Structures of 6-108:

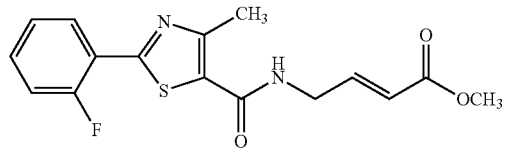

6

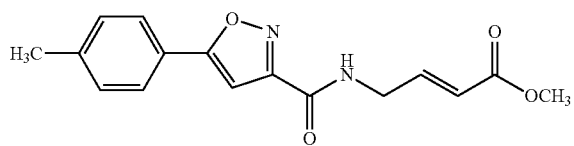

7

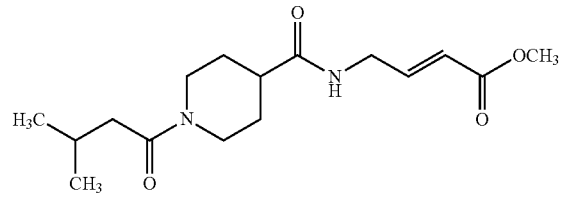

8

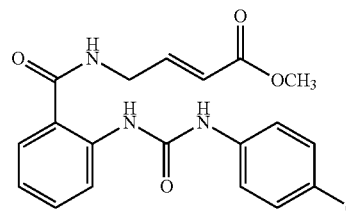

9

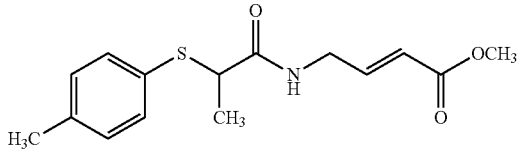

10

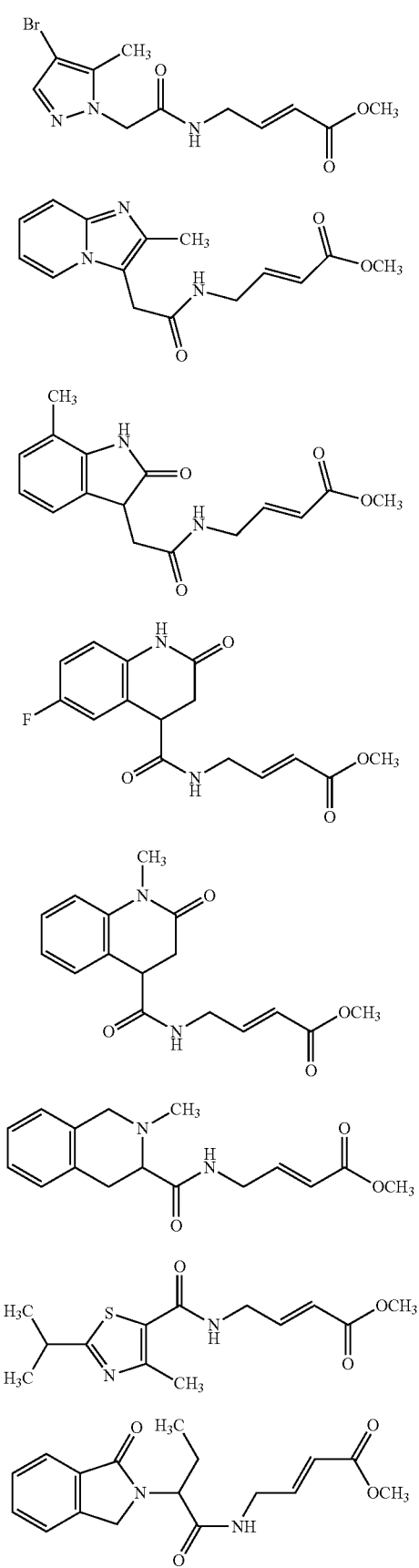

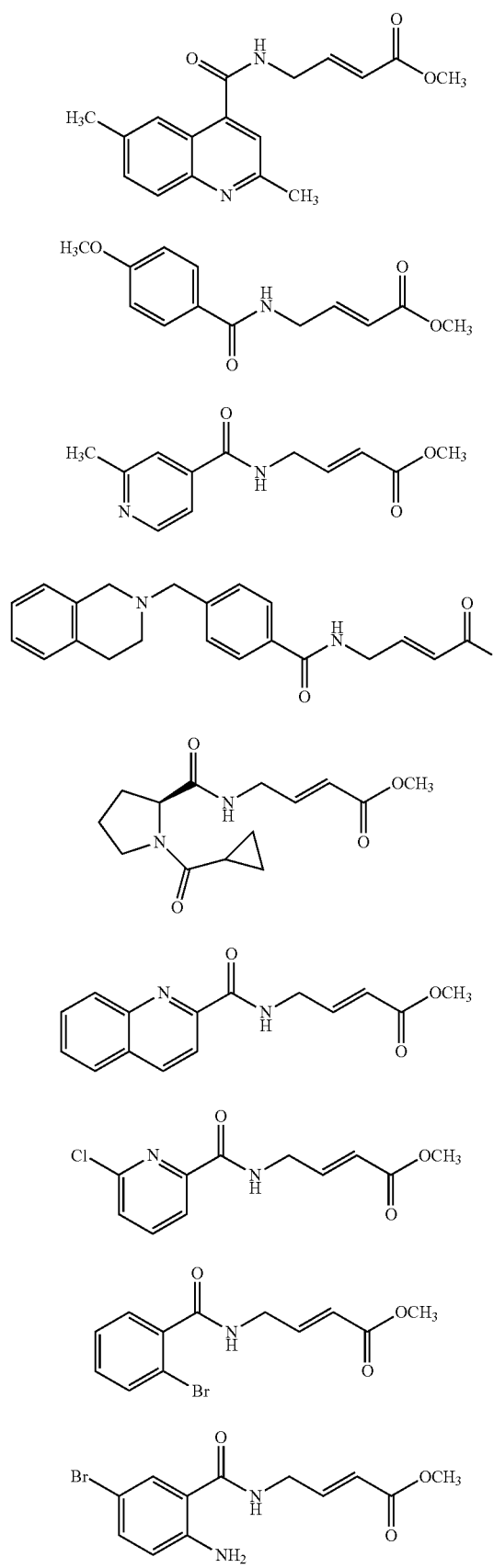
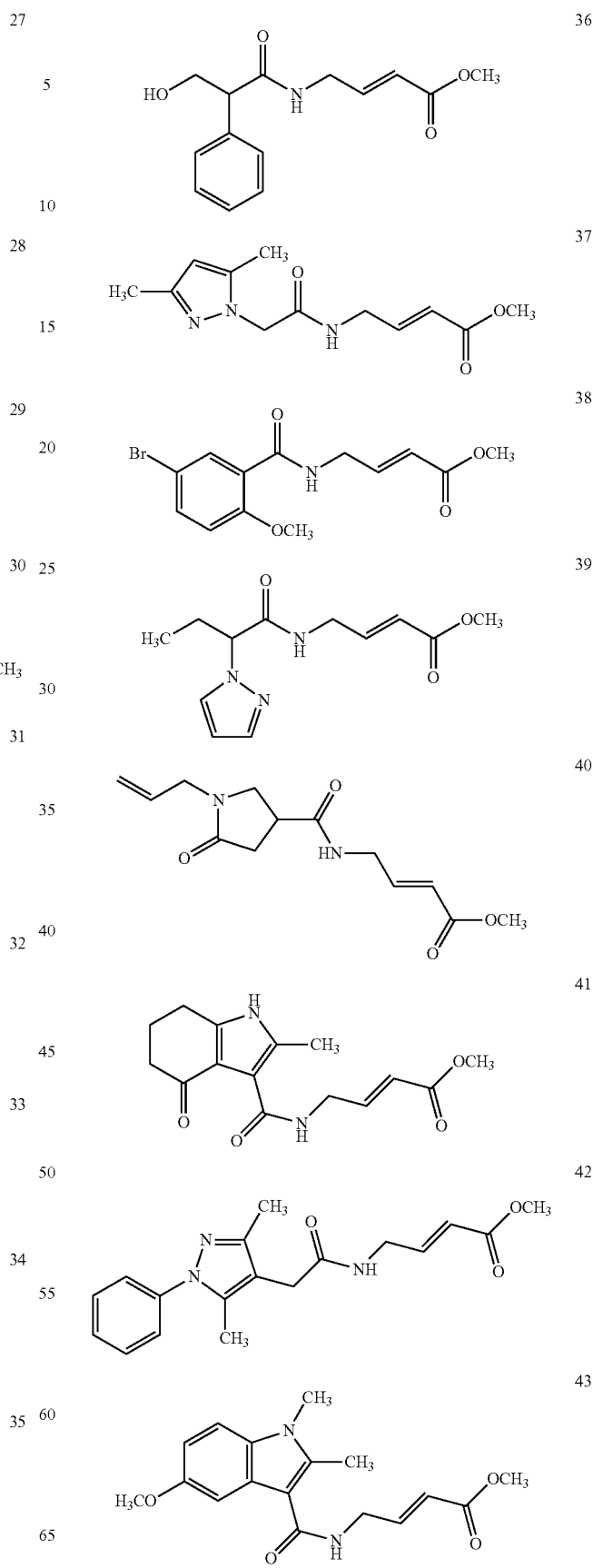

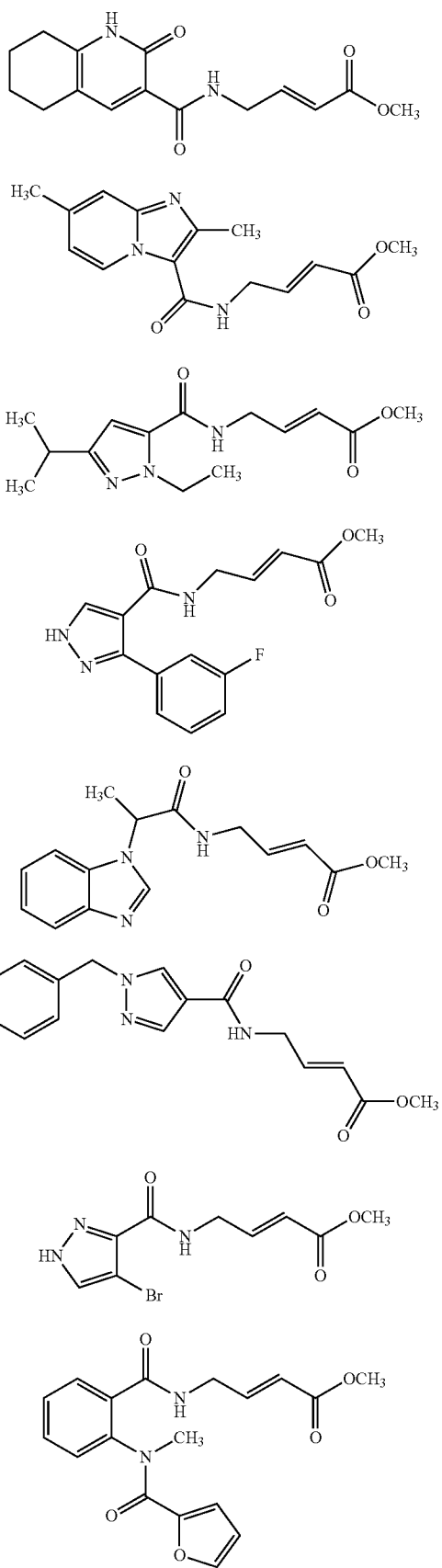
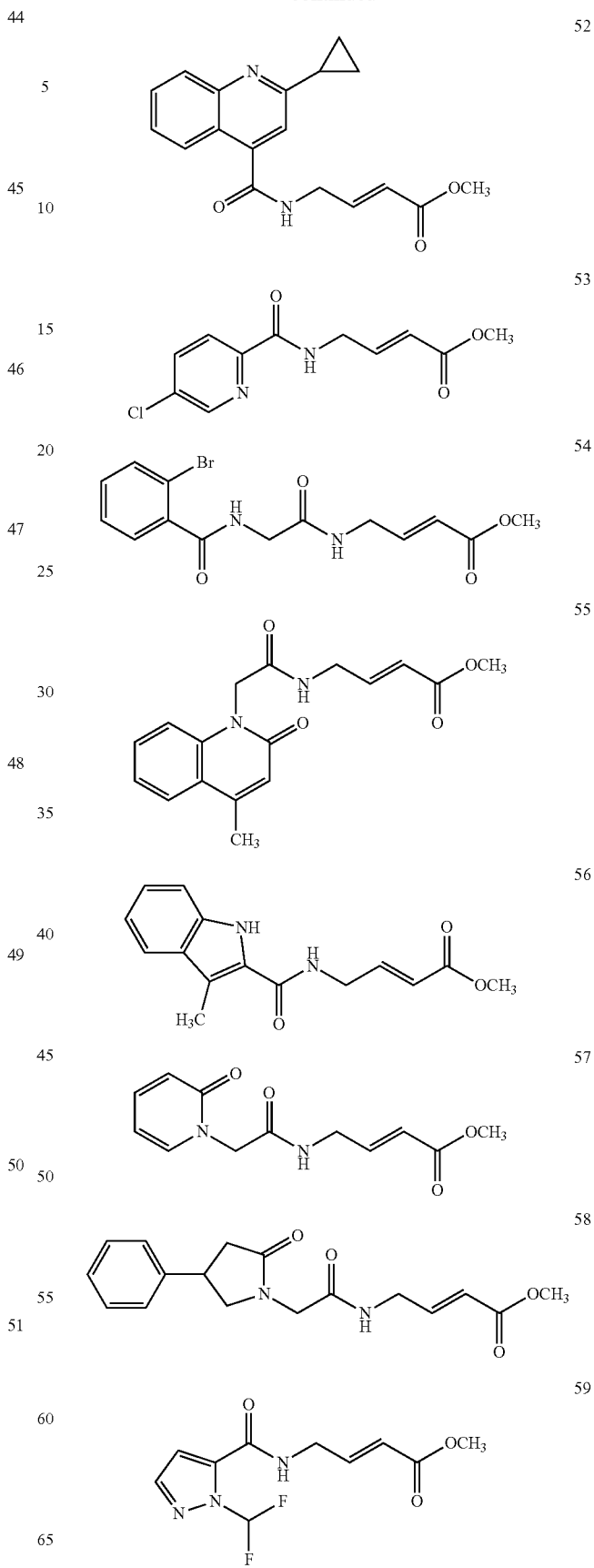

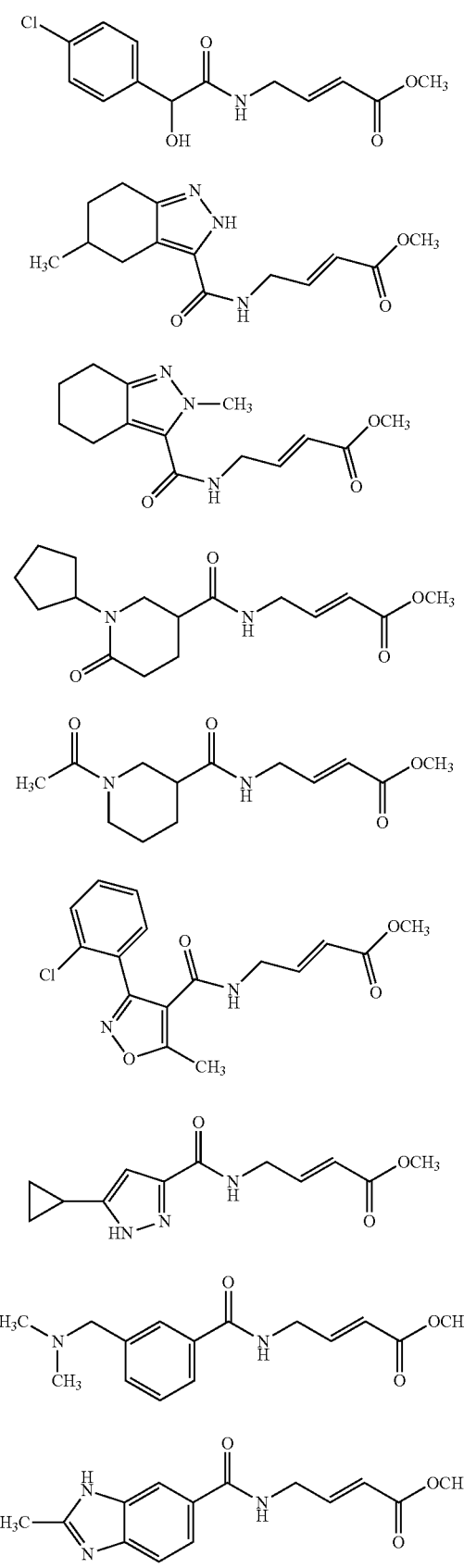
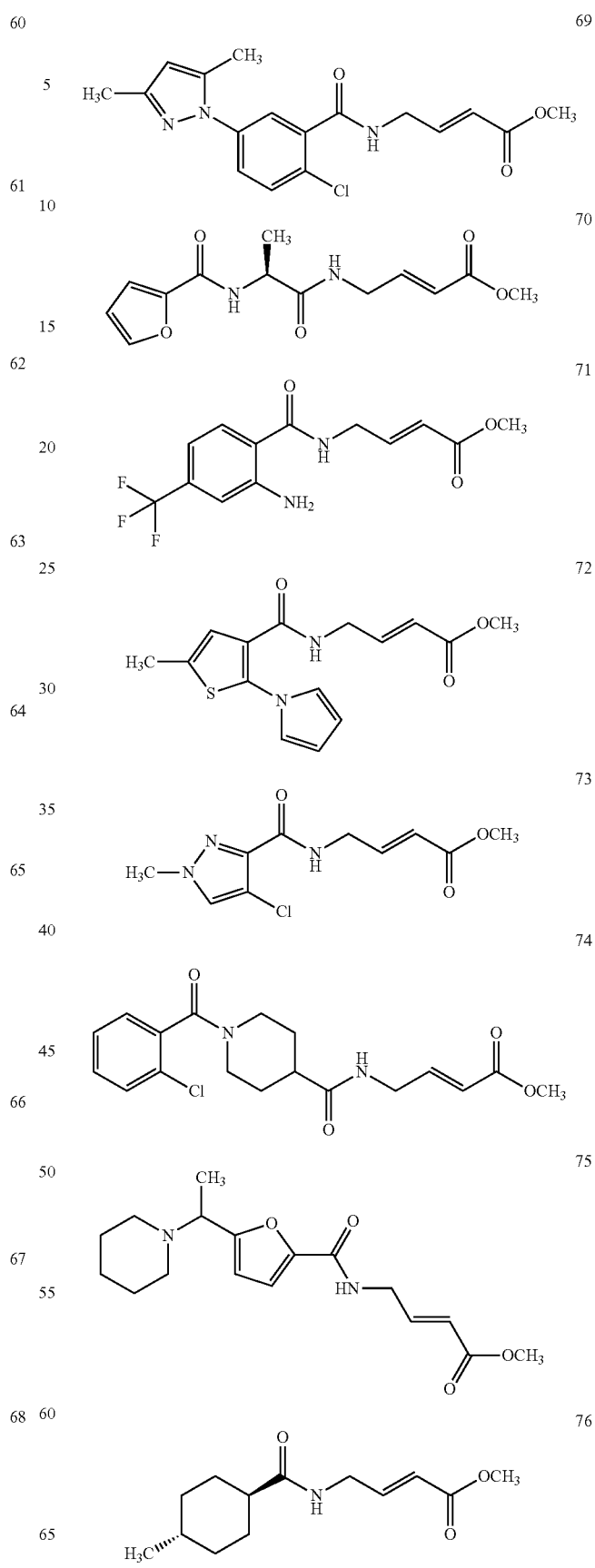

77
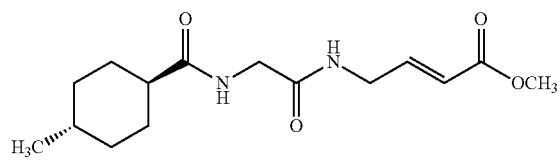
78
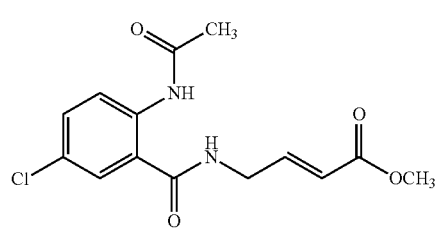
79
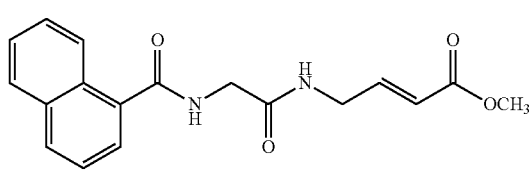
80
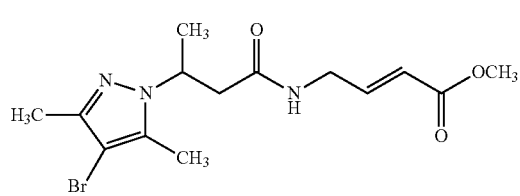
81
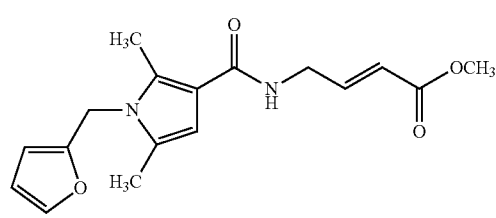
82
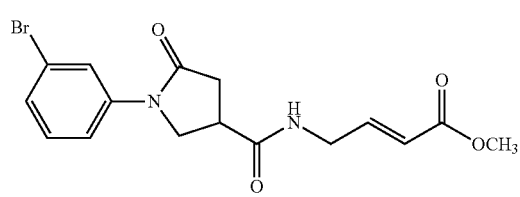
83
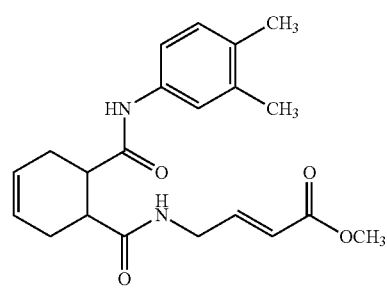
84
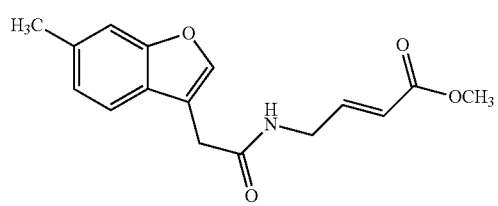
85
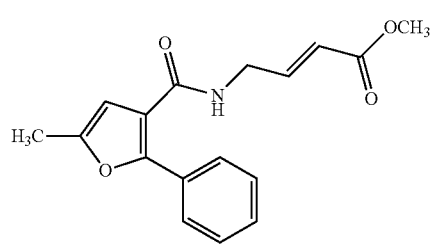
86
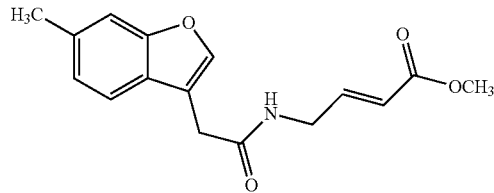
87
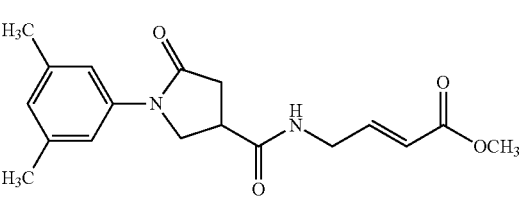
88
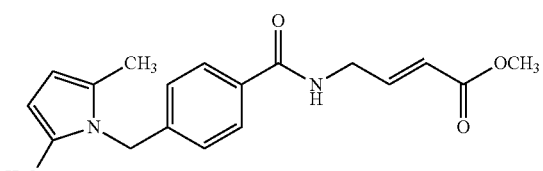
89
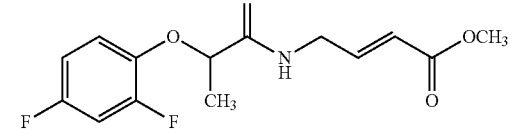
90
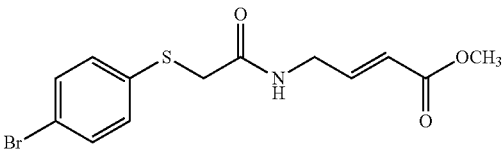
91
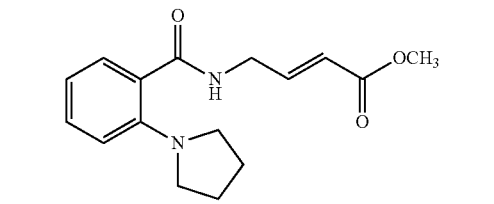

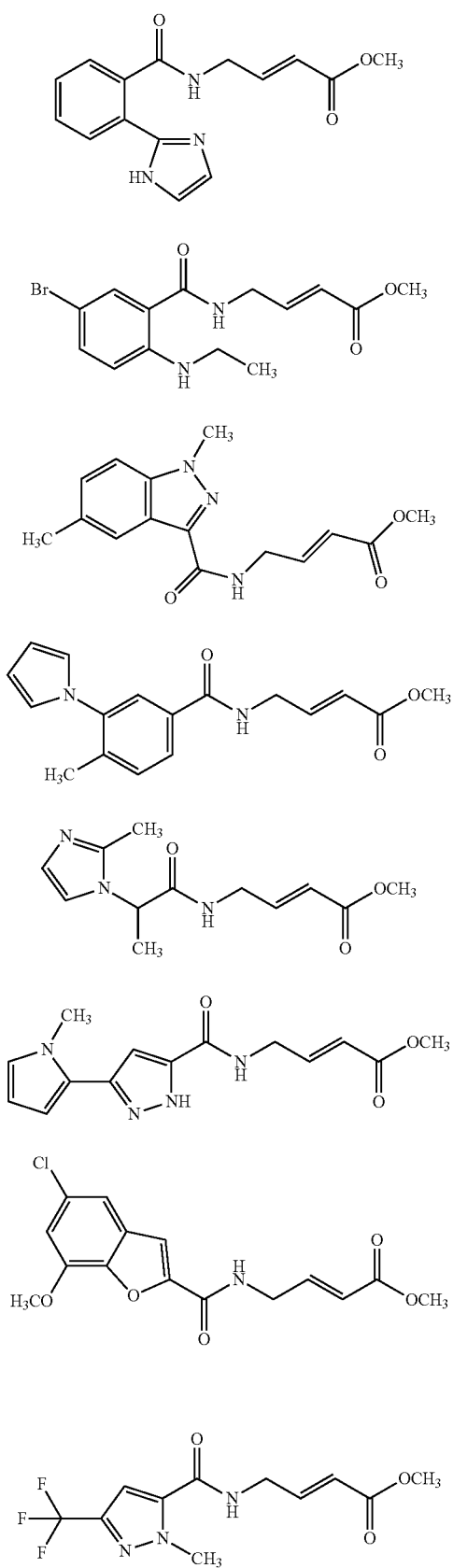
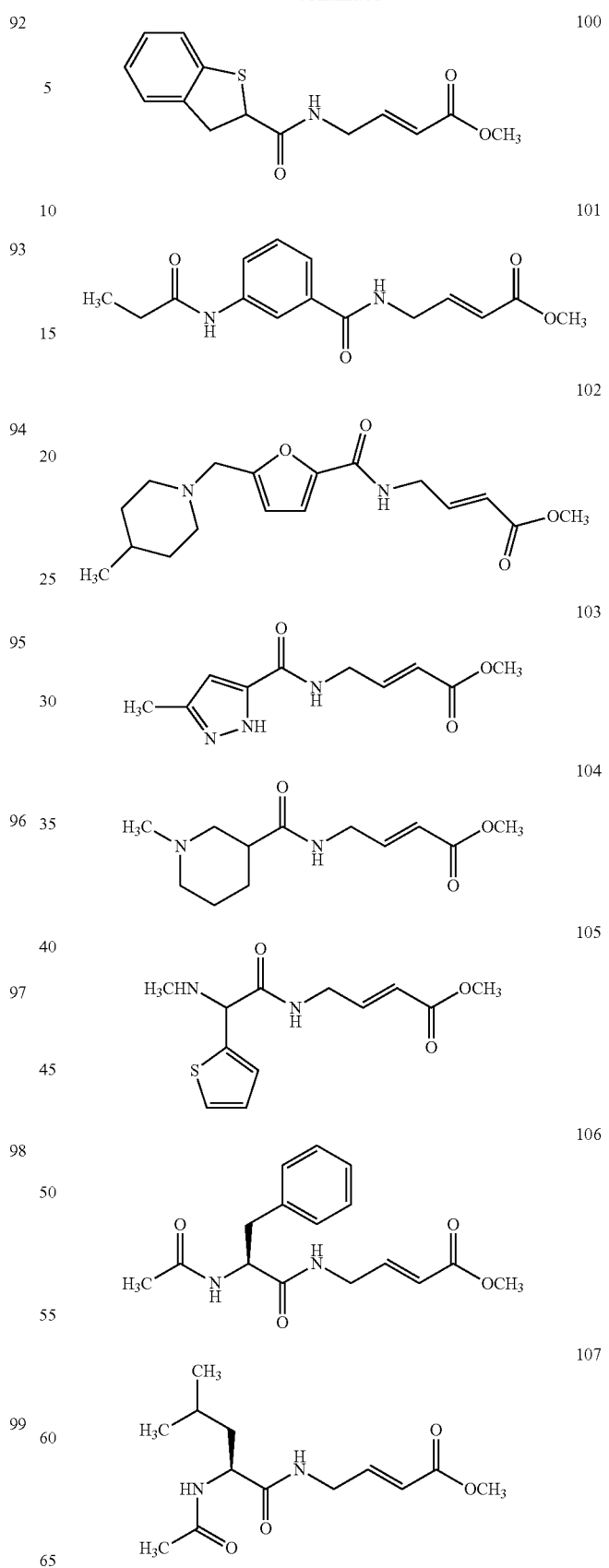

108

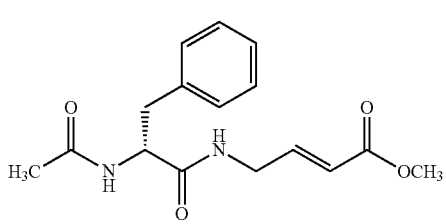

14. Characterization of compounds tested in enzymatic assays

6

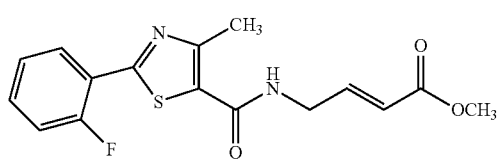

¹H NMR (500 MHz, CDCl₃) δ 8.29 (td, J=7.7, 1.8 Hz, 1H), 7.41 (dddd, J=8.7, 7.3, 5.3, 1.8 Hz, 1H), 7.24 (td, J=7.9, 1.4 Hz, 1H), 7.17 (ddd, J=11.4, 8.1, 1.2 Hz, 1H), 6.95 (dt, J=15.7, 5.2 Hz, 1H), 6.07-5.75 (m, 2H), 4.20 (td, J=5.6, 1.9 Hz, 2H), 3.71 (s, 3H), 2.75 (s, 3H). ¹³C NMR (126 MHz, CDCl₃) δ 166.29, 161.82, 161.22, 159.39, 156.23, 143.55, 132.07, 128.98, 125.44, 124.78, 122.00, 120.57, 116.22, 51.75, 40.69, 17.38. [M+Na]: 357.1 Da. HPLC purity: 95%.

7

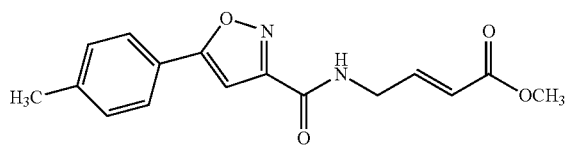

¹H NMR (500 MHz, CDCl₃) δ 7.63 (d, J=8.1 Hz, 2H), 7.23 (d, J=8.0 Hz, 2H), 6.98 (t, J=6.3 Hz, 1H), 6.93 (dt, J=15.7, 5.1 Hz, 1H), 6.86 (s, 1H), 5.96 (d, J=15.7 Hz, 1H), 4.20 (ddd, J=6.5, 5.1, 1.9 Hz, 2H), 3.68 (s, 3H), 2.35 (s, 3H). ¹³C NMR (126 MHz, CDCl₃) δ 172.07, 166.25, 159.05, 158.64, 143.10, 141.27, 129.84, 125.90, 123.99, 121.99, 98.50, 51.73, 39.98, 21.55. [M+H]: 301.1 Da. HPLC purity: 97%.

8

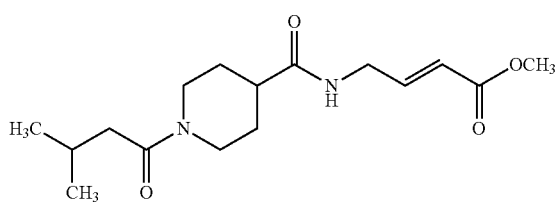

¹H NMR (500 MHz, CDCl₃) δ 6.87 (d, J=15.7 Hz, 1H), 6.05-5.57 (m, 2H), 4.03 (t, J=5.5 Hz, 2H), 3.71 (s, 3H), 3.03 (s, 1H), 2.63 (s, 1H), 2.44-2.27 (m, 1H), 2.19 (d, J=6.8 Hz, 2H), 2.07 (dt, J=13.4, 6.7 Hz, 1H), 1.87 (d, J=11.3 Hz, 3H), 1.64 (s, 3H), 0.94 (d, J=6.6 Hz, 6H). ¹³C NMR (126 MHz, CDCl₃) δ 173.93, 171.03, 166.31, 144.04, 121.52, 51.72, 43.11, 42.12, 40.03, 25.84, 22.76. [M+H]: 311.2 Da. HPLC purity: 98%.

19

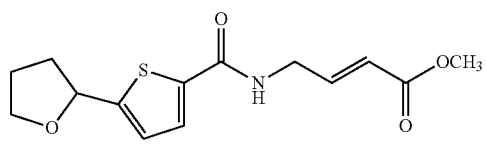

¹H NMR (500 MHz, CDCl₃) δ 7.24 (d, J=3.8 Hz, 1H), 6.80 (dt, J=15.7, 5.1 Hz, 1H), 6.74 (dd, J=3.8, 0.9 Hz, 1H), 6.08-5.96 (m, 1H), 5.81 (d, J=15.7 Hz, 1H), 4.97 (t, J=6.6 Hz, 1H), 4.18-3.99 (m, 2H), 3.89 (dd, J=7.6, 5.9 Hz, 1H), 3.74 (dd, J=7.5, 1.0 Hz, 1H), 3.56 (s, 3H), 2.34-2.04 (m, 1H), 1.93-1.69 (m, 4H). ¹³C NMR (126 MHz, CDCl₃) δ 166.38, 161.88, 153.36, 144.00, 136.10, 128.68, 123.75, 121.66, 68.64, 51.70, 40.47, 34.77, 25.84. [M+Na]: 318.1 Da. HPLC purity: 95%.

106

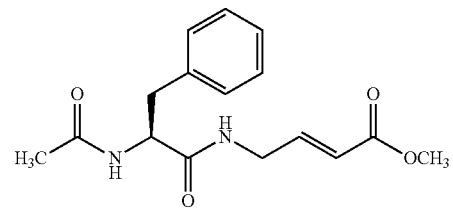

¹H NMR (500 MHz, CDCl₃) δ 7.55-7.00 (m, 5H), 6.72 (dt, J=15.7, 5.2 Hz, 1H), 6.07 (d, J=7.8 Hz, 1H), 5.94 (s, 1H), 5.69 (dt, J=15.9, 1.7 Hz, 1H), 4.60 (td, J=8.0, 6.2 Hz, 1H), 4.04-3.80 (m, 2H), 3.71 (s, 3H), 3.21-2.78 (m, 2H), 1.98 (s, 3H). ¹³C NMR (126 MHz, CDCl₃) δ 170.85, 170.20, 166.27, 143.28, 136.39, 129.18, 128.87, 127.25, 121.61, 54.83, 51.66, 40.03, 38.24, 23.21. [M+Na]: 327.1 Da. HPLC purity: 95%.

107

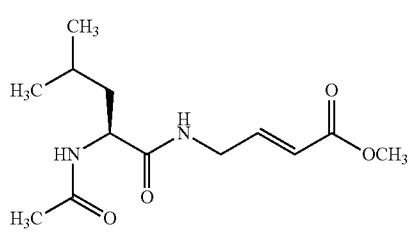

¹H NMR (500 MHz, CDCl₃) δ 7.33-7.19 (m, 1H), 7.11 (dt, J=15.8, 5.0 Hz, 1H), 6.52 (d, J=8.4 Hz, 1H), 6.13 (dt, J=15.9, 1.9 Hz, 1H), 4.74 (td, J=8.5, 5.9 Hz, 1H), 4.24 (dt, J=5.8, 3.0 Hz, 2H), 3.95 (s, 3H), 2.23 (s, 3H), 1.89 (tt, J=13.2, 6.2 Hz, 2H), 1.84-1.71 (m, 1H), 1.17 (dd, J=11.5, 6.1 Hz, 6H). ¹³C NMR (126 MHz, CDCl₃) δ 172.34, 170.54, 166.42, 143.91, 121.38, 51.69 (d, J=7.5 Hz), 40.86, 40.05, 24.80, 23.12, 22.82, 22.25. [M+Na]: 293.1 Da. HPLC purity: 95%.

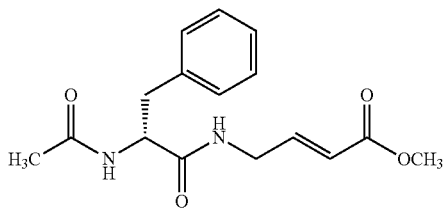

108

$^1$H NMR (500 MHz, CDCl$_3$) δ 7.51-7.12 (m, 5H), 6.80 (dt, J=15.7, 5.0 Hz, 2H), 6.61 (d, J=8.0 Hz, 1H), 5.76 (dd, J=15.8, 2.0 Hz, 1H), 4.78 (q, J=7.6 Hz, 1H), 4.09-3.86 (m, 2H), 3.76 (s, 3H), 3.10 (dd, J=7.5, 1.9 Hz, 2H), 2.00 (s, 3H). 13C NMR (126 MHz, CDCl$_3$) δ 171.24, 170.32, 166.35, 143.55, 136.46, 129.22, 128.70, 127.11, 121.40, 54.75, 51.63, 39.99, 38.56, 23.10. [M+Na]: 327.1 Da. HPLC purity: 99%.

B. Methods

1. Dialysis Experiments (FIG. 9)

200 µL of papain and compound 6-8 adducts were prepared separately as described above in "irreversible tethering screening assay" by incubating papain (10 µM) with 100 µM of compounds 6-8 in 1% DMSO 50 mM HEPES 150 mM NaCl 0.1 mM EDTA pH 7.5. The adducts were loaded into Slide-A-Lyzer dialysis cassettes (Thermo). The cassettes were dialyzed against 500 mL of 50 mM HEPES 150 Mm NaCl 0.1 mM EDTA pH 7.5 for 16 h, then 20 µL were extracted and analyzed by ESI-MS. The buffer was then replaced with fresh buffer and samples continued and switched again after another 24 h, with 20 µL samples extracted for MS analysis prior to each buffer switch.

2. Recombinant Expression of GST-HRV3C Protease in E. coli

GST-HRV3C protease in a PGEX4T vector plasmid (GST-UbcH7) was transformed into Rosetta (DE3)pLysS cells (Millipore). 1 L LB media containing 100 µg/ml ampicillin was inoculated with 50 mL overnight cell culture and incubated at 37° C. until OD reached ~0.5. Then, IPTG (0.5 mM final concentration) was added to the cell culture media at 28° C., followed by 5 hour incubation at the same temperature. Cells were then harvested and lysed by sonication in phosphate buffered saline (PBS) with 1 mM DTT and 1 mM PMSF. The supernatant was incubated with glutathione agarose beads (Pierce Biotechnology) for 1 hour at 4° C. The beads were washed three times with PBS+1 mM DTT+1 mM PMSF. The protease was then eluted with 100 mM Tris pH 8.0, 100 mM NaCl, 10 mM GSH (reduced), 1 mM DTT. The pooled fractions were then dialyzed three times (300, 400, 300 mL) versus 50 mM Tris Ph 8.5, 150 mM NaCl, 5 mM DTT, 20% glycerol.

3. Recombinant Expression of UbcH7 in E. coli

UbcH7 in a PGEX6P1 vector plasmid (GST-UbcH7) was transformed into BL21 cells (Novagen). 1 L LB media containing 100 µg/ml ampicillin was inoculated with 50 mL overnight cell culture and incubated at 37° C. until OD reached ~1.2. Then, IPTG (1.0 mM final concentration) was added to the cell culture media at 30° C., followed by 4 hour incubation at the same temperature. Cells were then harvested and lysed by sonication in phosphate buffered saline (PBS) with protease inhibitors (Complete Mini Protease Inhibitor Cocktail, Roche). The supernatant was incubated with glutathione agarose beads (Pierce Biotechnology) for 1 hour at 4° C. The beads were washed three times with PBS and incubated with PreScission Protease overnight at 4° C. to elute UbcH7 (50 mM HEPES, 150 mM NaCl, 0.1 mM EDTA).

4. Recombinant Expression of USPO8 Catalytic Domain in E. coli

USPO8 catalytic domain in a PET21a-LIC vector plasmid (6×His-USP08, Addgene) was transformed into BL21 (DE3) cells (Invitrogen). 1 L TB media containing 100 µM kanamycin and 600p1 antifoam 204 (Sigma A-8311) was inoculated with 50 ml overnight culture and incubated at 37° C. until OD reached ~3. Then, IPTG (100 µM final concentration) was added to the cell culture media at 15° C. The culture was incubated overnight at the same temperature. Cells were then harvested and lysed by sonication in 10 mM Tris-HCl pH 7.0, 0.5 M NaCl 5% glycerol 2 mM imidazole 1 mM β-mercaptoethanol 0.1 µM PMSF. The cleared lysate was then loaded onto TALON metal-affinity beads at 4° C. Beads were washed three times with 10 mM Tris-HCl, pH 7.0 0.5 M NaCl 5% glycerol 10 mM imidazole 1 mM β-mercaptoethanol 0.05% Tween 20. The protein was then eluted with 10 mM Tris-HCl pH 7.0, 0.5 M NaCl 5% glycerol 200 mM imidazole 1 mM β-mercaptoethanol before being exchanged into 50 mM HEPES 150 mM NaCl 0.1 mM EDTA pH 7.5 with PD10 columns (GE Healthcare). MS analysis of USPO8 showed that the resulting protein had a cleaved N-terminal methionine residue, and ~50% of the protein had been further modified by gluconic acid at the N-terminus.

References (1) Scott, D. E.; Coyne, A. G.; Hudson, S. A.; Abell, C. Fragment-Based Approaches in Drug Discovery and Chemical Biology. *Biochemistry* 2012, 51, 4990-5003.

(2) Erlanson, D. A.; Braisted, A. C.; Raphael, D. R.; Randal, M.; Stroud, R. M.; Gordon, E. M.; Wells, J. A. Site-directed ligand discovery. *PNAS* 2000, 97, 9367-9372.

(3) Erlanson, D. A.; Wells, J. A; Braisted, A. C. Tethering: fragment-based drug discovery. *Annu. Rev. Biophys. Biomol. Struct.* 2004, 33, 199-223.

(4) Miller, R. M.; Paavilainen, V. O.; Krishnan, S.; Serafimova, I. M.; Taunton, J. Electrophilic fragment based design of reversible covalent kinase inhibitors. *J. Am. Chem. Soc.* 2013, 135, 5298-5301.

(5) Singh, J.; Petter, R. C.; Baillie, T. A.; Whitty, A. The resurgence of covalent drugs. *Nat. Rev. Drug. Discov.* 2011, 10, 307-317.

(6) Zartler, E.; Shapiro, M. *Fragment-Based Drug Discovery: A Practical Approach*, Wiley: 2008.

(7) Cardoso, R.; Love, R.; Nilsson, C. L.; Bergqvist, S.; Nowlin, D.; Yan, J.; Liu, K. K.; Zhu, J.; Chen, P.; Deng, Y. L.; Dyson, H. J.; Greig, M. J.; Broouun, A. Identification of Cys255 in HIF-1α as a novel site for development of covalent inhibitors of HIF-1α/ARNT PasB domain protein—protein interaction. *Protein. Sci.* 2012, 21, 1885-1896.

(8) Weerapana, E.; Wang, C.; Simon, G. M.; Richter, F.; Khare, S.; Dillon, M. B.; Bachovchin, D. A.; Mowen, K.; Baker, D.; Cravatt, B. F. Quantitative reactivity profiling predicts functional cysteines in proteomes. *Nature* 2010, 468, 790-795.

(9) Nonoo, R. H.; Armstrong, A.; Mann, D. J. Kinetic Template-Guided Tethering of Fragments. *ChemMedChem* 2012, 7, 2082-2086.

(10) Rosenthal, P. J. Falcipains and other cysteine proteases of malaria parasites. *Adv. Exp. Med. Biol.* 2011, 712, 30-48.

(11) Reddick, J. J.; Cheng, J.; Roush, W. R. Relative Rates of Michael Reactions of 2'-(Phenethyl)thiol with Vinyl Sulfones, Vinyl Sulfonate Esters, and Vinyl Sulfonamides Relevant to Vinyl Sulfonyl Cysteine Protease Inhibitors. *Org. Lett.* 2003, 5, 1967-1970.

(12) Chen, G.; Heim, A.; Riether, D.; Yee, D.; Milgrom, Y.; Gawinowicz, M. A.; Sames. D. Reactivity of Functional Groups on the Protein Surface: Development of Epoxide Probes for Protein Labeling. *J. Am. Chem. Soc.* 2003, 125, 8130-8133.

(13) a) Hanzlik, R. P.; Thompson, S. A. Vinylogous Amino Acid Esters: A New Class of Inactivators for Thiol Proteases. *J. Med. Chem.* 1984, 27, 711-712. b) Ettari, R.; Micale, N.; Schirmeister, T.; Gelhaus, C.; Leippe, M.; Nizi, E.; Di Francesco, M. E.; Grasso, S.; Zappala, M. Novel Peptidomimetics Containing a Vinyl Ester Moiety as Highly Potent and Selective Falcipain-2 Inhibitors. *J. Med. Chem.* 2009, 52, 2157-60.

(14) Patick, A. K.; Brothers, M. A.; Maldonado, F.; Binford, S.; Maldonado, O.; Fuhrman, S.; Petersen, A.; Smith III, G. J.; Zalman, L. S.; Burns-Naas, L. A.; Tran, J. Q. In Vitro Antiviral Activity and Single-Dose Pharmacokinetics in Humans of a Novel, Orally Bioavailable Inhibitor of Human Rhinovirus 3C Protease. *Antimicrob. Agents Chemother.* 2005, 49, 2267-2275.

(15) Congreve, M.; Carr, R.; Murray, C.; Jhoti, H. A. *Drug Discovery Today* 2003, 8, 876-877.

(16) Rosenthal, P. J. Falcipains and other cysteine proteases of malaria parasites. *Adv. Exp. Med. Biol.* 2011, 712, 30-48.

(17) Liu, S.; Hanzlik, R. P. Structure-activity relationships for inhibition of papain by peptide Michael acceptors. *J. Med. Chem.* 1992, 35, 1067-1075.

(18) Krippendorff, B. F.; Neuhaus, R.; Lienau, P.; Reichel, A.; Huisinga, W. Mechanism-Based Inhibition: Deriving KI and kinact Directly from Time-Dependent IC50 Values. *J. Biomol. Screen.* 2009, 14, 913-23.

(19) Powers, J. C.; Asgian, J. L.; Ekici, 0. D.; James, K. E. Irreversible Inhibitors of Serine, Cysteine, and Threonine Proteases. *Chem. Rev.* 2002, 102, 4639-4750

(20) Renukuntla, J.; Vadlapudi, A. D.; Patel, A.; Boddu, S. H.; Mitra, A. K. Approaches for enhancing oral bioavailability of peptides and proteins. *Int. J. Pharm.* 2013, 447, 75-93.

(21) Byun, S.; Lee, S. Y.; Lee, J.; Jeong, C. H.; Farrand, L.; Lim, S.; Reddy, K.; Kim, J. Y.; Lee, M. H.; Lee, H. J.; Bode, A. M.; Lee, K. W.; Dong, Z. USP8 is a novel target for overcoming gefitinib-resistance in lung cancer. *Clin. Cancer Res.* 2013, 19, 3894-904.

(22) Whitcomb, E. A.; Dudek, E. J.; Liu, Q.; Taylor, A. Novel control of S phase of the cell cycle by ubiquitin-conjugating enzyme H7. *Mol. Biol. Cell.* 2009, 20, 1-9.

(23) Kitz, R.; Wilson, I. B. Esters of Methanesulfonic Acid as Irreversible Inhibitors of Acetylcholinesterase. *J. Biol. Chem.* 1962, 237, 3245-3249.

Example 2—Methods to Screen for the Binding of Chemical Entities

Abstract

Ubiquitin ligases are a large family of enzymes with substantial roles in human disease. While the importance of ubiquitin ligases in human disease rivals protein kinases, unfortunately few small molecule inhibitors of ubiquitin ligases have been disclosed. Herein we disclose small molecule inhibitors of HECT-type ubiquitin ligase. More specifically, herein we disclose small molecule inhibitors of the HECT-type ubiquitin ligase NEDD4-1. The small molecule inhibitors disclosed herein serve as therapies for the multitude of diseases in which NEDD4-1 is a factor, including but not limited to, cancer, neurodegenerative diseases and the spreading of HIV.

Background and Introduction

Many researchers study the importance of protein kinases in the regulation of disease. On the other hand, another important means to study the regulation of disease is through the control of ubiquitin ligases. Ubiquitin ligases are a large family of enzymes with substantial roles in human disease and their importance in biology rivals that of protein kinases.

For example, NEDD4-1 is overexpressed in a wide variety of cancers and is a promising drug target for these diseases. It is proposed that NEDD4-1 "ubiquitinate" and degrade tumor suppressors p53, LATS, and PTEN, which contributes to its oncogenic properties. In addition NEDD4-1 is involved in the degradation of α-synuclein, a key player in Parkinson's disease. Small molecule activators of NEDD4-1 will serve as therapeutics to treat Parkinson's disease. Lastly, NEDD4-1 and its closely related homolog NEDD4-2, which is also a likely target of our inhibitors, have been shown to be essential host proteins for the budding of HIV viruses from the host cell. Therefore, they are promising host targets for HIV. Lastly NEDD4-1$^{+/-}$ heterozygous mice gained less weight when placed on the high fat diet, indicating NEDD4-1 to be a promising drug target to treat obesity.

Unlike protein kinases, efforts to develop small molecule inhibitors of ubiquitin ligases have been mostly unsuccessful. Herein we disclose small molecule inhibitors of the HECT-type ubiquitin ligase NEDD4-1, an enzyme for which there are no reported inhibitors. These compounds serve as therapies for the multitude of diseases in which NEDD4-1 is a factor including, but not limited to, cancer, neurodegenerative disease and spreading of HIV.

Experimental

In some embodiments, the compounds of this example have a generic structure as indicated below:

Generic structure:

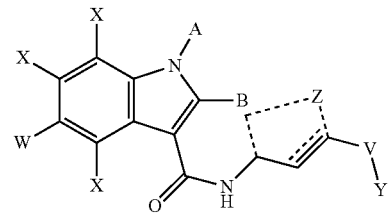

A = aryl, alkyl rings
B = aryl, alkyl rings and chains
Z = CH$_2$, CH$_2$CH$_2$
V = COY, SO$_2$Y, CN
Y = CR$_1$R$_2$R$_3$, OR, NR$_1$R$_2$
R = aryl, alkyl rings and chains
W = OMe, SMe, SH, NH$_2$, NHMe
X = F, Cl, Br In other embodiments, the compounds of this example may be chosen from the group consisting of:

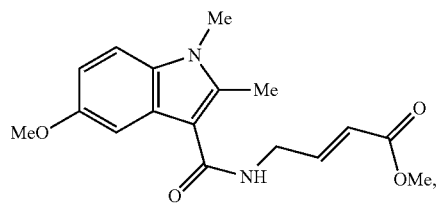

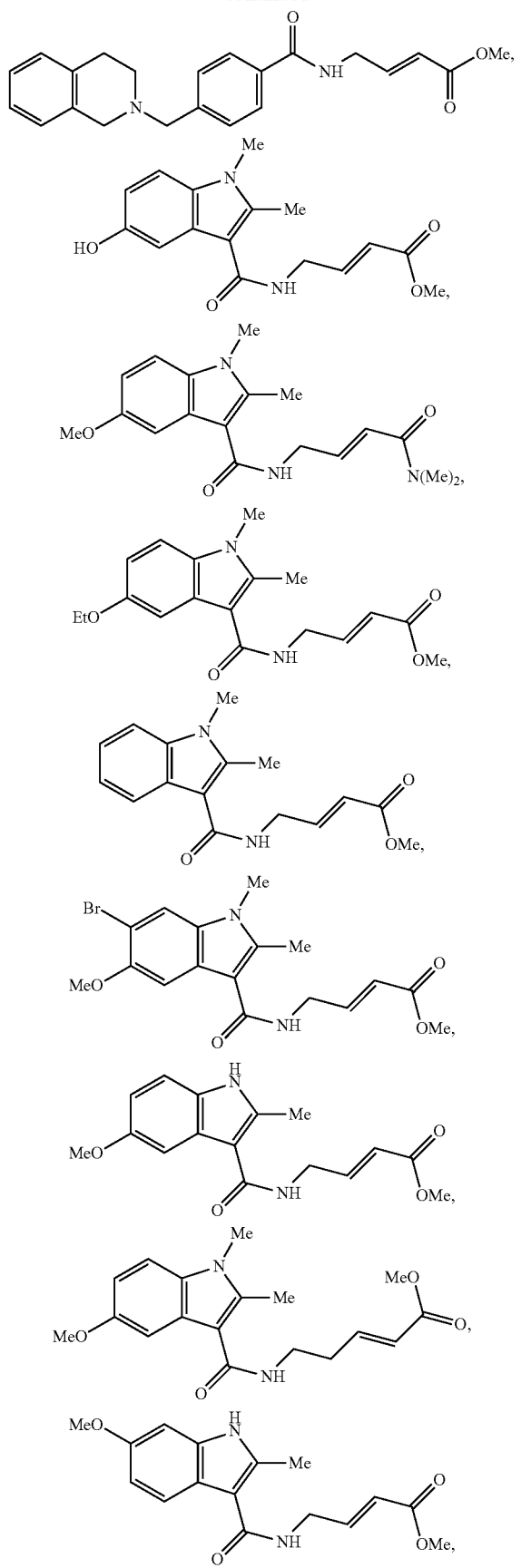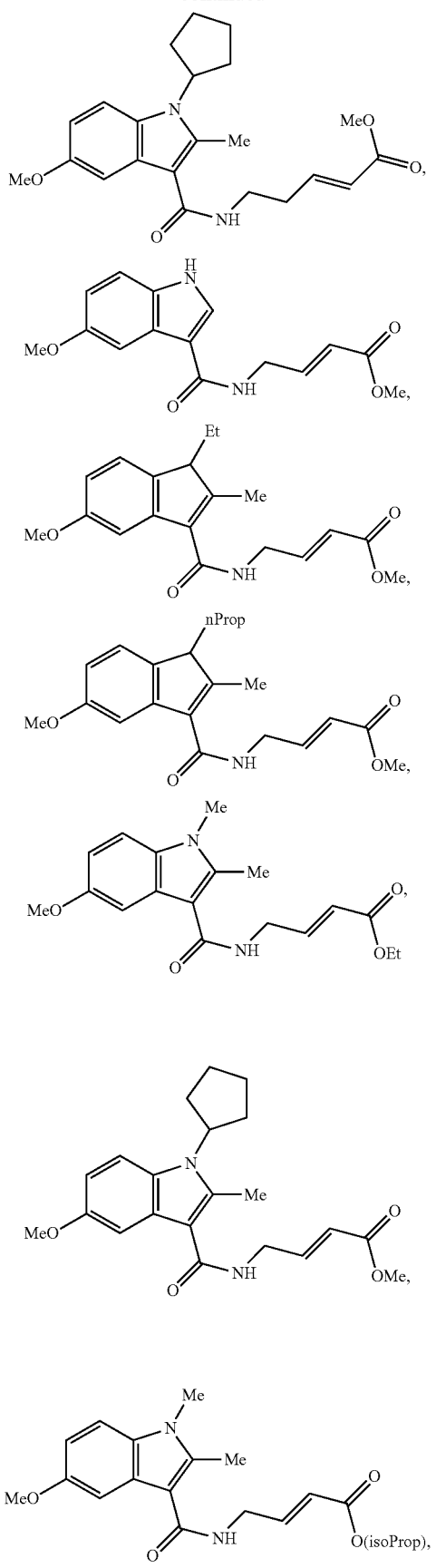

61

-continued

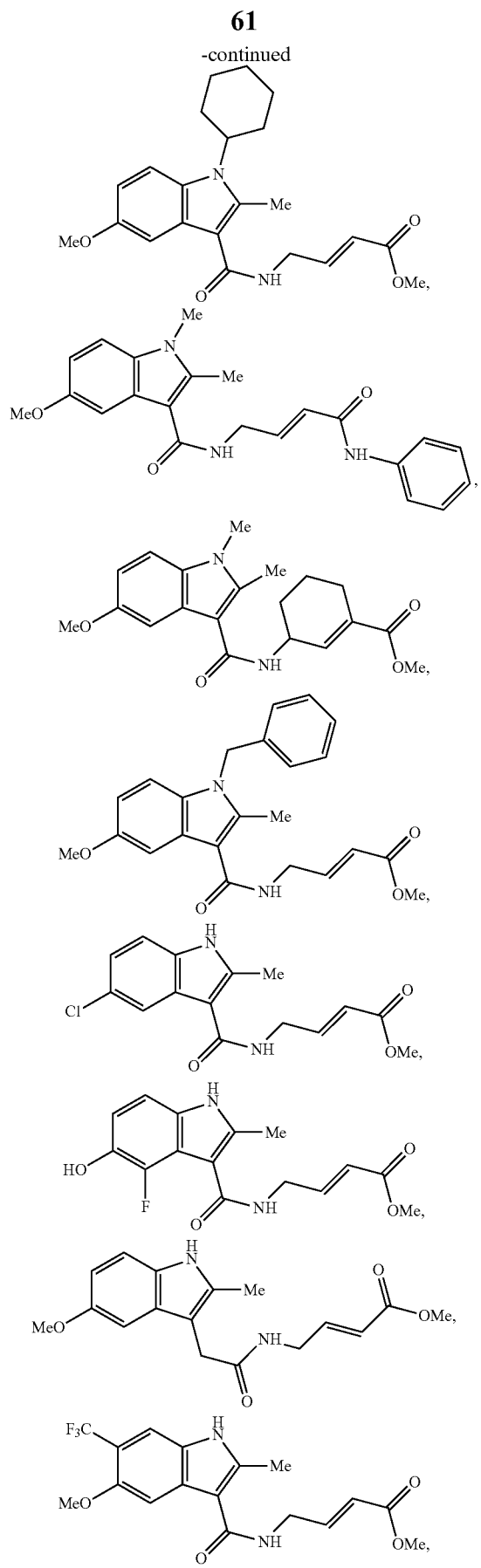

62

-continued

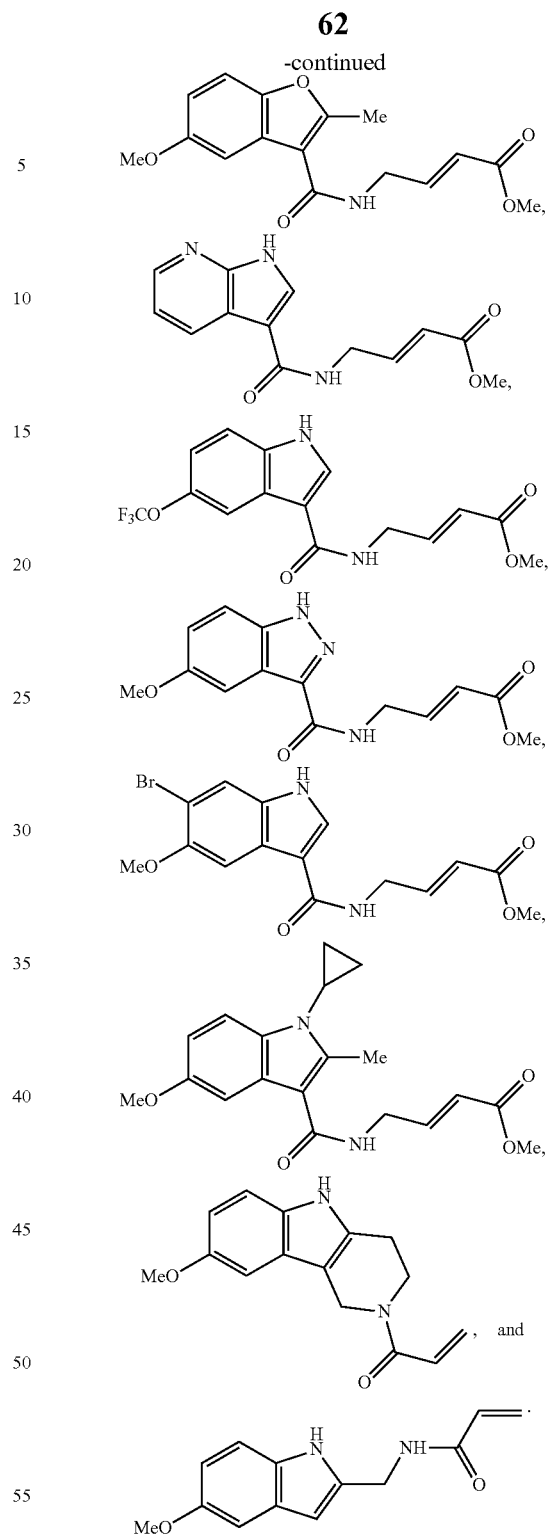

A. Chemical Synthesis of NEDD4-1 Inhibitors i. General Information

Methanol (ACS grade), ethyl acetate (ACS grade), chloroform (ACS grade), toluene (ACS grade), and diethyl ether (ACS grade), and hexanes (ACS grade) were purchased from Fisher Scientific and used without further purification. Dichloromethane, tetrahydrofuran and dimethylformamide were purified by passing over activated alumina. Commercially available reagents were used without further purification. Unless otherwise specified, all reagents were purchased from Sigma-Aldrich. Reactions were monitored by thin-layer chromatography (TLC) on pre-coated glass backed plates (60 Å silica gel, 0.25 mm, Whatman), and components were visualized by UV light (254 and 365 nm) or by treating the plates with anisaldehyde, KMnO4, and ninhydrin stains followed by heating. Flash column chromatography was performed over ultra pure silica gel (230-400 mesh) from Silicycle. 1H and 13C NMR spectra were obtained on a Bruker AVANCE III 500 MHz spectrometer or an Agilent DDR2 400 MHz spectrometer (Funded by NSF CHE-1048773, 2010). Chemical shifts were reported in ppm relative to the residual solvent peak (CDCl3 or DMSO-d6). Multiplicity was indicated as follows: s (singlet); d (doublet); t (triplet); q (quartet); m (multiplet); dd (doublet of doublets); ddd (doublet of doublet of doublets); dt (doublets of triplets); td (triplet of doublets); brs (broad singlet). Coupling constants were reported in Hz.

ii. General Synthesis Scheme

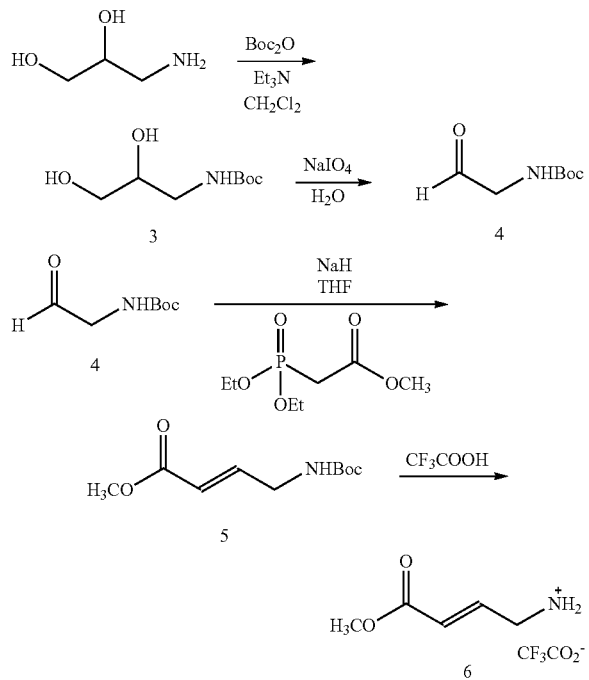

iii. Synthesis of 3

(±)-3-amino-1,2-propanediol (11.29 g, 124 mmol) was dissolved in CH$_2$Cl$_2$:CH$_3$OH (1:5) (1M) and triethylamine (2 mL, 14.7 mmol) was added. Di-tert-butyl dicarbonate (32.5 g, 149 mmol) was dissolved in dichloromethane (0.8M, 186 mL) and added slowly to the reaction mixture. The resulting reaction was stirred at 23° C. for 2 h, followed by TLC analysis that showed a full consumption of the starting material. The reaction mixture was evaporated under reduced pressure, and the residue was purified by column chromatography with EtOAc:Hexanes 1:4, then dried on high vacuum to yield 3 as a white solid (23.7 g, 94% yield). $^1$H NMR (500 MHz, CDCl$_3$) δ 5.28-4.96 (m, 1H), 3.83-3.73 (m, 1H), 3.60 (qd, J=11.7, 4.9 Hz, 2H), 3.44 (s, 1H), 3.27 (dt, J=12.9, 6.0 Hz, 2H), 1.46 (s, 9H). $^{13}$C NMR (126 MHz, Chloroform-d) δ 157.45, 80.13, 71.37, 63.58, 28.35, 27.42.

iv. Synthesis of 4

3 (10 g, 52 mmol) was suspended in H$_2$O (0.6M, 87.2 mL) and the flask was covered in foil (to protect NaIO4 from light). NaIO4 (13.4 g, 62.8 mmol) was then added and the reaction was stirred for 1 h. A white precipitate had formed after 1 h, and TLC analysis showed full consumption of the starting material. The precipitate was filtered off, and the aqueous layer was extracted with CHCl3 (8×50 mL). The organic layer was dried with MgSO4, filtered, and evaporated to yield 4 as a yellow oil, which was used immediately without further purification (7.7 g, 93% yield). 1H NMR (500 MHz, CDCl3) δ 9.68 (s, 1H), 5.23 (s, 1H), 4.10 (d, J=5.2 Hz, 2H), 1.47 (s, 9H). 13C NMR (126 MHz, CDCl3) δ 197.21, 155.67, 80.19, 51.39, 28.28. v. Synthesis of 5 Sodium hydride (60% dispersion in mineral oil) (1.9 g, 46.6 mmol) in tetrahydrofuran (0.17 M, 274 mL) was cooled to 0° C., then triethylphosphonoacetate (8.5 mL, 46.6 mmol) in THF was added dropwise. The reaction was stirred at 0° C. for 20 min, then 4 (7.4 g, 46.6 mmol) in THF was added. The reaction was allowed to warm to 23° C. and was stirred for 1 h. TLC showed a full consuption of the starting materials and conversion to product. THF was removed under reduced pressure, and the residue was then diluted with ethyl acetate (200 mL) and water (200 mL). The layers were separated, followed by the extraction of the aqueous layer with EtOAc (2×100 mL). The organic layer was then dried over MgSO4, filtered, and evaporated. The residue was purified by flash column chromatography with an ethyl acetate/hexanes gradient 25% EtOAc→50% EtOAc to yield 5 (6.6 g, 66% yield). $^1$H NMR (500 MHz, CDCl$_3$) δ 6.94 (dt, J=15.7, 4.8 Hz, 1H), 5.97 (dt, J=15.8, 1.9 Hz, 1H), 4.73 (s, 1H), 3.95 (t, J=5.6 Hz, 2H), 3.76 (s, 3H), 1.48 (s, 9H). $^{13}$C NMR (126 MHz, CDCl$_3$) δ 166.55, 145.26, 120.71, 79.73, 60.37, 51.58, 41.28, 28.30.

vi. Synthesis of 6

5 (6.66 g, 30.8 mmol) was dissolved in trifluoroacetic acid (47 mL, 617 mmol) and stirred at 23° C. for 30 min. TLC at 30 min showed conversion to product. TFA was evaporated and azeotroped with toluene (2×100 mL). The residue was then dried on high vacuum for 2 hours, dissolved in 2 mL methanol and dropped into ice cold diethyl ether (200 mL). The ether was then filtered to collect 6 as the TFA salt (6.2 g, 88% yield). $^1$H NMR (500 MHz, DMSO-d6) δ 8.08 (s, 3H), 6.86 (dt, J=15.9, 5.6 Hz, 1H), 6.15 (dt, J=16.0, 1.7 Hz, 1H), 3.70 (s, 3H), 3.70 (d, J=1.8 Hz, 2H). $^{13}$C NMR (126 MHz, DMSO-d6) δ 165.33, 140.61, 123.22, 51.72.

vii. Synthesis of 1

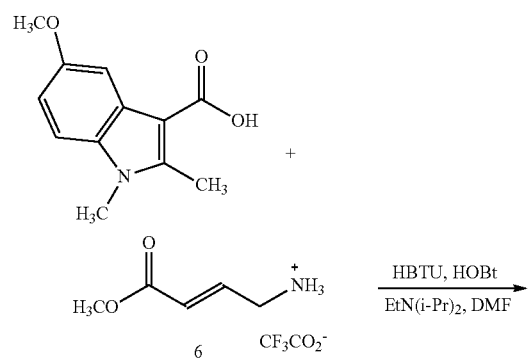

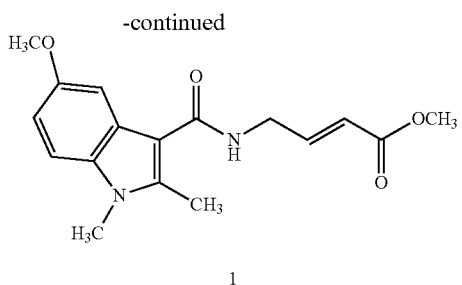

5-methoxy-1,2-dimethyl-1H-indole-3-carboxylic acid (Chembridge) (0.2 mmol) was dissolved in dimethylformamide (0.2M, 1 mL), then 6 (46 mg, 0.2 mmol), HBTU (73.8 mg, 0.16 mmol), and HOBt (29.8 mg, 0.22 mmol) were added, followed by EtN(i-Pr)2 (100.7 µL, 0.6 mmol). The reaction was stirred at 23° C. for 16 h. TLC at 16 h showed conversion to product. The reaction was quenched with H2O (5 mL) and extracted three times with $CH_2Cl_2$ (5 mL). The combined organic layers were washed with 1M HCl (10 mL), saturated aqueous $NaHCO_3$ (10 mL), and saturated aqueous NaCl (10 mL). The organic layer was dried over MgSO4, filtered, and evaporated. Purified by flash column chromatography with a 50-100% EtOAc/Hexanes gradient to yield compound 1 (31.6 mg, 50.2% yield). $^1$H NMR (500 MHz, Chloroform-d) δ 7.29-7.22 (m, 2H), 7.11 (dt, J=15.7, 4.9 Hz, 1H), 6.91 (dd, J=8.8, 2.4 Hz, 1H), 6.07 (d, J=15.7 Hz, 1H), 6.00 (d, J=6.2 Hz, 1H), 4.40-4.22 (m, 2H), 3.91 (s, 3H), 3.76 (s, 3H), 3.70 (s, 3H), 2.74 (s, 3H). $^{13}$C NMR (126 MHz, Chloroform-d) δ 166.57, 166.28, 155.32, 145.26, 142.70, 131.76, 125.59, 121.15, 110.59, 110.30, 106.82, 101.91, 56.05, 51.67, 40.16, 29.68, 11.84. [M+H]: 317.1 Da.

viii. Synthesis of 2

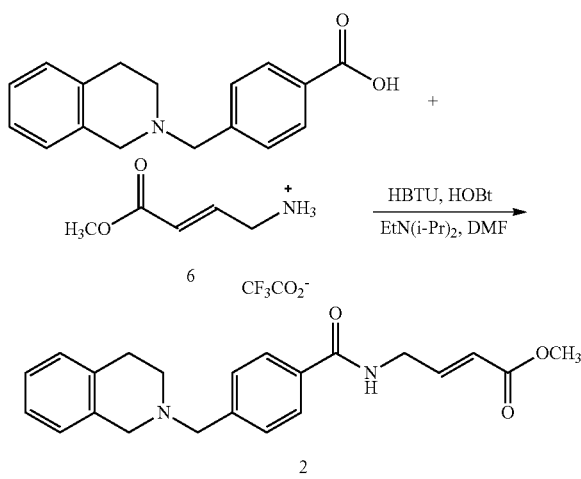

4-((3,4-dihydroisoquinolin-2(1H)-yl)methyl)benzoic acid (Chembridge) (0.2 mmol) was dissolved in dimethylformamide (0.2M, 1 mL), then 6 (46 mg, 0.2 mmol), HBTU (73.8 mg, 0.16 mmol), and HOBt (29.8 mg, 0.22 mmol) were added, followed by EtN(i-Pr)2 (100.7 µL, 0.6 mmol). The reaction was stirred at 23° C. for 16 h. TLC at 16 h showed conversion to product. The reaction was quenched with $H_2O$ (5 mL) and extracted three times with $CH_2Cl_2$ (5 mL). The combined organic layers were washed with saturated aqueous $NaHCO_3$ (10 mL) and saturated aqueous NaCl (10 mL). The organic layer was dried over MgSO4, filtered, and evaporated. Purified by flash column chromatography with a 75-100% EtOAc/Hexanes gradient to yield compound 2 (58.8 mg, 80.7% yield). $^1$H NMR (500 MHz, DMSO-d6) δ 8.82 (t, J=5.7 Hz, 1H), 7.87 (d, J=8.2 Hz, 2H), 7.47 (d, J=8.2 Hz, 2H), 7.16-7.04 (m, 3H), 7.00 (d, J=6.7 Hz, 1H), 6.95 (dt, J=15.7, 4.8 Hz, 1H), 6.03-5.80 (m, 1H), 3.71 (s, 2H), 3.66 (s, 2H), 3.55 (s, 3H), 2.83 (t, J=5.8 Hz, 2H), 2.56-2.46 (m, 2H). $^{13}$C NMR (126 MHz, DMSO-d6) δ 166.08, 165.89, 146.28, 142.08, 134.66, 134.00, 132.69, 128.51, 128.42, 127.26, 126.32, 125.97, 125.45, 119.93, 61.35, 59.73, 55.40, 51.37, 50.25, 38.21, 28.64, 20.74, 14.06. [M+H]: 365.2 Da.

B. Inhibition of NEDD4-1

Figure 11A:
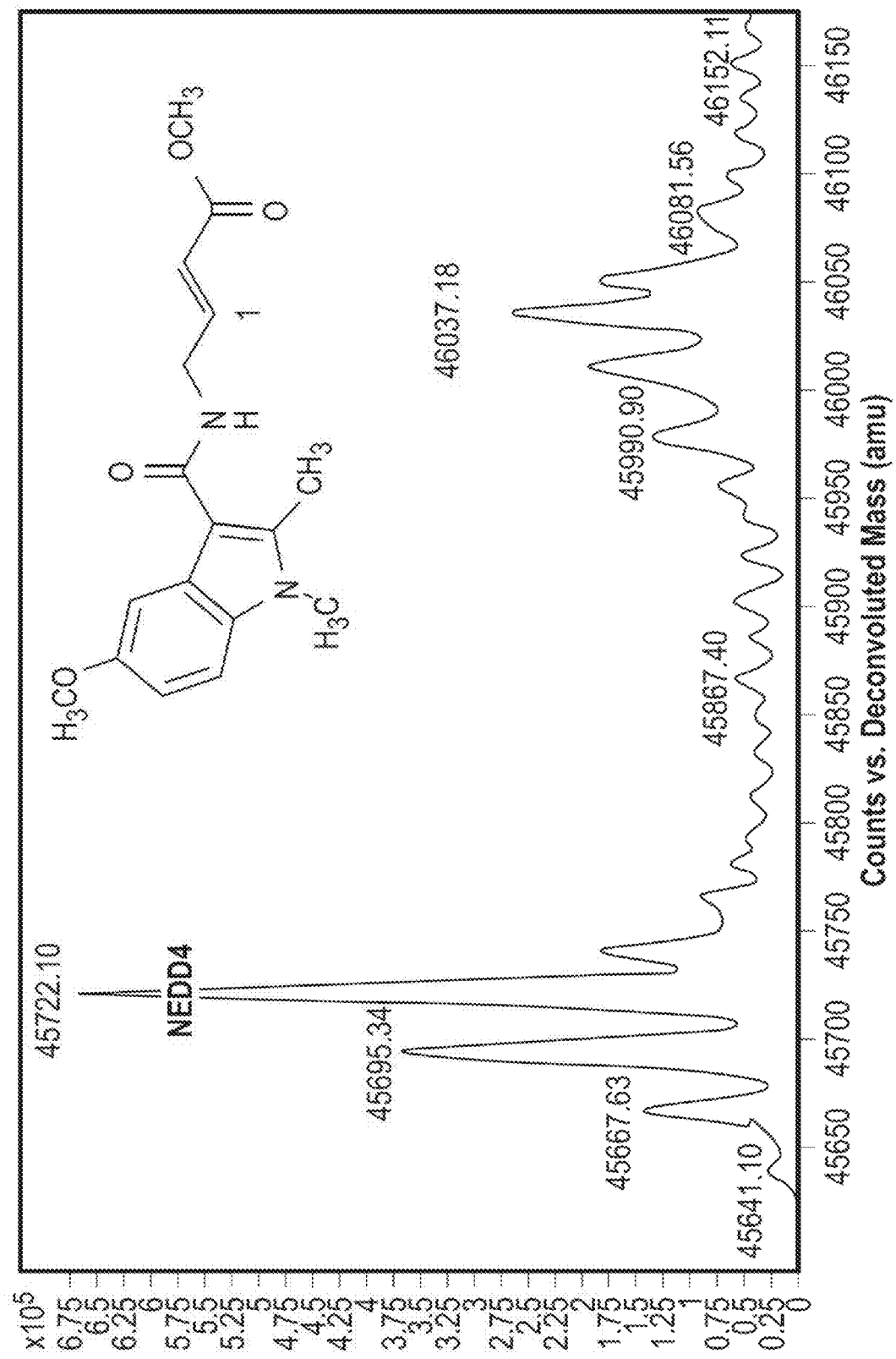
FIG. 11A and FIG. 11B. ESI-MS of NEDD4-1 HECT domain covalent labeled by 1 (FIG. 11A) and 2 (FIG. 11B).
Figure 11B:
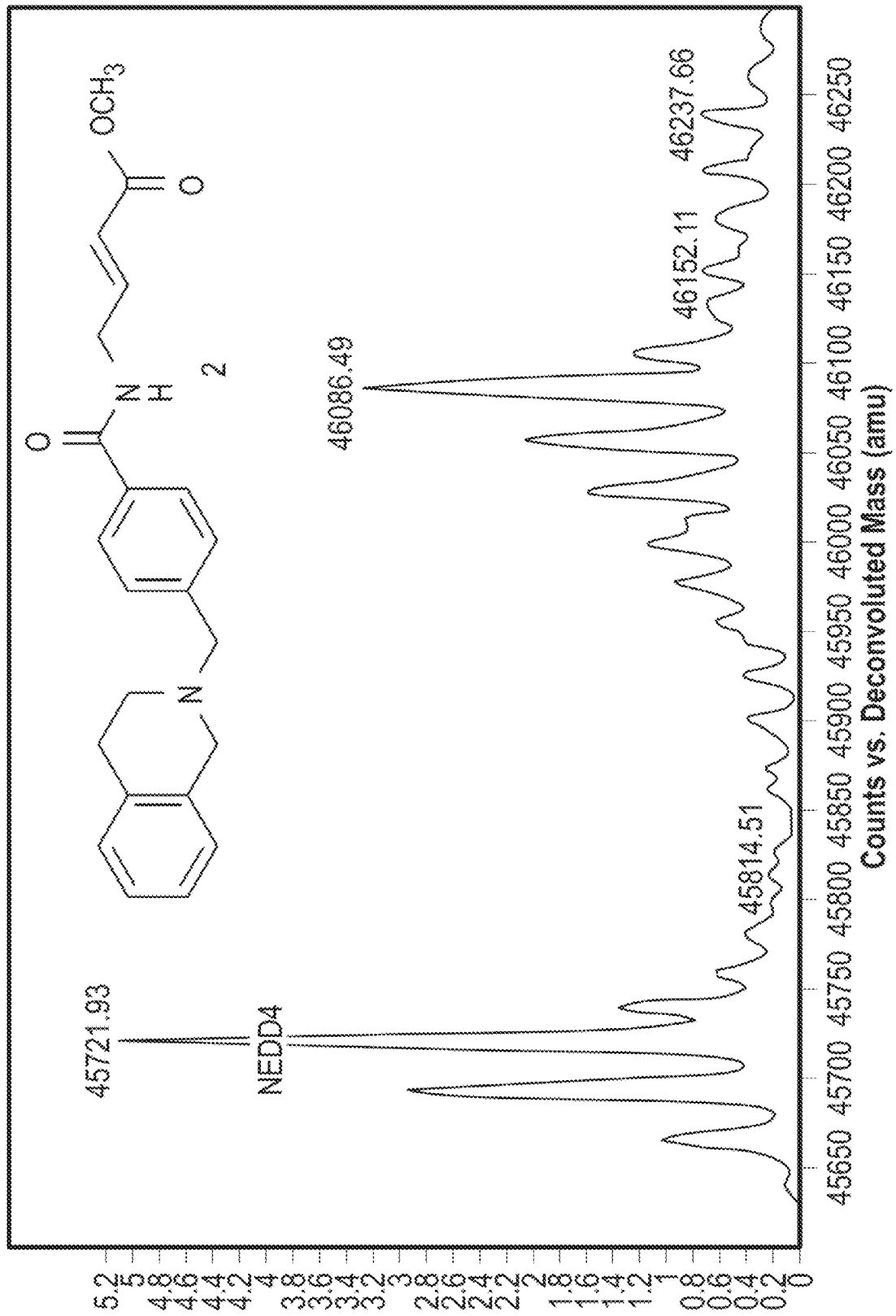
Figure 12:
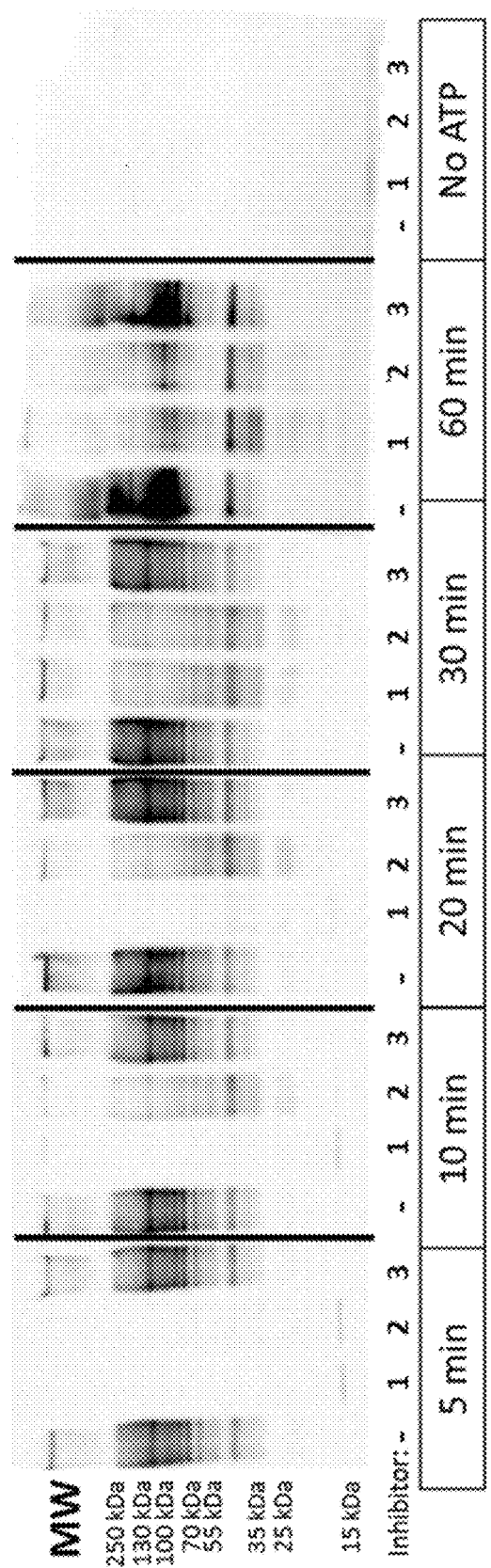
FIG. 12. Ubiquitin western blot showing inhibition of polyubiquitization by 1 and 2 in vitro. 3 is a non-hit control molecule.

We developed an irreversible tethering screening technology for discovering novel cysteine-reactive inhibitor fragments. We applied this technology to screening against catalytic HECT domain of the ubiquitin ligase NEDD4-1 and discovered two inhibitor fragments of this enzyme (FIG. 11): methyl (E)-4-(5-methoxy-1,2-dimethyl-1H-indole-3-carboxamido)but-2-enoate (compound 1) and methyl (E)-4-(4-((3,4-dihydroisoquinolin-2(1H)-yl)methyl)benzamido) but-2-enoate (compound 2). Surprisingly, we found that these electrophilic fragments do not react with the more reactive catalytic cysteine of NEDD4-1 (Cys867) but with a non-catalytic surface cysteine (Cys 627) that is part of the interface for non-covalent binding to ubiquitin. The binding interaction with ubiquitin is essential for polyubiquitination, so we reasoned that if we could disrupt this interaction we could inhibition NEDD4-1 polyubiquitination, but not monoubiquitination since monoubiquitination occurs independently of this interaction. Indeed, we found that NEDD4-1 labeled with our two fragments has reduced binding affinity for ubiquitin (as measured by fluorescence polarization), and NEDD4-1 labeled with our hits has impaired polyubiquitination kinetics (FIG. 12). Counter-screens have showed that our inhibitors do not react with the cysteine protease papain, the E2 enzyme UbcH7, the deubiquitinase USP08, and the HECT ligase E6-AP. These are the first known selective inhibitors of NEDD4-1, which is a promising drug target in cancer because it is thought to degrade the tumor suppressor PTEN, as well as another tumor suppressor LATS. In addition NEDD4-1 promotes polyubiquitination and degradation of another tumor suppressor p53. Notably, since our molecules inhibit polyubiquitination but not monoubiquitination, we can inhibit PTEN polyubiquitination and degradation but not PTEN monoubiquitination, which is necessary for PTEN import to the nucleus, which in turn is essential for PTEN tumor suppressive properties. We are currently optimizing the potency of NEDD4-1 inhibitors to use for subsequent cellular and in vivo studies.

Example 3—Discovery and Structural Characterization of a Covalent Inhibitor of NEDD4-1 Ubiquitin Ligase Abstract Homologous to E6-AP Carboxyl Terminus (HECT) E3 ubiquitin ligases are implicated in neurodegenerative diseases, autoimmune diseases, hypertensive disorders, and viral budding, and are frequently misregulated in human cancers. Despite their significance, there are few small molecules that modulate the activity of HECT E3s. This paper reports the discovery of a covalent inhibitor of the HECT E3 neural precursor-cell expressed developmentally downregulated gene 4-1 (NEDD4-1), which impairs its ability to polyubiquitinate protein substrates. This is the first reported inhibitor of E3 ligase processivity, and is the first known covalent inhibitor of an E3 ligase. We also report the first crystal structure of a HECT E3 bound to an inhibitor. Our studies outline the path forward towards inhibitors of HECT E3s with unique mechanisms of action.

Introduction, Results, and Discussion

Protein ubiquitination is a highly conserved post-translational modification that regulates many cellular processes.[1] The specificity of protein ubiquitination is controlled by E3 ubiquitin ligases, which can mono- or polyubiquitinate their protein substrates.[2] Remarkably, protein monoubiquitination and polyubiquitination can lead to disparate physiological outcomes. For example, monoubiquitination of the tumor suppressor phosphatase and tensin homolog deleted from chromosome 10 (PTEN) is tumor suppressive,[3] while polyubiquitination and degradation of PTEN is oncogenic.[4] Thus, there is an unmet need for pharmacological probes that decouple protein mono- and polyubiquitination.

To develop such probes, we focused on NEDD4-1, a member of the HECT E3 ligase family.[5] NEDD4-1 is a promising drug target to treat viral infections, Parkinson's disease, and cancers.[6] NEDD4-1 contains a calcium-binding C2 domain, four WW domains, and a catalytic HECT domain. The HECT domain of NEDD4-1 is composed of two subdomains, the C- and N-lobes, which are connected via a flexible hinge region.[7,8]

Figure 13:
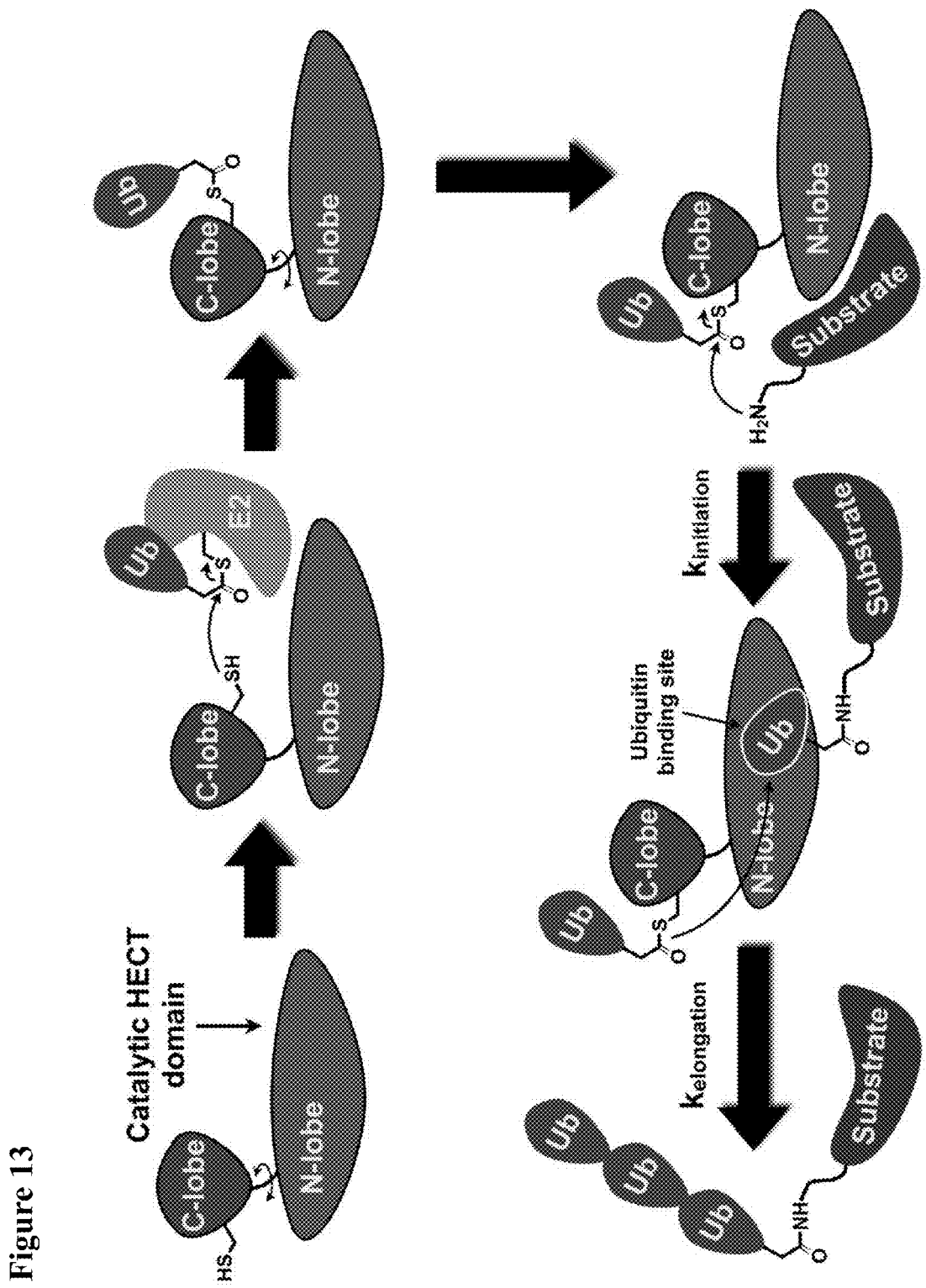
FIG. 13. A simplified model of NEDD4-1 HECT domain mediated ubiquitination.

The C-lobe contains the catalytic cysteine, which forms a thioester with ubiquitin (Ub), while the N-lobe contains the E2 enzyme binding site and the second, non-covalent Ub-binding site. The second Ub binding site controls the polyubiquitin chain growth rate, also known as the processivity of the ligase, and has essential functions in vivo.[9,10] Current X-ray and biochemical studies suggest the following simplified ubiquitination model (FIG. 13).[11] In this model, the last Ub of the growing polyubiquitin chain binds the N-lobe of the HECT domain, where it is held proximal to the active site of HECT E3 for the subsequent addition of another Ub molecule.

Figure 14A:
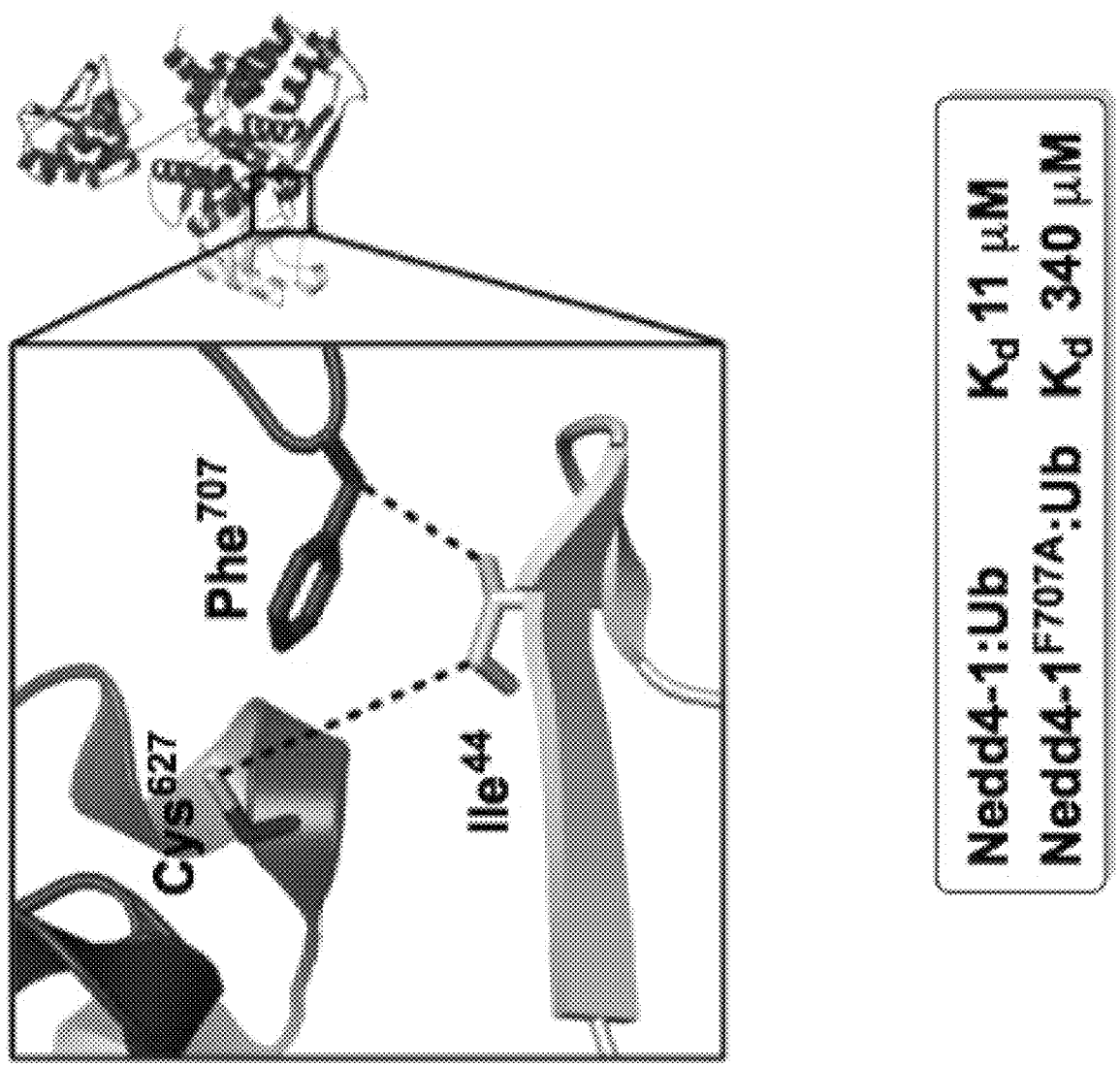
FIG. 14A, FIG. 14B, FIG. 14C and FIG. 14D.

The crystal structure of the NEDD4-1 HECT domain with Ub (PDB ID: 2XBB) has two solvent-exposed Cys residues: the catalytic $Cys^{867}$, and the non-catalytic $Cys^{627}$ (FIG. 14A).[7] $Cys^{627}$ is positioned at the N-lobe of NEDD4-1 near $Phe^{707}$ and $Ile^{44}$ of Ub, which are two critical residues that form hydrophobic contacts that are essential for Ub binding.[7] Mutation of $Phe^{707}$ to Ala in NEDD4-1 disrupts NEDD4-1:Ub binding and affects the kinetics of polyubiquitin chain growth. We therefore envisioned two types of covalent NEDD4-1 inhibitors: type I that covalently modify the catalytic $Cys^{867}$ and inhibit the enzyme entirely, and type II that covalently modify $Cys^{627}$ and inhibit the ability of NEDD4-1 to build long polyubiquitin chains.

Figure 14B:
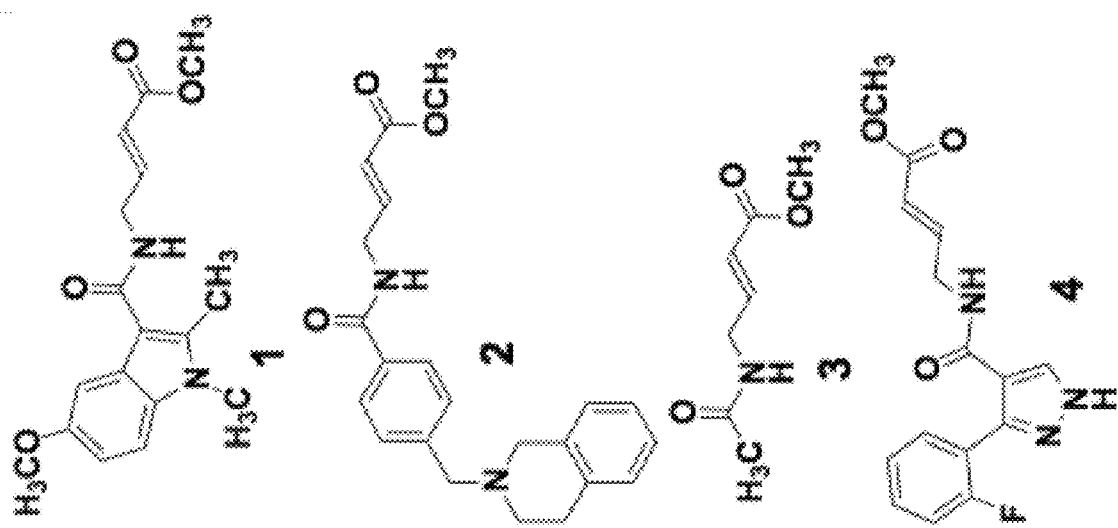
Figure 14C:
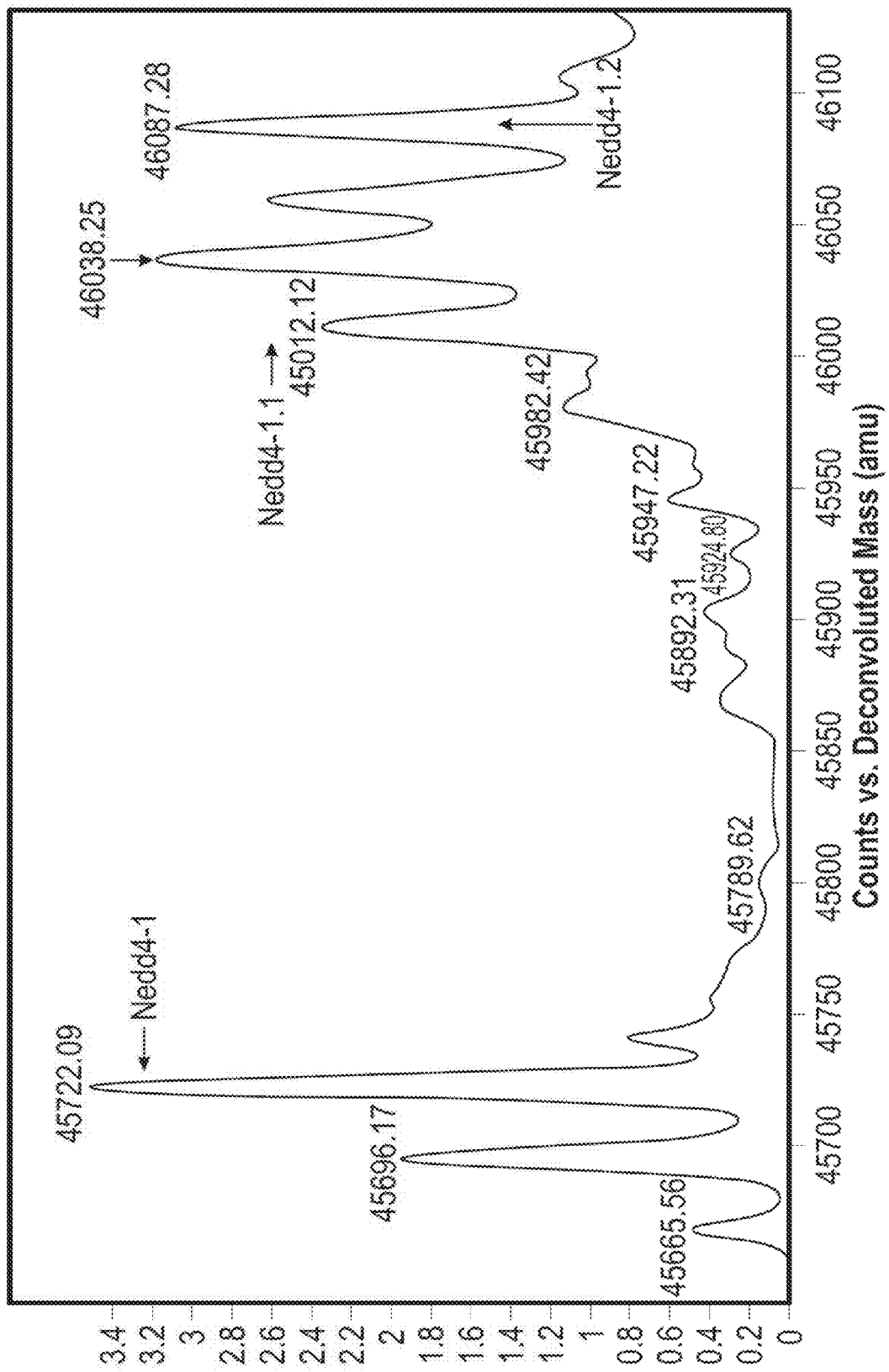
Figure 14D:
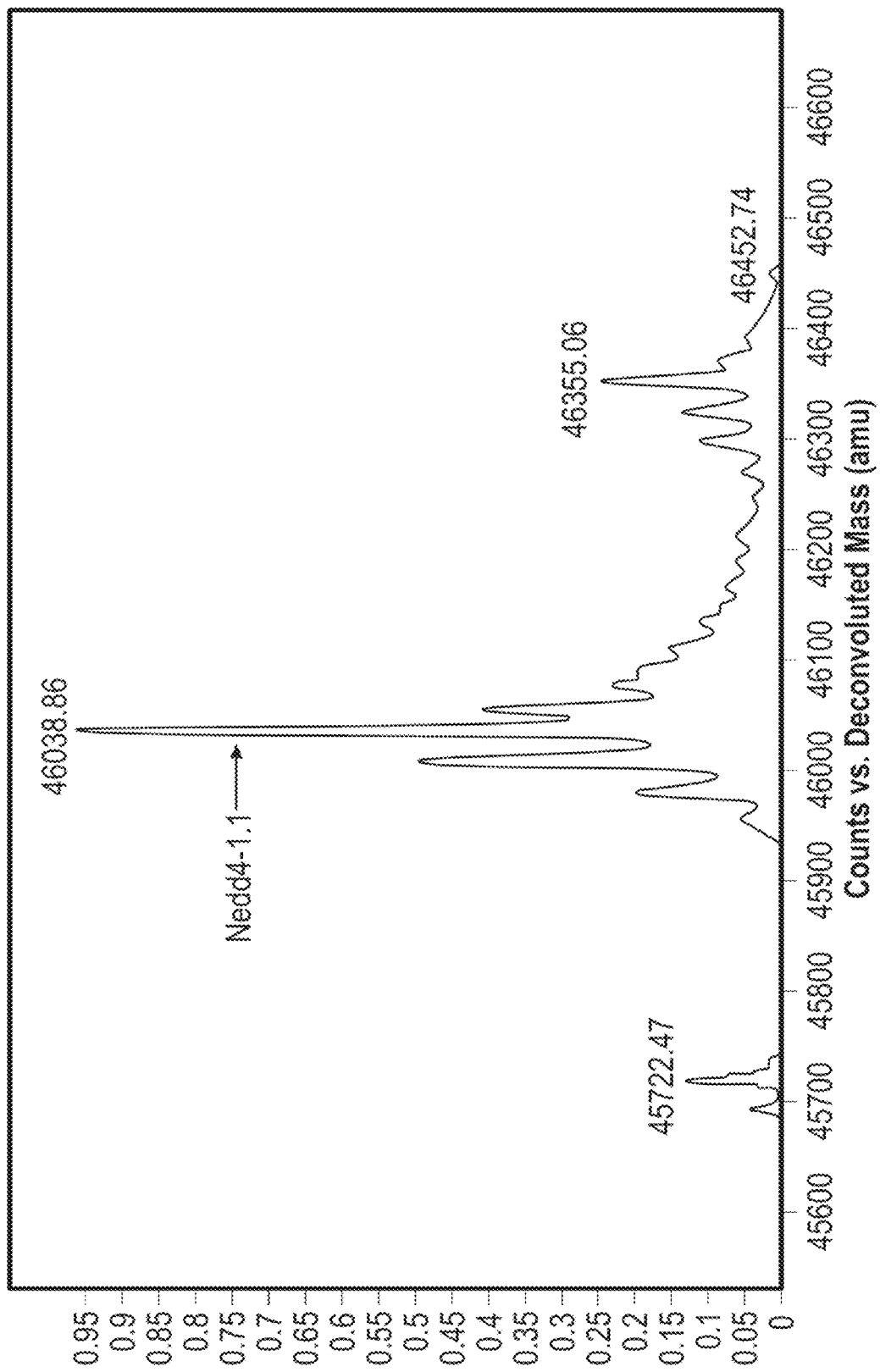

To discover these inhibitors we used our previously reported irreversible tethering method.[2] The HECT domain of NEDD4-1 was treated with ten mixtures of ten drug-like acrylate fragments and then analyzed by mass spectrometry (MS) (FIG. 17), which identified compounds 1 and 2 as weak covalent modifiers of NEDD4-1 (FIG. 14B-14C). Although we expected to discover covalent inhibitors of the more reactive catalytic cysteine, cysteine point mutation studies revealed that 1 and 2 selectively react with the non-catalytic $Cys^{627}$ (FIG. 18). Covalent modification of NEDD4-1 with 1 and 2 was both time- and concentration-dependent (FIG. 19), and we observed a complete modification upon treatment with 1 mM of compounds 1 and 2 for 3-4 h (FIG. 14D, FIG. 19).

Interestingly, the catalytic $Cys^{867}$ of NEDD4-1 was more reactive than $Cys^{627}$ with the non-specific N-acetyl electrophile 3 (FIG. 20), which suggests that compounds 1 and 2 are specific hits that covalently modify the less reactive non-catalytic cysteine in the presence of the more reactive catalytic cysteine. Moreover, labeling by compound 1 was either tolerant of or sensitive to structural changes in 1, a further indication that covalent labeling of NEDD4-1 by 1 was specific (FIG. 21).

Figure 15A:
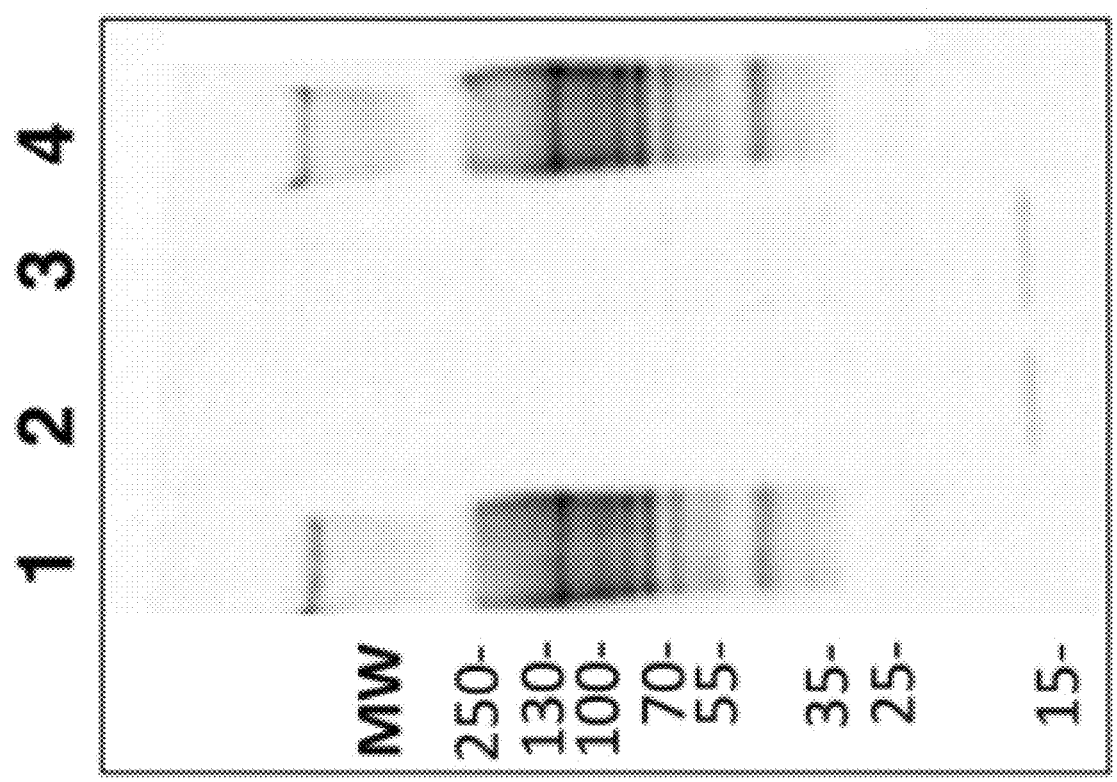
FIG. 15A, FIG. 15B and FIG. 15C.
Figure 15B:
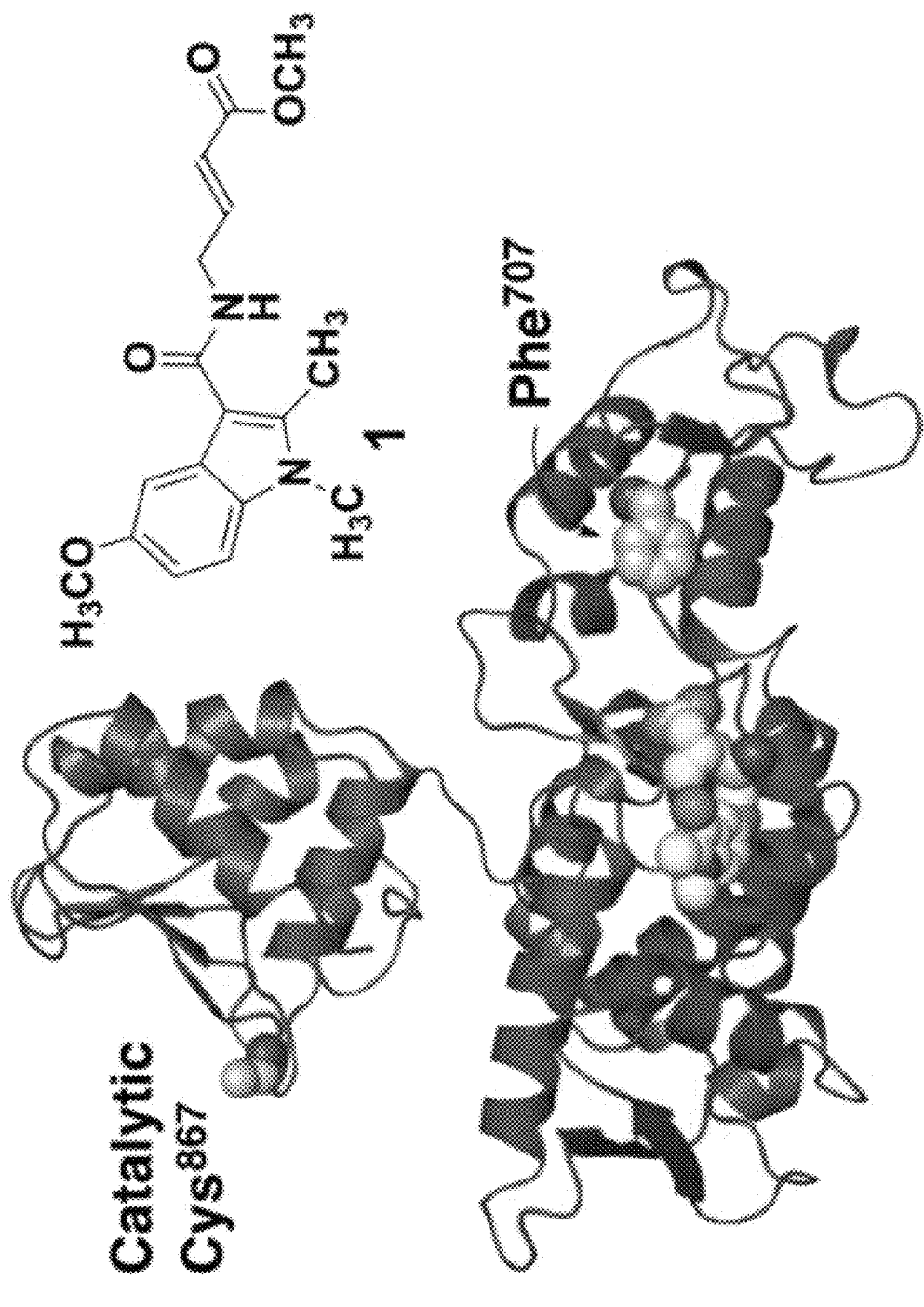

Since $Cys^{627}$ of NEDD4-1 is adjacent to the NEDD4-1:Ub hot spot, we investigated if the covalent modification of $Cys^{627}$ led to impaired enzymatic activity of NEDD4-1. As expected, NEDD4-1 covalently modified with compound 1 or 2 was defective at assembling polyubiquitin chains, while the negative control electrophilic molecule 4 did not affect NEDD4-1 activity (FIG. 15A). To understand how compounds 1 and 2 might inhibit NEDD4-1, we crystallized NEDD4-1 covalently modified by 1 and solved the structure to 2.44 Å resolution (PDB ID: 4PFL) (FIG. 15B, FIG. 22).

| Crystallographic table | |
|---|---|
| | NEDD4-1•compound 1 |
| Data collection | |
| Space group | C2 |
| Cell dimensions | |
| a, b, c (Å) | 175.20, 38.73, 60.36 |
| α, β, γ (°) | 90.00, 93.13, 90.00 |
| Resolution (Å) | 32.20-2.44 (2.50-2.44) |
| $R_{merge}$ (%) | 9.1 (60.2) |
| I/σ (I) | 11.2 (2.0) |
| Completeness (%) | 98.2 (98.7) |
| Multiplicity | 3.2 (3.1) |
| CC(1/2) | 0.994 (0.626) |
| Refinement | |
| Resolution (Å) | 31.86-2.44 |
| No. reflections | 14371 |
| $R_{work}/R_{free}$ | 0.248/0.298 |
| No. atoms | |
| Protein | 3175 |
| N-lobe (residues 519-780) | 2239 |
| C-lobe (residues 780-893) | 936 |
| Ligand/ion | 23 |
| Water | 7 |
| Average B-factors (Å$^2$) | |
| Protein | 50.842 |
| N-lobe (residues 519-780) | 42.472 |
| C-lobe (residues 780-893) | 70.864 |
| Ligand/ion | 63.217 |
| Water | 35.437 |
| R.m.s. deviations | |
| Bond lengths (Å) | 0.005 |
| Bond angles (°) | 1.036 |
| Ramachandran plot (%) | 95.4/4.3/0.3 |

Figure 15C:
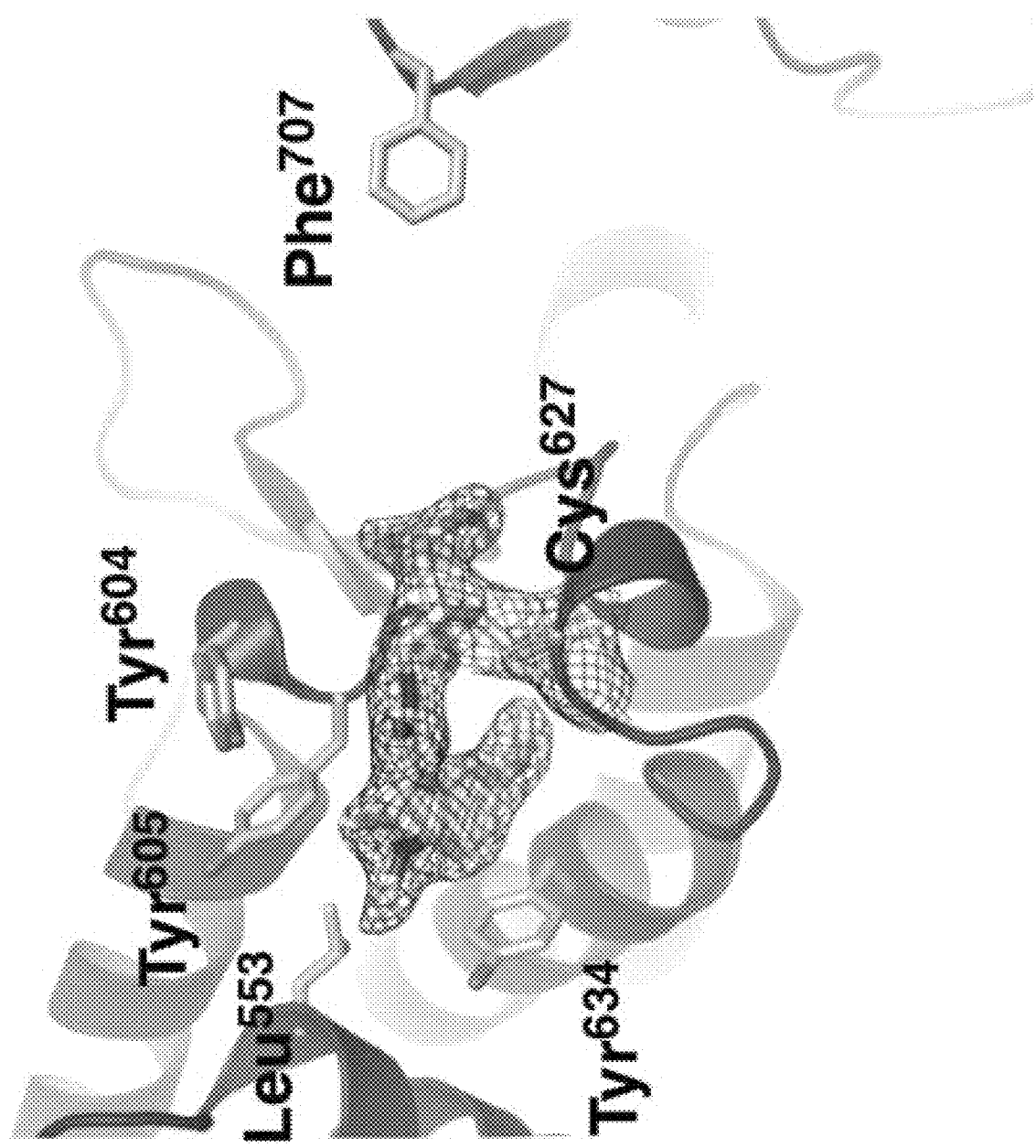

Notably, this structure is the first of a HECT E3 ubiquitin ligase bound to a small molecule inhibitor. The overall conformation is virtually identical to the previously reported structure of NEDD4-1 (root-mean-square deviation (rmsd): 0.316 Å; FIG. 23).[7] Our structure confirms that 1 forms a stable covalent bond with $Cys^{627}$ and reveals that the hydrophobic indole core of 1 is oriented towards a pocket of the N-lobe formed by residues $Leu^{553}$, $Glu^{554}$, $Asn^{602}$, $Tyr^{604}$, $Tyr^{605}$, $Leu^{607}$, and $Tyr^{634}$ (FIG. 15C).

This ligand orientation explains why compound 10 that contains a $CH_3CH_2O$-group on the indole core did not label NEDD4-1, since the ligand binding pocket cannot accommodate this sterically bulkier group (FIG. 21). The aromatic edge-to-face interactions of $Tyr^{605}$ and $Tyr^{634}$ with the indole moiety of 1 provide further stabilization of the ligand conformation, while a hydrogen bond between the backbone carbonyl oxygen of Tyr$^{605}$ and the amide NH of 1 positions the connecting region between Cys$^{627}$ and the indole group. The ester methoxy group points inward and towards the E2 binding site, into a small cavity formed by Gly$^{606}$O, Asn$^{621}$N, Asn$^{623}$O, and Asn$^{623}$Cβ, which are within 3.4-4.4 Å of the methyl group. However, since the methyl ester group is freely rotatable around the C—C bond, our crystallographic data cannot exclude a partial conformation in which the methoxy and the carbonyl groups are exchanged. Interestingly, it was previously shown that the mutation of Tyr$^{605}$ of NEDD4-1 to Ala also disrupts non-covalent Ub binding and inhibits the formation of long polyubiquitin chains by NEDD4-1.[7] Since 1 forms an edge-to-face interaction with Tyr$^{605}$, the ligand should block the essential binding interaction between Leu$^{73}$ of Ub and Tyr$^{605}$ of NEDD4-1 observed in the NEDD4-1 HECT:Ub complex structure.

Our initial experiments showed that the reaction of NEDD4-1 with 1 could be completely inhibited by 60 μM of Ub (FIG. 24). Given that the intracellular concentration of Ub is ~80 μM,[13] further improvements in the potency of 1 were necessary. Since our initial structure-activity relationship studies indicated that the N-methyl group of the indole in 1 might tolerate substitutions (FIG. 21), we prepared a series of N-substituted analogues 5-8 (FIG. 25). Of these, the N-cyclopentyl analogue 6 and N-cyclohexyl analogue 7 were the most potent, and at 100 μM they were able to completely label 10 μM of NEDD4-1 after one hour. By comparison, 100 μM of the original hit 1 only labeled ~40% of 10 μM NEDD4-1 after 4 h. Compound 6 did not label the HECT domain of the related ligases WWP1 or E6-AP (FIG. 26), but it was effective at labeling the highly homologous HECT ligase Nedd4-2, which has an almost identical non-covalent Ub-binding site (FIG. 27). Compound 6 also did not react with the deubiquitinase USPO8 or Human Rhinovirus 3C protease, both of which have catalytic cysteines (FIG. 28).

Fluorescence polarization (FP) experiments using fluorescein-Ub showed that 6 disrupts NEDD4-1:Ub binding in a concentration- and time-dependent manner with a $K_I$ of 29.3 μM and a $k_{inact}$ of 5.8×10$^{-5}$ s$^{-1}$ ($k_{inact}/K_I$=1.98 M$^{-1}$ s$^{-1}$) (FIG. 16A), while the N-cyclohexyl analogue 7 was less potent (FIG. 29). The $k_{obs}$ vs [6] plot showed a two-step mechanism for the covalent modification of NEDD4-1, in which the initial reversible NEDD4-1:6 complex is formed, followed by the covalent bond formation step (FIG. 30).[14] It should be noted that the FP assay requires a high concentration of NEDD4-1 (8 μM) to be close to its $K_d$ with ubiquitin (11 μM). Therefore, with a $K_I$ of 29.3 μM we are achieving half-maximal covalent inhibition at a 3.66-fold excess of inhibitor relative to NEDD4-1. Remarkably, in contrast to the original hit 1, indole 6 was able to robustly label NEDD4-1 even in the presence of 60 μM ubiquitin, which is significantly above the NEDD4-1:Ub $K_d$ value (FIG. 31).

To investigate if indole 6 affects the ability of NEDD4-1 to assemble long polyubiquitin chains we used Wbp2-C-K222 as a substrate. Wbp2-C-K222 has only one acceptor lysine residue (Lys$^{222}$), and a cysteine residue that we modified with 5-iodoacetamidofluorescein for quantification purposes (FIG. 32).[10] Remarkably, we observed that NEDD4-1 covalently modified with compound 6 had a dramatically impaired ability to build long polyubiquitin chains on Wbp2-C-K222, as compared to DMSO or the negative control molecule 4 (FIG. 16B-16C, FIG. 33).

Altogether, these results suggest that 6 inhibits the ability of NEDD4-1 to elongate polyubiquitin chains, and it does so by acting as a covalent inhibitor of the NEDD4-1 HECT:Ub protein-protein interaction. Compound 6 promotes the dissociation of the ubiquitinated substrate from the enzyme, thereby slowing the rate of polyubiquitin chain elongation. Indeed, after 5 min, we observed the addition of three ubiquitins to Wbp2, but after 30 min, only up to 5 ubiquitins were added to Wbp2. Thus polyubiquitination takes place but at a much slower rate compared to the unmodified enzyme. Compound 6 also affects the initial ubiquitin conjugation, but this effect is also observed in the NEDD4-1 F707A mutant under identical conditions (FIG. 34). It is significant that the NEDD4-1:6 covalent complex behaves identically to the F707A mutant in vitro, since the corresponding mutation in Rsp5, the yeast homolog of NEDD4-1, results in temperature-sensitive growth defects.[9,10] Therefore, even though our inhibitors do not completely inhibit NEDD4-1 function it is likely that disrupting its ability to form long polyubiquitin chains will have unique physiological consequences.

Finally, to evaluate the cell permeability and selectivity of compound 6 we prepared an alkyne tagged analog 15 (FIG. 35). We treated TC71 Ewing's sarcoma cells (NEDD4-1 positive),[6b] with 2 μM of compound 15, followed by lysis, click reaction with rhodamine azide, and in-gel fluorescence.[15] Pretreatment with compound 6, but not the inactive analog 11, abolished the labeling of a ~120 kDa band, which corresponds to the molecular weight of NEDD4-1 by Western blot, along with another specific off-target band at >250 kDa (FIG. 36). Covalent labeling of the ~120 kDa band was completely inhibited upon pretreatment with 50 μM 6 for 1 h, and was ~50% reduced after pretreatment with 10 μM 6 for 1 h. Therefore compound 6 and the probe 15 demonstrate good selectivity in TC71 cells at micromolar concentrations. However, we envision that further optimizations are needed to achieve better selectivity and potency in cells.

In summary, we have taken the first steps toward the rational design of covalent small molecule inhibitors of HECT E3s, an important yet unexploited class of drug targets. Although a handful of HECT E3 inhibitors have recently been reported,[16] E3 inhibitors are still greatly lacking when compared to the 19,000 known ATP competitive kinase inhibitors.[17] Importantly, E3 inhibitors that preferentially inhibit the formation of long but not short polyubiquitin chains are not known. We anticipate that our crystal structure and novel mechanism of action will help inform future drug discovery efforts for E3 ligases that target the chain elongation step. Further studies of the NEDD4-1 inhibitors and their use to probe the role of NEDD4-1 processivity in human cells will be reported in the near future.

References

[1] A. Hershko, A. Ciechanover, *Annu. Rev. Biochem.* 1998, 67, 425-479.

[2] D. Komander, M. Rape, *Annu. Rev. Biochem.* 2012, 81, 203-229.

[3] M. S. Song, A. Carracedo, L. Salmena, S. J. Song, A. Egia, M. Malumbres, P. P. Pandolfi, *Cell* 2011, 144, 187-199.

[4] a) X. J. Wang et al., *Cell* 2007, 128, 129-139; b) S. Maddika, S. Kavela, N. Rani, V. R. Palicharla, J. L. Pokorny, J. N. Sarkaria, J. J. Chen, *Nat. Cell Biol.* 2011, 13, 728-U224.

[5] D. Rotin, S. Kumar, *Nat. Rev. Mol. Cell Biol.* 2009, 10, 398-409.

[6] a) N. A. Boase, S. Kumar, Gene 2015, 557, 113-122; b) Y.J. Shi, J. Wang, S. Chandarlapaty, J. Cross, C. Thompson, N. Rosen, X. Jiang, *Nat. Struct. Mol. Biol.* 2014.

[7] E. Maspero, S. Mari, E. Valentini, A. Musacchio, A. Fish, S. Pasqualato, S. Polo, *EMBO Rep* 2011, 12, 342-349.

[8] E. Maspero, E. Valentini, S. Mari, V. Cecatiello, P. Soffientini, S. Pasqualato, S. Polo, *Nat. Struct. Mol. Biol.* 2013, 20, 696-701.

[9] M. E. French, B. R. Kretzmann, L. Hicke, *J. Biol. Chem.* 2009, 284, 12071-12079.

[10] H. C. Kim, A. M. Steffen, M. L. Oldham, J. Chen, J. Huibregtse, *EMBO Rep.* 2011, 12, 334-341.

[11] a) H. B. Kamadurai et al., *Elife* 2013, 2:e00828; b) H. B. Kamadurai, J. Souphron, D. C. Scott, D. M. Duda, D. J. Miller, D. Stringer, R. C. Piper, B. A. Schulman, *Mol. Cell.* 2009, 36, 1095-1102.

[12] S. G. Kathman, Z. Xu, A. V. Statsyuk, *J. Med. Chem.* 2014, 57, 4969-4974.

[13] S. E. Kaiser, B. E. Riley, T. A. Shaler, R. S. Trevino, C. H. Becker, H. Schulman, R. R. Kopito, *Nat. Methods* 2011, 8, 691-U129.

[14] R. A. Copeland, *Evaluation of Enzyme Inhibitors in Drug Discovery: A Guide for Medicinal Chemists and Pharmacologists*, 2nd Edition, Wiley, p. 347-348.

[15] B. R. Lanning et al., *Nat. Chem. Biol.* 2014, 10, 760-767.

[16] a) Y. Cao, C. Wang, X. Zhang, G. Xing, K. Lu, Y. Gu, F. He, L. Zhang, *Sci. Rep.* 2014, 4, 4965; b) T. Mund, M. J. Lewis, S. Maslen, H. R. Pelham, *Proc. Natl. Acad. Sci.* 2014, 111, 16736-16741; c) S. Peter et al., *EMBO Mol. Med.* 2014, 6, 1525-1541 d) M. Rossi et al., *Cell Death Dis.* 2014, 5:e1203; e) Z. Y. Han et al. *J. Virol.* 2014, 88, 7294-7306.

[17] Y. Hu, N. Furtmann, J. Bajorath, *J. Med. Chem.* 2015, 58, 30-40

Supplemental Information

Materials and Methods

Recombinant Expression of NEDD4-1 HECT Domain in *E. coli*.

NEDD4-1 HECT domain in a PGEX6P1 vector plasmid (GST-NEDD4-1 HECT) was transformed into BL21 cells (Novagen). 1 L TB media containing 100 µg/ml ampicillin was inoculated with 50 mL overnight cell culture and incubated at 37° C. until OD reached ~3. Then, IPTG (1.0 mM final concentration) was added to the cell culture media at 18° C., followed by 16 hour incubation at the same temperature. Cells were then harvested and lysed by sonication in phosphate buffered saline (PBS) with protease inhibitors (Complete Mini Protease Inhibitor Cocktail, Roche). The supernatant was incubated with glutathione agarose beads (Pierce Biotechnology) for 1 hour at 4° C. The beads were washed three times with PBS and incubated with PreScission Protease (GE Healthcare) for 4 h at 23° C. to elute NEDD4-1 HECT domain (50 mM HEPES, 150 mM NaCl, 0.1 mM EDTA 1 mM DTT). NEDD4-1 HECT sequence (SEQ ID NO:5):

```
GPLGSRDYKRKYEFFRRKLKKQNDIPNKFEMKLRRATVLEDSYRRIMGVK

RADFLKARLWIEFDGEKGLDYGGVAREWFFLISKEMFNPYYGLFEYSATD

NYTLQINPNSGLCNEDHLSYFKFIGRVAGMAVYHGKLLDGFFIRPFYKMM

LHKPITLHDMESVDSEYYNSLRWILENDPTELDLRFIIDEELFGQTHQHE

LKNGGSEIVVTNKNKKEYIYLVIQWRFVNRIQKQMAAFKEGFFELIPQDL
```

-continued
```
IKIFDENELELLMCGLGDVDVNDWREHTKYKNGYSANHQVIQWFWKAVLM

MDSEKRIRLLQFVTGTSRVPMNGFAELYGSNGPQSFTVEQWGTPEKLPRA

HTCFNRLDLPPYESFEELWDKLQMAIENTQGFDGVD
```

Irreversible Tethering Screening Assay with NEDD4-1 HECT Domain.

10 µM of NEDD4-1 HECT domain in 50 mM HEPES 150 mM NaCl 0.1 mM EDTA 1 mM DTT pH 7.5 was treated with a mixture of ten fragments (from 10 mM each DMSO stock solution mixtures; final concentrations: 100 µM of each fragment, and 1% DMSO). Fragment structures and mixture compositions were the same as reported previously. The reaction mixture was incubated for 4 h at 23° C. before being passed through Zeba gel filtration columns (Thermo, 7K MWCO) to remove unreacted fragments. The protein solution was then immediately analyzed by whole protein LC/ESI-MS.

LC/ESI-MS Protocol.

Accurate-mass data were obtained on an Agilent 6210A LC-TOF mass spectrometer in positive ion mode using electrospray ionization. Samples were chromatographed on the LC-TOF instrument using a Poroshell 120 EC-C18 HPLC column (2.1*50 mm, 2.7 micron), an Agilent Series 1200 HPLC binary pump, and an Agilent Series 1200 autoinjector. The HPLC column was held at 45° C. and the autosampler was held at 8° C. Mobile Phase A was a solution of 0.1% formic acid in water:acetonitrile (19:1). Mobile Phase B was a solution of 0.1% formic acid in acetonitrile. The flow rate was set to 250 µL/min. The gradient used was 0% B for 2 minutes, ramping linearly to 90% B from 2 minutes to 5 minutes, holding at 90% B from 5 minutes to 7 minutes, and then returning to 0% B at 7.1 minutes. The column was allowed to equilibrate for 2.7 minutes before the next injection was initiated. The eluent from the column was diverted to waste for the first 2 minutes. The spectra were acquired from 301 to 3200 daltons using a gas temperature of 340° C., a gas flow of 7 liters/min, and the nebulizer gas at 35 psi. The following voltages were used: capillary 4200 V, fragmentor 230V, skimmer 64V, and octapole RF peak 250V. Spectra were acquired at a rate of 1 spectra/sec. The data was processed using MassHunter software version B.02.00. Maximum entropy deconvolutions were performed with a Mass Step of 1, S/N Threshold of 30, Average Mass at 90% of Peak Height, and 5 Charge States Minimum.

Preparation of Fully Labeled NEDD4-1•Inhibitor Complexes for Crystallography and Enzymatic Assays.

10 µM of NEDD4-1 HECT domain in 50 mM HEPES 150 mM NaCl 0.1 mM EDTA 1 mM DTT pH 7.5 was treated with 1 mM of inhibitor 1 or 2 (from 100 mM DMSO stock solution; final concentrations: 1 mM of inhibitor, 1% DMSO, and 0.2% CHAPS to solubilize the inhibitors at 1 mM). The reaction mixture was incubated for 4 h at 23° C. before being passed through Zeba gel filtration columns (Thermo, 7K MWCO) to remove unreacted inhibitor. The protein solution was then immediately used for crystallization or enzymatic assay.

Crystallization.

Crystals of the Nedd4 HECT:inhibitor 1 complex were obtained by the sitting-drop vapor diffusion method using MiTeGen-XtalQuest Plates with a 1:1 ratio of protein (6.3 mg/mL) and reservoir solution at 20° C. The precipitant was similar to that used previously[1], and consisted of 100 mM 2-(N-morpholino)ethanesulfonic acid (MES), pH 6.5, 35 mM $CaCl_2$, 5 mM tris(2-carboxyethyl)phosphine (TCEP), 6% polyethylene glycol (PEG) 400. Crystals were soaked in cryoprotectant (100 mM MES, pH 6.0, 6% PEG 400, 20% ethylene glycol) for 1 min, mounted on loops, and flash frozen in $N_{2(1)}$.

Data Collection and Structure Determination.

Native data sets were collected using synchrotron radiation at the LS-CAT 21-ID-D beamline at the Advanced Photon Source, Argonne National Laboratory, using a Mar 300 CCD detector. The datasets were processed using Xia2[2] and solved by molecular replacement using Phaser[3]. The coordinates of the Nedd4 HECT structure with Protein Data Bank (PDB) ID 2XBF were used as a starting model. Descriptions of the inhibitor and link were generated with the program JLigand[4] utilizing the appropriate library obtained from the Grade Web Server[5]. Model building and refinement were performed with Coot[6] and REFMAC5[7,8], respectively. The new chiral center generated upon covalent binding of the inhibitor to the Cys side chain was initially modeled as both S and R enantiomers. Since the refinement with the S enantiomer resulted in a lower $R_{work}/R_{free}$, we modeled this center as the S stereoisomer. However, we note that further experimental evidence is necessary to determine the absolute stereochemistry at this site. Translation liberation screw-rotation (TLS)[7,9] parameters and restrained refinement options in REFMAC5 were used for the final refinement cycles. Ramachandran plots were calculated with PROCHECK[7,10], and validation was performed using both PHENIX[11] and SFCHECK[12]. Data collection and refinement statistics are shown in Table 51. Electron density maps were calculated using FFT[7,13], and figures were prepared using PyMOL[14]. The atomic coordinates have been deposited in the PDB, Research Collaboratory for Structural Bioinformatics at Rutgers University, ID 4PFL.

Fluorescence Polarization Assay.

NEDD4-1 HECT (7.98 µM) and ubiquitin-fluorescein (50 nM, Lifesensors) in 50 mM HEPES pH 7.5 150 mM NaCl 0.1 mM EDTA were treated with DMSO or varying concentrations of inhibitor in 1% DMSO in black 96 well plates. Changes in fluorescence polarization were monitored over 1 h with a Biotek Synergy 4 plate reader. Slopes of ln(polarization) vs. time were plotted with GraphPad Prism and used to determine the pseudo-first order rate contstant $k_{obs}$ for a given concentration of inhibitor. The values of $k_{inact}/K_I$ for each inhibitor were then determined by fitting the $k_{obs}$ vs. [inhibitor] plot to the equation $k_{obs}=k_{inact}*[inhibitor]/([inhibitor]+K_I)$. All reactions were performed in triplicate and plotted as mean±s.e.m.

Preparation of Fluorescein-Wbp2-C-K222.

Wbp2-C-K222 in a PGEX6P1 vector plasmid (GST-Wbp2-C-K222) was transformed into BL21 cells (Novagen). 1 L LB media containing 100 µg/ml ampicillin was inoculated with 50 mL overnight cell culture and incubated at 37° C. until OD reached ~0.6. Then, IPTG (0.1 mM final concentration) was added to the cell culture media at 18° C., followed by 16 hour incubation at the same temperature. Cells were then harvested and lysed by sonication in phosphate buffered saline (PBS) with protease inhibitors (Complete Mini Protease Inhibitor Cocktail, Roche). The supernatant was incubated with glutathione agarose beads (Pierce Biotechnology) for 1 hour at 4° C. The beads were washed three times with PBS and incubated with PreScission Protease (GE Healthcare) for 16 h at 4° C. to elute Wbp2-C-K222 (50 mM HEPES, 150 mM NaCl, 0.1 mM EDTA 1 mM DTT). Wbp2-C-K222 was then treated with 1 mM TCEP for 15 min, then 5-iodoacetamidofluorescein (Santa Cruz Biotechnology) in DMSO was added (final concentration: 3 mM, 5% DMSO). The reaction was rocked at 4° C. for 90 min in the dark, then passed through a Zeba gel filtration column (Thermo, 7K MWCO). The tagged protein was further purified by size exclusion with an S75 column (GE Healthcare). Elution buffer: 20 mM Tris-HCl pH 8.0 200 mM NaCl 1 mM EDTA 5% glycerol 1 mM DTT.

In Vitro Ubiquitination Assays.

Reaction mixtures were composed of 80 nM Ube1 E1 enzyme (Boston Biochem), 1.5 µM UbcH5a E2 enzyme (Boston Biochem), 1.5 µM NEDD4-1 HECT domain, 0.5 µM substrate (Sic60-GFP[15] or fluorescein-Wbp2-C-K222, recombinantly expressed), 6 µM ubiquitin (Sigma-Aldrich), and ATP in 25 mM HEPES pH 7.6 100 mM NaCl 4 mM $MgCl_2$. 30 µL reactions were quenched with 6X Laemmli buffer and 3 µL beta-mercaptoethanol and analyzed by SDS-PAGE. Fluorescent gels were imaged with a Typhoon 9400 (GE Healthcare, NCRR #S10RR027842 at Northwestern's Keck Biophysics Facility) and fluorescent bands were quantified with ImageQuant TL. Western blots were performed with anti-ubiquitin antibody from Cell Signaling (3933S).

Cell-Based Selectivity Studies with Alkyne Probe 15, Click Reaction, and in-Gel Fluorescence.

TC71 cells were cultured in Iscove's Modified Dulbecco's Medium (IMDM), 20% (v/v) FBS, 4 mM glutamine, and lx ITS (5 µg/mL insulin, 5 µg/mL transferrin, 5 ng/mL selenous acid). Cells were grown to confluence in 6-well plates (9.6 cm² per well). The growth medium was aspirated off and replaced with 2 mL serum-free IMDM containing 0.1% DMSO or the indicated concentration of inhibitor in 0.1% DMSO. After 1 h incubation time at 37° C., cells were treated with 0.1% DMSO or 2 µM of probe 15 in 0.1% DMSO for an additional hour. The medium was then aspirated off and cells were washed with Dulbecco's Phosphate Buffered Saline 3×2 mL. 300 µL of lysis buffer containing Tris HCl (25 mM, pH 7.6), NaCl (150 mM), 1% NP40, 1% sodium deoxycholate, 0.1% SDS, and protease inhibitors (Sigma-Aldrich, P8340, 1:100 v/v) was added to each well, and cells were lysed by rocking at 4° C. for 10 min. Cellular debris was cleared by centrifugation (21,000×g) for 45 min at 4° C. The total protein concentration of each cell lysate was normalized to 1.0 mg/mL using the Bradford assay. 20 µL of each cell lysate was then treated for 30 min in the dark with the click chemistry reagents: $CuSO_4$ (final conc. 1 mM), TBTA (final conc. 100 µM), sodium ascorbate (final conc. 1 mM), TCEP (final conc. 1 mM), and Azide-Fluor-585 (final conc. 100 µM). Proteins were then resolved by SDS-PAGE 7.5% or 15% acrylamide gels, and subjected to in-gel scanning fluorescence imaging on the Typhoon 9400 at 610 nm excitation. The gel was then stained with Coomassie Brilliant Blue to visualize all proteins. Western blots were performed with anti-NEDD4-1 antibody from Cell Signaling (2740S).

Chemical Synthesis

General Information.

Methanol (ACS grade), ethyl acetate (ACS grade), chloroform (ACS grade), toluene (ACS grade), and diethyl ether (ACS grade), acetonitrile (HPLC grade), and hexanes (ACS grade) were purchased from Fisher Scientific and used without further purification. Dichloromethane, tetrahydrofuran and dimethylformamide were purified by passing over activated alumina. Commercially available reagents were used without further purification. Unless otherwise specified, all reagents were purchased from Sigma-Aldrich. Reactions were monitored by thin-layer chromatography (TLC) on pre-coated glass backed plates (60 Å silica gel, 0.25 mm, Whatman), and components were visualized by UV light (254 and 365 nm) or by treating the plates with anisaldehyde, $KMnO_4$, and ninhydrin stains followed by heating.

Flash column chromatography was performed over ultra pure silica gel (230-400 mesh) from Silicycle. $^1$H and $^{13}$C NMR spectra were obtained on a Bruker AVANCE III 500 MHz spectrometer or an Agilent DDR2 400 MHz spectrometer (Funded by NSF CHE-1048773, 2010) at Northwestern's Integrated Molecular Structure Education and Research Center. Chemical shifts were reported in ppm relative to the residual solvent peak (CDCl$_3$ or DMSO-d$_6$). Multiplicity was indicated as follows: s (singlet); d (doublet); t (triplet); q (quartet); m (multiplet); dd (doublet of doublets); ddd (doublet of doublet of doublets); dt (doublets of triplets); td (triplet of doublets). Coupling constants were reported in Hz. Small molecule ESI-MS was performed on a Bruker AmaZon SL quadropole ion trap instrument.

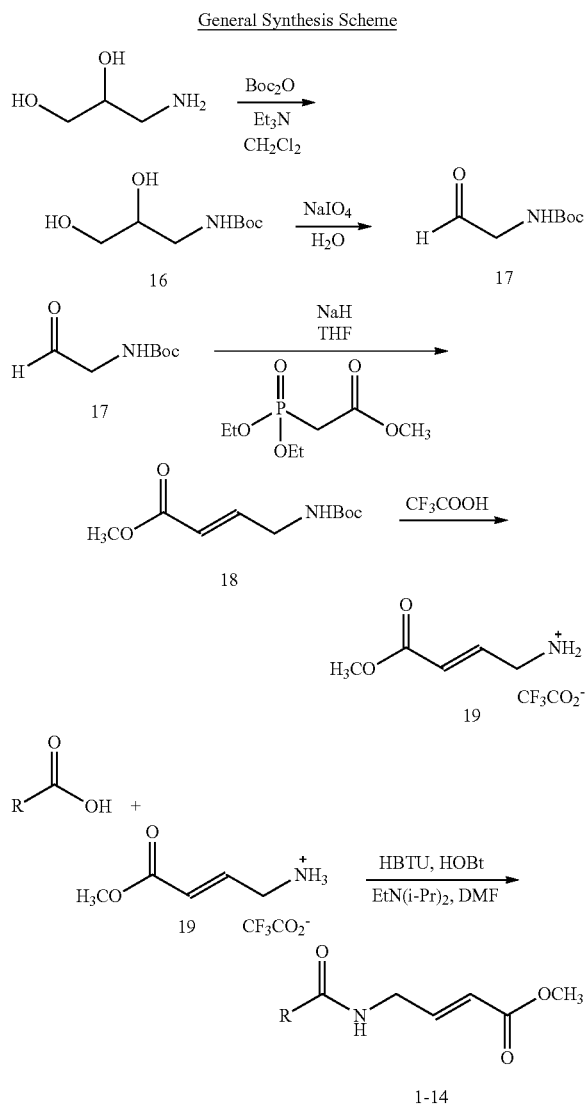

Synthesis of 16.

(±)-3-amino-1,2-propanediol (11.29 g, 124 mmol) was dissolved in CH$_2$Cl$_2$:CH$_3$OH (1:5) (1M) and triethylamine (2 mL, 14.7 mmol) was added. Di-tert-butyl dicarbonate (32.5 g, 149 mmol) was dissolved in dichloromethane (0.8M, 186 mL) and added slowly to the reaction mixture. The resulting reaction was stirred at 23° C. for 2 h, followed by TLC analysis that showed a full consumption of the starting material. The reaction mixture was evaporated under reduced pressure, and the residue was purified by column chromatography with EtOAc:Hexanes 1:4, then dried on high vacuum to yield 16 as a white solid (23.7 g, 94% yield). $^1$H NMR (500 MHz, CDCl$_3$) δ 5.28-4.96 (m, 1H), 3.83-3.73 (m, 1H), 3.60 (qd, J=11.7, 4.9 Hz, 2H), 3.44 (s, 1H), 3.27 (dt, J=12.9, 6.0 Hz, 2H), 1.46 (s, 9H). $^{13}$C NMR (126 MHz, Chloroform-d) δ 157.45, 80.13, 71.37, 63.58, 28.35, 27.42.

Synthesis of 17.

16 (10 g, 52 mmol) was suspended in H$_2$O (0.6M, 87.2 mL) and the flask was covered in foil (to protect NaIO$_4$ from light). NaIO$_4$ (13.4 g, 62.8 mmol) was then added and the reaction was stirred for 1 h. A white precipitate had formed after 1 h, and TLC analysis showed full consuption of the starting material. The precipitate was filtered off, and the aqueous layer was extracted with CHCl$_3$ (8×50 mL). The organic layer was dried with MgSO$_4$, filtered, and evaporated to yield 17 as a yellow oil, which was used immediately without further purification (7.7 g, 93% yield). $^1$H NMR (500 MHz, CDCl$_3$) δ 9.68 (s, 1H), 5.23 (s, 1H), 4.10 (d, J=5.2 Hz, 2H), 1.47 (s, 9H). $^{13}$C NMR (126 MHz, CDCl$_3$) δ 197.21, 155.67, 80.19, 51.39, 28.28.

Synthesis of 18.

Sodium hydride (60% dispersion in mineral oil) (1.9 g, 46.6 mmol) in tetrahydrofuran (0.17 M, 274 mL) was cooled to 0° C., then triethylphosphonoacetate (8.5 mL, 46.6 mmol) in THF was added dropwise. The reaction was stirred at 0° C. for 20 min, then 17 (7.4 g, 46.6 mmol) in THF was added. The reaction was allowed to warm to 23° C. and was stirred for 1 h. TLC showed a full consuption of the starting materials and conversion to product. THF was removed under reduced pressure, and the residue was then diluted with ethyl acetate (200 mL) and water (200 mL). The layers were separated, followed by the extraction of the aqueous layer with EtOAc (2×100 mL). The organic layer was then dried over MgSO$_4$, filtered, and evaporated. The residue was purified by flash column chromatography with an ethyl acetate/hexanes gradient 25% EtOAc 50% EtOAc to yield 18 (6.6 g, 66% yield). $^1$H NMR (500 MHz, CDCl$_3$) δ 6.94 (dt, J=15.7, 4.8 Hz, 1H), 5.97 (dt, J=15.8, 1.9 Hz, 1H), 4.73 (s, 1H), 3.95 (t, J=5.6 Hz, 2H), 3.76 (s, 3H), 1.48 (s, 9H). $^{13}$C NMR (126 MHz, CDCl$_3$) δ 166.55, 145.26, 120.71, 79.73, 60.37, 51.58, 41.28, 28.30.

Synthesis of 19.

18 (6.6 g, 30.8 mmol) was dissolved in trifluoroacetic acid (47 mL, 617 mmol) and stirred at 23° C. for 30 min. TLC at 30 min showed conversion to product. TFA was evaporated and azeotroped with toluene (2×100 mL). The residue was then dried on high vacuum for 2 hours, dissolved in 2 mL methanol and dropped into ice cold diethyl ether (200 mL). The ether was then filtered to collect 19 as the TFA salt (6.2 g, 88% yield). $^1$H NMR (500 MHz, DMSO-d$_6$) δ 8.08 (s, 3H), 6.86 (dt, J=15.9, 5.6 Hz, 1H), 6.15 (dt, J=16.0, 1.7 Hz, 1H), 3.70 (s, 3H), 3.70 (d, J=1.8 Hz, 2H). $^{13}$C NMR (126 MHz, DMSO-d$_6$) δ 165.33, 140.61, 123.22, 51.72.

3

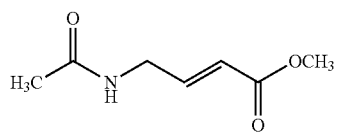

Synthesis of 3 (methyl (E)-4-acetamidobut-2-enoate) 19.

TFA (50 mg, 0.218 mmol) and triethylamine (77.8 μL, 0.558 mmol) were dissolved in anhydrous $CH_2Cl_2$ (2.4 mL, 0.09M), then acetic anhydride (32.1 μL, 0.34 mmol) was added dropwise. The reaction was stirred at 23° C. for 24 h, at which point TLC showed conversion to product. The reaction was quenched with 10 mL saturated $NH_4Cl$, then extracted with 10% $CH_3OH/CH_2Cl_2$ (3×10 mL). The combined organic layers were dried over $MgSO_4$, filtered, and evaporated. Purification with flash column chromatography with $CH_3OH/CH_2Cl_2$ ($CH_3OH$ gradient 0→5%) yielded compound 3 (23.3 mg, 68% yield). $^1H$ NMR (500 MHz, $CDCl_3$) δ 6.93 (dt, J=15.7, 5.1 Hz, 1H), 5.95 (dt, J=15.8, 1.8 Hz, 1H), 5.68 (s, 1H), 4.08 (td, J=5.8, 1.8 Hz, 2H), 3.76 (s, 3H), 2.07 (s, 3H). $^{13}C$ NMR (126 MHz, $CDCl_3$) δ 169.98, 166.39, 144.13, 121.48, 51.70, 40.21, 23.14. [M+Na]: 179.828 Da.

Synthesis of 1, 2, 3-14.

The commercially available carboxylic acid starting material (0.35 mmol) was dissolved in dimethylformamide (0.2M, 1.75 mL), then 19, TFA (80.2 mg, 0.35 mmol), HBTU (128 mg, 0.34 mmol), and HOBT (51.8 mg, 0.38 mmol) were added, followed by diisopropylethylamine (175 μL, 1.047 mmol). The reaction was stirred at 23° C. for 16 h. TLC at 16 h showed conversion to product. The reaction was quenched with $H_2O$ (5 mL) and extracted with DCM (3×5 mL). The combined organic layers were washed with 1M HCl (10 mL), saturated aqueous $NaHCO_3$ (10 mL), and saturated aqueous NaCl (10 mL). The organic layer was dried over $MgSO_4$, filtered, and evaporated. Purification with flash column chromatography with $CH_3OH/CH_2Cl_2$ ($CH_3OH$ gradient 05%) yielded compounds 1, 2, 3-14.

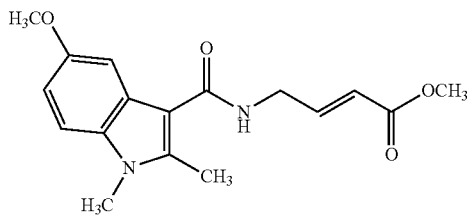

Methyl(E)-4-(5-methoxy-1,2-dimethyl-1H-indole-3-carboxamido)but-2-enoate (compound 1). Carboxylic acid starting material purchased from ChemBridge. 55.6 mg, 50.2% yield. $^1H$ NMR (500 MHz, $CDCl_3$) δ 7.28-7.21 (m, 2H), 7.11 (dt, J=15.7, 4.9 Hz, 1H), 6.91 (dd, J=8.8, 2.4 Hz, 1H), 4.34 (ddd, J=6.1, 4.9, 2.0 Hz, 2H), 3.91 (s, 3H), 3.76 (s, 3H), 3.70 (s, 3H), 2.74 (s, 3H). $^{13}C$ NMR (126 MHz, $CDCl_3$) δ 166.57, 166.28, 155.32, 145.26, 142.70, 131.76, 125.59, 121.15, 110.59, 110.30, 106.82, 101.91, 56.05, 51.67, 40.16, 29.68, 11.84. [M+Na]: 339.244 Da.

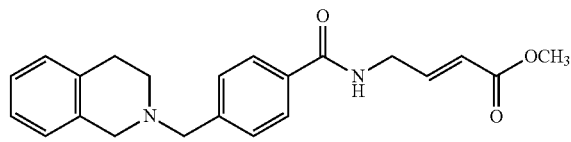

Methyl(E)-4-(4-((3,4-dihydroisoquinolin-2(1H)-yl)methyl)benzamido)but-2-enoate (Compound 2)

Carboxylic acid starting material purchased from ChemBridge. 103.22 mg, 80.7% yield. $^1H$ NMR (500 MHz, DMSO-$d_6$) δ 8.82 (t, J=5.7 Hz, 1H), 7.87 (d, J=8.2 Hz, 2H), 7.47 (d, J=8.2 Hz, 2H), 7.18-7.04 (m, 3H), 7.04-6.86 (m, 2H), 5.92 (dt, J=15.7, 1.9 Hz, 1H), 4.23-3.99 (m, 2H), 3.71 (s, 2H), 3.66 (s, 3H), 3.55 (s, 2H), 2.82 (d, J=5.8 Hz, 2H), 2.69 (s, 3H). $^{13}C$ NMR (126 MHz, DMSO-$d_6$) δ 166.08, 165.89, 146.28, 142.08, 134.66, 134.00, 132.69, 128.51, 128.42, 127.26, 126.32, 125.97, 125.45, 119.93, 61.35, 55.40, 51.37, 50.25, 38.21, 28.64. [M+H]: 363.255 Da.

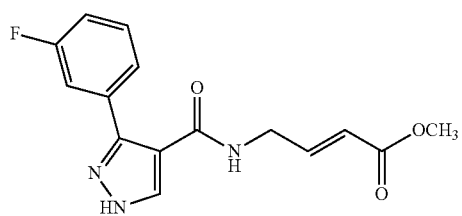

Methyl(E)-4-(3-(3-fluorophenyl)-1H-pyrazole-4-carboxamido)but-2-enoate (Compound 4)

Carboxylic acid starting material purchased from ChemBridge. 56.9 mg, 53.4% yield. $^1H$ NMR (500 MHz, $CDCl_3$) δ 8.11 (s, 1H), 7.55-7.43 (m, 2H), 7.41 (ddd, J=9.5, 2.6, 1.5 Hz, 1H), 7.20 (tdd, J=8.4, 2.7, 1.2 Hz, 1H), 6.92 (dt, J=15.7, 5.1 Hz, 1H), 5.85 (dt, J=15.7, 1.9 Hz, 1H), 5.79 (t, J=6.0 Hz, 1H), 4.15 (ddd, J=6.1, 5.2, 1.9 Hz, 2H), 3.76 (s, 3H). $^{13}C$ NMR (126 MHz, $CDCl_3$) δ 166.46, 163.73, 163.16, 161.77, 143.89, 130.58, 130.52, 124.66, 124.63, 121.45, 116.47, 116.30, 116.10, 115.92, 115.09, 55.59, 51.73, 43.53, 40.18, 18.56, 17.21, 12.42. [M+Na]: 325.846 Da.

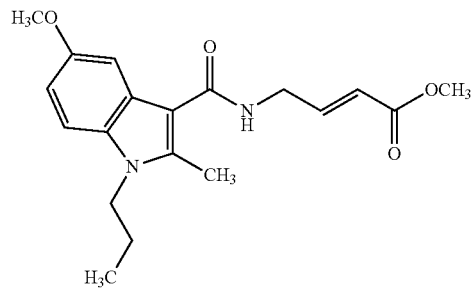

Methyl(E)-4-(5-methoxy-2-methyl-1-propyl-1H-indole-3-carboxamido)but-2-enoate (Compound 5)

Carboxylic acid starting material purchased from Enamine. 57.4 mg, 47.6% yield. $^1H$ NMR (500 MHz, $CDCl_3$) δ 7.24 (d, J=1.5 Hz, 1H), 7.10 (dt, J=15.7, 4.9 Hz, 1H), 6.89 (dd, J=8.8, 2.4 Hz, 1H), 6.07 (d, J=15.7 Hz, 1H), 6.03 (dd, J=12.2, 5.7 Hz, 1H), 4.33 (ddd, J=6.0, 4.9, 1.9 Hz, 2H), 4.06 (t, J=7.4 Hz, 2H), 3.89 (s, 3H), 3.75 (s, 3H), 2.72 (s, 3H), 1.81 (q, J=7.4 Hz, 2H), 0.98 (t, J=7.4 Hz, 3H). $^{13}C$ NMR (126 MHz, $CDCl_3$) δ 166.54, 166.34, 155.26, 145.23, 142.21, 131.15, 125.77, 121.19, 110.62, 110.57, 106.90, 101.93, 56.05, 51.63, 44.83, 40.17, 23.16, 11.80, 11.44. [M+Na]: 366.934 Da.

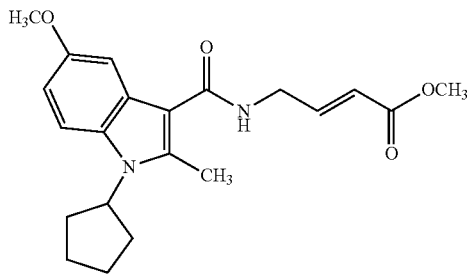

6

Methyl(E)-4-(1-cyclopentyl-5-methoxy-2-methyl-1H-indole-3-carboxamido)but-2-enoate (Compound 6)

Carboxylic acid starting material purchased from Enamine. 78.8 mg, 60.8%. $^1$H NMR (500 MHz, CDCl$_3$) δ 7.33 (d, J=8.9 Hz, 1H), 7.24 (d, J=2.4 Hz, 1H), 7.08 (dt, J=15.7, 4.9 Hz, 1H), 6.83 (dd, J=8.9, 2.4 Hz, 1H), 6.05 (dt, J=15.6, 1.7 Hz, 1H), 6.01-5.90 (m, 1H), 4.82 (t, J=9.0 Hz, 1H), 4.31 (td, J=5.6, 1.8 Hz, 2H), 3.87 (s, 3H), 3.74 (s, 3H), 2.72 (s, 3H), 2.24 (td, J=8.6, 5.3 Hz, 2H), 2.06 (dt, J=10.7, 7.2 Hz, 5H), 1.81 (q, J=6.5 Hz, 2H). $^{13}$C NMR (126 MHz, CDCl$_3$) δ 166.53, 154.88, 145.17, 142.29, 129.10, 126.85, 121.19, 112.42, 110.16, 107.19, 102.08, 56.00, 55.96, 51.63, 40.21, 29.99, 25.38, 12.28. [M+Na]: 392.971 Da.

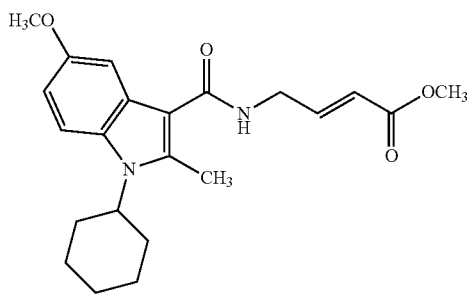

7

Methyl(E)-4-(1-cyclohexyl-5-methoxy-2-methyl-1H-indole-3-carboxamido)but-2-enoate (Compound 7)

Carboxylic acid starting material purchased from Enamine. 63.5 mg, 47.2% yield $^1$H NMR (500 MHz, CDCl$_3$) δ 7.50 (d, J=9.1 Hz, 1H), 7.24 (d, J=2.5 Hz, 1H), 7.14-7.03 (m, 1H), 6.85 (dd, J=9.0, 2.5 Hz, 1H), 6.07 (d, J=15.7 Hz, 1H), 6.02 (d, J=7.0 Hz, 1H), 4.33 (ddd, J=5.9, 4.9, 2.0 Hz, 2H), 4.24 (tt, J=12.3, 4.1 Hz, 1H), 3.89 (s, 3H), 3.76 (s, 3H), 2.74 (s, 3H), 2.43-2.19 (m, 2H), 2.00 (dt, J=14.0, 3.3 Hz, 2H), 1.87 (ddd, J=24.5, 12.7, 4.0 Hz, 4H), 1.57-1.43 (m, 2H). $^{13}$C NMR (126 MHz, CDCl$_3$) δ 166.53, 154.73, 145.16, 141.62, 121.19, 110.19, 101.74, 55.95, 51.63, 40.22, 31.25, 26.37, 25.47. [M+Na]: 406.993 Da.

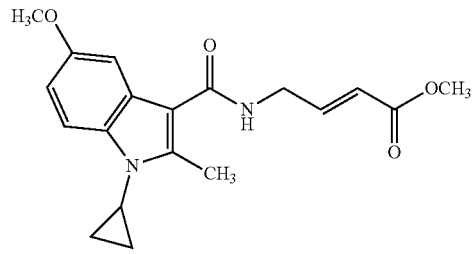

8

Methyl(E)-4-(1-cyclopropyl-5-methoxy-2-methyl-1H-indole-3-carboxamido)but-2-enoate (Compound 8)

Carboxylic acid starting material purchased from Enamine. 71.2 mg, 59.4% yield. $^1$H NMR (500 MHz, CDCl$_3$) δ 7.51 (d, J=8.9 Hz, 1H), 7.24 (d, J=2.2 Hz, 1H), 7.09 (ddd, J=15.7, 5.8, 4.7 Hz, 1H), 6.89 (ddd, J=9.2, 2.3, 1.1 Hz, 1H), 6.06 (dd, J=16.0, 1.9 Hz, 1H), 6.02 (d, J=7.0 Hz, 1H), 4.32 (td, J=5.4, 4.7, 1.6 Hz, 2H), 3.89 (d, J=1.1 Hz, 3H), 3.76 (d, J=1.2 Hz, 3H), 3.15 (dt, J=7.0, 3.1 Hz, 1H), 2.79 (d, J=1.2 Hz, 3H), 1.25 (dt, J=6.9, 1.6 Hz, 2H), 1.15-0.96 (m, 2H). $^{13}$C NMR (126 MHz, CDCl$_3$) δ 166.51, 155.35, 145.09, 144.42, 132.36, 125.68, 121.23, 111.81, 110.62, 56.03, 51.64, 40.18, 24.95, 12.96, 7.54. [M+Na]: 364.920 Da.

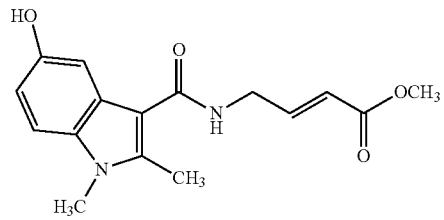

9

Methyl(E)-4-(5-hydroxy-1,2-dimethyl-1H-indole-3-carboxamido)but-2-enoate (Compound 9)

Carboxylic acid starting material purchased from Chembridge. 26.2 mg, 24.7% yield. $^1$H NMR (400 MHz, CDCl$_3$) δ 7.19-7.10 (m, 2H), 7.04 (dt, J=15.7, 5.1 Hz, 1H), 6.78 (dd, J=8.7, 2.4 Hz, 1H), 6.01 (dt, J=15.6, 1.9 Hz, 1H), 4.27 (td, J=5.5, 1.9 Hz, 2H), 3.72 (s, 3H), 3.64 (s, 3H), 2.68 (s, 3H).

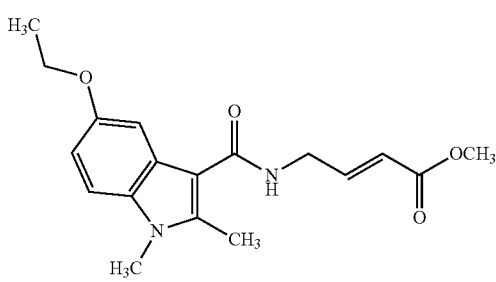

10

Methyl(E)-4-(5-ethoxy-1,2-dimethyl-1H-indole-3-carboxamido)but-2-enoate (Compound 10)

Carboxylic acid starting material purchased from Chembridge. 48.3 mg, 41.6% yield. $^1$H NMR (400 MHz, CDCl$_3$) δ 7.23-7.16 (m, 2H), 7.06 (dt, J=15.7, 5.0 Hz, 1H), 6.91-6.79 (m, 1H), 6.02 (d, J=15.7 Hz, 1H), 5.99-5.91 (m, 1H), 4.28 (ddd, J=5.9, 5.0, 1.9 Hz, 2H), 4.08 (q, J=7.0 Hz, 2H), 3.72 (s, 3H), 3.65 (s, 3H), 2.69 (s, 3H), 1.43 (t, J=7.0 Hz, 3H). $^{13}$C NMR (126 MHz, CDCl$_3$) δ 166.56, 166.27, 154.61, 145.27, 142.83, 131.80, 125.59, 121.15, 111.08, 110.22, 106.76, 103.03, 64.42, 51.62, 40.16, 29.62, 15.06, 11.79. [M+Na]: 352.952 Da.

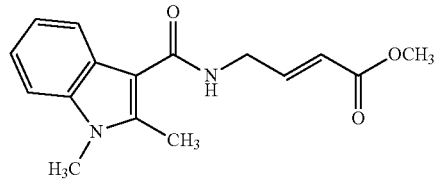

Methyl(E)-4-(1,2-dimethyl-1H-indole-3-carboxamido)but-2-enoate (Compound 11)

Carboxylic acid starting material purchased from Chembridge. 71.05 mg, 70.7% yield. $^1$H NMR (400 MHz, CDCl$_3$) δ 7.75-7.58 (m, 1H), 7.41-7.28 (m, 1H), 7.27-7.15 (m, 3H), 7.06 (dt, J=15.7, 5.0 Hz, 1H), 6.08 (s, 1H), 6.02 (dt, J=15.7, 1.9 Hz, 1H), 4.30 (ddd, J=5.9, 5.0, 1.9 Hz, 2H), 3.72 (s, 3H), 3.69 (s, 3H), 2.73 (s, 3H). $^{13}$C NMR (126 MHz, CDCl$_3$) δ 166.58, 166.17, 145.14, 142.87, 136.52, 124.83, 121.31, 118.31, 109.73, 106.97, 51.64, 40.18, 29.53, 11.67. [M+Na]: 308.858 Da.

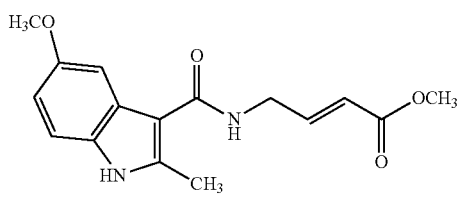

Methyl(E)-4-(5-methoxy-2-methyl-1H-indole-3-carboxamido)but-2-enoate (Compound 12)

Carboxylic acid starting material purchased from Matrix Scientific. 43.3 mg, 40.88%. $^1$H NMR (400 MHz, CDCl$_3$) δ 7.23-7.17 (m, 2H), 7.05 (dt, J=15.7, 5.0 Hz, 1H), 6.82 (dd, J=8.7, 2.4 Hz, 1H), 6.03 (d, J=15.7 Hz, 0H), 5.96 (t, J=6.1 Hz, 1H), 4.29 (ddd, J=6.0, 5.0, 1.9 Hz, 2H), 3.85 (s, 3H), 3.72 (s, 3H), 2.68 (s, 3H).

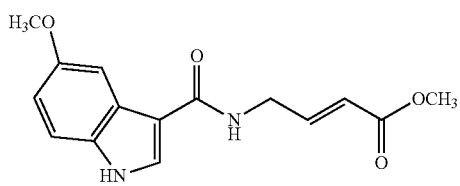

Methyl(E)-4-(5-methoxy-1H-indole-3-carboxamido)but-2-enoate (Compound 13)

Carboxylic acid starting material purchased from Sigma-Aldrich. 17.1 mg, 16.9% yield. $^1$H NMR (400 MHz, CDCl$_3$) δ 8.36 (s, 1H), 7.66 (d, J=3.0 Hz, 1H), 7.55 (d, J=2.5 Hz, 1H), 7.30 (dd, J=8.9, 0.6 Hz, 1H), 7.04 (dt, J=15.7, 5.0 Hz, 1H), 6.92 (dd, J=8.9, 2.4 Hz, 1H), 6.03 (d, J=15.7 Hz, 1H), 5.97 (s, 1H), 4.28 (ddd, J=6.0, 5.0, 1.9 Hz, 2H), 3.88 (s, 3H), 3.72 (s, 3H). $^{13}$C NMR (126 MHz, CDCl$_3$) δ 166.93, 166.00, 155.39, 145.31, 131.49, 131.34, 128.13, 127.96, 125.89, 125.86, 113.09, 112.62, 112.57, 110.68, 110.63, 102.23, 55.85, 51.68, 39.96. [M+Na]: 310.842 Da.

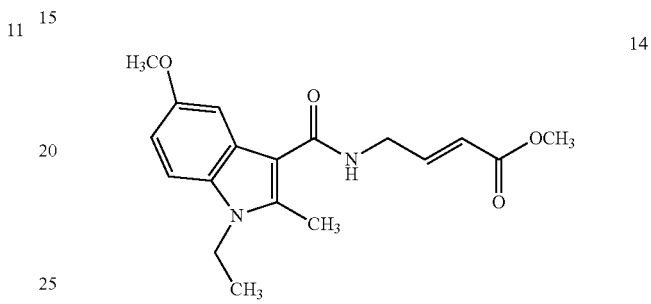

Methyl(E)-4-(1-ethyl-5-methoxy-2-methyl-1H-indole-3-carboxamido)but-2-enoate (Compound 14)

Carboxylic acid starting material purchased from Enamine. 68.95 mg, 59.4% yield. $^1$H NMR (400 MHz, CDCl$_3$) δ 7.22 (d, J=10.8 Hz, 1H), 7.06 (dt, J=15.7, 5.0 Hz, 1H), 6.86 (dd, J=8.8, 2.4 Hz, 1H), 6.03 (d, J=15.7 Hz, 1H), 5.96 (t, J=5.9 Hz, 1H), 4.29 (ddd, J=5.9, 5.0, 1.9 Hz, 2H), 4.11 (t, J=7.2 Hz, 2H), 3.86 (s, 3H), 3.71 (s, 3H), 2.69 (s, 3H), 1.33 (t, J=7.2 Hz, 3H). $^{13}$C NMR (126 MHz, CDCl$_3$) δ 166.50, 155.36, 144.97, 142.00, 130.63, 125.84, 121.32, 110.71, 110.37, 102.00, 56.06, 51.65, 40.27, 37.98, 29.73, 14.94, 11.59. [M+Na]: 352.918 Da.

Scheme for synthesis of probe 15

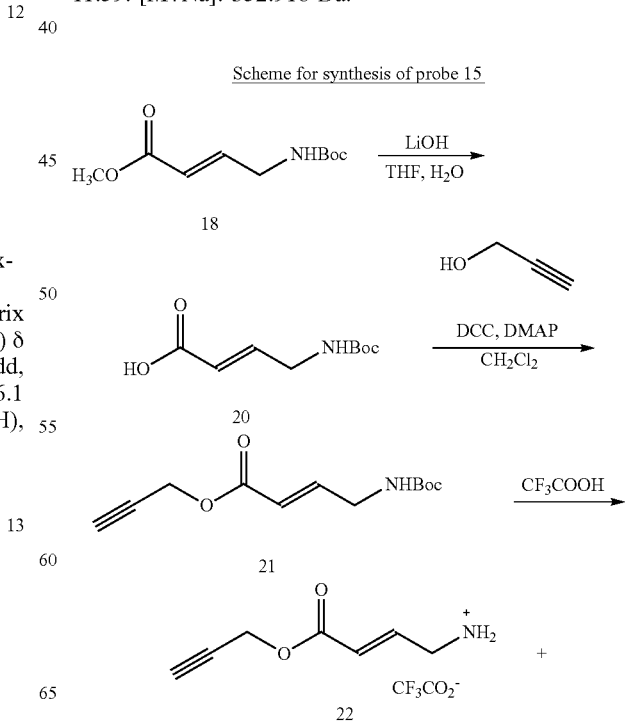

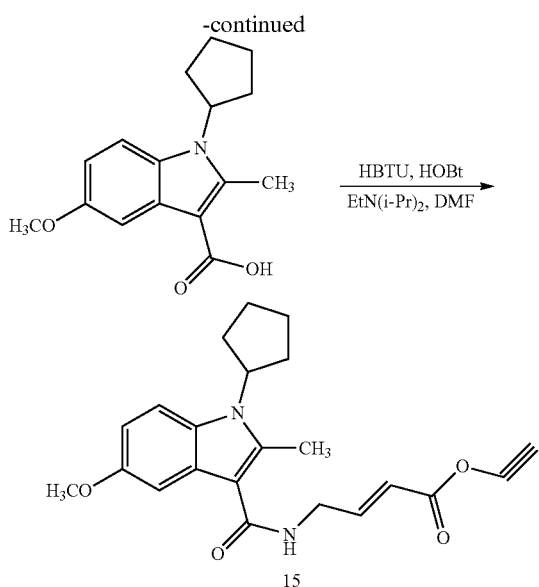

Synthesis of 20.

18 (1.5 g, 7 mmol) was dissolved in THF (37 mL). Lithium hydroxide monohydrate (971 mg, 23 mmol) dissolved in water (22 mL) was then added. TLC at 3 h showed full conversion to product. THF was evaporated under reduced pressure and the aqueous residue was adjusted to pH 3 with 1M HCl. The product was extracted with DCM (3×30 mL). The combined organic layers were dried over MgSO$_4$, filtered, and evaporated to yield 20 (1.3 g, 91%). $^1$H NMR (400 MHz, DMSO-d$_6$) δ 12.23 (s, 1H), 7.13 (t, J=5.8 Hz, 1H), 6.70 (dt, J=15.7, 4.7 Hz, 1H), 5.72 (d, J=15.8 Hz, 1H), 3.67 (t, J=4.7 Hz, 2H), 1.35 (s, 9H).

Synthesis of 21.

20 (200 mg, 1 mmol) was dissolved in CH$_2$Cl$_2$ (5 mL, 0.2M). DCC (199 mg, 1 mmol) and DMAP (21 mg, 0.17 mmol) were then added, followed by propargyl alcohol (179 μL, 3 mmol). The reaction was stirred for 1 h at room temperature, at which point TLC showed conversion to product. The white precipitate was then filtered off and washed with CHCl$_3$ (2×5 mL). The filtrate was then evaporated, and the residue was purified by flash column chromatography with an ethyl acetate/hexanes gradient 25% EtOAc 50% EtOAc to yield 21 (120 mg, 50% yield). $^1$H NMR (500 MHz, CDCl$_3$) δ 7.22 (dt, J=15.9, 4.7 Hz, 1H), 6.21 (dt, J=15.7, 2.0 Hz, 1H), 5.01 (s, 1H), 4.98 (d, J=1.7 Hz, 2H), 4.17 (d, J=5.8 Hz, 2H), 2.72 (d, J=2.4 Hz, 1H), 1.69 (s, 9H).

Synthesis of 22.

21 (120 mg, 0.5 mmol) was dissolved in trifluoroacetic acid (766 μL, 10 mmol) and stirred at 23° C. for 30 min. TLC at 30 min showed conversion to product. TFA was evaporated and azeotroped with toluene (2×100 mL). The residue was then dried on high vacuum for 2 hours to yield 22 as the TFA salt (109 mg, 86% yield). $^1$H NMR (500 MHz, CDCl$_3$) δ 8.36 (s, 3H) 7.00 (s, 1H), 6.22 (s, 1H), 5.01 (s, 1H), 4.78 (s, 2H), 3.88 (s, 2H), 2.65 (s, 1H).

Synthesis of 15.

1-cyclopentyl-5-methoxy-2-methyl-1H-indole-3-carboxylic acid (117 mg, 0.43 mmol) was dissolved in dimethylformamide (0.2M, 2.14 mL), then 22, TFA (109 mg, 0.43 mmol), HBTU (158 mg, 0.41 mmol), and HOBT (63.6 mg, 0.47 mmol) were added, followed by diisopropylethylamine (215 μL, 1.28 mmol). The reaction was stirred at 23° C. for 16 h. TLC at 16 h showed conversion to product. The reaction was quenched with H$_2$O (5 mL) and extracted with DCM (3×5 mL). The combined organic layers were washed with 1M HCl (10 mL), saturated aqueous NaHCO$_3$ (10 mL), and saturated aqueous NaCl (10 mL). The organic layer was dried over MgSO$_4$, filtered, and evaporated. Purification with flash column chromatography with CH$_3$OH/CH$_2$Cl$_2$ (CH$_3$OH gradient 05%) yielded compound 15 as a yellow powder (55.4 mg, 33.8% yield). $^1$H NMR (500 MHz, CDCl$_3$) δ 7.34 (d, J=9.0 Hz, 1H), 7.24 (d, J=2.5 Hz, 1H), 7.15 (dt, J=15.7, 4.8 Hz, 1H), 6.84 (dd, J=9.0, 2.4 Hz, 1H), 6.08 (dt, J=15.8, 1.9 Hz, 1H), 6.02 (t, J=6.0 Hz, 1H), 4.82 (t, J=9.0 Hz, 1H), 4.74 (d, J=2.5 Hz, 2H), 4.32 (ddd, J=6.5, 4.9, 2.0 Hz, 2H), 3.88 (s, 3H), 2.73 (s, 3H), 2.48 (t, J=2.5 Hz, 1H), 2.31-2.17 (m, 2H), 2.06 (dd, J=9.2, 3.1 Hz, 4H), 1.81 (qd, J=5.1, 4.5, 2.2 Hz, 2H). $^{13}$C NMR (126 MHz, CDCl$_3$) δ 166.38, 165.11, 154.90, 146.57, 142.37, 129.10, 126.83, 120.42, 112.45, 110.19, 107.12, 102.05, 74.88, 56.01, 55.99, 51.98, 40.23, 29.99, 25.39, 12.29. [M+H]: 395.360 Da.

SUPPLEMENTARY REFERENCES

1. Maspero, E., et al. Structure of the HECT:ubiquitin complex and its role in ubiquitin chain elongation. *EMBO Rep.* 12 (4), 342-9 (2011).
2. Winter, G. Xia2: an expert system for macromolecular crystallography data reduction. *J. Appl. Cryst.* 43, 186-190 (2010).
3. McCoy, A. J., et al. Phaser crystallographic software. *J. Appl. Cryst.* 40, 658-674 (2007).
4. Lebedev, A. A. et al. JLigand: a graphical tool for the CCP4 template-restraint library. *Acta Cryst.* D 68, 431-440 (2012).
5. Smart, O. S. et al. (2011) grade, version 1.101. Cambridge, United Kingdom, Global Phasing Ltd. available at its website.
6. Emsley, P., Cowtan, K. Coot: model-building tools for molecular graphics. *Acta Cryst.* D 60, 2126-2132 (2004).
7. Winn, M. D. et al. Overview of the CCP4 suite and current developments. *Acta Cryst.* D 67, 235-242 (2011).
8. Murshudov, G. N., Vagin, A. A., Dodson, E. J. Refinement of macromolecular structures by the maximum-likelihood method. *Acta Cryst.* D 53, 240-255 (1997).
9. Winn, M. D., Isupov, M. N., Murshudov, G. N. Use of TLS parameters to model anisotropic displacements in macromolecular refinement. *Acta Cryst.* D 57, 122-133 (2001).
10. Laskowski, R. A., Rullmannn, J. A., MacArthur, M. W., Kaptein, R., Thornton, J. M. J. AQUA and PROCHECK-NMR: programs for checking the quality of protein structures solved by NMR. *Biomol. NMR* 8, 477-486 (1996).
11. Adams, P. D. et al. PHENIX: a comprehensive Python-based system for macromolecular structure solution. *Acta Cryst.* D 66, 213-221 (2010).
12. Vaguine, A. A., Richelle, J., Wodak, S. J. SFCHECK: a unified set of procedures for evaluating the quality of macromolecular structure-factor data and their agreement with the atomic model. *Acta Cryst.* D 55, 191-205 (1999).
13. Read, R. J., Schierbeek, A. J. J. A phased translation function. *J. Appl. Cryst.* 21, 490-495 (1988).
14. The PyMOL Molecular Graphics System, Version 1.3; Schrödinger, LLC.
15. Park, S., et al. Mechanism-based small molecule crosslinkers of HECT E3 ubiquitin ligase-substrate pairs. *Biochemistry* 51, 8327-8329 (2012).

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of preparing and selecting an inhibitor of an active biological molecule having a catalytic or non-catalytic cysteine residue, wherein the biological molecule is selected from the group consisting of HRV3C, NEDD4-1, NEDD4-2, and UbcH7, the method comprising:
    (a) selecting an electrophile that is reactive with cysteine residues;
    (b) preparing a library of candidate inhibitor molecules by covalently attaching the electrophile to a plurality of drug molecules, wherein the library of candidate inhibitor molecules thus prepared is reactive with cysteine residues;
    (c) contacting the library of candidate inhibitor molecules with the biological molecule;
    (d) detecting a reaction product formed from one or more of the candidate inhibitor molecules and the biological molecule;
    (e) detecting inhibitory activity of one or more of the candidate inhibitor molecules that form a reaction product with the biological molecule in an inhibition assay for the biological molecule and selecting the inhibitor based on the detected inhibitory activity; wherein the library of candidate inhibitor molecules comprises one or more molecules having a formula:

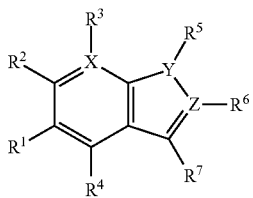

I wherein:
    X is CH or N; Y is N, O, or S; Z is C or N;
    $R^1$ is selected from hydrogen, hydroxyl, thiol, halogen, alkoxy, alkylthio, amino, alkylamino, haloalkyl, and haloalkoxy;
    $R^2$, $R^3$, and $R^4$ are the same or different and are selected from hydrogen, halogen, and alkoxy;
    $R^5$ and $R^6$ are the same or different and are selected from hydrogen, alkyl, cycloalkyl, aryl, and alkylaryl; and
    $R^7$ has a formula selected from:

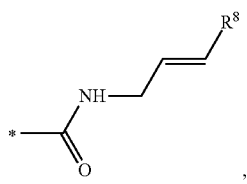

,

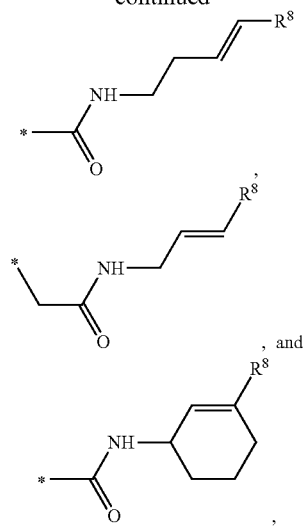

wherein $R^8$ is $COR^9$, COOR, $C(=O)NR_2$, $C(=O)NHR$, $SO_2R^9$ or CN, and $R^9$ is selected from alkyl, aryl, alkoxy, amino, alkylamino, and aniline.

2. The method of claim 1, wherein the biological molecule has a catalytic cysteine residue.

3. The method of claim 1, wherein the electrophile is not reactive with lysine residues or histidine residues.

4. The method of claim 1, wherein the electrophile is an electrophile selected from the group consisting of acrylamides, vinylsulfonamides, acrylates, methyl acrylates, vinyl sulfones, methyl vinyl sulfones, vinyl ketones, acrylonitriles, and propargyl ketones.

5. The method of claim 1, wherein the reaction product formed from the candidate inhibitor molecule and the biological molecule is formed via reaction of the electrophile of the candidate inhibitor molecule and the cysteine residue of the biological molecule.

6. The method of claim 1, wherein the reaction product formed from the candidate inhibitor molecule and the biological molecule is detected by performing electrospray ionization mass spectrometry (ESI-MS).

7. The method of claim 1, further comprising measuring the reaction rate of the library of candidate inhibitor molecules with a cysteine residue.

8. The method of claim 1, further comprising testing whether the selected inhibitor inhibits activity of a different biological molecule having a catalytic or non-catalytic cysteine residue and selecting the inhibitor if the inhibitor does not inhibit activity of the different biological molecule.

9. The method of claim 8, wherein the different biological molecule has a catalytic cysteine residue.

10. The method of claim 1, wherein:
    $R^1$ is selected from hydrogen, hydroxyl, halogen, alkoxy, haloalkyl, and haloalkoxy;

$R^7$ has a formula selected from:

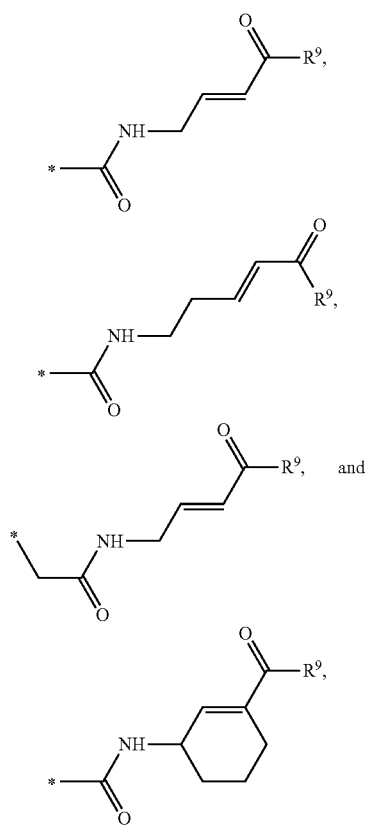

and $R^9$ is selected from alkoxy, amino, alkylamino, and anilino.

11. The method of claim 1, wherein the compound has a formula Ia:

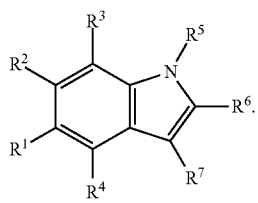

12. The method of claim 1, wherein $R^1$ is methoxy or ethoxy.

13. The method of claim 1, wherein $R^2$, $R^3$, and $R^4$ are hydrogen.

14. The method of claim 1, wherein $R^5$ and $R^6$ are the same or different and are selected from hydrogen, methyl, cyclopropyl, cyclobutyl, cyclopentyl, cyclohexyl, and benzyl.

15. The method of claim 13, wherein $R^7$ has a formula:

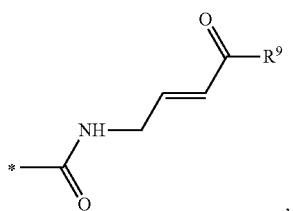

and $R^9$ is selected from alkoxy, amino, alkylamino, and anilino.

16. The method of claim 1, wherein $R^7$ has a formula:

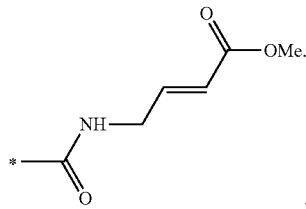

\* \* \* \* \*